US009198432B2

(12) United States Patent
Giencke et al.

(10) Patent No.: US 9,198,432 B2

(45) Date of Patent: Dec. 1, 2015

(54) 1,2,4-TRIAZOLYL-SUBSTITUTED KETOENOLS

(75) Inventors: Wolfgang Giencke, Hofheim (DE); Stefan Lehr, Lyons (FR); Reiner Fischer, Monheim (DE); David Stephen Lindell, Kelkheim (DE); Isolde Haeuser-Hahn, Leverkusen (DE); Ines Heinemann, Hofheim (DE); Elmar Gatzweiler, Bad Nauheim (DE); Christopher Hugh Rosinger, Hofheim (DE); Angela Becker, Dusseldorf (DE); Arnd Voerste, Cologne (DE); Ulrich D.I. Goergens, Ratingen (DE)

(73) Assignee: BAYER INTELLECTUAL PROPERTY GMBH, Monheim am Rhein (DE)

( * ) Notice: Subject to any disclaimer, the term of this patent is extended or adjusted under 35 U.S.C. 154(b) by 89 days.

(21) Appl. No.: 14/237,117

(22) PCT Filed: Aug. 10, 2012

(86) PCT No.: PCT/EP2012/065682

§ 371 (c)(1), (2), (4) Date: May 7, 2014

(87) PCT Pub. No.: WO2013/021044

PCT Pub. Date: Feb. 14, 2013

(65) Prior Publication Data

US 2014/0302988 A1 Oct. 9, 2014

(30) Foreign Application Priority Data

Aug. 11, 2011 (EP) .................................... 11177285

(51) Int. Cl.

| | |
|---|---|
| ***C07D 249/04*** | (2006.01) |
| ***A01N 43/90*** | (2006.01) |
| ***C07D 403/12*** | (2006.01) |
| ***A01N 43/653*** | (2006.01) |
| ***A01N 47/38*** | (2006.01) |
| ***C07D 403/04*** | (2006.01) |
| ***C07D 405/04*** | (2006.01) |
| ***C07D 405/12*** | (2006.01) |
| ***C07D 413/06*** | (2006.01) |
| ***C07D 249/08*** | (2006.01) |
| ***C07D 487/04*** | (2006.01) |
| ***C07D 487/10*** | (2006.01) |
| ***C07D 491/04*** | (2006.01) |
| ***C07D 491/10*** | (2006.01) |
| ***C07D 493/10*** | (2006.01) |
| ***A01N 43/76*** | (2006.01) |

(Continued)

(52) U.S. Cl.

CPC .............. *A01N 43/90* (2013.01); *A01N 43/653* (2013.01); *A01N 43/76* (2013.01); *A01N 43/82* (2013.01); *A01N 43/84* (2013.01); *A01N 47/38* (2013.01); *C07D 249/08* (2013.01); *C07D 403/04* (2013.01); *C07D 403/12* (2013.01); *C07D 405/04* (2013.01); *C07D 405/12* (2013.01); *C07D 413/06* (2013.01); *C07D 487/04* (2013.01); *C07D 487/10* (2013.01); *C07D 491/04* (2013.01); *C07D 491/10* (2013.01); *C07D 493/10* (2013.01)

(58) Field of Classification Search

CPC .................................................... C07D 249/04

See application file for complete search history.

(56) References Cited

U.S. PATENT DOCUMENTS

| | | | |
|---|---|---|---|
| 3,542,809 | A | 11/1970 | Nakanishi et al. |
| 4,024,149 | A | 5/1977 | Winters et al. |
| 4,623,727 | A | 11/1986 | Hubele et al. |

(Continued)

FOREIGN PATENT DOCUMENTS

| | | |
|---|---|---|
| DE | 1945703 | 7/1970 |
| EP | 0142924 | 9/1984 |

(Continued)

OTHER PUBLICATIONS

Mohamed, 1993, Pak. J. Sci. Ind. Res., vol. 36, No. 6-7, p. 223-227.*

(Continued)

*Primary Examiner* — Rebecca Anderson

*Assistant Examiner* — Karen Cheng

(74) *Attorney, Agent, or Firm* — Miles and Stockbridge

(57) ABSTRACT

The invention relates to novel compounds of the formula (I)

(I)

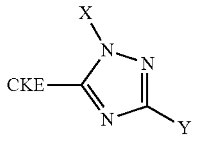

in which X, Y and CKE have the meanings given herein, to a plurality of processes and intermediates for their preparation, and to their use as pesticides and/or herbicides. The invention also relates to selective herbicidal compositions comprising the 1,2,4-triazolyl-substituted ketoenols and a crop plant compatibility-improving compound. The present invention further relates to boosting the action of said crop protection compositions through the addition of ammonium salts or phosphonium salts and optional penetrants to the corresponding compositions, to processes for producing said compositions, and to their application in crop protection as insecticides and/or acaricides and/or for preventing unwanted plant growth.

15 Claims, No Drawings

(51) Int. Cl.
*A01N 43/82* (2006.01)
*A01N 43/84* (2006.01)

(56) References Cited

U.S. PATENT DOCUMENTS

| | | | |
|---|---|---|---|
| 4,639,266 | A | 1/1987 | Heubach et al. |
| 4,678,501 | A | 7/1987 | Manning et al. |
| 4,881,966 | A | 11/1989 | Nyffeler et al. |
| 4,891,057 | A | 1/1990 | Sohn et al. |
| 4,902,340 | A | 2/1990 | Hubele et al. |
| 4,944,790 | A | 7/1990 | Moser et al. |
| 5,013,659 | A | 5/1991 | Bedbrook et al. |
| 5,215,570 | A | 6/1993 | Burckhardt et al. |
| 5,262,383 | A | 11/1993 | Fischer et al. |
| 5,314,863 | A | 5/1994 | Loher et al. |
| 5,332,720 | A | 7/1994 | Kruger et al. |
| 5,380,852 | A | 1/1995 | Schutze et al. |
| 5,401,700 | A | 3/1995 | Sohn et al. |
| 5,494,890 | A | 2/1996 | Cederbaum et al. |
| 5,500,367 | A | 3/1996 | Hain et al. |
| 5,516,750 | A | 5/1996 | Willms et al. |
| 5,689,046 | A | 11/1997 | Schroder et al. |
| 5,700,758 | A | 12/1997 | Rosch et al. |
| 5,703,008 | A | 12/1997 | Rosch et al. |
| 5,739,079 | A | 4/1998 | Holdgrun et al. |
| 5,840,661 | A | 11/1998 | Fischer et al. |
| 5,972,839 | A | 10/1999 | Ziemer et al. |
| 5,985,647 | A | 11/1999 | Schroder et al. |
| 6,133,296 | A | 10/2000 | Lieb et al. |
| 6,235,680 | B1 | 5/2001 | Ziemer et al. |
| 6,251,827 | B1 | 6/2001 | Ziemer et al. |
| 6,251,833 | B1 | 6/2001 | Erdelen et al. |
| 6,515,184 | B1 | 2/2003 | Fischer et al. |
| 6,569,810 | B1 | 5/2003 | Fischer et al. |
| 6,767,864 | B2 | 7/2004 | Fischer et al. |
| 6,974,827 | B2 | 12/2005 | Fischer et al. |
| 7,141,533 | B2 | 11/2006 | Fischer et al. |
| 7,230,116 | B2 | 6/2007 | Fischer et al. |
| 7,435,829 | B2 | 10/2008 | Fischer et al. |
| 7,595,404 | B2 | 9/2009 | Fischer et al. |
| 7,642,359 | B2 | 1/2010 | Fischer et al. |
| 8,058,452 | B2 | 11/2011 | Fischer et al. |
| 8,629,084 | B2 | 1/2014 | Fischer et al. |
| 2001/0004629 | A1 | 6/2001 | Lieb et al. |
| 2002/0010204 | A1 | 1/2002 | Lieb et al. |
| 2002/0022575 | A1 | 2/2002 | Fischer et al. |
| 2002/0151676 | A1 | 10/2002 | Desmazeau et al. |
| 2003/0073851 | A1 | 4/2003 | Lieb et al. |
| 2003/0171219 | A1 | 9/2003 | Lieb et al. |
| 2004/0009877 | A1 | 1/2004 | Fischer et al. |
| 2004/0097558 | A1 | 5/2004 | Fischer et al. |
| 2004/0102516 | A1 | 5/2004 | Fischer et al. |
| 2004/0220243 | A1 | 11/2004 | Fischer et al. |
| 2004/0224844 | A1 | 11/2004 | Bickers et al. |
| 2004/0242664 | A1 | 12/2004 | Fischer et al. |
| 2005/0037922 | A1 | 2/2005 | Bickers et al. |
| 2005/0049145 | A1 | 3/2005 | Bickers et al. |
| 2005/0070707 | A1 | 3/2005 | Fischer et al. |
| 2005/0164883 | A1 | 7/2005 | Maetzke et al. |
| 2005/0164885 | A1 | 7/2005 | Lieb et al. |
| 2005/0256000 | A1 | 11/2005 | Schaper et al. |
| 2007/0135630 | A1 | 6/2007 | Fischer et al. |
| 2007/0203101 | A1 | 8/2007 | Fischer et al. |
| 2008/0081807 | A1 | 4/2008 | Lieb et al. |
| 2008/0293573 | A1 | 11/2008 | Fischer et al. |
| 2010/0009850 | A1 | 1/2010 | Fischer et al. |
| 2010/0062942 | A1 | 3/2010 | Fischer et al. |
| 2011/0143942 | A1 | 6/2011 | Fischer et al. |

FOREIGN PATENT DOCUMENTS

| | | | |
|---|---|---|---|
| EP | 0174562 | | 9/1984 |
| EP | 0191736 | | 2/1985 |
| EP | 134985 | A | 3/1985 |
| EP | 0086750 | | 7/1987 |
| EP | 0346620 | | 12/1989 |
| EP | 0269806 | | 2/1991 |
| EP | 0193259 | | 12/1991 |
| EP | 0268554 | | 12/1991 |
| EP | 0309862 | | 8/1992 |
| EP | 0131624 | | 9/1992 |
| EP | 0221044 | B1 | 9/1992 |
| EP | 0242246 | | 11/1992 |
| EP | 0365484 | | 1/1993 |
| EP | 0333131 | | 10/1993 |
| EP | 0094349 | | 4/1994 |
| EP | 0242236 | | 8/1996 |
| EP | 0257993 | | 11/1996 |
| EP | 0492366 | | 3/1997 |
| EP | 0528156 | | 3/1997 |
| EP | 0508126 | | 5/1997 |
| EP | 0464461 | | 11/2000 |
| EP | 0582198 | | 2/2006 |
| JP | 60087254 | | 5/1985 |
| WO | WO-8402919 | | 8/1984 |
| WO | WO-8706766 | | 11/1987 |
| WO | WO-8910396 | | 11/1989 |
| WO | WO-9107874 | | 6/1991 |
| WO | WO-9108202 | | 6/1991 |
| WO | WO-9113972 | | 9/1991 |
| WO | WO-9119806 | | 12/1991 |
| WO | WO-9200377 | | 1/1992 |
| WO | WO-9211376 | | 7/1992 |
| WO | WO-9214827 | | 9/1992 |
| WO | WO-9216510 | | 10/1992 |
| WO | WO-9507897 | | 3/1995 |
| WO | WO-9601798 | | 1/1996 |
| WO | WO-9633270 | | 10/1996 |
| WO | WO-9635664 | | 11/1996 |
| WO | WO-9701535 | | 1/1997 |
| WO | WO-9702243 | | 1/1997 |
| WO | WO-9714667 | | 4/1997 |
| WO | WO-9736868 | | 10/1997 |
| WO | 9743275 | A2 | 11/1997 |
| WO | WO-9743275 | | 11/1997 |
| WO | WO-9745016 | | 12/1997 |
| WO | WO-9805638 | | 2/1998 |
| WO | WO-9813361 | | 4/1998 |
| WO | WO-9827049 | | 6/1998 |
| WO | WO-9838856 | | 9/1998 |
| WO | WO-9839281 | | 9/1998 |
| WO | WO-9900020 | | 1/1999 |
| WO | WO-9916744 | | 4/1999 |
| WO | WO-9943649 | | 9/1999 |
| WO | WO-9943699 | | 9/1999 |
| WO | WO-9947525 | | 9/1999 |
| WO | WO-9948869 | | 9/1999 |
| WO | WO-0117972 | | 3/2001 |
| WO | WO-0179204 | | 10/2001 |
| WO | 0196333 | A1 | 12/2001 |
| WO | WO-0196333 | | 12/2001 |
| WO | WO-0198288 | | 12/2001 |
| WO | 0288098 | A1 | 4/2002 |
| WO | WO-0234048 | | 5/2002 |
| WO | WO-02062791 | | 8/2002 |
| WO | WO-02088098 | | 11/2002 |
| WO | 03035643 | A1 | 5/2003 |
| WO | WO-03035643 | | 5/2003 |
| WO | WO-03048138 | | 6/2003 |
| WO | WO-2004084631 | | 10/2004 |
| WO | WO-2005015994 | | 2/2005 |
| WO | WO-2005016001 | | 2/2005 |
| WO | WO-2005112630 | | 12/2005 |
| WO | 2006029799 | A1 | 3/2006 |
| WO | WO-2006029799 | | 3/2006 |
| WO | WO-2007023719 | | 3/2007 |
| WO | WO-2007023764 | | 3/2007 |
| WO | WO-2007024782 | | 3/2007 |
| WO | WO-2007027777 | | 7/2007 |
| WO | 2009000533 | A1 | 12/2008 |
| WO | WO-2009000533 | | 12/2008 |
| WO | 2009015877 | A1 | 2/2009 |
| WO | WO-2009015877 | | 2/2009 |

(56) References Cited

FOREIGN PATENT DOCUMENTS

| | | | |
|---|---|---|---|
| WO | 2011012862 | A1 | 2/2011 |
| WO | WO-2011012862 | | 2/2011 |
| ZA | 9805601 | | 1/1999 |

OTHER PUBLICATIONS

International Search Report received in PCT/EP2012/065682, dated Dec. 13, 2012.

Gautier, J.A., "Addition Des Reactifs Nucleophiles Sur la Triple Liaison Nitrile", Am. Chi., 1970, pp. 11-27.

Zong, et al., "A Facile Synthesis of [1,2] Oxazinane-3,5-diones", Bull. Korean Chem Soc., 1999, vol. 20, No. 8, pp. 965-968.

Edward, et al., "Stereochemistry of the Bucherer-Bergs and Strecker Reactions of 4-tert-Butylcyclohexanone", Can. J. Chem, vol. 53, May 16, 1975, pp. 3339-3350.

Askani, Rainer, "Zur Reaktion von Cyclohexadien-(1.3) mit Azodicarbonsaure-diathylester", Eingegangen am, Feb. 17, 1965, pp. 2551-2555.

Harrison, et al., "Use of Molecular Sieves in the Methyl Esterification of Carboxylic Acids", Chemistry and Industry, Nov. 9, 1968, p. 1568.

Perry, et al., "Chemical Engineers' Handbook", Fourth Edition, McGraw-Hill Book Company, Inc., 4 pages.

Sonntag, Norman O.V., "The Reactions of Aliphatic Acid Chlorides", Colgate-Palmolive-Peet Company, Jersey City, New Jersey, Nov. 15, 1952, 180 pages.

Bruan, et al., "The General Mitochondrial Processing Peptidase from Potato is an Integral Part of Cytochrome c Reductase of the Respitory Chain", The EMBO Journal, vol. 11, No. 9, 1992, pp. 3219-3227.

Bhattacharya, Bhabatosh, "Isoquinoline Derivatives: Part XVIII-Formation of I-Alkyl-(or alkaryl or aryl)-3-Methyl-7-Chloro-(or 5-chloro)-Isoquinolines", Bengal Immunity Research Institute, Calcutta 16, Jan. 28, 1967, pp. 341-345.

J. Chemical Society, "Munday: Amino-acids of the", 1961, pp. 4372-4379.

Chambers, et al., "An Asymmetric Synthesis of Thiotetronic Acids using Chirality Transfer via an Allyl Xanthate-to-Dithiocarbonate Rearrangement. X-Ray Crystal Structure of (5R)-2,5-Dihydro-4-hydroxy-5-methyl-3-phenyl-5-prop-1'-enyl-2-oxothiophene", J. Chem. Soc. Chem. Comm. 1987, 3 pages.

Porter, et al., "Preparation of Unsymmetrically Labeled Hydroperoxides. A Hydroxamate Ester-Nitrosation Approach", J. Org. Chem., 1998, 63, pp. 5547-5554.

The Journal of Antibiotics, "Syntheses and Biological Activities of Thiotetromycin Analogs", vol. XXXVI, No. 11, 1983, pp. 1589-1591.

Diels, et al., Uber das aus Cyclopentadien und Azoester entstehende Endomethylen-piperidazin und seine Uberfuhrung in 1,3-Diamino-cyclopentan, Apr. 16, 1925, 11 pages.

Dannenberg, et al., "Versuche zur Synthese des,,Steranthrens" III. 3,4-Aceperinaphthan und 6,7-Aceperinaphthan, Justus Liebigs, Annalen Der Chemie, 1954, 8 pages.

Henecka, Houben-Weyl, "Methoden der organischen", Chemie 8, 1952, 4 pages.

Nakanishi, et al., "Synthesis of Chlorocarbonyl Ketenes", Organic Preparations and Procedures Int., 7(4), 1975, pp. 155-158.

Reaktionen mit metallorganischen Verbindungen, Organikum, 15, Berlin, 1977, 4 pages.

Reaktionen von Carbonsauren und Carbonsaurederivaten mit Basen, Organikum, Berlin, 1977, 1 page.

Reaktionen von Carbonylverbindungen, Organikum, Berlin, 1977, 9 pages.

Reaktionen von Carbonylverbindungen, Organikum, Berlin, 1977, 2 pages.

Bauer, et al., "Polydisperse Ethoxylated Fatty Alcohol Surfactants as Accelerators of Cuticular Penetration. 1. Effects of Ethoxy Chain length and the Size of the Penetrants", Pestic. Sci., 1997, 51, pp. 131-152.

Sonnewald, et al., "Transgenic tobacco plants expressing yeast-derived invertase in either the cytosol, vacuole or apoplast: a powerful tool for studying sucrose metabolism and sink/source interactions", The Plant Journal, 1991, 1(1), pp. 95-106.

Barton, et al., "Bacillus thuringiensis 0-Endotoxin Expressed in Transgenic Nicotiana tabacum Provides Resistance to Lepidopteran Insects", Plant Physiol., 1987, pp. 1103-1109.

Wolter, et al., "rbcS Genes in Solanum Tuberosum: Conservation of Transit Peptide and Exon Shuffling during Evolution", PNAS, 85, 1988, pp. 846-850.

Reaktionen der Organischen Chemie, 1978, 4 pages.

Prep'Yalov, et al., "Reactions of Unsaturated 1,3-Oxazines; I. Reaction of 6-Alkoxy-2-aryl-4H-1,3-oxazine-4-one with Hydrazine Derivatives", Synthesis 1999, No. 3, pp. 483-486.

Baciocchi, et al., "Dimethyl Arylmalonates from Cerium (IV) Ammonium Nitrate Promoted Reactions of Dimethyl Malonate with Aromatic Compounds in Methanol", Tetrahedron Letters, vol. 27, No. 24, 1986, pp. 2763-2766.

Christou, Paul, "Transformation Technology", Trends in Plant Science, vol. 1., No. 12, Dec. 1996, pp. 423-431.

Weed Control Handbook, "The Use of Herbicides in Potato", 5, 1968, pp. 101-103.

* cited by examiner

1,2,4-TRIAZOLYL-SUBSTITUTED KETOENOLS

CROSS REFERENCE TO RELATED APPLICATIONS

This application is a §371 National Stage Application of PCT/EP2012/065682, filed Aug. 10, 2012, which claims priority to EP 11177285.1, filed Aug. 11, 2011, and to U.S. Provisional Application No. 61/522,308, filed Aug. 11, 2011.

BACKGROUND OF THE INVENTION

1. Field of the Invention

The present invention relates to novel 1,2,4-triazolyl-substituted ketoenols, to a plurality of processes for their preparation and to their use as pesticides and/or herbicides. The invention also provides selective herbicidal compositions comprising, firstly, the 1,2,4-triazolyl-substituted ketoenols and, secondly, a crop plant compatibility-improving compound.

The present invention furthermore relates to the boosting of the action of crop protection compositions comprising, in particular, 1,2,4-triazolyl-substituted ketoenols, through the addition of ammonium salts or phosphonium salts and optionally penetrants, to the corresponding compositions, to processes for producing them and to their application in crop protection as insecticides and/or acaricides and/or for preventing unwanted plant growth.

2. Description of Relation Art

It is known that heteroaryl-substituted cyclic ketoenols have herbicidal and/or insecticidal properties (U.S. Pat. No. 4,678,501, EP-A-912547, EP-A-134985, WO 2001/96333, WO 2002/088098, WO 2003/035643, WO 2009/000533, WO 2009/015877, WO2011/012862).

However, the herbicidal and/or acaricidal and/or insecticidal activity and/or activity spectrum and/or the plant compatibility of the known compounds, in particular with respect to crop plants, is/are not always satisfactory.

SUMMARY

This invention now provides novel compounds of the formula (I)

(I)

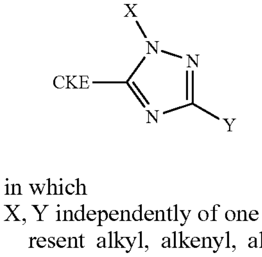

in which

X, Y independently of one another represent hydrogen, represent alkyl, alkenyl, alkynyl, cycloalkyl, cycloalkenyl, cycloalkylalkyl, cycloalkylalkenyl, cycloalkylalkinyl, cycloalkenylalkyl, each of which is optionally mono- or polysubstituted by halogen, alkoxy, alkyl-S(O)$_n$, haloalkoxy, halogenalkyl-S(O)$_n$, cyano or nitro, represent alkoxycarbonylalkyl, N,N-dialkylaminocarbonylalkyl, N,N-dialkylaminoalkyl, or represent aryl, arylalkyl, arylalkenyl, arylalkynyl, hetaryl, hetarylalkyl, hetarylalkenyl, hetarylalkynyl, heterocyclyl, heterocyclylalkyl, N-alkyl-N-arylaminocarbonylalkyl, N-alkyl-N-hetarylaminocarbonyl-alkyl, N-alkyl-N-arylaminoalkyl, each of which is optionally mono- or polysubstituted by halogen, alkyl, haloalkyl, alkoxy, haloalkoxy, alkyl-S(O)n, haloalkyl-S(O)$_n$, cyano or nitro, CKE represents one of the groups (1)

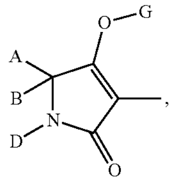

(2)

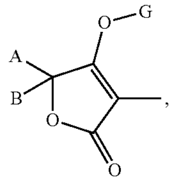

(3)

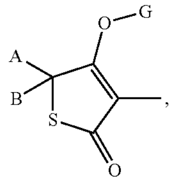

(4)

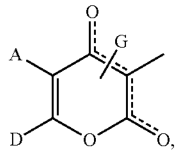

(5)

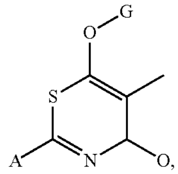

(6)

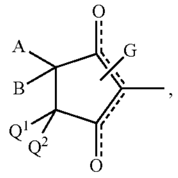

(7)

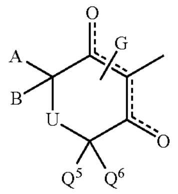

(8)

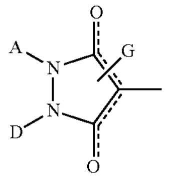

-continued (9)

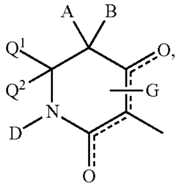

(10)

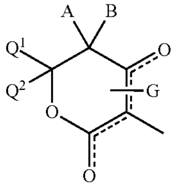

or (11)

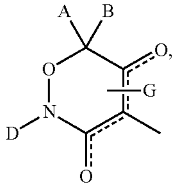

in which

U represents —S—, —S(O)—, —S($O)_2$—, —O—,

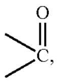

an S═N—, S(O)═N— or

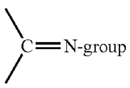

or represents $C_1$-$C_4$-alkylene which is optionally substituted by $Q^3$ and $Q^4$ and which may optionally be interrupted by oxygen, A represents hydrogen, represents in each case optionally halogen-substituted alkyl, alkenyl, alkoxyalkyl, alkylthioalkyl, saturated or unsaturated, optionally substituted cycloalkyl, in which optionally at least one ring atom is replaced by a heteroatom, or in each case optionally halogen-, alkyl-, haloalkyl-, alkoxy-, haloalkoxy-, cyano- or nitro-substituted aryl, arylalkyl or hetaryl, B represents hydrogen, alkyl, alkoxyalkyl or cycloalkyl, or A and B together with the carbon atom to which they are attached represent a saturated or unsaturated substituted or unsubstituted cycle which optionally contains at least one heteroatom, D represents hydrogen or an optionally substituted radical from the group consisting of alkyl, alkenyl, alkynyl, alkoxyalkyl, saturated or unsaturated cycloalkyl in which optionally one or more ring members are replaced by heteroatoms, represents in each case optionally substituted arylalkyl, aryl, hetarylalkyl or hetaryl or A and D together with the atoms to which they are attached represent a saturated or unsaturated cycle which is unsubstituted or substituted in the A,D moiety and optionally contains at least one (in the case of CKE=8 and 11 one further) heteroatom, or A and $Q^1$ together represent in each case optionally substituted alkanediyl or alkenediyl which may optionally be interrupted by at least one heteroatom, a

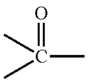

or substituted

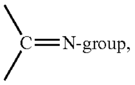

or

B and $Q^2$ together with the atoms to which they are attached represent a saturated or unsaturated cycle which is unsubstituted or substituted in the B, $Q^2$ moiety and optionally contains at least one heteroatom, or D and $Q^1$ together with the atoms to which they are attached represent a saturated or unsaturated cycle which is unsubstituted or substituted in the D, $Q^1$ moiety and optionally contains at least one heteroatom, n represents 0, 1 or 2, $Q^1$ represents hydrogen, alkyl, alkoxyalkyl, optionally substituted cycloalkyl in which one methylene group is optionally replaced by oxygen or sulphur, or represents optionally substituted phenyl, $Q^2$, $Q^4$, $Q^5$ and $Q^6$ independently of one another represent hydrogen or alkyl, $Q^3$ represents hydrogen, represents in each case optionally substituted alkyl, alkoxy, alkylthio, alkoxyalkyl, alkylthioalkyl, optionally substituted cycloalkyl in which optionally one or two methylene groups are replaced by oxygen or sulfur or represents optionally substituted phenyl, or $Q^1$ and $Q^2$ together with the carbon atom to which they are attached represent an unsubstituted or substituted cycle which optionally contains one heteroatom, or $Q^3$ and $Q^4$ together with the carbon atom to which they are attached represent a saturated or unsaturated substituted or unsubstituted cycle which optionally contains at least one heteroatom, or A and $Q^3$ together with the carbon atom to which they are attached represent a saturated or unsaturated substituted or unsubstituted cycle which optionally contains at least one heteroatom, or A and $Q^5$ together with the carbon atom to which they are attached represent a saturated or unsaturated substituted or unsubstituted cycle which optionally contains at least one heteroatom, G represents hydrogen (a) or represents one of the groups (b)

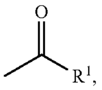

-continued (c)

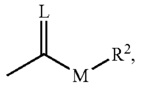

(d)

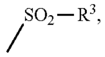

(e)

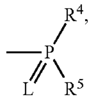

(f)

E or (g)

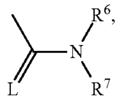

in which

E represents a metal ion equivalent or an ammonium ion,

L represents oxygen or sulfur,

M represents oxygen or sulfur, $R^1$ represents in each case optionally halogen-substituted alkyl, alkenyl, alkoxyalkyl, alkylthioalkyl, polyalkoxyalkyl or represents optionally halogen-, alkyl- or alkoxy-substituted cycloalkyl which may be interrupted by at least one heteroatom, represents in each case optionally substituted phenyl, phenylalkyl, hetaryl, phenoxyalkyl or hetaryloxyalkyl, $R^2$ represents in each case optionally halogen-substituted alkyl, alkenyl, alkoxyalkyl, polyalkoxyalkyl or represents in each case optionally substituted cycloalkyl, phenyl or benzyl, $R^3$, $R^4$ and $R^5$ independently of one another represent in each case optionally halogen-substituted alkyl, alkoxy, alkylamino, dialkylamino, alkylthio, alkenylthio, cycloalkylthio or represent in each case optionally substituted phenyl, benzyl, phenoxy or phenylthio, $R^6$ and $R^7$ independently of one another represent hydrogen, represent in each case optionally halogen-substituted alkyl, cycloalkyl, alkenyl, alkoxy, alkoxyalkyl, optionally substituted phenyl, optionally substituted benzyl, or together with the nitrogen atom to which they are attached represent a cycle which is optionally interrupted by oxygen or sulfur.

DETAILED DESCRIPTION OF A PREFERRED EMBODIMENT

Depending inter alia on the nature of the substituents, the compounds of the formula (I) can be present as geometrical and/or optical isomers or isomer mixtures of varying composition which, if desired, can be separated in a customary manner. Both the pure isomers and the isomer mixtures can be employed in the compositions according to the invention, and their activity can be enhanced by ammonium or phosphonium salts according to the invention. For the sake of simplicity, compounds of the formula (I) are always referred to below, although both the pure compounds and also, if appropriate, mixtures having different proportions of isomeric compounds are meant.

Taking into account the meanings (1) to (11) of the group CKE, the following principal structures (I-1) to (I-11) are obtained:

I-(1)

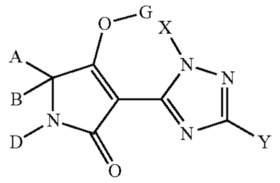

I-(2)

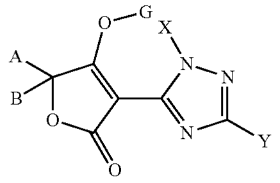

I-(3)

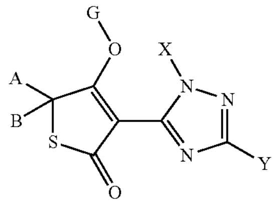

I-(4)

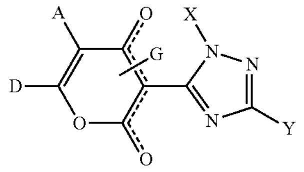

I-(5)

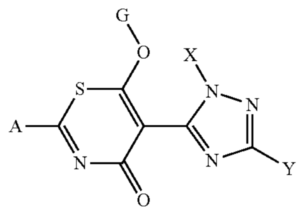

I-(6)

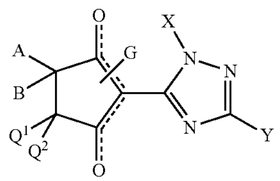

I-(7)

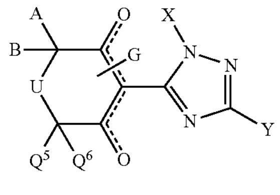

I-(8)

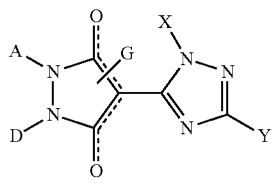

-continued

I-(9)

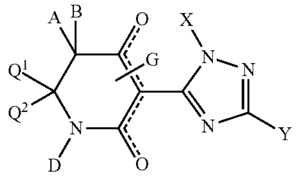

I-(10)

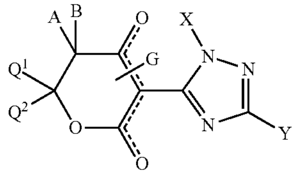

and

I-(11)

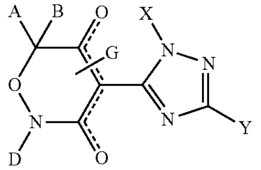

in which

A, B, D, G, $Q^1$, $Q^2$, $Q^5$, $Q^6$, U, X and Y have the meaning given above.

Taking into account the various meanings (a), (b), (c), (d), (e), (f) and (g) of group G, the following principal structures (I-1-a) to (I-1-g) are obtained if CKE represents group (1)

(I-1-a)

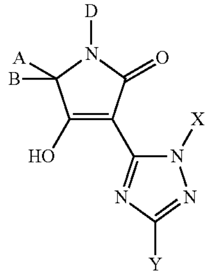

(I-1-b)

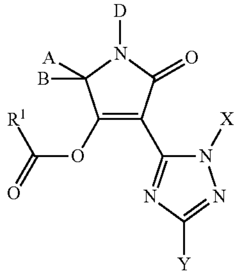

(I-1-c)

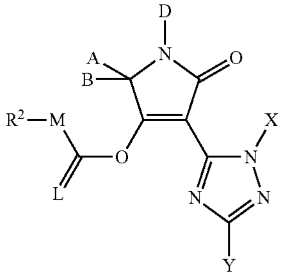

-continued (I-1-d)

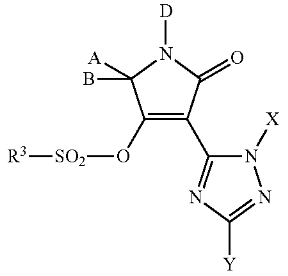

(I-1-e)

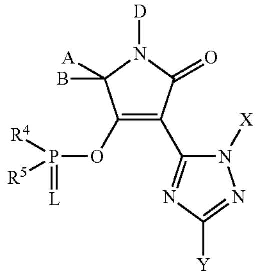

(I-1-f)

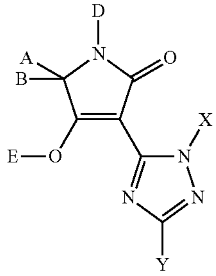

(I-1-g)

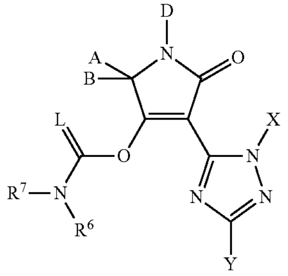

in which

A, B, D, E, L, M, X, Y, $R^1$, $R^2$, $R^3$, $R^4$, $R^5$, $R^6$ and $R^7$ have the meanings given above.

It has been found that, in the crystal, the triazole moiety of the compounds of the formula (I-1-a) is present in non-aromatized form, resulting in the structure below:

(I-1-a')

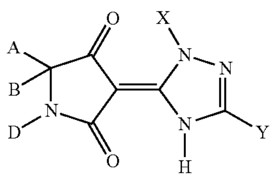

where X, Y, A, B and D have the meanings given above.

Thus, in addition to the compounds of the formula (I-1-a), the present invention also encompasses the compounds of the formula (I-1-a').

Taking into account the various meanings (a), (b), (c), (d), (e), (f) and (g) of group G, the following principal structures (I-2-a) to (I-2-g) are obtained if CKE represents group (2)

(I-2-a)

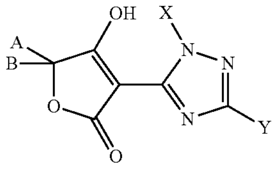

(I-2-b)

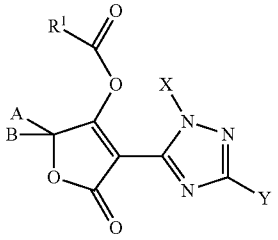

(I-2-c)

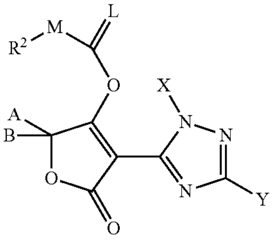

(I-2-d)

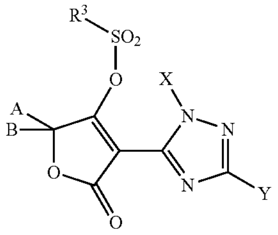

(I-2-e)

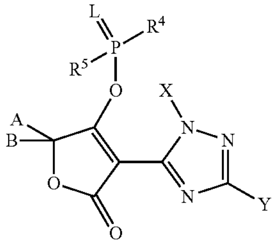

(I-2-f)

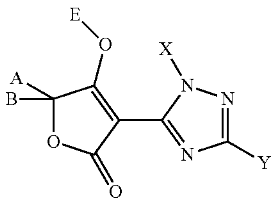

-continued (I-2-g)

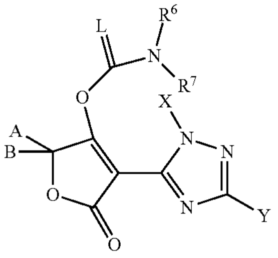

in which

A, B, D, E, L, M, X, Y, $R^1$, $R^2$, $R^3$, $R^4$, $R^5$, $R^6$ and $R^7$ have the meaning given above.

Taking into account the various meanings (a), (b), (c), (d), (e), (f) and (g) of group G, the following principal structures (I-3-a) to (I-3-g) are obtained if CKE represents group (3)

(I-3-a)

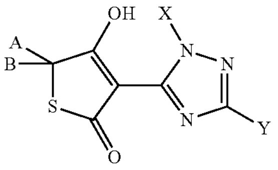

(I-3-b)

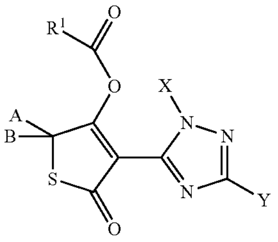

(I-3-c)

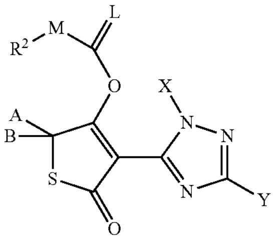

(I-3-d)

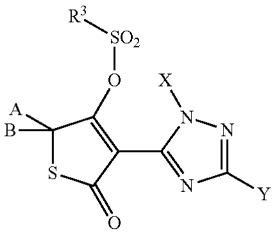

-continued (I-3-e)

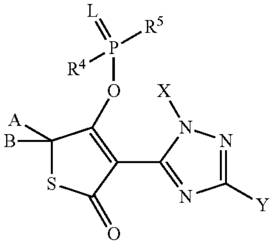

(I-3-f)

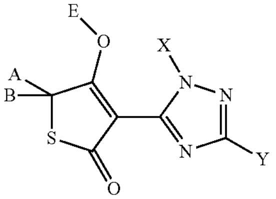

(I-3-g)

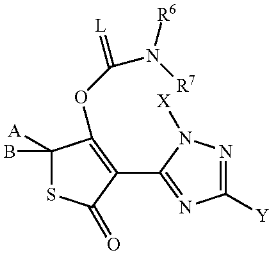

in which

A, B, D, E, L, M, X, Y, $R^1$, $R^2$, $R^3$, $R^4$, $R^5$, $R^6$ and $R^7$ have the meaning given above.

Depending on the position of the substituent G, the compounds of the formula (I-4) can exist in the two isomeric forms of the formulae (I-4-A) and (I-4-B)

(I-4-A)

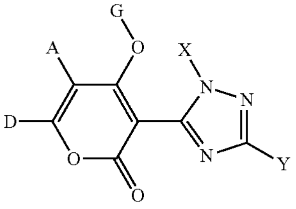

(I-4-B)

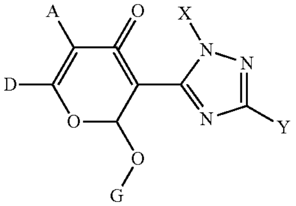

which is expressed by the broken line in formula (I-4).

The compounds of the formulae (I-4-A) and (I-4-B) can exist not only as mixtures, but also in the form of their pure isomers. If appropriate, mixtures of the compounds of the formulae (I-4-A) and (I-4-B) can be separated in a manner known per se by physical methods, for example by chromatographic methods.

The following text will only mention in each case one of the isomers which are possible, for the sake of clarity. This does not exclude that, if appropriate, the compounds may exist in the form of the isomer mixtures or in the respective other isomeric form.

Taking into account the various meanings (a), (b), (c), (d), (e), (f) and (g) of group G, the following principal structures (I-4-a) to (I-4-g) are obtained if CKE represents group (4)

(I-4-a)

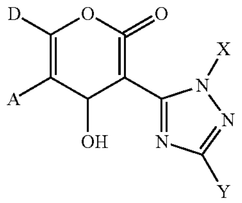

(I-4-b)

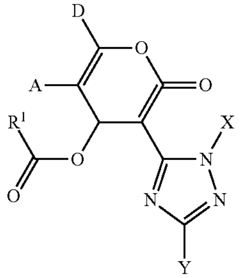

(I-4-c)

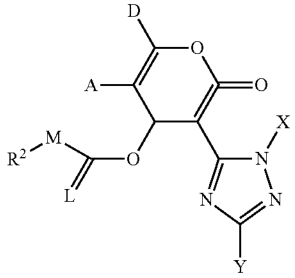

(I-4-d)

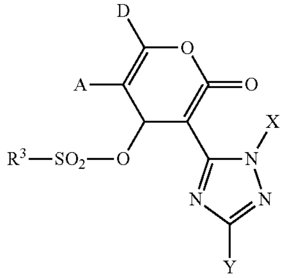

(I-4-e)

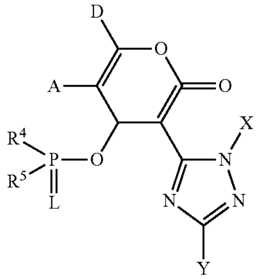

-continued (I-4-f)

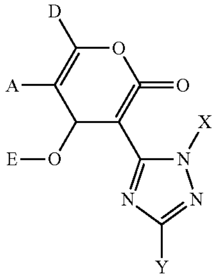

(I-4-g)

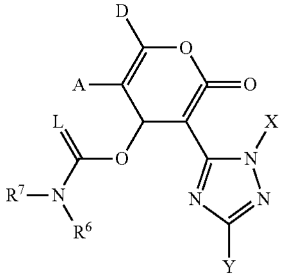

in which

A, B, D, E, L, M, X, Y, $R^1$, $R^2$, $R^3$, $R^4$, $R^5$, $R^6$ and $R^7$ have the meanings given above.

Taking into account the various meanings (a), (b), (c), (d), (e), (f) and (g) of group G, the following principal structures (I-5-a) to (I-5-g) are obtained if CKE represents group (5)

(I-5-a)

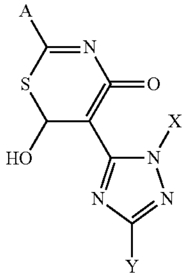

(I-5-b)

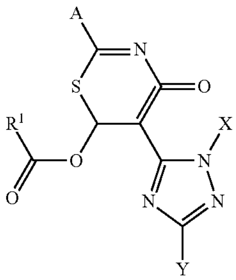

(I-5-c)

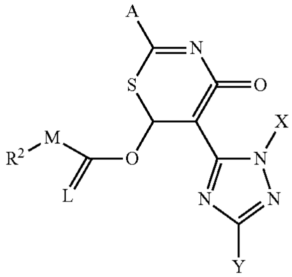

-continued (I-5-d)

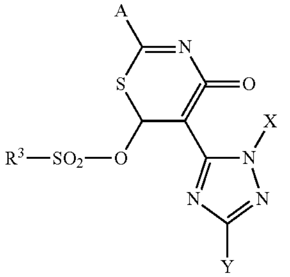

(I-5-e)

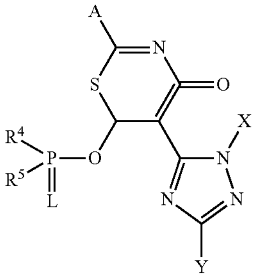

(I-5-f)

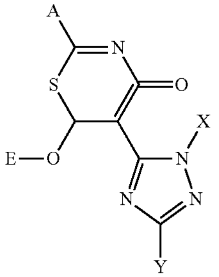

(I-5-g)

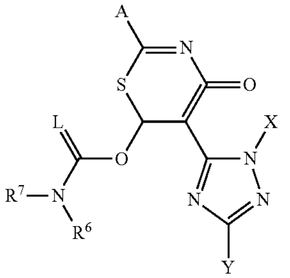

in which

A, B, D, E, L, M, X, Y, $R^1$, $R^2$, $R^3$, $R^4$, $R^5$, $R^6$ and $R^7$ have the meanings given above.

Depending on the position of the substituent G, the compounds of the formula (I-6) can exist in the two isomeric forms of the formulae (I-6-A) and (I-6-B)

(I-6-A)

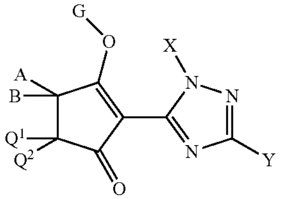

-continued (I-6-B)

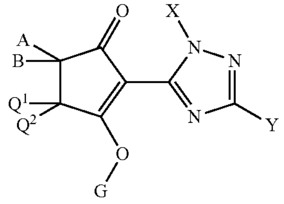

which is expressed by the broken line in formula (I-6).

The compounds of the formulae (I-6-A) and (I-6-B) can exist not only as mixtures, but also in the form of their pure isomers. If appropriate, mixtures of the compounds of the formulae (I-6-A) and (I-6-B) can be separated by physical methods, for example by chromatographic methods.

The following text will only mention in each case one of the isomers which are possible, for the sake of clarity. This does not exclude that, if appropriate, the compounds may exist in the form of the isomer mixtures or in the respective other isomeric form.

Taking into account the various meanings (a), (b), (c), (d), (e), (f) and (g) of group G, the following principal structures (I-6-a) to (I-6-g) are obtained if CKE represents group (6)

(I-6-a)

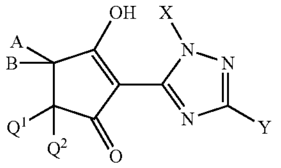

(I-6-b)

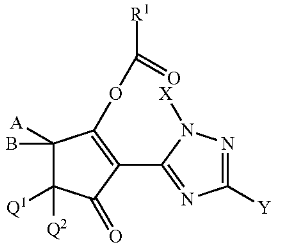

(I-6-c)

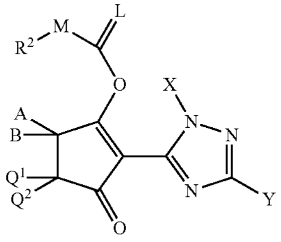

(I-6-d)

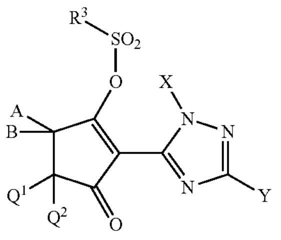

-continued (I-6-e)

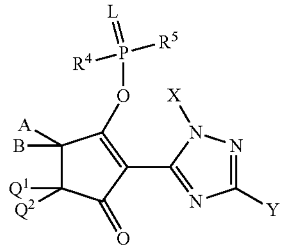

(I-6-f)

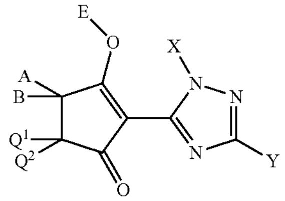

(I-6-g)

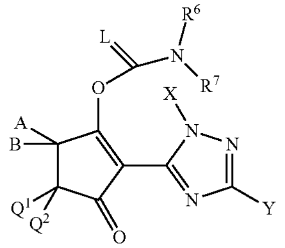

in which

A, B, D, E, L, M, X, Y, $R^1$, $R^2$, $R^3$, $R^4$, $R^5$, $R^6$ and $R^7$ have the meanings given above.

Depending on the position of the substituent G, the compounds of the formula (I-7) can exist in the two isomeric forms of the formulae (I-7-A) and (I-7-B), which is expressed by the broken line in formula (I-7):

(I-7-A)

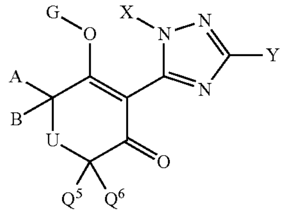

(I-7-B)

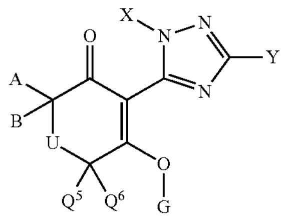

The compounds of the formulae (I-7-A) and (I-7-B) can exist not only as mixtures, but also in the form of their pure isomers. If appropriate, mixtures of the compounds of the formulae (I-7-A) and (I-7-B) can be separated by physical methods, for example by chromatographic methods.

The following text will only mention in each case one of the isomers which are possible, for the sake of clarity. This includes that the compound in question may optionally be present as an isomer mixture or in the respective other isomeric form.

Taking into account the various meanings (a), (b), (c), (d), (e), (f) and (g) of group G, the following principal structures (I-7-a) to (I-7-g) are obtained if CKE represents group (7)

(I-7-a)

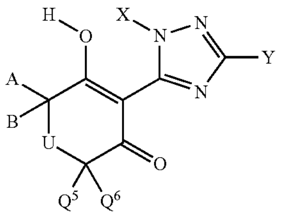

(I-7-b)

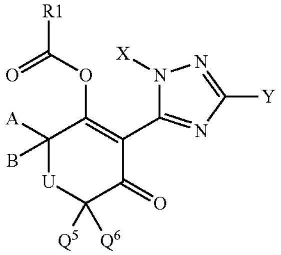

(I-7-c)

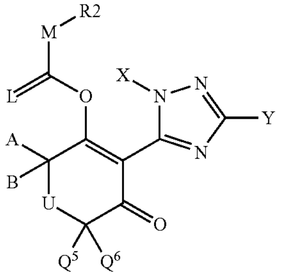

(I-7-d)

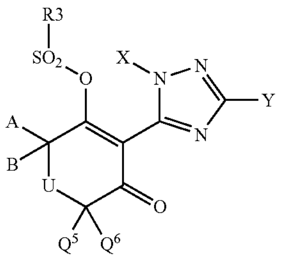

(I-7-e)

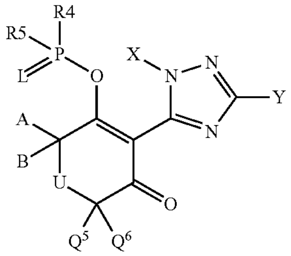

-continued (I-7-f)

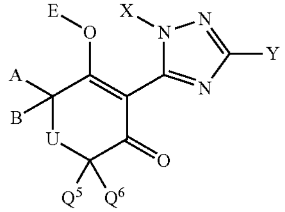

(I-7-g)

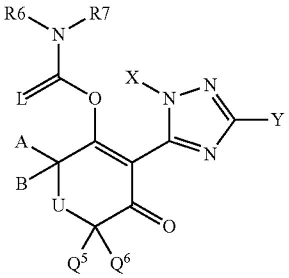

in which

A, B, D, E, L, M, X, Y, $R^1$, $R^2$, $R^3$, $R^4$, $R^5$, $R^6$ and $R^7$ have the meanings given above.

Depending on the position of the substituent G, the compounds of the formula (I-8) can exist in the two isomeric formulae (I-8-A) and (I-8-B)

(I-8-A)

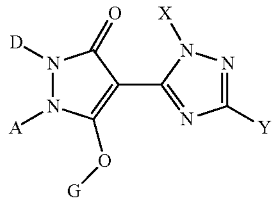

(I-8-B)

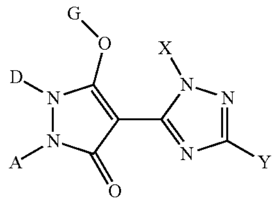

which is expressed by the broken line in formula (I-8).

The compounds of the formulae (I-8-A) and (I-8-B) can exist not only as mixtures, but also in the form of their pure isomers. If appropriate, mixtures of the compounds of the formula (I-8-A) and (I-8-B) can be separated in a manner known per se by physical methods, for example by chromatographic methods.

The following text will only mention in each case one of the isomers which are possible, for the sake of clarity. This does not exclude that, if appropriate, the compounds may exist in the form of the isomer mixtures or in the respective other isomeric form.

Taking into account the various meanings (a), (b), (c), (d), (e), (f) and (g) of group G, the following principal structures (I-8-a) to (I-8-g) are obtained if CKE represents group (8)

(I-8-a)

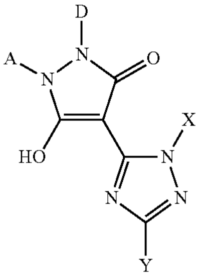

(I-8-b)

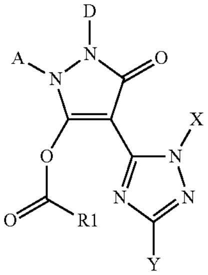

(I-8-c)

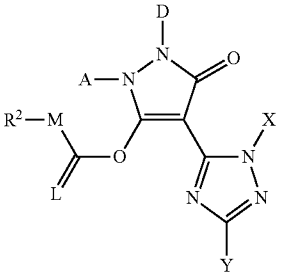

(I-8-d)

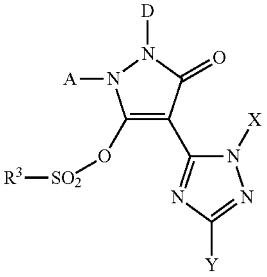

(I-8-e)

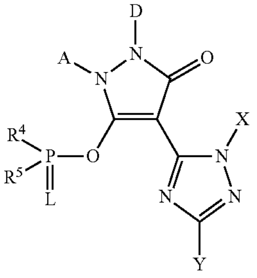

-continued (I-8-f)

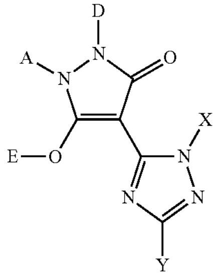

(I-8-g)

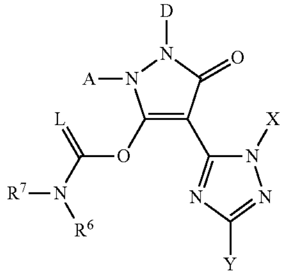

in which

A, B, D, E, L, M, X, Y, $R^1$, $R^2$, $R^3$, $R^4$, $R^5$, $R^6$ and $R^7$ have the meanings given above.

Depending on the position of the substituent G, the compounds of the formula (I-9) can exist in the two isomeric forms of the formulae (I-9-A) and (I-9-B), which is expressed by the broken line in formula (I-9):

(I-9-A)

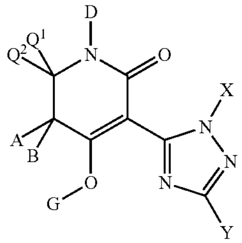

(I-9-B)

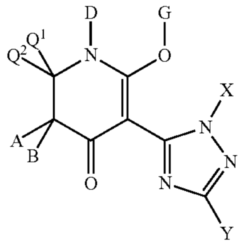

The compounds of the formulae (I-9-A) and (I-9-B) can exist not only as mixtures, but also in the form of their pure isomers. If appropriate, mixtures of the compounds of the formulae (I-9-A) and (I-9-B) can be separated in a manner known per se by physical methods, for example by chromatographic methods.

The following text will only mention in each case one of the isomers which are possible, for the sake of clarity. This does not exclude that, if appropriate, the compounds may exist in the form of the isomer mixtures or in the respective other isomeric form.

Taking into account the various meanings (a), (b), (c), (d), (e), (f) and (g) of group G, the following principal structures (I-9-a) to (I-9-g) are obtained if CKE represents group (9)

(I-9-a)

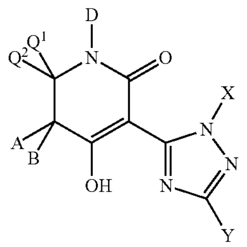

(I-9-b)

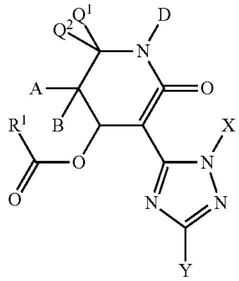

(I-9-c)

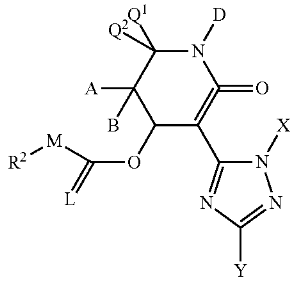

(I-9-d)

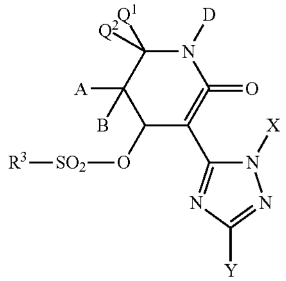

(I-9-e)

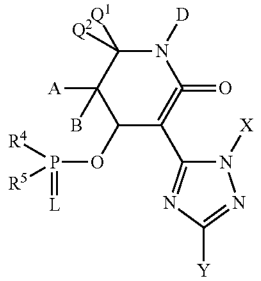

-continued (I-9-f)

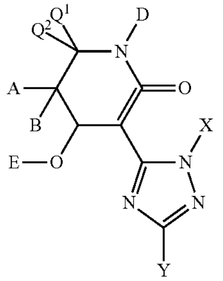

(I-9-g)

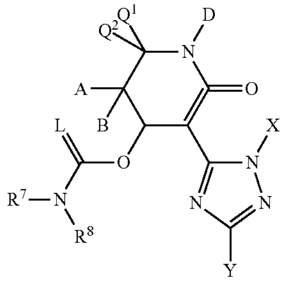

in which

A, B, D, E, L, M, $Q^1$, $Q^2$, X, Y, $R^1$, $R^2$, $R^3$, $R^4$, $R^5$, $R^6$ and $R^7$ have the meanings given above.

Depending on the position of the substituent G, the compounds of the formula (I-10) can exist in the two isomeric forms of the formulae (I-10-A) and (I-10-B)

(I-10-A)

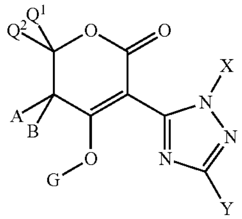

(I-10-B)

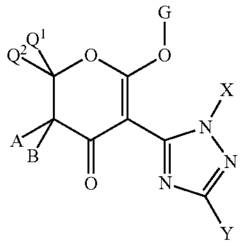

which is expressed by the broken line in formula (I-10).

The compounds of the formulae (I-10-A) and (I-10-B) can exist not only as mixtures, but also in the form of their pure isomers. If appropriate, mixtures of the compounds of the formulae (I-10-A) and (I-10-B) can be separated in a manner known per se by physical methods, for example by chromatographic methods.

The following text will only mention in each case one of the isomers which are possible, for the sake of clarity. This does not exclude that, if appropriate, the compounds may exist in the form of the isomer mixtures or in the respective other isomeric form.

Taking into account the various meanings (a), (b), (c), (d), (e), (f) and (g) of group G, the following principal structures (I-10-a) to (I-10-g) are obtained if CKE represents group (10)

(I-10-a)

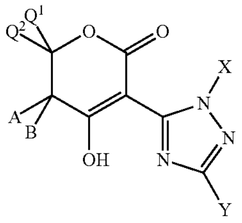

(I-10-b)

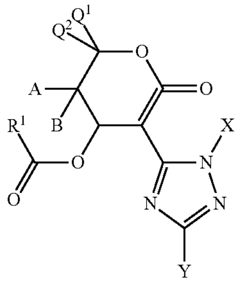

(I-10-c)

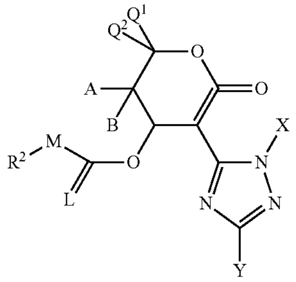

(I-10-d)

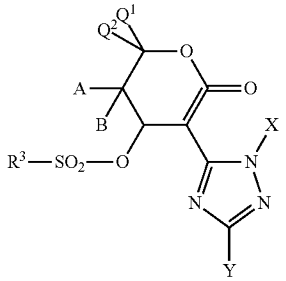

(I-10-e)

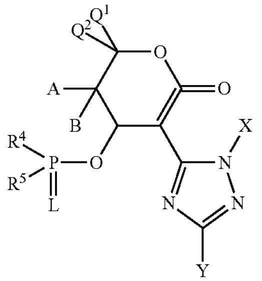

-continued (I-10-f)

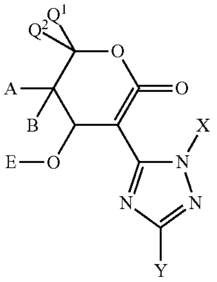

(I-10-g)

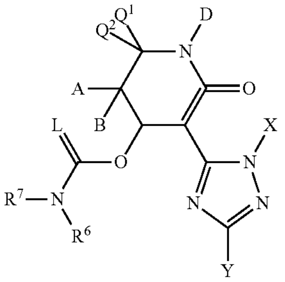

in which

A, B, E, L, M, $Q^1$, $Q^2$, X, Y, $R^1$, $R^2$, $R^3$, $R^4$, $R^5$, $R^6$ and $R^7$ have the meanings given above.

Depending on the position of the substituent G, the compounds of the formula (I-11) can exist in the two isomeric forms of the formulae (I-11-A) and (I-11-B), which is expressed by the broken line in formula (I-11):

(I-11-A)

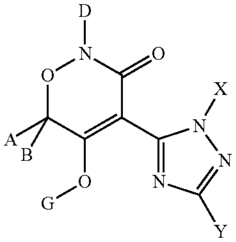

(I-11-B)

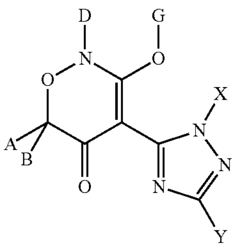

The compounds of the formulae (I-11-A) and (I-11-B) can exist not only as mixtures, but also in the form of their pure isomers. If appropriate, mixtures of the compounds of the formulae (I-11-A) and (I-11-B) can be separated in a manner known per se by physical methods, for example by chromatographic methods.

The following text will only mention in each case one of the isomers which are possible, for the sake of clarity. This does not exclude that, if appropriate, the compounds may exist in the form of the isomer mixtures or in the respective other isomeric form.

Taking into account the various meanings (a), (b), (c), (d), (e), (f) and (g) of group G, the following principal structures (I-11-a) to (I-11-g) are obtained if CKE represents group (11)

(I-11-a)

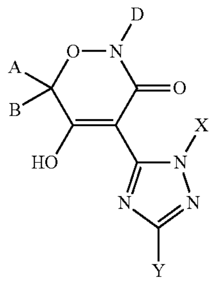

(I-11-b)

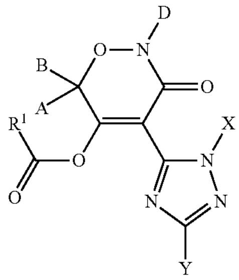

(I-11-c)

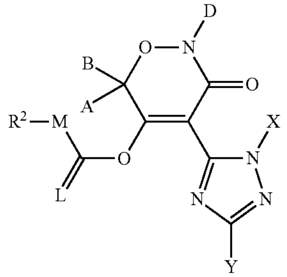

(I-11-d)

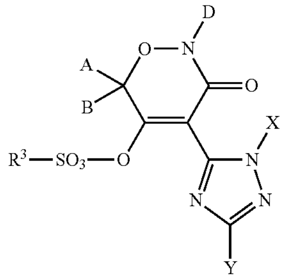

(I-11-e)

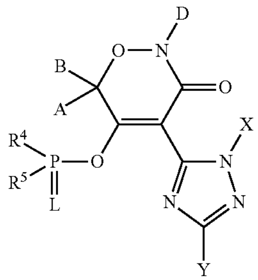

-continued (I-11-f)

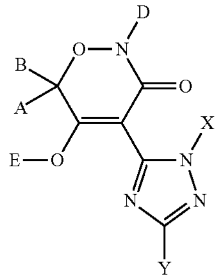

(I-11-g)

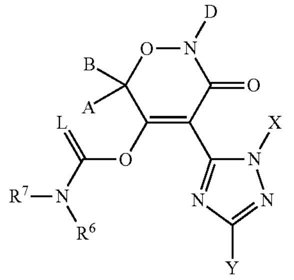

in which

A, B, D, E, L, M, X, Y, $R^1$, $R^2$, $R^3$, $R^4$, $R^5$, $R^6$ and $R^7$ have the meanings given above.

It has been found that, in the crystal, the triazole moiety of the compounds of the formulae (I-1-a), (I-2-a), (I-3-a), (I-4-a), (I-5-a), (I-6-a), (I-7-a), (I-8-a), (I-9-a), (I-10-a) and (I-11-a) is present in non-aromatized form, resulting in the structures below:

(I-1-a')

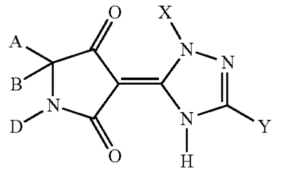

(I-2-a')

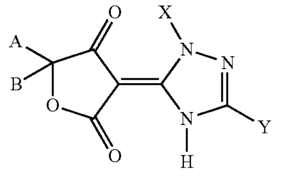

(I-3-a')

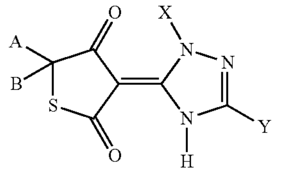

(I-4-a')

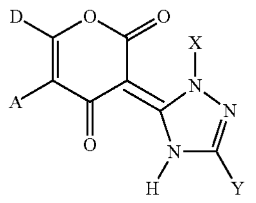

-continued (I-5-a')

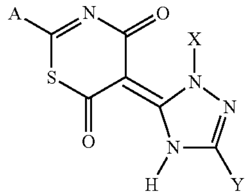

(I-6-a')

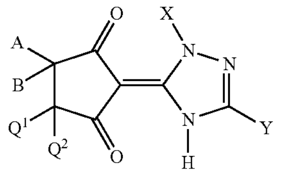

(I-7-a')

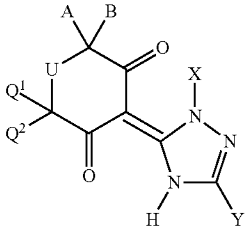

(I-8-a')

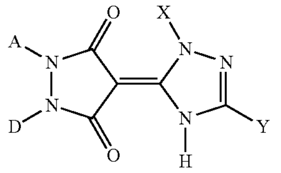

(I-9-a')

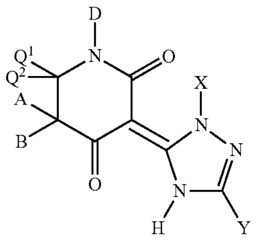

(I-10-a')

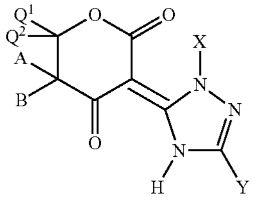

(I-11-a')

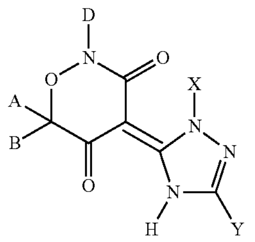

where X, Y, A, B, D, $Q^1$ and $Q^2$ have the meanings given above.

Thus, in addition to the compounds of the formulae (I-1-a), (I-2-a), (I-3-a), (I-4-a), (I-5-a), (I-6-a), (I-7-a), (I-8-a), (I-9-a), (I-10-a) and (I-11-a), the present invention also encompasses the compounds of the formulae (I-1-a'), (I-2-a'), (I-3-a'), (I-4-a'), (I-5-a'), (I-6-a'), (I-7-a'), (I-8-a'), (I-9-a'), (I-10-a') and (I-11-a').

With regard to the compounds according to the invention, the terms used above and further below will be elucidated. These are familiar to the person skilled in the art and especially have the definitions elucidated hereinafter:

"Alkoxy" is an alkyl radical bonded via an oxygen atom, alkenyloxy is an alkenyl radical bonded via an oxygen atom, alkynyloxy is an alkynyl radical bonded via an oxygen atom, cycloalkyloxy is a cycloalkyl radical bonded via an oxygen atom, and cycloalkenyloxy is a cycloalkenyl radical bonded via an oxygen atom.

The term "aryl" means a mono-, bi- or polycyclic aromatic system having preferably 6 to 14, in particular 6 to 10, carbon ring atoms, for example phenyl, naphthyl, anthryl, phenanthrenyl and the like, preferably phenyl.

The term "aryl" also includes polycyclic systems, such as tetrahydronaphthyl, indenyl, indanyl, fluorenyl, biphenylyl, where the point of attachment is on the aromatic system. In systematic terms, "aryl" is generally also encompassed by the term "optionally substituted phenyl".

A heterocyclic radical (heterocyclyl) comprises at least one heterocyclic ring (=carbocyclic ring in which at least one carbon atom is replaced by a heteroatom, preferably by a heteroatom from the group consisting of N, O, S, P, B, Si, Se), which is saturated, unsaturated, partially saturated or heteroaromatic and may be unsubstituted or substituted, where the point of attachment is located at a ring atom. If the heterocyclyl radical or the heterocyclic ring is optionally substituted, it can be fused to other carbocyclic or heterocyclic rings. Optionally substituted heterocyclyl also includes polycyclic systems, such as, for example, 8-aza-bicyclo[3.2.1]octanyl or 1-aza-bicyclo[2.2.1]heptyl. In the case of optionally substituted heterocyclyl, spirocyclic systems are also included, for example 1-oxa-5-azaspiro[2.3]hexyl. Unless defined differently, the heterocyclic ring contains preferably 3 to 9 ring atoms and in particular 3 to 6 ring atoms and one or more, preferably 1 to 4 and in particular 1, 2 or 3 heteroatoms in the heterocyclic ring, preferably from the group consisting of N, O and S, although no two oxygen atoms should be directly adjacent, for example, with one heteroatom from the group consisting of N, O and S, 1- or 2- or 3-pyrrolidinyl, 3,4-dihydro-2H-pyrrol-2- or 3-yl, 2,3-dihydro-1H-pyrrol-1- or 2- or 3- or 4- or 5-yl; 2,5-dihydro-1H-pyrrol-1- or 2- or 3-yl, 1- or 2- or 3- or 4-piperidinyl; 2,3,4,5-tetrahydropyridin-2- or 3- or 4- or 5-yl or 6-yl; 1,2,3,6-tetrahydropyridin-1- or 2- or 3- or 4- or 5- or 6-yl; 1,2,3,4-tetrahydropyridin-1- or 2- or 3- or 4- or 5- or 6-yl; 1,4-dihydropyridin-1- or 2- or 3- or 4-yl; 2,3-dihydropyridin-2- or 3- or 4- or 5- or 6-yl; 2,5-dihydropyridin-2- or 3- or 4- or 5- or 6-yl, 1- or 2- or 3- or 4-azepanyl; 2,3,4,5-tetrahydro-1H-azepin-1- or 2- or 3- or 4- or 5- or 6- or 7-yl; 2,3,4,7-tetrahydro-1H-azepin-1- or 2- or 3- or 4- or 5- or 6- or 7-yl; 2,3,6,7-tetrahydro-1H-azepin-1- or 2- or 3- or 4-yl; 3,4,5,6-tetrahydro-2H-azepin-2- or 3- or 4- or 5- or 6- or 7-yl; 4,5-dihydro-1H-azepin-1- or 2- or 3- or 4-yl; 2,5-dihydro-1H-azepin-1- or -2- or 3- or 4- or 5- or 6- or 7-yl; 2,7-dihydro-1H-azepin-1- or -2- or 3- or 4-yl; 2,3-dihydro-1H-azepin-1- or -2- or 3- or 4- or 5- or 6- or 7-yl; 3,4-dihydro-2H-azepin-2- or 3- or 4- or 5- or 6- or 7-yl; 3,6-dihydro-2H-azepin-2- or 3- or 4- or 5- or 6- or 7-yl; 5,6-dihydro-2H-azepin-2- or 3- or 4- or 5- or 6- or 7-yl; 4,5-dihydro-3H-azepin-2- or 3- or 4- or 5- or 6- or 7-yl; 1H-azepin-1- or -2- or 3- or 4- or 5- or 6- or 7-yl; 2H-azepin-2- or 3- or 4- or 5- or 6- or 7-yl; 3H-azepin-2- or 3- or 4- or 5- or 6- or 7-yl; 4H-azepin-2- or 3- or 4- or 5- or 6- or 7-yl, 2- or 3-oxolanyl (=2- or 3-tetrahydrofuranyl); 2,3-dihydrofuran-2- or 3- or 4- or 5-yl; 2,5-dihydrofuran-2- or 3-yl, 2- or 3- or 4-oxanyl (=2- or 3- or 4-tetrahydropyranyl); 3,4-dihydro-2H-pyran-2- or 3- or 4- or 5- or 6-yl; 3,6-dihydro-2H-pyran-2- or 3- or 4- or 5- or 6-yl; 2H-pyran-2- or 3- or 4- or 5- or 6-yl; 4H-pyran-2- or 3- or 4-yl, 2- or 3- or 4-oxepanyl; 2,3,4,5-tetrahydrooxepin-2- or 3- or 4- or 5- or 6- or 7-yl; 2,3,4,7-tetrahydrooxepin-2- or 3- or 4- or 5- or 6- or 7-yl; 2,3,6,7-tetrahydrooxepin-2- or 3- or 4-yl; 2,3-dihydrooxepin-2- or 3- or 4- or 5- or 6- or 7-yl; 4,5-dihydrooxepin-2- or 3- or 4-yl; 2,5-dihydrooxepin-2- or 3- or 4- or 5- or 6- or 7-yl; oxepin-2- or 3- or 4- or 5- or 6- or 7-yl; 2- or 3-tetrahydrothiophenyl; 2,3-dihydrothiophen-2- or 3- or 4- or 5-yl; 2,5-dihydrothiophen-2- or 3-yl; tetrahydro-2H-thiopyran-2- or 3- or 4-yl; 3,4-dihydro-2H-thiopyran-2- or 3- or 4- or 5- or 6-yl; 3,6-dihydro-2H-thiopyran-2- or 3- or 4- or 5- or 6-yl; 2H-thiopyran-2- or 3- or 4- or 5- or 6-yl; 4H-thiopyran-2- or 3- or 4-yl. Preferred 3-membered and 4-membered heterocycles are, for example, 1- or 2-aziridinyl, oxiranyl, thiiranyl, 1- or 2- or 3-azetidinyl, 2- or 3-oxetanyl, 2- or 3-thietanyl, 1,3-dioxetan-2-yl. Further examples of “heterocyclyl” are a partly or fully hydrogenated heterocyclic radical having two heteroatoms from the group of N, O and S, for example 1- or 2- or 3- or 4-pyrazolidinyl; 4,5-dihydro-3H-pyrazol-3- or 4- or 5-yl; 4,5-dihydro-1H-pyrazol-1- or 3- or 4- or 5-yl; 2,3-dihydro-1H-pyrazol-1- or 2- or 3- or 4- or 5-yl; 1- or 2- or 3- or 4-imidazolidinyl; 2,3-dihydro-1H-imidazol-1- or 2- or 3- or 4-yl; 2,5-dihydro-1H-imidazol-1- or 2- or 4- or 5-yl; 4,5-dihydro-1H-imidazol-1- or 2- or 4- or 5-yl; hexahydropyridazin-1- or 2- or 3- or 4-yl; 1,2,3,4-tetrahydropyridazin-1- or 2- or 3- or 4- or 5- or 6-yl; 1,2,3,6-tetrahydropyridazin-1- or 2- or 3- or 4- or 5- or 6-yl; 1,4,5,6-tetrahydropyridazin-1- or 3- or 4- or 5- or 6-yl; 3,4,5,6-tetrahydropyridazin-3- or 4- or 5-yl; 4,5-dihydropyridazin-3- or 4-yl; 3,4-dihydropyridazin-3- or 4- or 5- or 6-yl; 3,6-dihydropyridazin-3- or 4-yl; 1,6-dihydropyridazin-1- or 3- or 4- or 5- or 6-yl; hexahydropyrimidin-1- or 2- or 3- or 4-yl; 1,4,5,6-tetrahydropyrimidin-1- or 2- or 4- or 5- or 6-yl; 1,2,5,6-tetrahydropyrimidin-1- or 2- or 4- or 5- or 6-yl; 1,2,3,4-tetrahydropyrimidin-1- or 2- or 3- or 4- or 5- or 6-yl; 1,6-dihydropyrimidin-1- or 2- or 4- or 5- or 6-yl; 1,2-dihydropyrimidin-1- or 2- or 4- or 5- or 6-yl; 2,5-dihydropyrimidin-2- or 4- or 5-yl; 4,5-dihydropyrimidin-4- or 5- or 6-yl; 1,4-dihydropyrimidin-1- or 2- or 4- or 5- or 6-yl; 1- or 2- or 3-piperazinyl; 1,2,3,6-tetrahydropyrazin-1- or 2- or 3- or 5- or 6-yl; 1,2,3,4-tetrahydropyrazin-1- or 2- or 3- or 4- or 5- or 6-yl; 1,2-dihydropyrazin-1- or 2- or 3- or 5- or 6-yl; 1,4-dihydropyrazin-1- or 2- or 3-yl; 2,3-dihydropyrazin-2- or 3- or 5- or 6-yl; 2,5-dihydropyrazin-2- or 3-yl; 1,3-dioxolan-2- or 4- or 5-yl; 1,3-dioxol-2- or 4-yl; 1,3-dioxan-2- or 4- or 5-yl; 4H-1,3-dioxin-2- or 4- or 5- or 6-yl; 1,4-dioxan-2- or 3- or 5- or 6-yl; 2,3-dihydro-1,4-dioxin-2- or 3- or 5- or 6-yl; 1,4-dioxin-2- or 3-yl; 1,2-dithiolan-3- or 4-yl; 3H-1,2-dithiol-3- or 4- or 5-yl; 1,3-dithiolan-2- or 4-yl; 1,3-dithiol-2- or 4-yl; 1,2-dithian-3- or 4-yl; 3,4-dihydro-1,2-dithiin-3- or 4- or 5- or 6-yl; 3,6-dihydro-1,2-dithiin-3- or 4-yl; 1,2-dithiin-3- or 4-yl; 1,3-dithian-2- or 4- or 5-yl; 4H-1,3-dithiin-2- or 4- or 5- or 6-yl; isoxazolidin-2- or 3- or 4- or 5-yl; 2,3-dihydroisoxazol-2- or 3- or 4- or 5-yl; 2,5-dihydroisoxazol-2- or 3- or 4- or 5-yl; 4,5-dihydroisoxazol-3- or 4- or 5-yl; 1,3-oxazolidin-2- or 3- or 4- or 5-yl; 2,3-dihydro-1,3-oxazol-2- or 3- or 4- or 5-yl; 2,5-dihydro-1,3-oxazol-2- or 4- or 5-yl; 4,5-dihydro-1,3-oxazol-2- or 4- or 5-yl; 1,2-oxazinan-2- or 3- or 4- or 5- or 6-yl; 3,4-dihydro-2H-1,2-oxazin-2- or 3- or 4- or 5- or 6-yl; 3,6-dihydro-2H-1,2-oxazin-2- or 3- or 4- or 5- or 6-yl; 5,6-dihydro-2H-1,2-oxazin-2- or 3- or 4- or 5- or 6-yl; 5,6-dihydro-4H-1,2-oxazin-3- or 4- or 5- or 6-yl; 2H-1,2-oxazin-2- or 3- or 4- or 5- or 6-yl; 6H-1,2-oxazin-3- or 4- or 5- or 6-yl; 4H-1,2-oxazin-3- or 4- or 5- or 6-yl; 1,3-oxazinan-2- or 3- or 4- or 5- or 6-yl; 3,4-dihydro-2H-1,3-oxazin-2- or 3- or 4- or 5- or 6-yl; 3,6-dihydro-2H-1,3-oxazin-2- or 3- or 4- or 5- or 6-yl; 5,6-dihydro-2H-1,3-oxazin-2- or 4- or 5- or 6-yl; 5,6-dihydro-4H-1,3-oxazin-2- or 4- or 5- or 6-yl; 2H-1,3-oxazin-2- or 4- or 5- or 6-yl; 6H-1,3-oxazin-2- or 4- or 5- or 6-yl; 4H-1,3-oxazin-2- or 4- or 5- or 6-yl; morpholin-2- or 3- or 4-yl; 3,4-dihydro-2H-1,4-oxazin-2- or 3- or 4- or 5- or 6-yl; 3,6-dihydro-2H-1,4-oxazin-2- or 3- or 5- or 6-yl; 2H-1,4-oxazin-2- or 3- or 5- or 6-yl; 4H-1,4-oxazin-2- or 3-yl; 1,2-oxazepan-2- or 3- or 4- or 5- or 6- or 7-yl; 2,3,4,5-tetrahydro-1,2-oxazepin-2- or 3- or 4- or 5- or 6- or 7-yl; 2,3,4,7-tetrahydro-1,2-oxazepin-2- or 3- or 4- or 5- or 6- or 7-yl; 2,3,6,7-tetrahydro-1,2-oxazepin-2- or 3- or 4- or 5- or 6- or 7-yl; 2,5,6,7-tetrahydro-1,2-oxazepin-2- or 3- or 4- or 5- or 6- or 7-yl; 4,5,6,7-tetrahydro-1,2-oxazepin-3- or 4- or 5- or 6- or 7-yl; 2,3-dihydro-1,2-oxazepin-2- or 3- or 4- or 5- or 6- or 7-yl; 2,5-dihydro-1,2-oxazepin-2- or 3- or 4- or 5- or 6- or 7-yl; 2,7-dihydro-1,2-oxazepin-2- or 3- or 4- or 5- or 6- or 7-yl; 4,5-dihydro-1,2-oxazepin-3- or 4- or 5- or 6- or 7-yl; 4,7-dihydro-1,2-oxazepin-3- or 4- or 5- or 6- or 7-yl; 6,7-dihydro-1,2-oxazepin-3- or 4- or 5- or 6- or 7-yl; 1,2-oxazepin-3- or 4- or 5- or 6- or 7-yl; 1,3-oxazepan-2- or 3- or 4- or 5- or 6- or 7-yl; 2,3,4,5-tetrahydro-1,3-oxazepin-2- or 3- or 4- or 5- or 6- or 7-yl; 2,3,4,7-tetrahydro-1,3-oxazepin-2- or 3- or 4- or 5- or 6- or 7-yl; 2,3,6,7-tetrahydro-1,3-oxazepin-2- or 3- or 4- or 5- or 6- or 7-yl; 2,5,6,7-tetrahydro-1,3-oxazepin-2- or 4- or 5- or 6- or 7-yl; 4,5,6,7-tetrahydro-1,3-oxazepin-2- or 4- or 5- or 6- or 7-yl; 2,3-dihydro-1,3-oxazepin-2- or 3- or 4- or 5- or 6- or 7-yl; 2,5-dihydro-1,3-oxazepin-2- or 4- or 5- or 6- or 7-yl; 2,7-dihydro-1,3-oxazepin-2- or 4- or 5- or 6- or 7-yl; 4,5-dihydro-1,3-oxazepin-2- or 4- or 5- or 6- or 7-yl; 4,7-dihydro-1,3-oxazepin-2- or 4- or 5- or 6- or 7-yl; 6,7-dihydro-1,3-oxazepin-2- or 4- or 5- or 6- or 7-yl; 1,3-oxazepin-2- or 4- or 5- or 6- or 7-yl; 1,4-oxazepan-2- or 3- or 5- or 6- or 7-yl; 2,3,4,5-tetrahydro-1,4-oxazepin-2- or 3- or 4- or 5- or 6- or 7-yl; 2,3,4,7-tetrahydro-1,4-oxazepin-2- or 3- or 4- or 5- or 6- or 7-yl; 2,3,6,7-tetrahydro-1,4-oxazepin-2- or 3- or 5- or 6- or 7-yl; 2,5,6,7-tetrahydro-1,4-oxazepin-2- or 3- or 5- or 6- or 7-yl; 4,5,6,7-tetrahydro-1,4-oxazepin-2- or 3- or 4- or 5- or 6- or 7-yl; 2,3-dihydro-1,4-oxazepin-2- or 3- or 5- or 6- or 7-yl; 2,5-dihydro-1,4-oxazepin-2- or 3- or 5- or 6- or 7-yl; 2,7-dihydro-1,4-oxazepin-2- or 3- or 5- or 6- or 7-yl; 4,5-dihydro-1,4-oxazepin-2- or 3- or 4- or 5- or 6- or 7-yl; 4,7-dihydro-1,4-oxazepin-2- or 3- or 4- or 5- or 6- or 7-yl; 6,7-dihydro-1,4-oxazepin-2- or 3- or 5- or 6- or 7-yl; 1,4-oxazepin-2- or 3- or 5- or 6- or 7-yl; isothiazolidin-2- or 3- or 4- or 5-yl; 2,3-dihydroisothiazol-2- or 3- or 4- or 5-yl; 2,5-dihydroisothiazol-2- or 3- or 4- or 5-yl; 4,5-dihydroisothiazol-3- or 4- or 5-yl; 1,3-thiazolidin-2- or 3- or 4- or 5-yl; 2,3-dihydro-1,3-thiazol-2- or 3- or 4- or 5-yl; 2,5-dihydro-1,3-thiazol-2- or 4- or 5-yl; 4,5-dihydro-1,3-thiazol-2- or 4- or 5-yl; 1,3-thiazinan-2- or 3- or 4- or 5- or 6-yl; 3,4-dihydro-2H-1,3-thiazin-2- or 3- or 4- or 5- or 6-yl; 3,6-dihydro-2H-1,3-thiazin-2- or 3- or 4- or 5- or 6-yl; 5,6-dihydro-2H-1,3-thiazin-2- or 4- or 5- or 6-yl; 5,6-dihydro-4H-1,3-thiazin-2- or 4- or 5- or 6-yl; 2H-1,3-thiazin-2- or 4- or 5- or 6-yl; 6H-1,3-thiazin-2- or 4- or 5- or 6-yl; 4H-1,3-thiazin-2- or 4- or 5- or 6-yl. Further examples of “heterocyclyl” are a partly or fully hydrogenated heterocyclic radical having 3 heteroatoms from the group of N, O and S, for example 1,4,2-dioxazolidin-2- or 3- or 5-yl; 1,4,2-dioxazol-3- or 5-yl; 1,4,2-dioxazinan-2- or -3- or 5- or 6-yl; 5,6-dihydro-1,4,2-dioxazin-3- or 5- or 6-yl; 1,4,2-dioxazin-3- or 5- or 6-yl; 1,4,2-dioxazepan-2- or 3- or 5- or 6- or 7-yl; 6,7-dihydro-5H-1,4,2-dioxazepin-3- or 5- or 6- or 7-yl; 2,3-dihydro-7H-1,4,2-dioxazepin-2- or 3- or 5- or 6- or 7-yl; 2,3-dihydro-5H-1, 4,2-dioxazepin-2- or 3- or 5- or 6- or 7-yl; 5H-1,4,2-dioxazepin-3- or 5- or 6- or 7-yl; 7H-1,4,2-dioxazepin-3- or 5- or 6- or 7-yl.

When a base structure is substituted "by one or more radicals" from a list of radicals (=group) or a generically defined group of radicals, this in each case includes simultaneous substitution by a plurality of identical and/or structurally different radicals.

In the case of a partly or fully saturated nitrogen heterocycle, this may be joined to the remainder of the molecule either via carbon or via the nitrogen.

According to the invention, the expression "hetaryl" represents heteroaromatic compounds, i.e. fully unsaturated aromatic heterocyclic compounds, preferably 5- to 7-membered rings having 1 to 4, preferably 1 or 2, identical or different heteroatoms, preferably O, S or N. Heteroaryls according to the invention are, for example, 1H-pyrrol-1-yl; 1H-pyrrol-2-yl; 1H-pyrrol-3-yl; furan-2-yl; furan-3-yl; thien-2-yl; thien-3-yl, 1H-imidazol-1-yl; 1H-imidazol-2-yl; 1H-imidazol-4-yl; 1H-imidazol-5-yl; 1H-pyrazol-1-yl; 1H-pyrazol-3-yl; 1H-pyrazol-4-yl; 1H-pyrazol-5-yl, 1H-1,2,3-triazol-1-yl, 1H-1,2,3-triazol-4-yl, 1H-1,2,3-triazol-5-yl, 2H-1,2,3-triazol-2-yl, 2H-1,2,3-triazol-4-yl, 1H-1,2,4-triazol-1-yl, 1H-1,2,4-triazol-3-yl, 4H-1,2,4-triazol-4-yl, 1,2,4-oxadiazol-3-yl, 1,2,4-oxadiazol-5-yl, 1,3,4-oxadiazol-2-yl, 1,2,3-oxadiazol-4-yl, 1,2,3-oxadiazol-5-yl, 1,2,5-oxadiazol-3-yl, azepinyl, pyridin-2-yl, pyridin-3-yl, pyridin-4-yl, pyrazin-2-yl, pyrazin-3-yl, pyrimidin-2-yl, pyrimidin-4-yl, pyrimidin-5-yl, pyridazin-3-yl, pyridazin-4-yl, 1,3,5-triazin-2-yl, 1,2,4-triazin-3-yl, 1,2,4-triazin-5-yl, 1,2,4-triazin-6-yl, 1,2,3-triazin-4-yl, 1,2,3-triazin-5-yl, 1,2,4-, 1,3,2-, 1,3,6- and 1,2,6-oxazinyl, isoxazol-3-yl, isoxazol-4-yl, isoxazol-5-yl, 1,3-oxazol-2-yl, 1,3-oxazol-4-yl, 1,3-oxazol-5-yl, isothiazol-3-yl, isothiazol-4-yl, isothiazol-5-yl, 1,3-thiazol-2-yl, 1,3-thiazol-4-yl, 1,3-thiazol-5-yl, oxepinyl, thiepinyl, 1,2,4-triazolonyl and 1,2,4-diazepinyl, 2H-1,2,3,4-tetrazol-5-yl, 1H-1,2,3,4-tetrazol-5-yl, 1,2,3,4-oxatriazol-5-yl, 1,2,3,4-thiatriazol-5-yl, 1,2,3,5-oxatriazol-4-yl, 1,2,3,5-thiatriazol-4-yl. The heteroaryl groups according to the invention may also be substituted by one or more identical or different radicals. When two adjacent carbon atoms are part of a further aromatic ring, the systems are fused heteroaromatic systems, such as benzofused or polyannulated heteroaromatics. Preferred examples are quinolines (e.g. quinolin-2-yl, quinolin-3-yl, quinolin-4-yl, quinolin-5-yl, quinolin-6-yl, quinolin-7-yl, quinolin-8-yl); isoquinolines (e.g. isoquinolin-1-yl, isoquinolin-3-yl, isoquinolin-4-yl, isoquinolin-5-yl, isoquinolin-6-yl, isoquinolin-7-yl, isoquinolin-8-yl); quinoxaline; quinazoline; cinnoline; 1,5-naphthyridine; 1,6-naphthyridine; 1,7-naphthyridine; 1,8-naphthyridine; 2,6-naphthyridine; 2,7-naphthyridine; phthalazine; pyridopyrazines; pyridopyrimidines; pyridopyridazines; pteridines; pyrimidopyrimidines. Examples of heteroaryl are also 5- or 6-membered benzofused rings from the group of 1H-indol-1-yl, 1H-indol-2-yl, 1H-indol-3-yl, 1H-indol-4-yl, 1H-indol-5-yl, 1H-indol-6-yl, 1H-indol-7-yl, 1-benzofuran-2-yl, 1-benzofuran-3-yl, 1-benzofuran-4-yl, 1-benzofuran-5-yl, 1-benzofuran-6-yl, 1-benzofuran-7-yl, 1-benzothiophen-2-yl, 1-benzothiophen-3-yl, 1-benzothiophen-4-yl, 1-benzothiophen-5-yl, 1-benzothiophen-6-yl, 1-benzothiophen-7-yl, 1H-indazol-1-yl, 1H-indazol-3-yl, 1H-indazol-4-yl, 1H-indazol-5-yl, 1H-indazol-6-yl, 1H-indazol-7-yl, 2H-indazol-2-yl, 2H-indazol-3-yl, 2H-indazol-4-yl, 2H-indazol-5-yl, 2H-indazol-6-yl, 2H-indazol-7-yl, 2H-isoindol-2-yl, 2H-isoindol-1-yl, 2H-isoindol-3-yl, 2H-isoindol-4-yl, 2H-isoindol-5-yl, 2H-isoindol-6-yl; 2H-isoindol-7-yl, 1H-benzimidazol-1-yl, 1H-benzimidazol-2-yl, 1H-benzimidazol-4-yl, 1H-benzimidazol-5-yl, 1H-benzimidazol-6-yl, 1H-benzimidazol-7-yl, 1,3-benzoxazol-2-yl, 1,3-benzoxazol-4-yl, 1,3-benzoxazol-5-yl, 1,3-benzoxazol-6-yl, 1,3-benzoxazol-7-yl, 1,3-benzothiazol-2-yl, 1,3-benzothiazol-4-yl, 1,3-benzothiazol-5-yl, 1,3-benzothiazol-6-yl, 1,3-benzothiazol-7-yl, 1,2-benzisoxazol-3-yl, 1,2-benzisoxazol-4-yl, 1,2-benzisoxazol-5-yl, 1,2-benzisoxazol-6-yl, 1,2-benzisoxazol-7-yl, 1,2-benzisothiazol-3-yl, 1,2-benzisothiazol-4-yl, 1,2-benzisothiazol-5-yl, 1,2-benzisothiazol-6-yl, 1,2-benzisothiazol-7-yl.

The term "halogen" means, for example, fluorine, chlorine, bromine or iodine.

If the term is used for a radical, "halogen" means, for example, a fluorine, chlorine, bromine or iodine atom.

According to the invention, "alkyl" means a straight-chain or branched open-chain saturated hydrocarbyl radical.

"Haloalkyl" means alkyl which is partially or fully substituted by identical or different halogen atoms such as, for example, $CH_2CH_2Cl$, $CH_2CH_2Br$, $CHClCH_3$, $CH_2Cl$, $CH_2F$, perhaloalkyl such as, for example, $CCl_3$, $CClF_2$, $CFCl_2$, $CF_2CClF_2$, $CF_2CClFCF_3$, polyhaloalkyl such as, for example, $CH_2CHFCl$, $CF_2CClFH$, $CF_2CBrFH$, $CH_2CF_3$.

Furthermore, it has been found that the novel compounds of the formula (I) are obtained by one of the processes described below:

(A) Substituted 3-(1-2-4-triazolyl)pyrrolidine-2,4-diones or their enols of the formula (I-1-a)

(I-1-a)

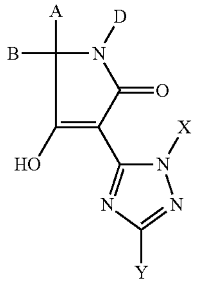

in which

A, B, D, X and Y have the meanings given above, are obtained when

N-acylamino acid esters of the formula (II)

(II)

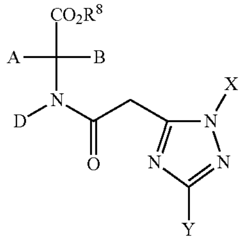

in which

A, B, D, X and Y have the meanings given above, and $R^8$ represents alkyl (preferably $C_1$-$C_6$-alkyl), are condensed intramolecularly in the presence of a diluent and in the presence of a base.

(B) Moreover, it has been found that substituted 3-(1-2-4-triazolyl)-4-hydroxy-Δ3-dihydrofuranone derivatives of the formula (I-2-a)

(I-2-a)

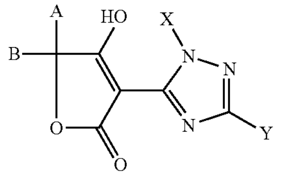

in which

A, B, X and Y have the meanings given above, are obtained when carboxylic esters of the formula (III)

(III)

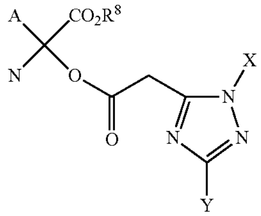

in which

A, B, X, Y and $R^8$ have the meanings given above, are condensed intramolecularly in the presence of a diluent and in the presence of a base.

(C) Furthermore, it has been found that substituted 3-(1,2,4-triazolyl)-4-hydroxy-$\Delta^3$-dihydrothiophenone derivatives of the formula (I-3-a)

(I-3-a)

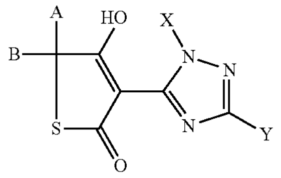

in which

A, B, X and Y have the meanings given above, are obtained when

β-ketocarboxylic esters of the formula (IV)

(IV)

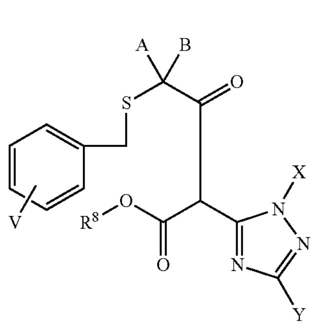

in which

A, B, X, Y and $R^8$ have the meanings given above and

V represents hydrogen, halogen, alkyl (preferably $C_1$-$C_6$-alkyl) or alkoxy (preferably $C_1$-$C_8$-alkoxy), are cyclized intramolecularly, if appropriate in the presence of a diluent and in the presence of a base.

(D) Furthermore, it has been found that the novel substituted 3-(1,2,4-triazolyl) derivatives of the formula (I-4-a)

(I-4-a)

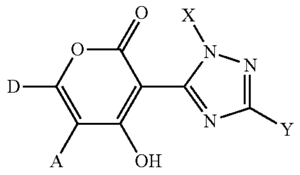

in which

A, D, X and Y have the meanings given above, are obtained when carbonyl compounds of the formula (V)

(V)

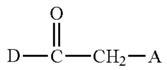

in which

A and D have the meanings given above, or silylenol ethers thereof of the formula (Va)

(Va)

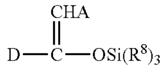

in which

A, D and $R^8$ have the meaning given above, are reacted with ketene acid halides of the formula (VI)

(VI)

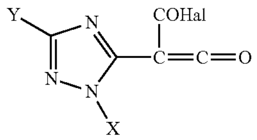

in which

X and Y have the meanings given above and

Hal represents halogen (preferably chlorine or bromine), if appropriate in the presence of a diluent and if appropriate in the presence of an acid acceptor.

Furthermore, it has been found (E) that the novel substituted triazolyl-1,3-thiazine derivatives of the formula (I-5-a)

(I-5-a)

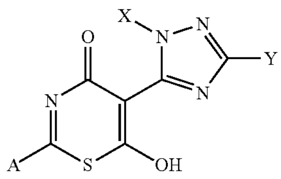

in which

A, X and Y have the meaning given above are obtained when thioamides of the formula (VII)

(VII)

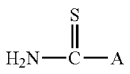

in which

A has the meaning given above are reacted with ketene acid halides of the formula (VI)

(VI)

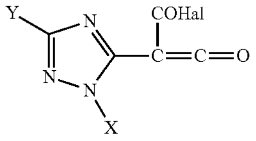

in which

Hal, X and Y have the meanings given above, if appropriate in the presence of a diluent and if appropriate in the presence of an acid acceptor.

Furthermore, it has been found (F) that compounds of the formula (I-6-a)

(I-6-a)

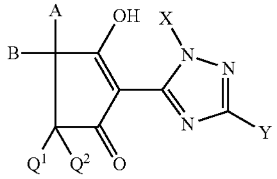

in which

A, B, $Q^1$, $Q^2$, X and Y have the meaning given above are obtained when ketocarboxylic esters of the formula (VIII)

(VIII)

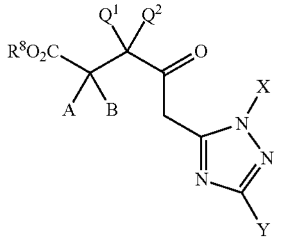

in which

A, B, $Q^1$, $Q^2$, X and Y have the meaning given above and

R8 represents alkyl (in particular $C_1$-$C_8$-alkyl), are cyclized intramolecularly, if appropriate in the presence of a diluent and in the presence of a base.

Moreover, it has been found (G) that compounds of the formula (I-7-a)

(I-7-a)

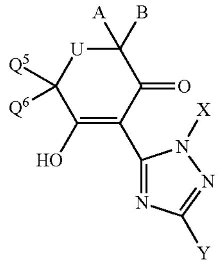

in which

A, B, $Q^5$, $Q^6$, U, X and Y have the meaning given above are obtained when 6-triazolyl-5-ketohexanoic esters of the formula (IX)

(IX)

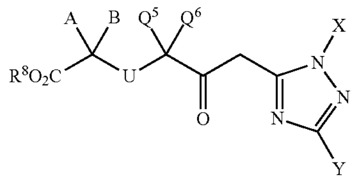

in which

A, B, $Q^5$, $Q^6$, U, X and Y have the meaning given above and $R^8$ represents alkyl (preferably $C_1$-$C_6$-alkyl)

are condensed intramolecularly in the presence of a diluent and in the presence of a base.

(H) Furthermore, it has been found that compounds of the formula (I-8-a)

(I-8-a)

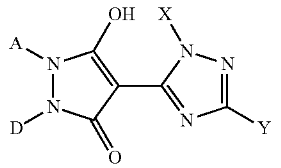

in which

A, D, X and Y have the meanings given above, are obtained when compounds of the formula (X)

(X)

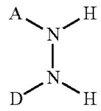

in which

A and D have the meaning given above

α) are reacted with compounds of the formula (VI)

(VI)

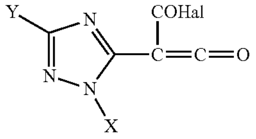

in which

Hal, X and Y have the meanings given above, if appropriate in the presence of a diluent and if appropriate in the presence of an acid acceptor, or β) are reacted with compounds of the formula (XI)

(XI)

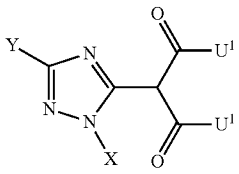

in which

X and Y have the meaning given above and $U^1$ represents $NH_2$ or O—$R^8$, where $R^8$ has the meaning mentioned above, if appropriate in the presence of a diluent and if appropriate in the presence of a base, or γ) are reacted with compounds of the formula (XII)

(XII)

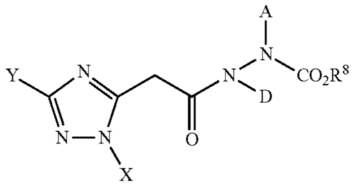

in which

A, D, X, Y and $R^8$ have the meaning given above, if appropriate in the presence of a diluent and if appropriate in the presence of a base.

Moreover, it has been found that the novel compounds of the formula (I-9-a) are obtained by one of the processes described below:

(I) Substituted tetrahydropyridine-2,4-diones or their enols of the formula (I-9-a)

(I-9-a)

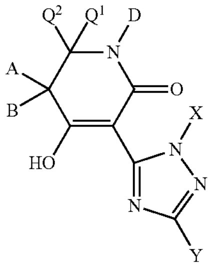

in which

A, B, D, $Q^1$, $Q^2$, X and Y have the meanings given above are obtained when

N-acylamino acid esters of the formula (XIII)

(XIII)

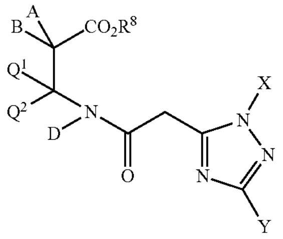

in which

A, B, D, $Q^1$, $Q^2$, X and Y have the meanings given above and $R^8$ represents alkyl (preferably $C_1$-$C_6$-alkyl), are condensed intramolecularly in the presence of a diluent and in the presence of a base.

Furthermore, it has been found (J) that substituted 5,6-dihydropyrones of the formula (I-10-a)

(I-10-a)

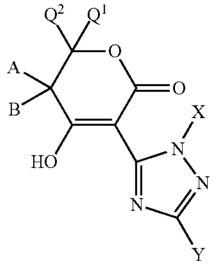

in which

A, B, $Q^1$, $Q^2$, X and Y have the meanings given above are obtained when

O-acylhydroxycarboxylic esters of the formula (XIV)

(XIV)

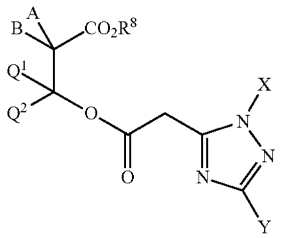

in which

A, B, $Q^1$, $Q^2$, X and Y have the meanings given above and $R^8$ represents alkyl (preferably $C_1$-$C_6$-alkyl), are reacted, if appropriate in the presence of a diluent and if appropriate in the presence of a base.

Furthermore, it has been found that the novel compounds of the formula (I-11-a) are obtained by one of the processes described below:

(K) Substituted oxazine-3,5-diones or their enols of the formula (I-11-a)

(I-11-a)

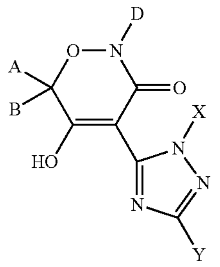

in which

A, B, D, X and Y have the meanings given above are obtained when

N-acylamino acid esters of the formula (XV)

(XV)

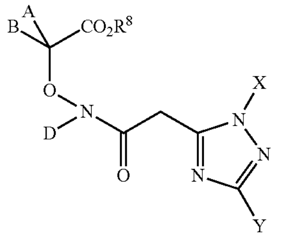

in which

A, B, D, X and Y have the meanings given above and $R^8$ represents alkyl (preferably $C_1$-$C_6$-alkyl), are condensed intramolecularly in the presence of a diluent and in the presence of a base.

Moreover, it has been found (L) that the compounds of the formulae (I-1-b) to (1-11-b) shown above in which A, B, D, $Q^1$, $Q^2$, $Q^5$, $Q^6$, $R^1$, U, X and Y have the meanings given above are obtained when compounds of the formulae (I-1-a) to (I-11-a) shown above in which A, B, D, $Q^1$, $Q^2$, $Q^5$, $Q^6$, U, X and Y have the meanings given above are in each case reacted (α) with acid halides of the formula (XVI)

(XVI)

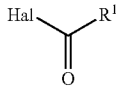

in which $R^1$ has the meaning given above and

Hal represents halogen (in particular chlorine or bromine)

or (β) with carboxylic anhydrides of the formula (XVII)

$R^1$—CO—O—CO—$R^1$ (XVII)

in which $R^1$ has the meaning given above, if appropriate in the presence of a diluent and if appropriate in the presence of an acid binder;

(M) that the compounds of the formulae (I-1-c) to (I-11-c) shown above in which A, B, D, $Q^1$, $Q^2$, $Q^5$, $Q^6$, $R^2$, M, U, X and Y have the meanings given above and L represents oxygen are obtained when compounds of the formulae (I-1-a) to (I-11-a) shown above in which A, B, D, $Q^1$, $Q^2$, $Q^5$, $Q^6$, U, X and Y have the meanings given above are in each case reacted with chloroformic esters or chloroformic thioesters of the formula (XVIII)

$R^2$-M-CO—Cl (XVIII)

in which $R^2$ and M have the meanings given above, if appropriate in the presence of a diluent and if appropriate in the presence of an acid binder;

(N) that compounds of the formulae (I-1-c) to (I-11-c) shown above in which A, B, D, $Q^1$, $Q^2$, $Q^5$, $Q^6$, $R^2$, M, U, X and Y have the meanings given above and L represents sulfur are obtained when compounds of the formulae (I-1-a) to (I-11-a) shown above in which A, B, D, $Q^1$, $Q^2$, $Q^5$, $Q^6$, U, X and Y have the meanings given above are in each case reacted with chloromonothioformic esters or chlorodithioformic esters of the formula (XIX)

(XIX)

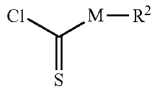

in which

M and $R^2$ have the meanings given above, if appropriate in the presence of a diluent and if appropriate in the presence of an acid binder, and (O) that the compounds of the formulae (I-1-d) to (I-11-d) shown above in which A, B, D, $Q^1$, $Q^2$, $Q^5$, $Q^6$, $R^3$, U, X and Y have the meanings given above are obtained when compounds of the formulae (I-1-a) to (I-11-a) shown above in which A, B, D, $Q^1$, $Q^2$, $Q^5$, $Q^6$, U, X and Y have the meanings given above are in each case reacted with sulfonyl chlorides of the formula (XX)

$R^3$—$SO_2$—Cl (XX)

in which $R^3$ has the meaning given above, if appropriate in the presence of a diluent and if appropriate in the presence of an acid binder, (P) that the compounds of the formulae (I-1-e) to (I-11-e) shown above in which A, B, D, L, $Q^1$, $Q^2$, $Q^5$, $Q^6$, $R^4$, $R^5$, U, X and Y have the meanings given above are obtained when compounds of the formulae (I-1-a) to (I-11-a) shown above in which A, B, D, $Q^1$, $Q^2$, $Q^5$, $Q^6$, U, X and Y have the meanings given above are in each case reacted with phosphorus compounds of the formula (XXI)

(XXI)

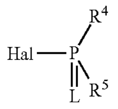

in which

L, $R^4$ and $R^5$ have the meanings given above and

Hal represents halogen (in particular chlorine or bromine), if appropriate in the presence of a diluent and if appropriate in the presence of an acid binder, (O) that the compounds of the formulae (I-1-f) to (I-11-f) shown above in which A, B, D, E, $Q^1$, $Q^2$, $Q^5$, $Q^6$, R3, U, X and Y have the meanings given above are obtained when compounds of the formulae (I-1-a) to (I-11-a) shown above in which A, B, D, $Q^1$, $Q^2$, $Q^5$, $Q^6$, U, X and Y have the meanings given above are in each case reacted with metal compounds or amines of the formulae (XXII) or (XXIII)

$Me(OR^{10})_t$ (XXII)

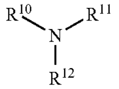

(XXIII)

in which

Me represents a monovalent or divalent metal (preferably an alkali metal or alkaline earth metal such as lithium, sodium, potassium, magnesium or calcium), or represents an ammonium ion,

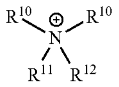

t represents the number 1 or 2 and $R^{10}$, $R^{11}$, $R^{12}$ independently of one another represent hydrogen or alkyl (preferably $C_1$-$C_8$-alkyl), if appropriate in the presence of a diluent, (R) that the compounds of the formulae (I-1-g) to (I-11-g) shown above in which A, B, D, L, $Q^1$, $Q^2$, $Q^5$, $Q^6$, $R^6$, $R^7$, U, X and Y have the meanings given above are obtained when compounds of the formulae (I-1-a) to (I-11-a) shown above in which A, B, D, $Q^1$, $Q^2$, $Q^5$, $Q^6$, U, X and Y have the meanings given above are in each case (α) reacted with isocyanates or isothiocyanates of the formula (XXIV)

$R^6$—N═C═L (XXIV)

in which $R^6$ and L have the meanings given above, if appropriate in the presence of a diluent and if appropriate in the presence of a catalyst, or (β) reacted with carbamoyl chlorides or thiocarbamoyl chlorides of the formula (XXV)

(XXV)

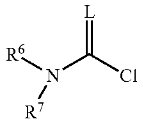

in which

L, $R^6$ and $R^7$ have the meanings given above, if appropriate in the presence of a diluent and if appropriate in the presence of an acid binder, Furthermore, it has been found that the new compounds of the formula (I) have very good activity as pesticides, preferably as insecticides, acaricides and/or herbicides.

Surprisingly, it has now also been found that certain 1,2,4-triazolyl-substituted ketoenols, when used together with the crop plant compatibility-improving compounds (safeners/antidotes) described below, efficiently prevent damage to the crop plants and can be used in a particularly advantageous manner as broad-spectrum combination preparations for the selective control of unwanted plants in crops of useful plants, such as, for example, in cereals, but also in corn, oilseed rape, soybeans and rice.

The invention also provides selective herbicidal compositions comprising an effective amount of an active compound combination comprising, as components, a') at least one compound of the formula (I) in which CKE, X and Y have the meaning given above and (b') at least one crop plant compatibility-improving compound (safener).

The safeners are preferably selected from the group consisting of:

S1) compounds of the formula (S1)

(S1)

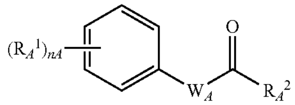

where the symbols and indices are each defined as follows:

$n_A$ is a natural number from 0 to 5, preferably 0 to 3;

$R_A^1$ is halogen, ($C_1$-$C_4$)-alkyl, ($C_1$-$C_4$)-alkoxy, nitro or ($C_1$-$C_4$)-haloalkyl;

$W_A$ is an unsubstituted or substituted divalent heterocyclic radical from the group of the partially unsaturated or aromatic five-membered heterocycles having 1 to 3 ring heteroatoms of the N or O type, where at least one nitrogen atom and at most one oxygen atom is present in the ring, preferably a radical from the group of ($W_A^1$) to ($W_A^4$),

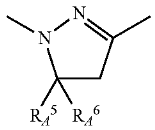

($W_A^1$)

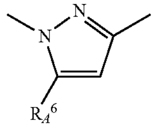

($W_A^2$)

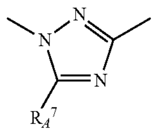

($W_A^3$)

-continued

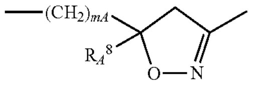

$(W_A{}^4)$ $m_A$ is 0 or 1;

$R_A{}^2$ is $OR_A{}^3$, $SR_A{}^3$ or $NR_A{}^3R_A{}^4$ or a saturated or unsaturated 3- to 7-membered heterocycle having at least one nitrogen atom and up to 3 heteroatoms, preferably from the group of O and S, which is joined to the carbonyl group in (S1) via the nitrogen atom and is unsubstituted or substituted by radicals from the group of $(C_1-C_4)$-alkyl, $(C_1-C_4)$-alkoxy or optionally substituted phenyl, preferably a radical of the formula $OR_A{}^3$, $NHR_A{}^4$ or $N(CH_3)_2$, especially of the formula $OR_A{}^3$;

$R_A{}^3$ is hydrogen or an unsubstituted or substituted aliphatic hydrocarbyl radical preferably having a total of 1 to 18 carbon atoms;

$R_A{}^4$ is hydrogen, $(C_1-C_6)$-alkyl, $(C_1-C_6)$-alkoxy or substituted or unsubstituted phenyl;

$R_A{}^5$ is H, $(C_1-C_8)$-alkyl, $(C_1-C_8)$-haloalkyl, $(C_1-C_4)$-alkoxy-$(C_1-C_8)$-alkyl, cyano or $COOR_A{}^9$, where $R_A{}^9$ is hydrogen, $(C_1-C_8)$-alkyl, $(C_1-C_8)$-haloalkyl, $(C_1-C_4)$-alkoxy-$(C_1-C_4)$-alkyl, $(C_1-C_6)$-hydroxyalkyl, $(C_3-C_{12})$-cycloalkyl or tri-$(C_1-C_4)$-alkylsilyl;

$R_A{}^6$, $R_A{}^7$, $R_A{}^8$ are identical or different and are hydrogen, $(C_1-C_8)$-alkyl, $(C_1-C_8)$-haloalkyl, $(C_3-C_{12})$-cycloalkyl or substituted or unsubstituted phenyl;

preferably:

a) compounds of the dichlorophenylpyrazoline-3-carboxylic acid type ($S1^a$), preferably compounds such as 1-(2,4-dichlorophenyl)-5-(ethoxycarbonyl)-5-methyl-2-pyrazoline-3-carboxylic acid, ethyl 1-(2,4-dichlorophenyl)-5-(ethoxycarbonyl)-5-methyl-2-pyrazoline-3-carboxylate (S1-1) ("mefenpyr-diethyl"), and related compounds as described in WO-A-91/07874;

b) derivatives of dichlorophenylpyrazolecarboxylic acid ($S1^b$), preferably compounds such as ethyl 1-(2,4-dichlorophenyl)-5-methylpyrazole-3-carboxylate (S1-2), ethyl 1-(2,4-dichlorophenyl)-5-isopropylpyrazole-3-carboxylate (S1-3), ethyl 1-(2,4-dichlorophenyl)-5-(1,1-dimethylethyl)pyrazole-3-carboxylate (S1-4) and related compounds as described in EP-A-333 131 and EP-A-269 806;

c) derivatives of 1,5-diphenylpyrazole-3-carboxylic acid ($S1^c$), preferably compounds such as ethyl 1-(2,4-dichlorophenyl)-5-phenylpyrazole-3-carboxylate (S1-5), methyl 1-(2-chlorophenyl)-5-phenylpyrazole-3-carboxylate (S1-6) and related compounds as described in EP-A-268 554, for example;

d) compounds of the triazolecarboxylic acid type ($S1^d$), preferably compounds such as fenchlorazole (ethyl ester), i.e. ethyl 1-(2,4-dichlorophenyl)-5-trichloromethyl-(1H)-1,2,4-triazole-3-carboxylate (S1-7), and related compounds as described in EP-A-174 562 and EP-A-346 620;

e) compounds of the 5-benzyl- or 5-phenyl-2-isoxazoline-3-carboxylic acid or of the 5,5-diphenyl-2-isoxazoline-3-carboxylic acid type ($S1^e$), preferably compounds such as ethyl 5-(2,4-dichlorobenzyl)-2-isoxazoline-3-carboxylate (S1-8) or ethyl 5-phenyl-2-isoxazoline-3-carboxylate (S1-9) and related compounds as described in WO-A-91/08202, or 5,5-diphenyl-2-isoxazolinecarboxylic acid (S1-10) or ethyl 5,5-diphenyl-2-isoxazolinecarboxylate (51-11) ("isoxadifen-ethyl") or n-propyl 5,5-diphenyl-2-isoxazolinecarboxylate (S1-12) or ethyl 5-(4-fluorophenyl)-5-phenyl-2-isoxazoline-3-carboxylate (S1-13), as described in patent application WO-A-95/07897.

S2) Quinoline derivatives of the formula (S2)

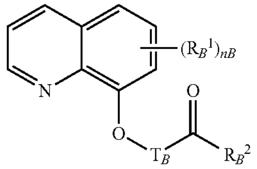

(S2)

where the symbols and indices are each defined as follows:

$R_B{}^1$ is halogen, $(C_1-C_4)$-alkyl, $(C_1-C_4)$-alkoxy, nitro or $(C_1-C_4)$-haloalkyl;

$n_B$ is a natural number from 0 to 5, preferably 0 to 3;

$R_B{}^2$ is $OR_B{}^3$, $SR_B{}^3$ or $NR_B{}^3R_B{}^4$ or a saturated or unsaturated 3- to 7-membered heterocycle having at least one nitrogen atom and up to 3 heteroatoms, preferably from the group of O and S, which is joined to the carbonyl group in (S2) via the nitrogen atom and is unsubstituted or substituted by radicals from the group of $(C_1-C_4)$-alkyl, $(C_1-C_4)$-alkoxy or optionally substituted phenyl, preferably a radical of the formula $OR_B{}^3$, $NHR_B{}^4$ or $N(CH_3)_2$, especially of the formula $OR_B{}^3$;

$R_B{}^3$ is hydrogen or an unsubstituted or substituted aliphatic hydrocarbyl radical preferably having a total of 1 to 18 carbon atoms;

$R_B{}^4$ is hydrogen, $(C_1-C_6)$-alkyl, $(C_1-C_6)$-alkoxy or substituted or unsubstituted phenyl;

$T_B$ is a ($C_1$ or $C_2$)-alkanediyl chain which is unsubstituted or substituted by one or two $(C_1-C_4)$-alkyl radicals or by $[(C_1-C_3)$-alkoxy]carbonyl;

preferably:

a) compounds of the 8-quinolinoxyacetic acid type ($S2^a$), preferably 1-methylhexyl (5-chloro-8-quinolinoxy)acetate ("cloquintocet-mexyl") (S2-1), 1,3-dimethylbut-1-yl (5-chloro-8-quinolinoxy)acetate (S2-2), 4-allyloxybutyl (5-chloro-8-quinolinoxy)acetate (S2-3), 1-allyloxyprop-2-yl (5-chloro-8-quinolinoxy)acetate (S2-4), ethyl (5-chloro-8-quinolinoxy)acetate (S2-5), methyl (5-chloro-8-quinolinoxy)acetate (S2-6), allyl (5-chloro-8-quinolinoxy)acetate (S2-7), 2-(2-propylideneiminoxy)-1-ethyl (5-chloro-8-quinolinoxy)acetate (S2-8), 2-oxoprop-1-yl (5-chloro-8-quinolinoxy) acetate (S2-9) and related compounds, as described in EP-A-86 750, EP-A-94 349 and EP-A-191 736 or EP-A-0 492 366, and also (5-chloro-8-quinolinoxy)acetic acid (S2-10), hydrates and salts thereof, for example the lithium, sodium, potassium, calcium, magnesium, aluminum, iron, ammonium, quaternary ammonium, sulfonium or phosphonium salts thereof, as described in WO-A-2002/34048;

b) compounds of the (5-chloro-8-quinolinoxy)malonic acid type ($S2^b$), preferably compounds such as diethyl (5-chloro-8-quinolinoxy)malonate, diallyl (5-chloro-8-quinolinoxy)malonate, methyl ethyl (5-chloro-8-quinolinoxy)malonate and related compounds, as described in EP-A-0 582 198.

S3) Compounds of the formula (S3)

(S3)

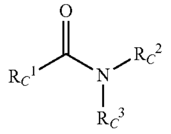

where the symbols and indices are each defined as follows:

$R_C^1$ is $(C_1-C_4)$-alkyl, $(C_1-C_4)$-haloalkyl, $(C_2-C_4)$-alkenyl, $(C_2-C_4)$-haloalkenyl, $(C_3-C_7)$-cycloalkyl, preferably dichloromethyl;

$R_C^2$, $R_C^3$ are identical or different and are hydrogen, $(C_1-C_4)$-alkyl, $(C_2-C_4)$-alkenyl, $(C_2-C_4)$-alkynyl, $(C_1-C_4)$-haloalkyl, $(C_2-C_4)$-haloalkenyl, $(C_1-C_4)$-alkylcarbamoyl-$(C_1-C_4)$-alkyl, $(C_2-C_4)$-alkenylcarbamoyl-$(C_1-C_4)$ alkyl, $(C_1-C_4)$-alkoxy-$(C_1-C_4)$-alkyl, dioxolanyl-$(C_1-C_4)$-alkyl, thiazolyl, furyl, furylalkyl, thienyl, piperidyl, substituted or unsubstituted phenyl, or $R_C^2$ and $R_C^3$ together form a substituted or unsubstituted heterocyclic ring, preferably an oxazolidine, thiazolidine, piperidine, morpholine, hexahydropyrimidine or benzoxazine ring;

preferably:

active compounds of the dichloroacetamide type, which are frequently used as pre-emergence safeners (soil-acting safeners), for example "dichlormid" (N,N-diallyl-2,2-dichloroacetamide) (S3-1), "R-29148" (3-dichloroacetyl-2,2,5-trimethyl-1,3-oxazolidine) from Stauffer (S3-2), "R-28725" (3-dichloroacetyl-2,2-dimethyl-1,3-oxazolidine) from Stauffer (S3-3), "benoxacor" (4-dichloroacetyl-3,4-dihydro-3-methyl-2H-1,4-benzoxazine) (S3-4), "PPG-1292" (N-allyl-N-[(1,3-dioxolan-2-yl)methyl]dichloroacetamide) from PPG Industries (S3-5), "DKA-24" (N-allyl-N-[(allylaminocarbonyl)methyl]dichloroacetamide) from Sagro-Chem (S3-6), "AD-67" or "MON 4660" (3-dichloroacetyl-1-oxa-3-azaspiro[4,5]decane) from Nitrokemia or Monsanto (S3-7), "TI-35" (1-dichloroacetylazepane) from TRI-Chemical RT (S3-8), "diclonon" (dicyclonone) or "BAS145138" or "LAB145138" (S3-9) (3-dichloroacetyl-2,5,5-trimethyl-1,3-diazabicyclo[4.3.0]nonane) from BASF, "furilazole" or "MON 13900" ((RS)-3-dichloroacetyl-5-(2-furyl)-2,2-dimethyloxazolidine) (S3-10); and the (R) isomer thereof (S3-11).

S4) N-Acylsulfonamides of the formula (S4) and salts thereof, (S4)

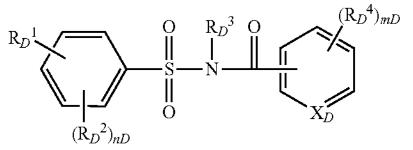

in which the symbols and indices are each defined as follows:

$X_D$ is CH or N;

$R_D^1$ is CO—$NR_D^5R_D^6$ or NHCO—$R_D^7$;

$R_D^2$ is halogen, $(C_1-C_4)$-haloalkyl, $(C_1-C_4)$-haloalkoxy, nitro, $(C_1-C_4)$-alkyl, $(C_1-C_4)$-alkoxy, $(C_1-C_4)$-alkylsulfonyl, $(C_1-C_4)$-alkoxycarbonyl or $(C_1-C_4)$-alkylcarbonyl;

$R_D^3$ is hydrogen, $(C_1-C_4)$-alkyl, $(C_2-C_4)$-alkenyl or $(C_2-C_4)$-alkynyl;

$R_D^4$ is halogen, nitro, $(C_1-C_4)$-alkyl, $(C_1-C_4)$-haloalkyl, $(C_1-C_4)$-haloalkoxy, $(C_3-C_6)$-cycloalkyl, phenyl, $(C_1-C_4)$-alkoxy, cyano, $(C_1-C_4)$-alkylthio, $(C_1-C_4)$-alkylsulfinyl, $(C_1-C_4)$-alkylsulfonyl, $(C_1-C_4)$-alkoxycarbonyl or $(C_1-C_4)$-alkylcarbonyl;

$R_D^5$ is hydrogen, $(C_1-C_6)$-alkyl, $(C_3-C_6)$-cycloalkyl, $(C_2-C_6)$-alkenyl, $(C_2-C_6)$-alkynyl, $(C_5-C_6)$-cycloalkenyl, phenyl or 3- to 6-membered heterocyclyl containing $v_D$ heteroatoms from the group of nitrogen, oxygen and sulfur, where the seven latter radicals are each substituted by $v_D$ substituents from the group of halogen, $(C_1-C_6)$-alkoxy, $(C_1-C_6)$-haloalkoxy, $(C_1-C_2)$-alkylsulfinyl, $(C_1-C_2)$-alkylsulfonyl, $(C_3-C_6)$-cycloalkyl, $(C_1-C_4)$-alkoxycarbonyl, $(C_1-C_4)$-alkylcarbonyl and phenyl, and in the case of cyclic radicals also $(C_1-C_4)$-alkyl and $(C_1-C_4)$-haloalkyl;

$R_D^6$ is hydrogen, $(C_1-C_6)$-alkyl, $(C_2-C_6)$-alkenyl or $(C_2-C_6)$-alkynyl, where the three latter radicals are each substituted by $v_D$ radicals from the group of halogen, hydroxyl, $(C_1-C_4)$-alkyl, $(C_1-C_4)$-alkoxy and $(C_1-C_4)$-alkylthio, or $R_D^5$ and $R_D^6$ together with the nitrogen atom which bears them form a pyrrolidinyl or piperidinyl radical;

$R_D^7$ is hydrogen, $(C_1-C_4)$-alkylamino, di-$(C_1-C_4)$-alkylamino, $(C_1-C_6)$-alkyl, $(C_3-C_6)$-cycloalkyl, where the 2 latter radicals are substituted by $v_D$ substituents from the group of halogen, $(C_1-C_4)$-alkoxy, $(C_1-C_6)$-haloalkoxy and $(C_1-C_4)$-alkylthio, and in the case of cyclic radicals also $(C_1-C_4)$-alkyl and $(C_1-C_4)$-haloalkyl;

$n_D$ is 0, 1 or 2;

$m_D$ is 1 or 2;

$v_D$ is 0, 1, 2 or 3;

among these, preference is given to compounds of the N-acylsulfonamide type, for example of the formula ($S4^a$) below, which are known, for example, from WO-A-97/45016

(S4a)

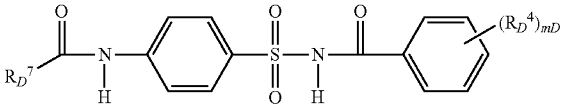

in which $R_D^7$ is $(C_1-C_6)$-alkyl, $(C_3-C_6)$-cycloalkyl, where the 2 latter radicals are substituted by $v_D$ substituents from the group of halogen, $(C_1-C_4)$-alkoxy, $(C_1-C_6)$-haloalkoxy and $(C_1-C_4)$-alkylthio, and in the case of cyclic radicals also $(C_1-C_4)$-alkyl and $(C_1-C_4)$-haloalkyl;

$R_D^4$ is halogen, $(C_1-C_4)$-alkyl, $(C_1-C_4)$-alkoxy, $CF_3$, $m_D$ is 1 or 2;

$v_D$ is 0, 1, 2 or 3;

and acylsulfamoylbenzamides, for example of the formula ($S4^b$) below, which are known, for example, from WO-A-99/16744, (S4b)

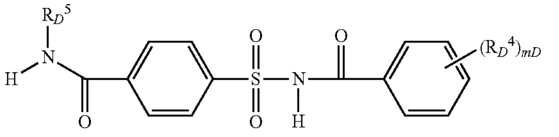

for example those in which $R_D^5$=cyclopropyl and $(R_D^4)$=2-OMe ("cyprosulfamide", S4-1), $R_D^5$=cyclopropyl and $(R_D^4)$=5-Cl-2-OMe (S4-2), $R_D^5$=ethyl and $(R_D^4)$=2-OMe (S4-3), $R_D^5$=isopropyl and $(R_D^4)$=5-Cl-2-OMe (S4-4) and $R_D^5$=isopropyl and $(R_D^4)$=2-OMe (S4-5), and compounds of the N-acylsulfamoylphenylurea type, of the formula ($S4^c$), which are known, for example, from EP-A-365484, (S4c)

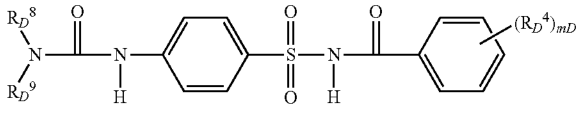

in which $R_D^8$ and $R_D^9$ are each independently hydrogen, $(C_1$-$C_8)$-alkyl, $(C_3$-$C_8)$-cycloalkyl, $(C_3$-$C_6)$-alkenyl, $(C_3$-$C_6)$-alkynyl, $R_D^4$ is halogen, $(C_1$-$C_4)$-alkyl, $(C_1$-$C_4)$-alkoxy, $CF_3$ $m_D$ is 1 or 2;

for example

1-[4-(N-2-methoxybenzoylsulfamoyl)phenyl]-3-methylurea,

1-[4-(N-2-methoxybenzoylsulfamoyl)phenyl]-3,3-dimethylurea,

1-[4-(N-4,5-dimethylbenzoylsulfamoyl)phenyl]-3-methylurea.

S5) Active compounds from the class of the hydroxyaromatics and aromatic-aliphatic carboxylic acid derivatives (S5), for example ethyl 3,4,5-triacetoxybenzoate, 3,5-dimethoxy-4-hydroxybenzoic acid, 3,5-dihydroxybenzoic acid, 4-hydroxysalicylic acid, 4-fluorosalicyclic acid, 2-hydroxycinnamic acid, 1,2-dihydro-2-oxo-6-trifluoromethylpyridine-3-carboxamide, 2,4-dichlorocinnamic acid, as described in WO-A-2004/084631, WO-A-2005/015994, WO-A-2005/016001.

S6) Active compounds from the class of the 1,2-dihydroquinoxalin-2-ones (S6), for example 1-methyl-3-(2-thienyl)-1,2-dihydroquinoxalin-2-one, 1-methyl-3-(2-thienyl)-1,2-dihydroquinoxaline-2-thione, 1-(2-aminoethyl)-3-(2-thienyl)-1,2-dihydroquinoxalin-2-one hydrochloride, 1-[2-(diethylamino)ethyl]-6,7-dimethyl-3-thiophen-2-ylquinoxalin-2(1H)-one, 1-(2-methylsulphonylaminoethyl)-3-(2-thienyl)-1,2-dihydroquinoxalin-2-one, as described in WO-A-2005/112630.

S7) Compounds of the formula (S7), as described in WO-A-1998/38856, (S7)

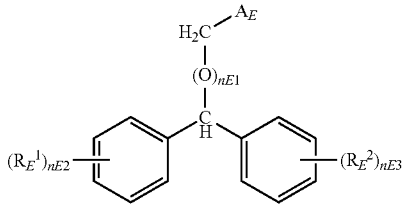

in which the symbols and indices are each defined as follows:

$R_E^1$, $R_E^2$ are each independently halogen, $(C_1$-$C_4)$-alkyl, $(C_1$-$C_4)$-alkoxy, $(C_1$-$C_4)$-haloalkyl, $(C_1$-$C_4)$-alkylamino, di-$(C_1$-$C_4)$-alkylamino, nitro;

$A_E$ is $COOR_E^3$ or $COSR_E^4$ $R_E^3$, $R_E^4$ are each independently hydrogen, $(C_1$-$C_4)$-alkyl, $(C_2$-$C_6)$-alkenyl, $(C_2$-$C_4)$-alkynyl, cyanoalkyl, $(C_1$-$C_4)$-haloalkyl, phenyl, nitrophenyl, benzyl, halobenzyl, pyridinylalkyl and alkylammonium, $n_E^1$ is 0 or 1

$n_E^2$, $n_E^3$ are each independently of one another 0, 1 or 2, preferably:

diphenylmethoxyacetic acid, ethyl diphenylmethoxyacetate, methyl diphenylmethoxyacetate (CAS reg. no. 41858-19-9) (S7-1).

S8) Compounds of the formula (S8), as described in WO-A-98/27049, (S8)

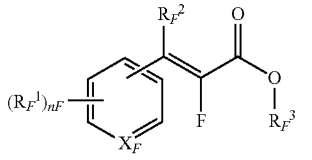

in which $X_F$ is CH or N, $n_F$ in the case that $X_F$=N is an integer from 0 to 4 and in the case that $X_F$=CH is an integer from 0 to 5, $R_F^1$ is halogen, $(C_1$-$C_4)$-alkyl, $(C_1$-$C_4)$-haloalkyl, $(C_1$-$C_4)$-alkoxy, $(C_1$-$C_4)$-haloalkoxy, nitro, $(C_1$-$C_4)$-alkylthio, $(C_1$-$C_4)$-alkylsulfonyl, $(C_1$-$C_4)$-alkoxycarbonyl, optionally substituted phenyl, optionally substituted phenoxy, $R_F^2$ is hydrogen or $(C_1$-$C_4)$-alkyl, $R_F^3$ is hydrogen, $(C_1$-$C_8)$-alkyl, $(C_2$-$C_4)$-alkenyl, $(C_2$-$C_4)$-alkynyl, or aryl, where each of the aforementioned carbon-containing radicals is unsubstituted or substituted by one or more, preferably up to three identical or different radicals from the group consisting of halogen and alkoxy; or salts thereof.

preferably compounds in which $X_F$ is CH, $n_F$ is an integer from 0 to 2, $R_F^1$ is halogen, $(C_1$-$C_4)$-alkyl, $(C_1$-$C_4)$-haloalkyl, $(C_1$-$C_4)$-alkoxy, $(C_1$-$C_4)$-haloalkoxy, $R_F^2$ is hydrogen or $(C_1$-$C_4)$-alkyl, $R_F^3$ is hydrogen, ($C_1$-$C_8$)-alkyl, ($C_2$-$C_4$)-alkenyl, ($C_2$-$C_4$)-alkynyl, or aryl, where each of the aforementioned carbon-containing radicals is unsubstituted or substituted by one or more, preferably up to three identical or different radicals from the group consisting of halogen and alkoxy; or salts thereof.

S9) Active compounds from the class of the 3-(5-tetrazolylcarbonyl)-2-quinolones (S9), for example 1,2-dihydro-4-hydroxy-1-ethyl-3-(5-tetrazolylcarbonyl)-2-quinolone (CAS reg. no.: 219479-18-2), 1,2-dihydro-4-hydroxy-1-methyl-3-(5-tetrazolylcarbonyl)-2-quinolone (CAS reg. no. 95855-00-8), as described in WO-A-1999/000020.

S10) Compounds of the formulae ($S10^a$) or ($S10^b$)
as described in WO-A-2007/023719 and WO-A-2007/023764, (S10a)

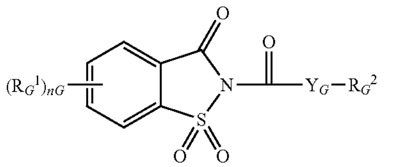

($S10^b$)

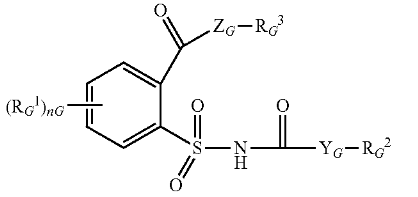

in which $R_G^1$ is halogen, ($C_1$-$C_4$)-alkyl, methoxy, nitro, cyano, $CF_3$, $OCF_3$, $Y_G$, $Z_G$ are each independently of one another O or S, $n_G$ is an integer from 0 to 4, $R_G^2$ is ($C_1$-$C_{16}$)-alkyl, ($C_2$-$C_6$)-alkenyl, ($C_3$-$C_6$)-cycloalkyl, aryl; benzyl, halobenzyl, $R_G^3$ is hydrogen or ($C_1$-$C_6$)-alkyl.

S11) Active compounds of the type of the oxyimino compounds (S11), which are known as seed dressings, such as, for example, "oxabetrinil" ((Z)-1,3-dioxolan-yl-methoxyimino(phenyl)acetonitrile) (S11-1), which is known as seed dressing safener for millet against metolachlor damage, "fluxofenim" (1-(4-chlorophenyl)-2,2,2-trifluoro-1-ethanone O-(1,3-dioxolan-2-ylmethyl)oxime) (S11-2), which is known as a seed-dressing safener for millet against metolachlor damage, and "cyometrinil" or "CGA-43089" ((Z)-cyanomethoxy-imino(phenyl)acetonitrile) (S11-3), which is known as a seed-dressing safener for millet against metolachlor damage.

S12) Active compounds from the class of the isothiochromanones (S12), for example methyl [(3-oxo-1H-2-benzothiopyran-4(3H)-ylidene)methoxy]acetate (CAS reg. no. 205121-04-6) (S12-1) and related compounds from WO-A-1998/13361.

S13) One or more compounds from group (S13):

"naphthalic anhydride" (1,8-naphthalenedicarboxylic anhydride) (S13-1), which is known as a seed-dressing safener for corn against thiocarbamate herbicide damage, "fenclorim" (4,6-dichloro-2-phenylpyrimidine) (S13-2), which is known as a safener for pretilachlor in sown rice, "flurazole" (benzyl 2-chloro-4-trifluoromethyl-1,3-thiazole-5-carboxylate) (S13-3), which is known as a seed-dressing safener for millet against alachlor and metolachlor damage, "CL 304415" (CAS reg. no. 31541-57-8) (4-carboxy-3,4-dihydro-2H-1-benzopyran-4-acetic acid) (S13-4) from American Cyanamid, which is known as a safener for corn against damage by imidazolinones, "MG 191" (CAS reg. no. 96420-72-3) (2-dichloromethyl-2-methyl-1,3-dioxolane) (S13-5) from Nitrokemia, which is known as a safener for corn, "MG-838" (CAS reg. no. 133993-74-5) (2-propenyl 1-oxa-4-azaspiro[4.5]decane-4-carbodithioate) (S13-6) from Nitrokemia, "disulfoton" (O,O-diethyl S-2-ethylthioethyl phosphorodithioate) (S13-7), "dietholate" (O,O-diethyl O-phenyl phosphorothioate) (S13-8), "mephenate" (4-chlorophenyl methylcarbamate) (S13-9).

S14) Active compounds which, in addition to herbicidal action against harmful plants, also have safener action on crop plants such as rice, for example "dimepiperate" or "MY-93" (S-1-methyl-1-phenylethylpiperidine-1-carbothioate), which is known as a safener for rice against damage by the herbicide molinate, "daimuron" or "SK 23" (1-(1-methyl-1-phenylethyl)-3-p-tolylurea), which is known as safener for rice against imazosulfuron herbicide damage, "cumyluron"="JC-940" (3-(2-chlorophenylmethyl)-1-(1-methyl-1-phenylethyl)urea, see JP-A-60087254), which is known as safener for rice against damage by some herbicides, "methoxyphenone" or "NK 049" (3,3'-dimethyl-4-methoxybenzophenone), which is known as safener for rice against damage by some herbicides, "CSB" (1-bromo-4-(chloromethylsulphonyl)benzene) from Kumiai, (CAS reg. no. 54091-06-4), which is known as a safener against damage by some herbicides in rice.

S15) Active compounds which are used primarily as herbicides but also have safener action on crop plants, for example (2,4-dichlorophenoxy)acetic acid (2,4-D),
(4-chlorophenoxy)acetic acid,
(R,S)-2-(4-chloro-o-tolyloxy)propionic acid (mecoprop),
4-(2,4-dichlorophenoxy)butyric acid (2,4-DB),
(4-chloro-o-tolyloxy)acetic acid (MCPA),
4-(4-chloro-o-tolyloxy)butyric acid,
4-(4-chlorophenoxy)butyric acid,
3,6-dichloro-2-methoxybenzoic acid (dicamba),
1-(ethoxycarbonyl)ethyl 3,6-dichloro-2-methoxybenzoate (lactidichlor-ethyl).

Most preferred as crop plant compatibility-improving compound [component (b')] are cloquintocet-mexyl, fenchlorazole-ethyl, isoxadifen-ethyl, mefenpyr-diethyl, fenclorim, cumyluron, S4-1 and S4-5, and particular emphasis is given to mefenpyr-diethyl. Cyprosulfamide (S4-1) is likewise emphasized.

Surprisingly, it has now been found that the active compound combinations defined above of compounds of the general formula (I) and safeners (antidotes) from the group (b') set out above combine very good useful plant tolerance with a particularly high herbicidal activity and can be used in various crops, in particular in cereals (especially wheat), but also in soybeans, potatoes, corn and rice, for the selective control of weeds.

In this context it is to be considered surprising that, from a multiplicity of known safeners or antidotes capable of antagonizing the damaging effect of a herbicide on the crop plants, it is specifically the compounds of group (b') set out above which are suitable for compensating—almost completely—the damaging effect of compounds of the formula (I) on the crop plants, without at the same time having any critical adverse effect on the herbicidal activity against the weeds.

Emphasis may be given here to the particularly advantageous effect of the particularly preferred and most preferred combination partners from group (b'), in particular with regard to the gentle treatment of cereal plants, such as wheat, barley and rye, for example, but also corn and rice, as crop plants.

A general definition of the compounds of the invention is provided by the formula (I). Preferred substituents or ranges of the radicals given under the formulae shown above and below are illustrated below:

X, Y independently of one another preferably represent hydrogen, represent $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkenyl, $C_3$-$C_8$-cycloalkyl-$C_1$-$C_4$-alkyl, $C_3$-$C_8$-cycloalkyl-$C_2$-$C_4$-alkenyl, $C_3$-$C_8$-cycloalkyl-$C_2$-$C_4$-alkynyl, $C_3$-$C_8$-cycloalkenyl-$C_1$-$C_4$-alkyl, each of which is optionally mono- or polysubstituted by halogen, alkoxy, alkyl-S(O)$_n$, haloalkoxy, haloalkyl-S(O)$_n$, cyano or nitro, represent $C_1$-$C_4$-alkoxycarbonyl-$C_1$-$C_4$-alkyl, N,N—$C_1$-$C_4$-dialkylaminocarbonyl-$C_1$-$C_4$-alkyl, N,N—$C_1$-$C_4$-dialkylamino-$C_1$-$C_4$-alkyl, or represent aryl, aryl-$C_1$-$C_4$-alkyl, aryl-$C_2$-$C_4$-alkenyl, aryl-$C_2$-$C_4$-alkynyl, hetaryl, hetaryl-$C_1$-$C_4$-alkyl, hetaryl-$C_2$-$C_4$-alkenyl, hetaryl-$C_2$-$C_4$-alkynyl, heterocyclyl, heterocyclyl-$C_1$-$C_4$-alkyl, N—$C_1$-$C_4$-alkyl-N-arylaminocarbonyl-$C_1$-$C_4$-alkyl, N—$C_1$-$C_4$-alkyl-N-hetarylaminocarbonyl-$C_1$-$C_4$-alkyl, N—$C_1$-$C_4$-alkyl-N-arylamino-$C_1$-$C_4$-alkyl, each of which is optionally mono- or polysubstituted by halogen, $C_1$-$C_4$-alkyl, halo-$C_1$-$C_4$-alkyl, $C_1$-$C_4$-alkoxy, halo-$C_1$-$C_4$-alkoxy, $C_1$-$C_4$-alkyl-S(O)n, halo-$C_1$-$C_4$-alkyl-S(O)$_n$, cyano or nitro, where n represents 0, 1 or 2, CKE preferably represents one of the groups (1)

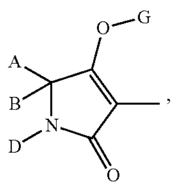

(2)

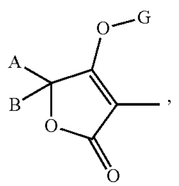

-continued (3)

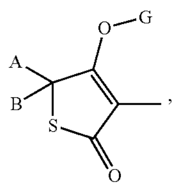

(4)

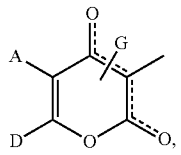

(5)

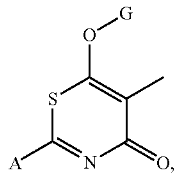

(6)

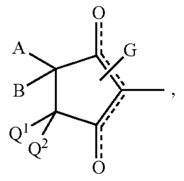

(7)

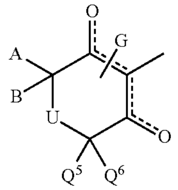

(8)

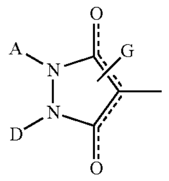

(9)

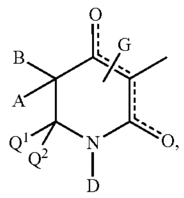

(10)

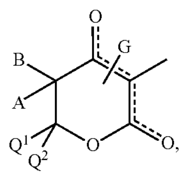

or

-continued

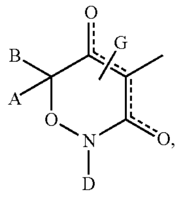

(11)

U preferably represents —S—, —S(O)—, —$S(O)_2$—, —O—,

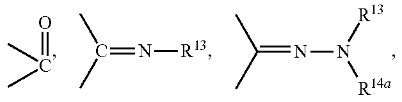

$S{=}N-R^{13}$, $S(O){=}N-R^{13}$ or

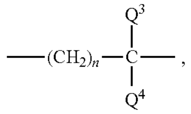

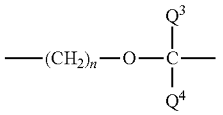

in which n represents the number 0, 1 or 2,

A preferably represents hydrogen or in each case optionally halogen-substituted $C_1$-$C_{12}$-alkyl, $C_3$-$C_8$-alkenyl, $C_1$-$C_{10}$-alkoxy-$C_1$-$C_8$-alkyl, $C_1$-$C_{10}$-alkylthio-$C_1$-$C_6$-alkyl, optionally halogen-, $C_1$-$C_6$-alkyl- or $C_1$-$C_6$-alkoxy-substituted $C_3$-$C_8$-cycloalkyl in which optionally one or two not directly adjacent ring members are replaced by oxygen and/or sulfur or represents in each case optionally halogen-, $C_1$-$C_6$-alkyl-, $C_1$-$C_6$-haloalkyl-, $C_1$-$C_6$-alkoxy-, $C_1$-$C_6$-haloalkoxy-, cyano- or nitro-substituted phenyl, naphthyl, hetaryl having 5 to 6 ring atoms (for example furanyl, pyridyl, imidazolyl, triazolyl, pyrazolyl, pyrimidyl, thiazolyl or thienyl), phenyl-$C_1$-$C_6$-alkyl or naphthyl-$C_1$-$C_6$-alkyl, B preferably represents hydrogen, $C_1$-$C_{12}$-alkyl or $C_1$-$C_8$-alkoxy-$C_1$-$C_6$-alkyl or $C_3$-$C_8$-cycloalkyl, or A, B and the carbon atom to which they are attached preferably represent saturated $C_3$-$C_{10}$-cycloalkyl or unsaturated $C_5$-$C_{10}$-cycloalkyl in which optionally one ring member is replaced by nitrogen, oxygen, sulfur, C═O or C═N—O—$C_1$-$C_4$-alkyl and which are optionally mono- or disubstituted by $C_1$-$C_8$-alkyl, $C_1$-$C_8$-alkoxy, $C_3$-$C_8$-alkenyloxy, $C_1$-$C_6$-alkoxy-$C_1$-$C_6$-alkyl, $C_3$-$C_6$-cycloalkyl-$C_1$-$C_2$-alkoxy, $C_3$-$C_{10}$-cycloalkyl, $C_1$-$C_8$-haloalkyl, $C_2$-$C_6$-haloalkoxy, $C_1$-$C_6$-alkoxy-$C_1$-$C_4$-alkoxy, where the radicals mentioned above are also suitable as N-substituents, or A, B and the carbon atom to which they are attached preferably represent $C_3$-$C_6$-cycloalkyl which is substituted by an alkylenediyl group, which optionally contains one or two not directly adjacent oxygen and/or sulfur atoms and is optionally substituted by $C_1$-$C_4$-alkyl, or by an alkylenedioxy group or by an alkylenedithioyl group which, together with the carbon atom to which it is attached, forms a further five- to eight-membered ring or A, B and the carbon atom to which they are attached preferably represent $C_3$-$C_8$-cycloalkyl or $C_5$-$C_8$-cycloalkenyl in which two substituents together with the carbon atoms to which they are attached form $C_2$-$C_6$-alkanediyl, $C_2$-$C_6$-alkenediyl or $C_4$-$C_6$-alkanedienediyl, each of which is optionally substituted by $C_1$-$C_6$-alkyl, $C_1$-$C_6$-alkoxy or halogen and in which optionally one methylene group is replaced by oxygen or sulfur, D preferably represents hydrogen, in each case optionally halogen-substituted $C_1$-$C_{12}$-alkyl, $C_3$-$C_8$-alkenyl, $C_3$-$C_8$-alkynyl, $C_1$-$C_{10}$-alkoxy-$C_1$-$C_8$-alkyl, optionally halogen-, $C_1$-$C_4$-alkyl-, $C_1$-$C_4$-alkoxy- or $C_1$-$C_4$-haloalkyl-substituted $C_3$-$C_8$-cycloalkyl in which optionally one ring member is replaced by oxygen or sulfur or in each case optionally halogen-, $C_1$-$C_6$-alkyl-, $C_1$-$C_6$-haloalkyl-, $C_1$-$C_6$-alkoxy-, $C_1$-$C_6$-haloalkoxy-, cyano- or nitro-substituted phenyl, hetaryl having 5 or 6 ring atoms (for example furanyl, imidazolyl, pyridyl, thiazolyl, pyrazolyl, pyrimidyl, pyrrolyl, thienyl or triazolyl), phenyl-$C_1$-$C_6$-alkyl or hetaryl-$C_1$-$C_6$-alkyl having 5 or 6 ring atoms (for example furanyl, imidazolyl, pyridyl, thiazolyl, pyrazolyl, pyrimidyl, pyrrolyl, thienyl or triazolyl) or A and D together preferably represent in each case optionally substituted $C_3$-$C_6$-alkanediyl or $C_3$-$C_6$-alkenediyl in which optionally one methylene group is replaced by a carbonyl group, oxygen or sulfur, and possible substituents being in each case:

halogen, hydroxy, mercapto or in each case optionally halogen-substituted $C_1$-$C_{10}$-alkyl, $C_1$-$C_6$-alkoxy, $C_1$-$C_6$-alkylthio, $C_3$-$C_7$-cycloalkyl, phenyl or benzyloxy, or a further $C_3$-$C_6$-alkanediyl grouping, $C_3$-$C_6$-alkenediyl grouping or a butadienyl grouping which is optionally substituted by $C_1$-$C_6$-alkyl or in which optionally two adjacent substituents together with the carbon atoms to which they are attached form a further saturated or unsaturated cycle which has 5 or 6 ring atoms (in the case of the compound of the formula (I-1) A and D together with the atoms to which they are attached then represent, for example, the groups AD-1 to AD-10 mentioned further below), which may contain oxygen or sulfur or in which optionally one of the groups below

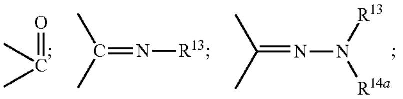

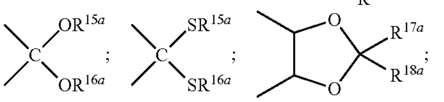

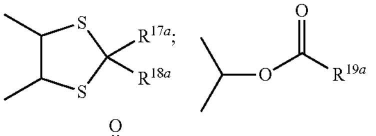

or

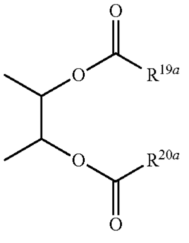

is present, or

A and $Q^1$ together with the carbon atoms to which they are attached preferably represent $C_3$-$C_6$-alkanediyl or $C_4$-$C_6$-alkenediyl (each of which is optionally mono- or disubstituted by identical or different substituents from the group consisting of halogen, hydroxy; $C_1$-$C_{10}$-alkyl, $C_1$-$C_8$-alkenyl, $C_1$-$C_6$-alkoxy, $C_1$-$C_6$-alkylthio, $C_3$-$C_7$-cycloalkyl, each of which is optionally mono- to trisubstituted by identical or different halogen; and benzyloxy or phenyl, each of which is optionally mono- to trisubstituted by identical or different substituents from the group consisting of halogen, $C_1$-$C_6$-alkyl and $C_1$-$C_6$-alkoxy) and which also optionally contains one of the groups below

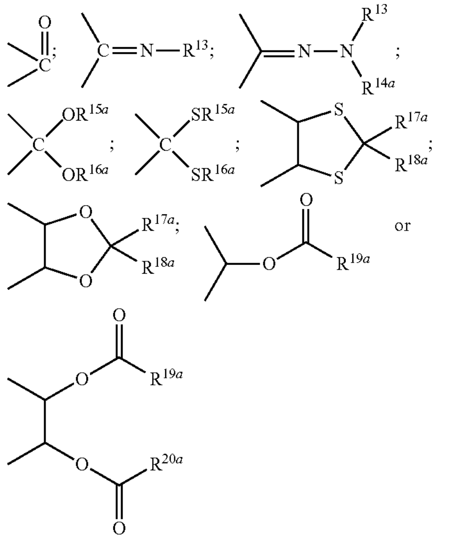

or is bridged by a $C_1$-$C_2$-alkanediyl group or by an oxygen atom or

B and $Q^2$ together preferably represent optionally $C_1$-$C_2$-alkyl-substituted $C_1$-$C_3$-alkanediyl which may optionally be interrupted by oxygen, or D and $Q^1$ together preferably represent $C_3$-$C_6$-alkanediyl which is optionally mono- or disubstituted by identical or different substituents from the group consisting of $C_1$-$C_4$-alkyl, $C_1$-$C_4$-alkoxy, or $Q^1$ preferably represents hydrogen, $C_1$-$C_6$-alkyl, $C_1$-$C_6$-alkoxy-$C_1$-$C_2$-alkyl, optionally fluorine-, chlorine-, $C_1$-$C_4$-alkyl, $C_1$-$C_2$-haloalkyl- or $C_1$-$C_4$-alkoxy-substituted $C_3$-$C_8$-cycloalkyl in which optionally one methylene group is replaced by oxygen or sulfur or optionally halogen-, $C_1$-$C_4$-alkyl-, $C_1$-$C_4$-alkoxy-, $C_1$-$C_2$-haloalkyl-, $C_1$-$C_2$-haloalkoxy-, cyano- or nitro-substituted phenyl, $Q^2$, $Q^4$, $Q^5$ and $Q^6$ independently of one another preferably represent hydrogen or $C_1$-$C_4$-alkyl, $Q^3$ preferably represents hydrogen, $C_1$-$C_6$-alkyl, $C_1$-$C_6$-alkoxy, $C_1$-$C_6$-alkylthio, $C_1$-$C_6$-alkoxy-$C_1$-$C_2$-alkyl, $C_1$-$C_6$-alkylthio-$C_1$-$C_2$-alkyl, optionally $C_1$-$C_4$-alkyl- or $C_1$-$C_4$-alkoxy-substituted $C_3$-$C_8$-cycloalkyl in which optionally one or two methylene groups are replaced by oxygen or sulfur or optionally halogen-, $C_1$-$C_4$-alkyl-, $C_1$-$C_4$-alkoxy-, $C_1$-$C_2$-haloalkyl-, $C_1$-$C_2$-haloalkoxy-, cyano- or nitro-substituted phenyl, or $Q^1$ and $Q^2$ together with the carbon atom to which they are attached preferably represent an optionally $C_1$-$C_6$-alkyl-, $C_1$-$C_6$-alkoxy- or $C_1$-$C_2$-haloalkyl-substituted $C_3$-$C_7$-ring in which optionally one ring member is replaced by oxygen or sulfur, $Q^3$ and $Q^4$ together with the carbon atom to which they are attached preferably represent an optionally $C_1$-$C_4$-alkyl-, $C_1$-$C_4$-alkoxy- or $C_1$-$C_2$-haloalkyl-substituted saturated or unsaturated $C_3$-$C_7$-ring in which optionally one or two ring member is/are replaced by oxygen or sulfur, A and $Q^3$ together with the carbon atoms to which they are attached preferably represent a saturated or unsaturated, optionally $C_1$-$C_4$-alkyl-, $C_1$-$C_4$-alkoxy- or $C_1$-$C_2$-haloalkyl-substituted $C_3$-$C_7$-ring in which optionally one or two ring member is/are replaced by oxygen or sulfur, A and $Q^5$ together with the carbon atoms to which they are attached preferably represent a saturated or unsaturated, optionally $C_1$-$C_4$-alkyl-, $C_1$-$C_4$-alkoxy- or $C_1$-$C_2$-haloalkyl-substituted $C_3$-$C_7$-ring in which optionally one ring member is replaced by oxygen or sulfur, G preferably represents hydrogen (a) or represents one of the groups (b)

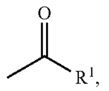

(c)

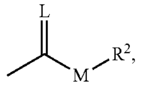

(d)

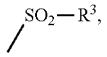

(e)

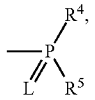

(f)

E or (g)

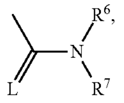

in particular (a), (b), (c) or (g)

in which

E represents a metal ion equivalent or an ammonium ion,

L represents oxygen or sulfur and

M represents oxygen or sulfur.

$R^1$ preferably represents in each case optionally halogen-substituted $C_1$-$C_{20}$-alkyl, $C_2$-$C_{20}$-alkenyl, $C_1$-$C_8$-alkoxy-$C_1$-$C_8$-alkyl, $C_1$-$C_8$-alkylthio-$C_1$-$C_8$-alkyl, poly-$C_1$-$C_8$-alkoxy-$C_1$-$C_8$-alkyl or represents optionally halogen-, $C_1$-$C_6$-alkyl- or $C_1$-$C_6$-alkoxy-substituted $C_3$-$C_8$-cycloalkyl in which optionally one or more (preferably not more than two) not directly adjacent ring members are replaced by oxygen and/or sulfur, represents optionally halogen-, cyano-, nitro-, $C_1$-$C_6$-alkyl-, $C_1$-$C_6$-alkoxy-, $C_1$-$C_6$-haloalkyl-, $C_1$-$C_6$-haloalkoxy-, $C_1$-$C_6$-alkylthio- or $C_1$-$C_6$-alkylsulfonyl-substituted phenyl, represents optionally halogen-, nitro-, cyano-, $C_1$-$C_6$-alkyl-, $C_1$-$C_6$-alkoxy-, $C_1$-$C_6$-haloalkyl- or $C_1$-$C_6$-haloalkoxy-substituted phenyl-$C_1$-$C_6$-alkyl, represents optionally halogen- or $C_1$-$C_6$-alkyl-substituted 5- or 6-membered hetaryl (for example pyrazolyl, thiazolyl, pyridyl, pyrimidyl, furanyl or thienyl), represents optionally halogen- or $C_1$-$C_6$-alkyl-substituted phenoxy-$C_1$-$C_6$-alkyl or represents optionally halogen-, amino- or $C_1$-$C_6$-alkyl-substituted 5- or 6-membered hetaryloxy-$C_1$-$C_6$-alkyl (for example pyridyloxy-$C_1$-$C_6$-alkyl, pyrimidyloxy-$C_1$-$C_6$-alkyl or thiazolyloxy-$C_1$-$C_6$-alkyl), $R^2$ preferably represents in each case optionally halogen-substituted $C_1$-$C_{20}$-alkyl, $C_2$-$C_{20}$-alkenyl, $C_1$-$C_8$-alkoxy-$C_2$-$C_8$-alkyl or poly-$C_1$-$C_8$-alkoxy-$C_2$-$C_8$-alkyl, represents optionally halogen-, $C_1$-$C_6$-alkyl- or $C_1$-$C_6$-alkoxy-substituted $C_3$-$C_8$-cycloalkyl or represents phenyl or benzyl, each of which is optionally substituted by halogen, cyano, nitro, $C_1$-$C_6$-alkyl, $C_1$-$C_6$-alkoxy, $C_1$-$C_6$-haloalkyl or $C_1$-$C_6$-haloalkoxy, $R^3$ preferably represents optionally halogen-substituted $C_1$-$C_8$-alkyl or represents in each case optionally halogen-, $C_1$-$C_6$-alkyl-, $C_1$-$C_6$-alkoxy-, $C_1$-$C_4$-haloalkyl-, $C_1$-$C_4$-haloalkoxy-, cyano- or nitro-substituted phenyl or benzyl, $R^4$ and $R^5$ preferably independently of one another represent in each case optionally halogen-substituted $C_1$-$C_8$-alkyl, $C_1$-$C_8$-alkoxy, $C_1$-$C_8$-alkylamino, di-($C_1$-$C_8$-alkyl)amino, $C_1$-$C_8$-alkylthio, $C_2$-$C_8$-alkenylthio, $C_3$-$C_7$-cycloalkylthio or represent in each case optionally halogen-, nitro-, cyano-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkyl- or $C_1$-$C_4$-haloalkyl-substituted phenyl, phenoxy or phenylthio, $R^6$ and $R^7$ independently of one another preferably represent hydrogen, represent in each case optionally halogen-substituted $C_1$-$C_8$-alkyl, $C_3$-$C_8$-cycloalkyl, $C_1$-$C_8$-alkoxy, $C_3$-$C_8$-alkenyl, $C_1$-$C_8$-alkoxy-$C_1$-$C_8$-alkyl, represent optionally halogen-, $C_1$-$C_8$-haloalkyl-, $C_1$-$C_8$-alkyl- or $C_1$-$C_8$-alkoxy-substituted phenyl, optionally halogen-, $C_1$-$C_8$-alkyl-, $C_1$-$C_8$-haloalkyl- or $C_1$-$C_8$-alkoxy-substituted benzyl or together represent an optionally $C_1$-$C_4$-alkyl-substituted $C_3$-$C_6$-alkylene radical in which optionally one carbon atom is replaced by oxygen or sulfur, $R^{13}$ preferably represents hydrogen, represents in each case optionally halogen-substituted $C_1$-$C_8$-alkyl or $C_1$-$C_8$-alkoxy (only in the case of the C═N—$R^{13}$ group), represents optionally halogen-, $C_1$-$C_4$-alkyl- or $C_1$-$C_4$-alkoxy-substituted $C_3$-$C_8$-cycloalkyl in which optionally one methylene group is replaced by oxygen or sulfur, or represents in each case optionally halogen-, $C_1$-$C_6$-alkyl-, $C_1$-$C_6$-alkoxy-, $C_1$-$C_4$-haloalkyl-, $C_1$-$C_4$-haloalkoxy-, nitro- or cyano-substituted phenyl, phenyl-$C_1$-$C_4$-alkyl, hetaryl-$C_1$-$C_4$-alkyl, or, only in the case of the C═N—$R^{13}$ group, represents phenyl-$C_1$-$C_4$-alkoxy or hetaryl-$C_1$-$C_4$-alkoxy, $R^{14a}$ preferably represents hydrogen or $C_1$-$C_8$-alkyl, or $R^{13}$ and $R^{14a}$ together preferably represent optionally $C_1$-$C_4$-alkyl-substituted $C_4$-$C_6$-alkanediyl which may optionally be interrupted by oxygen or sulfur, $R^{15a}$ and $R^{16a}$ are identical or different and preferably represent $C_1$-$C_6$-alkyl or $R^{15a}$ and $R^{16a}$ together preferably represent a $C_2$-$C_4$-alkanediyl radical or $C_4$-alkanediyl radical which is optionally substituted by $C_1$-$C_6$-alkyl, $C_1$-$C_6$-haloalkyl or by optionally halogen-, $C_1$-$C_6$-alkyl-, $C_1$-$C_4$-haloalkyl-, $C_1$-$C_6$-alkoxy-, $C_1$-$C_4$-haloalkoxy-, nitro- or cyano-substituted phenyl, $R^{17a}$ and $R^{18a}$ independently of one another preferably represent hydrogen, represent optionally halogen-substituted $C_1$-$C_8$-alkyl or represent optionally halogen-, $C_1$-$C_6$-alkyl-, $C_1$-$C_6$-alkoxy-, $C_1$-$C_4$-haloalkyl-, $C_1$-$C_4$-haloalkoxy-, nitro- or cyano-substituted phenyl or $R^{17a}$ and $R^{18a}$ together with the carbon atom to which they are attached preferably represent a carbonyl group or represent optionally halogen-, $C_1$-$C_4$-alkyl- or $C_1$-$C_4$-alkoxy-substituted $C_5$-$C_7$-cycloalkyl in which optionally one methylene group is replaced by oxygen or sulfur, $R^{19a}$ and $R^{20a}$ independently of one another preferably represent $C_1$-$C_{10}$-alkyl, $C_2$-$C_{10}$-alkenyl, $C_1$-$C_{10}$-alkoxy, $C_1$-$C_{10}$-alkylamino, $C_3$-$C_{10}$-alkenylamino, di-($C_1$-$C_{10}$-alkyl)amino or di-($C_3$-$C_{10}$-alkenyl)amino.

In the radical definitions mentioned as being preferred, halogen represents fluorine, chlorine, bromine and iodine, in particular fluorine, chlorine and bromine X particularly preferably represents in each case optionally halogen-substituted $C_1$-$C_6$-alkyl, $C_2$-$C_6$-alkenyl, $C_2$-$C_6$-alkynyl, $C_1$-$C_4$-alkoxy-$C_1$-$C_4$-alkyl, in each case saturated $C_3$-$C_8$-cycloalkyl, $C_3$-$C_8$-cycloalkyl-$C_1$-$C_4$-alkyl, in each case optionally halogen-, $C_1$-$C_4$-alkyl-, $C_1$-$C_4$-haloalkyl-, $C_1$-$C_4$-alkoxy-, $C_1$-$C_4$-haloalkoxy-, cyano- or nitro-substituted phenyl or represents phenyl-$C_1$-$C_2$-alkyl, Y particularly preferably represents in each case optionally halogen-, $C_1$-$C_4$-alkyl-, halo-$C_1$-$C_4$-alkyl-, $C_1$-$C_4$-alkoxy-, halo-$C_1$-$C_4$-alkoxy-, cyano- or nitro-substitued phenyl, phenyl-$C_1$-$C_4$-alkyl, pyridyl or pyridyl-$C_1$-$C_4$-alkyl, CKE particularly preferably represents one of the groups (1)

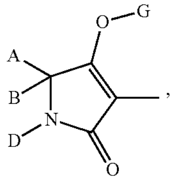

(2)

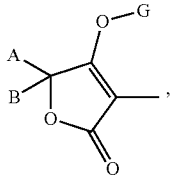

(3)

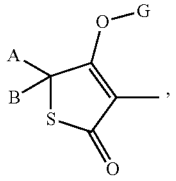

(4)

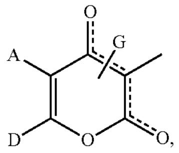

(5)

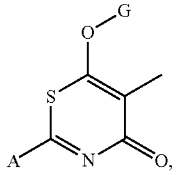

(6)

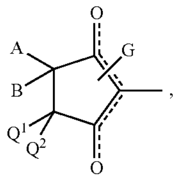

-continued (7)

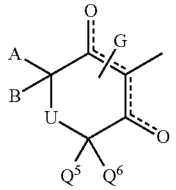

(8)

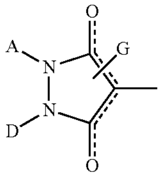

(9)

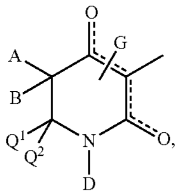

(10)

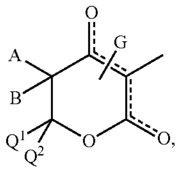

or (11)

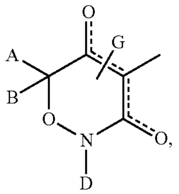

U particularly preferably represents —$CH_2$—, —$CH_2$—$CH_2$—, —O— or

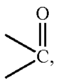

A particularly preferably represents hydrogen, represents $C_1$-$C_6$-alkyl, $C_1$-$C_4$-alkoxy-$C_1$-$C_2$-alkyl, each of which is optionally mono- to trisubstituted by fluorine or chlorine, represents $C_3$-$C_6$-cycloalkyl which is optionally mono- or disubstituted by $C_1$-$C_2$-alkyl or $C_1$-$C_2$-alkoxy and optionally interrupted by an oxygen atom or (but not in the case of the compounds of the formulae (I-3), (I-4), (I-6), (I-7), (I-9), (I-10) and (I-11)) represents phenyl, pyridyl or benzyl, each of which is optionally mono- or disubstituted by fluorine, chlorine, bromine, $C_1$-$C_4$-alkyl, $C_1$-$C_2$-haloalkyl, $C_1$-$C_4$-alkoxy, $C_1$-$C_2$-haloalkoxy, cyano or nitro, B particularly preferably represents hydrogen, $C_1$-$C_4$-alkyl, $C_1$-$C_2$-alkoxy-$C_1$-$C_2$-alkyl or $C_3$-$C_7$-cycloalkyl, or A, B and the carbon atom to which they are attached particularly preferably represent saturated or unsaturated $C_3$-$C_7$-cycloalkyl in which optionally one ring member is replaced by nitrogen, oxygen, sulfur, C═O or C═N—O—$C_1$-$C_2$- alkyl and which is optionally monosubstituted or disubstituted by $C_1$-$C_6$-alkyl, $C_1$-$C_4$-alkoxy-$C_1$-$C_2$-alkyl, trifluoromethyl, $C_1$-$C_6$-alkoxy, $C_3$-$C_6$-alkenyloxy, trifluoroethoxy, $C_1$-$C_3$-alkoxy-$C_1$-$C_3$-alkoxy or $C_3$-$C_6$-cycloalkylmethoxy, where the radicals mentioned above are also suitable as N-substituents, with the proviso that in this case $Q^3$ particularly preferably represents hydrogen or methyl, or A, B and the carbon atom to which they are attached particularly preferably represent $C_5$-$C_6$-cycloalkyl which is substituted by an alkylenediyl group, which optionally contains one or two not directly adjacent oxygen or sulfur atoms and is optionally substituted by methyl or ethyl, or by an alkylenedioxy group or by an alkylenedithiol group which, together with the carbon atom to which it is attached, forms a further five- or six-membered ring, with the proviso that in this case $Q^3$ particularly preferably represents hydrogen or methyl, or A, B and the carbon atom to which they are attached particularly preferably represent $C_3$-$C_6$-cycloalkyl or $C_5$-$C_6$-cycloalkenyl in which two substituents together with the carbon atoms to which they are attached form $C_2$-$C_4$-alkanediyl, $C_2$-$C_4$-alkenediyl or butadienediyl, each of which is optionally substituted by $C_1$-$C_2$-alkyl or $C_1$-$C_2$-alkoxy, with the proviso that in this case $Q^3$ particularly preferably represents hydrogen or methyl, D particularly preferably represents hydrogen, represents $C_1$-$C_6$-alkyl, $C_3$-$C_6$-alkenyl, $C_1$-$C_4$-alkoxy-$C_1$-$C_3$-alkyl, each of which is optionally mono- to trisubstituted by fluorine, represents $C_3$-$C_6$-cycloalkyl which is optionally mono- to disubstituted by $C_1$-$C_4$-alkyl, $C_1$-$C_4$-alkoxy or $C_1$-$C_2$-haloalkyl and in which optionally one methylene group is replaced by oxygen or (only in the case of the compounds of the formulae (I-4)) represents phenyl or pyridyl, each of which is optionally mono- to disubstituted by fluorine, chlorine, bromine, $C_1$-$C_4$-alkyl, $C_1$-$C_4$-haloalkyl, $C_1$-$C_4$-alkoxy or $C_1$-$C_4$-haloalkoxy, or A and D together particularly preferably represent $C_3$-$C_5$-alkanediyl which is optionally mono- to disubstituted and in which one methylene group may be replaced by a carbonyl group (but not in the case of the compounds of the formula (I-11)), oxygen or sulfur, possible substituents being $C_1$-$C_2$-alkyl or $C_1$-$C_2$-alkoxy, or A and D (in the case of the compounds of the formula (I-1)) together with the atoms to which they are attached represent one of the groups AD-1 to AD-10:

AD-1

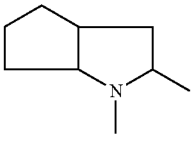

AD-2

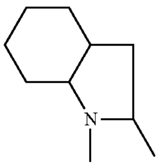

-continued

AD-3

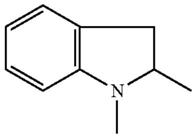

AD-4

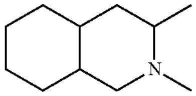

AD-5

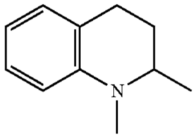

AD-6

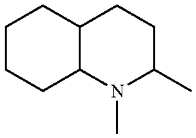

AD-7

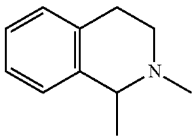

AD-8

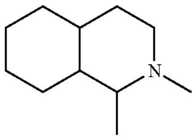

AD-9

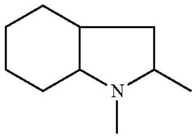

AD-10

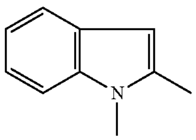

or

A and D together particularly preferably represent $C_3$-$C_5$-alkanediyl which is optionally substituted by an alkylenedioxy group which optionally contains two not directly adjacent oxygen atoms and is optionally mono- to tetra-substituted by $C_1$-$C_4$-alkyl or $C_1$-$C_3$-alkoxy-$C_1$-$C_2$-alkyl, thus forming a further 5- or 6-membered ring, or A and $Q^1$ together particularly preferably represent $C_3$-$C_4$-alkanediyl which is optionally mono- or disubstituted by identical or different substituents from the group consisting of $C_1$-$C_2$-alkyl and $C_1$-$C_2$-alkoxy and which optionally contains the group below:

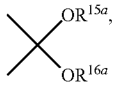

in which $R^{15a}$ and $R^{16a}$ are identical or different and particularly preferably represent methyl or ethyl, or $R^{15a}$ and $R^{16a}$ together particularly preferably represent a $C_2$-$C_4$-alkanediyl or $C_4$-alkenediyl radical which is optionally substituted by methyl or ethyl, or B and $Q^2$ together particularly preferably represent —$CH_2$—, —$CH_2$—$CH_2$— —$CH_2$—$CH_2$—$CH_2$—, or —$CH_2$—O—$CH_2$—, or D and $Q^1$ together particularly preferably represent $C_3$-$C_4$-alkanediyl, or $Q^1$ particularly preferably represents hydrogen, $C_1$-$C_4$-alkyl, $C_1$-$C_4$-alkoxy-$C_1$-$C_2$-alkyl or optionally methyl- or methoxy-substituted $C_3$-$C_6$-cycloalkyl in which optionally one methylene group is replaced by oxygen, $Q^2$ particularly preferably represents hydrogen, methyl or ethyl, $Q^4$, $Q^5$ and $Q^6$ independently of one another particularly preferably represent hydrogen or $C_1$-$C_3$-alkyl, $Q^3$ particularly preferably represents hydrogen, $C_1$-$C_4$-alkyl, $C_1$-$C_4$-alkoxy, or represents $C_3$-$C_6$-cycloalkyl which is optionally mono- or disubstituted by methyl or methoxy and is optionally interrupted by an oxygen atom, or $Q^1$ and $Q^2$ together with the carbon to which they are attached particularly preferably represent $C_3$-$C_6$-cycloalkyl which is optionally substituted by methyl or methoxy and in which one methylene group is optionally replaced by oxygen, with the proviso that in this case A and B independently of one another particularly preferably represent hydrogen or methyl, or $Q^3$ and $Q^4$ together with the carbon to which they are attached particularly preferably represent a saturated $C_5$-$C_6$-ring which is optionally substituted by $C_1$-$C_2$-alkyl or $C_1$-$C_2$-alkoxy and in which optionally one or two ring members are replaced by oxygen or sulfur, with the proviso that in this case A particularly preferably represents hydrogen or methyl, or A and $Q^3$ together with the carbon to which they are attached particularly preferably represent a saturated $C_5$-$C_6$-ring which is optionally substituted by $C_1$-$C_2$-alkyl or $C_1$-$C_2$-alkoxy and in which optionally one ring member is replaced by oxygen or sulfur, with the proviso that in this case B, $Q^4$, $Q^5$ and $Q^6$ independently of one another particularly preferably represent hydrogen or methyl, or A and $Q^5$ together with the carbon atoms to which they are attached particularly preferably represent an optionally $C_1$-$C_2$-alkyl- or $C_1$-$C_2$-alkoxy-substituted saturated or unsaturated $C_5$-$C_6$-ring, with the proviso that in this case B, $Q^3$, $Q^4$ and $Q^6$ independently of one another particularly preferably represent hydrogen or methyl, G particularly preferably represents hydrogen (a) or represents one of the groups (b)

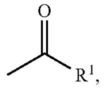

-continued (c)

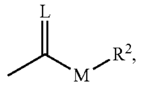

(d)

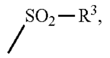

(e)

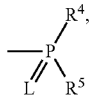

(f)

E or (g)

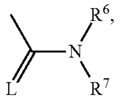

in particular (a), (b) or (c), in which

E represents a metal ion equivalent or an ammonium ion,

L represents oxygen or sulfur and

M represents oxygen or sulfur, $R^1$ particularly preferably represents $C_1$-$C_8$-alkyl, $C_2$-$C_8$-alkenyl, $C_1$-$C_4$-alkoxy-$C_1$-$C_2$-alkyl, $C_1$-$C_4$-alkylthio-$C_1$-$C_2$-alkyl, each of which is optionally mono- to trisubstituted by fluorine or chlorine, or represents $C_3$-$C_6$-cycloalkyl which is optionally mono- or disubstituted by fluorine, chlorine, $C_1$-$C_2$-alkyl or $C_1$-$C_2$-alkoxy and in which optionally one or two not directly adjacent ring members are replaced by oxygen, represents phenyl which is optionally mono- to disubstituted by fluorine, chlorine, bromine, cyano, nitro, $C_1$-$C_4$-alkyl, $C_1$-$C_4$-alkoxy, $C_1$-$C_2$-haloalkyl or $C_1$-$C_2$-haloalkoxy, $R^2$ particularly preferably represents $C_1$-$C_8$-alkyl, $C_2$-$C_8$-alkenyl or $C_1$-$C_4$-alkoxy-$C_2$-$C_4$-alkyl, each of which is optionally mono- to trisubstituted by fluorine, represents $C_3$-$C_6$-cycloalkyl which is optionally monosubstituted by $C_1$-$C_2$-alkyl or $C_1$-$C_2$-alkoxy or represents phenyl or benzyl, each of which is optionally mono- to disubstituted by fluorine, chlorine, bromine, cyano, nitro, $C_1$-$C_4$-alkyl, $C_1$-$C_3$-alkoxy, trifluoromethyl or trifluoromethoxy, $R^3$ particularly preferably represents $C_1$-$C_6$-alkyl which is optionally mono- to trisubstituted by fluorine, or represents phenyl which is optionally monosubstituted by fluorine, chlorine, bromine, $C_1$-$C_4$-alkyl, $C_1$-$C_4$-alkoxy, trifluoromethyl, trifluoromethoxy, cyano or nitro, $R^4$ particularly preferably represents $C_1$-$C_6$-alkyl, $C_1$-$C_6$-alkoxy, $C_1$-$C_6$-alkylamino, di-($C_1$-$C_6$-alkyl)amino, $C_1$-$C_6$-alkylthio, $C_3$-$C_4$-alkenylthio, $C_3$-$C_6$-cycloalkylthio, or represents phenyl, phenoxy or phenylthio, each of which is optionally monosubstituted by fluorine, chlorine, bromine, nitro, cyano, $C_1$-$C_3$-alkoxy, $C_1$-$C_3$-haloalkoxy, $C_1$-$C_3$-alkylthio, $C_1$-$C_3$-haloalkylthio, $C_1$-$C_3$-alkyl or trifluoromethyl, $R^5$ particularly preferably represents $C_1$-$C_6$-alkoxy or $C_1$-$C_6$-alkylthio, $R^6$ particularly preferably represents hydrogen, $C_1$-$C_6$-alkyl, $C_3$-$C_6$-cycloalkyl, $C_1$-$C_6$-alkoxy, $C_3$-$C_6$-alkenyl, $C_1$-$C_6$-alkoxy-$C_1$-$C_4$-alkyl, represents phenyl which is optionally monosubstituted by fluorine, chlorine, bromine, trifluoromethyl, $C_1$-$C_4$-alkyl or $C_1$-$C_4$-alkoxy, represents benzyl which is optionally monosubstituted by fluorine, chlorine, bromine, $C_1$-$C_4$-alkyl, trifluoromethyl or $C_1$-$C_4$-alkoxy, $R^7$ particularly preferably represents $C_1$-$C_6$-alkyl, $C_3$-$C_6$-alkenyl or $C_1$-$C_6$-alkoxy-$C_1$-$C_4$-alkyl, $R^6$ and $R^7$ together particularly preferably represent an optionally methyl- or ethyl-substituted $C_4$-$C_5$-alkylene radical in which optionally one methylene group is replaced by oxygen or sulfur.

In the radical definitions mentioned as being particularly preferred, halogen represents fluorine, chlorine and bromine, in particular fluorine and chlorine.

X very particularly preferably represents optionally halogen-substituted $C_1$-$C_4$-alkyl, in each case saturated $C_3$-$C_5$-cycloalkyl, $C_3$-$C_5$-cycloalkylalkyl, represents in each case optionally halogen-, $C_1$-$C_4$-alkyl-, halo-$C_1$-$C_4$-alkyl- or $C_1$-$C_4$-alkoxy-substituted phenyl, phenyl-$C_1$-$C_4$-alkyl, Y very particularly preferably represents in each case optionally halogen-, $C_1$-$C_4$-alkyl-, halo-$C_1$-$C_4$-alkyl- or $C_1$-$C_4$-alkoxy-substituted phenyl, phenyl-$C_1$-$C_4$-alkyl, CKE very particularly preferably represents one of the groups (1)

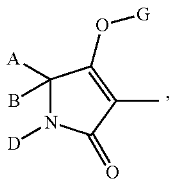

(2)

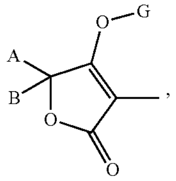

(3)

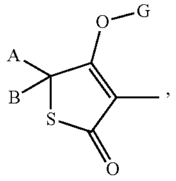

(4)

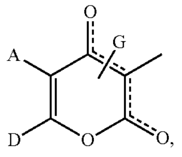

(5)

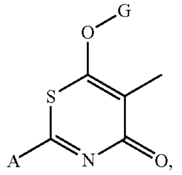

(6)

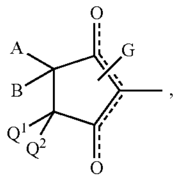

-continued (7)

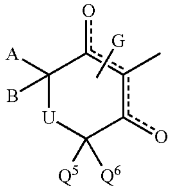

(8)

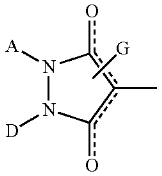

(9)

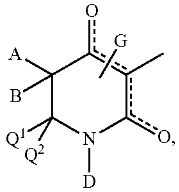

(10)

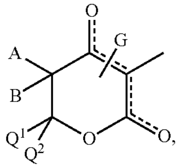

or (11)

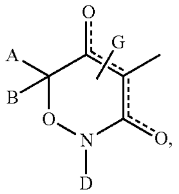

U very particularly preferably represents $-CH_2-$, $-CH_2-CH_2-$, $-O-$ or

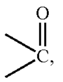

A very particularly preferably represents hydrogen, represents $C_1$-$C_4$-alkyl or $C_1$-$C_2$-alkoxy-$C_1$-$C_2$-alkyl, each of which is optionally mono- to trisubstituted by fluorine, represents cyclopropyl, cyclopentyl or cyclohexyl and, in the case of the compounds of the formula (I-5), represents phenyl which is optionally mono- to disubstituted by fluorine, chlorine, bromine, methyl, ethyl, n-propyl, isopropyl, methoxy, ethoxy, trifluoromethyl, trifluoromethoxy, cyano or nitro, B very particularly preferably represents hydrogen, methyl, ethyl or cyclopropyl or A, B and the carbon atom to which they are attached very particularly preferably represent saturated $C_5$-$C_6$-cycloalkyl in which optionally one ring member is replaced by nitrogen, oxygen, sulfur, C=O, C=N—O-methyl or C=N—O-ethyl and which is optionally mono- or disubstituted by methyl, ethyl, methoxymethyl, ethoxymethyl, methoxyethyl, ethoxyethyl, trifluoromethyl, methoxy, ethoxy, propoxy, butoxy, methoxyethoxy, ethoxyethoxy, allyloxy, trifluorethoxy or cyclopropylmethoxy, where the radicals mentioned above are also suitable as N-substituents, with the proviso that in this case $Q^3$ very particularly preferably represents hydrogen, or A, B and the carbon atom to which they are attached very particularly preferably represent $C_6$-cycloalkyl which is optionally substituted by an alkylenediyl group, which is optionally interrupted by an oxygen atom, or by an alkylenedioxy group, which contains two not directly adjacent oxygen atoms, thus forming a further 5- or 6-membered ring (which may optionally be mono- or disubstituted by methyl), with the proviso that in this case $Q^3$ very particularly preferably represents hydrogen, or A, B and the carbon atom to which they are attached very particularly preferably represent $C_5$-$C_6$-cycloalkyl or $C_5$-$C_6$-cycloalkenyl in which two substituents together with the carbon atoms to which they are attached represent $C_2$-$C_4$-alkanediyl or $C_2$-$C_4$-alkenediyl or butadienediyl, with the proviso that in this case $Q^3$ very particularly preferably represents hydrogen, D very particularly preferably represents hydrogen, represents $C_1$-$C_4$-alkyl, $C_3$-$C_4$-alkenyl, $C_1$-$C_4$-alkoxy-$C_1$-$C_3$-alkyl, each of which is optionally mono- to trisubstituted by fluorine, represents cyclopropyl, cyclopentyl or cyclohexyl or (in the case of the compounds of the formula (I-4)) represents phenyl or pyridyl, each of which is optionally monosubstituted by fluorine, chlorine, methyl, ethyl, n-propyl, isopropyl, methoxy, ethoxy or trifluoromethyl, or A and D together very particularly preferably represent $C_3$-$C_5$-alkanediyl which is optionally monosubstituted by methyl or methoxy and in which optionally one carbon atom is replaced by a carbonyl group (but not in the case of the compound of the formula (I-11)), oxygen or sulfur, or represents the group AD-1, or A and D together very particularly preferably represent $C_3$-$C_5$-alkanediyl which is optionally substituted by an alkylenedioxy group which optionally contains two not directly adjacent oxygen atoms and is optionally mono- to disubstituted by $C_1$-$C_2$-alkyl, thus forming a further 5-membered ring, or A and $Q^1$ together very particularly preferably represent $C_3$-$C_4$-alkanediyl which is optionally mono- or disubstituted by methyl or methoxy and which optionally contains the group below:

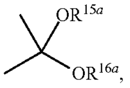

in which $R^{15a}$ and $R^{16a}$ together very particularly preferably represent a $C_2$-$C_4$-alkanediyl or $C_4$-alkenediyl radical, or B and $Q^2$ together very particularly preferably represent $-CH_2-CH_2-CH_2-$, or $-CH_2-O-CH_2-$, or D and $Q^1$ together very particularly preferably represent $C_3$-$C_4$-alkanediyl, or $Q^1$ very particularly preferably represents hydrogen, methyl, ethyl, propyl, isopropyl, cyclopropyl, cyclopentyl or cyclohexyl, $Q^2$ very particularly preferably represents hydrogen, methyl or ethyl, $Q^4$, $Q^5$ and $Q^6$ independently of one another very particularly preferably represent hydrogen or methyl, $Q^3$ very particularly preferably represents hydrogen, methyl, ethyl, propyl, methoxy or ethoxy, or represents $C_3$-$C_6$-cycloalkyl which is optionally monosubstituted by methyl or methoxy and optionally interrupted by an oxygen atom, or $Q^1$ and $Q^2$ together with the carbon atom to which they are attached very particularly preferably represent $C_5$-$C_6$-cycloalkyl which is optionally substituted by methyl or methoxy and in which one methylene group is optionally replaced by oxygen, with the proviso that A and B represent hydrogen, or $Q^3$ and $Q^4$ together with the carbon to which they are attached very particularly preferably represent a saturated $C_5$-$C_6$-ring which is optionally monosubstituted by methyl or methoxy and optionally interrupted by an oxygen atom, with the proviso that in this case A, B, $Q^5$ and $Q^6$ very particularly preferably represent hydrogen, G very particularly preferably represents hydrogen (a) or represents one of the groups (b)

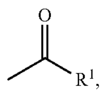

(c)

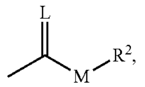

(d)

—$SO_2$—$R^3$ or (f)

E, in which

L represents oxygen or sulfur,

M represents oxygen or sulfur and

E represents a metal ion equivalent or an ammonium ion, $R^1$ very particularly preferably represents $C_1$-$C_6$-alkyl, $C_2$-$C_6$-alkenyl, $C_1$-$C_2$-alkoxy-$C_1$-alkyl, $C_1$-$C_2$-alkylthio-$C_1$-alkyl, each of which is optionally monosubstituted by chlorine, or represents cyclopropyl or cyclohexyl, each of which is optionally monosubstituted by fluorine, chlorine, methyl or methoxy, represents phenyl which is optionally monosubstituted by fluorine, chlorine, bromine, cyano, nitro, methyl, methoxy, trifluoromethyl or trifluoromethoxy, $R^2$ very particularly preferably represents $C_1$-$C_8$-alkyl, $C_2$-$C_6$-alkenyl, $C_1$-$C_4$-alkoxy-$C_2$-$C_3$-alkyl, phenyl or benzyl, each of which is optionally monosubstituted by fluorine, $R^3$ very particularly preferably represents $C_1$-$C_8$-alkyl, G also very particularly preferably represents group (g)

(g)

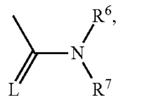

where L represents oxygen and $R^6$ and $R^7$ together represent a $C_4$-$C_5$-alkylene radical in which one carbon atom is replaced by oxygen.

X especially preferably represents methyl, ethyl, n-propyl, isopropyl, n-butyl, —$CH_2CF_3$ or cyclopropyl, Y especially preferably represents phenyl, 4-Cl-benzyl, 4-F-phenyl, 4-Cl-phenyl or 2,4-$Cl_2$-phenyl, CKE especially preferably represents one of the groups (1)

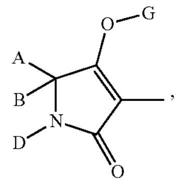

(2)

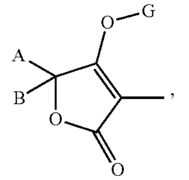

(6)

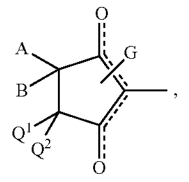

(8)

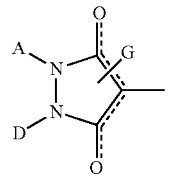

A especially preferably represents hydrogen, methyl, ethyl or cyclopropyl,

B especially preferably represents hydrogen, methyl or cyclopropyl,

A, B and the carbon atom to which they are attached especially preferably represent saturated $C_5$-$C_6$-cycloalkyl in which optionally one ring member is replaced by oxygen or nitrogen and which is optionally mono- or disubstituted by methyl, ethyl, methoxymethyl, methoxy, ethoxy, propoxy, butoxy, trifluorethoxy, trifluoromethyl or —O—$CH_2CHCH_2$, where methoxy or ethoxy are also suitable as N-substituents, or A, B and the carbon atom to which they are attached very particularly preferably represent $C_6$-cycloalkyl which is optionally substituted by an alkylenedioxy group which optionally contains two not directly adjacent oxygen atoms, thus forming a further 5- or 6-membered ring which may optionally be mono- or disubstituted by methyl, D especially preferably represents hydrogen or cyclopropyl, or A and D together especially preferably represent $C_3$-$C_5$-alkanediyl in which optionally one carbon atom is replaced by oxygen, or A and D together especially preferably represent $C_3$-$C_5$-alkanediyl which is optionally substituted by an alkylenedioxy group which optionally contains two not directly adjacent oxygen atoms and is optionally mono- or disubstituted by methyl, thus forming a further 5-membered ring, (with emphasis, A and D together represent $C_3$-$C_5$-alkanediyl which is optionally substituted by one or two not directly adjacent oxygen atoms, thus forming a further 5-membered ring), or A and $Q^1$ together especially preferably represent $C_3$-$C_4$-alkanediyl, $Q^2$ especially preferably represents hydrogen, G especially preferably represents hydrogen (a) or one of the groups (b)

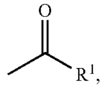

(c)

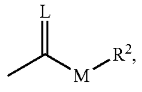

in which

L represents oxygen,

M represents oxygen, $R^1$ especially preferably represents $C_1$-$C_6$-alkyl, $R^2$ especially preferably represents $C_1$-$C_6$-alkyl, G also especially particularly preferably represents group (g)

(g)

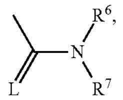

where L represents oxygen and $R^6$ and $R^7$ together represent a $C_5$-alkylene radical in which one carbon atom is replaced by oxygen.

X with emphasis represents methyl or ethyl,

Y with emphasis represents 4-F-phenyl or 4-Cl-phenyl,

CKE with emphasis represents one of the groups (1)

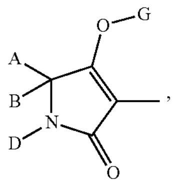

(2)

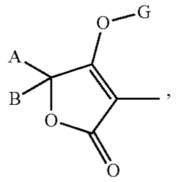

A with emphasis represents hydrogen or methyl,

B with emphasis represents hydrogen or methyl,

A, B and the carbon atom to which they are attached with emphasis represent saturated $C_6$-cycloalkyl in which optionally one ring member is replaced by oxygen and which is optionally monosubstituted by methyl or methoxy, D with emphasis represents hydrogen or cyclopropyl, or A and D together with emphasis represent $C_3$-alkanediyl, G with emphasis represents hydrogen (a).

X also with emphasis represents methyl, ethyl, isopropyl, n-propyl, n-butyl or $-CH_2-CF_3$, Y also with emphasis represents phenyl, 4-Cl-benzyl, 4-F-phenyl, 4-Cl-phenyl or 2,4-$Cl_2$-phenyl, CKE also with emphasis represents one of the groups (1)

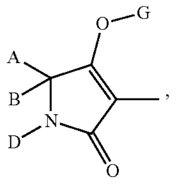

(2)

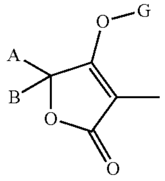

or (8)

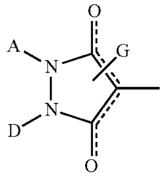

A also with emphasis represents hydrogen, methyl or cyclopropyl,

B also with emphasis represents hydrogen, methyl or cyclopropyl,

A, B and the carbon atom to which they are attached also with emphasis represent saturated $C_6$-cycloalkyl in which optionally one ring member is replaced by oxygen or nitrogen and which is optionally mono- or disubstituted by methyl, ethyl, methoxy, ethoxy, n-propoxy, trifluoromethyl or $-O-CH_2CHCH_2$, where methoxy or ethoxy are also suitable as N-substituents, A, B and the carbon atom to which they are attached also with emphasis represent $C_6$-cycloalkyl which is optionally substituted by an alkylenedioxy group which optionally contains two not directly adjacent oxygen atoms, thus forming a further 6-membered ring which may optionally be monosubstituted by methyl, D also with emphasis represents hydrogen or cyclopropyl, or A and D together also with emphasis represent $C_3$-alkanediyl, A and D in the case of CKE=group (8) together also with emphasis represent $-(CH_2)_2-O-(CH_2)_2-$, G also with emphasis represents hydrogen (a) or represents group (g)

(g)

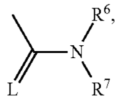

where L represents oxygen and $R^6$ and $R^7$ together represent a $C_5$-alkylene radical in which one carbon atom is replaced by oxygen.

The abovementioned general or preferred radical definitions or illustrations can be combined with one another as desired, i.e. including combinations between the respective ranges and preferred ranges. They apply both to the end products and, correspondingly, to precursors and intermediates.

Preference is given in accordance with the invention to the compounds of the formula (I) in which a combination of the definitions listed above as preferred (preferably) is present.

Particular preference is given in accordance with the invention to the compounds of the formula (I) in which a combination of the definitions listed above as more preferred is present.

Very particular preference is given in accordance with the invention to the compounds of the formula (I) in which a combination of the definitions listed above as even more preferred is present.

Special preference according to the invention is given to the compounds of the formula (I) which contain a combination of the meanings listed above as being especially preferred.

Most emphasized in accordance with the invention are the compounds of the formula (I) which contain a combination of the meanings stated above as being with emphasis.

Emphasis is likewise given to compounds of the formula (I) in which G represents hydrogen.

Saturated or unsaturated hydrocarbon radicals, such as alkyl, alkanediyl or alkenyl, can in each case be straight-chain or branched as far as this is possible, including in combination with heteroatoms, such as, for example, in alkoxy.

Unless indicated otherwise, optionally substituted radicals may be mono- or polysubstituted, where in the case of polysubstitutions the substituents may be identical or different.

In addition to the compounds mentioned in the examples, the following compounds may be specifically mentioned:

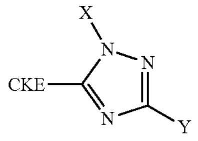

TABLE 1

| X | Y |
|---|---|
| $CH_3$ | Ph |
| $CH_3$ | 4-Cl—$C_6H_4$ |
| $CH_3$ | 4-F—$C_6H_4$ |
| $CH_3$ | 4-MeO—$C_6H_4$ |
| $CH_3$ | 4-$CF_3$—$C_6H_4$ |
| $CH_3$ | 3-Cl—$C_6H_4$ |
| $CH_3$ | 3-F—$C_6H_4$ |
| $CH_3$ | 3-$CF_3$—$C_6H_4$ |
| $CH_3$ | 3-MeO—$C_6H_4$ |
| $CH_3$ | 2-Cl—$C_6H_4$ |
| $CH_3$ | 2-MeO—$C_6H_4$ |
| $CH_3$ | 2-F—$C_6H_4$ |
| $CH_3$ | 2,4-$Cl_2$—$C_6H_3$ |
| $C_2H_5$ | Ph |
| $C_2H_5$ | 4-Cl—$C_6H_4$ |
| $C_2H_5$ | 4-F—$C_6H_4$ |
| $C_2H_5$ | 4-MeO—$C_6H_4$ |
| $C_2H_5$ | 4-$CF_3$—$C_6H_4$ |
| $C_2H_5$ | 3-Cl—$C_6H_4$ |
| $C_2H_5$ | 3-F—$C_6H_4$ |
| $C_2H_5$ | 3-$CF_3$—$C_6H_4$ |

TABLE 1-continued

| X | Y |
|---|---|
| $C_2H_5$ | 3-MeO—$C_6H_4$ |
| $C_2H_5$ | 2-Cl—$C_6$H4 |
| $C_2H_5$ | 2-MeO—$C_6H_4$ |
| $C_2H_5$ | 2-F—$C_6H_4$ |
| $C_2H_5$ | 2,4-$Cl_2$—$C_6H_3$ |
| $CH_2$—Ph | Ph |
| $CH_2$—Ph | 4-Cl—$C_6H_4$ |
| $CH_2$—Ph | 4-F—$C_6H_4$ |
| $CH_2$—Ph | 4-MeO—$C_6H_4$ |
| $CH_2$—Ph | 4-$CF_3$—$C_6H_4$ |
| $CH_2$—Ph | 3-Cl—$C_6H_4$ |
| $CH_2$—Ph | 3-F—$C_6H_4$ |
| $CH_2$—Ph | 3-$CF_3$—$C_6H_4$ |
| $CH_2$—Ph | 3-MeO—$C_6H_4$ |
| $CH_2$—Ph | 2-Cl—$C_6H_4$ |
| $CH_2$—Ph | 2-MeO—$C_6H_4$ |
| $CH_2$—Ph | 2-F—$C_6H_4$ |
| $CH_2$—Ph | 2,4-$Cl_2$—$C_6H_3$ |
| $CH(CH_3)_2$ | Ph |
| $CH(CH_3)_2$ | 4-Cl—$C_6H_4$ |
| $CH(CH_3)_2$ | 4-F—$C_6H_4$ |
| $CH(CH_3)_2$ | 4-MeO—$C_6H_4$ |
| $CH(CH_3)_2$ | 4-$CF_3$—$C_6H_4$ |
| $CH(CH_3)_2$ | 3-Cl—$C_6H_4$ |
| $CH(CH_3)_2$ | 3-F—$C_6H_4$ |
| $CH(CH_3)_2$ | 3-$CF_3$—$C_6H_4$ |
| $CH(CH_3)_2$ | 3-MeO—$C_6H_4$ |
| $CH(CH_3)_2$ | 2-Cl—$C_6H_4$ |
| $CH(CH_3)_2$ | 2-MeO—$C_6H_4$ |
| $CH(CH_3)_2$ | 2-F—$C_6H_4$ |
| $CH(CH_3)_2$ | 2,4-$Cl_2$—$C_6H_3$ |
| $CH_2COOCH_3$ | Ph |
| $CH_2COOCH_3$ | 4-Cl—$C_6H_4$ |
| $CH_2COOCH_3$ | 4-F—$C_6H_4$ |
| $CH_2COOCH_3$ | 4-MeO—$C_6H_4$ |
| $CH_2COOCH_3$ | 4-$CF_3$—$C_6H_4$ |
| $CH_2COOCH_3$ | 3-Cl—$C_6H_4$ |
| $CH_2COOCH_3$ | 3-F—$C_6H_4$ |
| $CH_2COOCH_3$ | 3-$CF_3$—$C_6H_4$ |
| $CH_2COOCH_3$ | 3-MeO—$C_6H_4$ |
| $CH_2COOCH_3$ | 2-Cl—$C_6H_4$ |
| $CH_2COOCH_3$ | 2-MeO—$C_6H_4$ |
| $CH_2COOCH_3$ | 2-F—$C_6H_4$ |
| $CH_2COOCH_3$ | 2,4-$Cl_2$—$C_6H_3$ |
| $CH_2$—c-Pr | Ph |
| $CH_2$—c-Pr | 4-Cl—$C_6H_4$ |
| $CH_2$—c-Pr | 4-F—$C_6H_4$ |
| $CH_2$—c-Pr | 4-MeO—$C_6H_4$ |
| $CH_2$—c-Pr | 4-$CF_3$—$C_6H_4$ |
| $CH_2$—c-Pr | 3-Cl—$C_6H_4$ |
| $CH_2$—c-Pr | 3-F—$C_6H_4$ |
| $CH_2$—c-Pr | 3-$CF_3$—$C_6H_4$ |
| $CH_2$—c-Pr | 3-MeO—$C_6H_4$ |
| $CH_2$—c-Pr | 2-Cl—$C_6H_4$ |
| $CH_2$—c-Pr | 2-MeO—$C_6H_4$ |
| $CH_2$—c-Pr | 2-F—$C_6H_4$ |
| $CH_2$—c-Pr | 2,4-$Cl_2$—$C_6H_3$ |
| c-Pr | Ph |
| c-Pr | 4-Cl—$C_6H_4$ |
| c-Pr | 4-F—$C_6H_4$ |
| c-Pr | 4-MeO—$C_6H_4$ |
| c-Pr | 4-$CF_3$—$C_6H_4$ |
| c-Pr | 3-Cl—$C_6H_4$ |
| c-Pr | 3-F—$C_6H_4$ |
| c-Pr | 3-$CF_3$—$C_6H_4$ |
| c-Pr | 3-MeO—$C_6H_4$ |
| c-Pr | 2-Cl—$C_6H_4$ |
| c-Pr | 2-MeO—$C_6H_4$ |
| c-Pr | 2-F—$C_6H_4$ |
| c-Pr | 2,4-$Cl_2$—$C_6H_3$ |
| $CH_2CH_2CH_3$ | Ph |
| $CH_2CH_2CH_3$ | 4-Cl—$C_6H_4$ |
| $CH_2CH_2CH_3$ | 4-F—$C_6H_4$ |
| $CH_2CH_2CH_3$ | 4-MeO—$C_6H_4$ |
| $CH_2CH_2CH_3$ | 4-$CF_3$—$C_6H_4$ |
| $CH_2CH_2CH_3$ | 3-Cl—$C_6H_4$ |
| $CH_2CH_2CH_3$ | 3-F—$C_6H_4$ |
| $CH_2CH_2CH_3$ | 3-$CF_3$—$C_6H_4$ |

TABLE 1-continued

| X | Y |
|---|---|
| $CH_2CH_2CH_3$ | 3-MeO—$C_6H_4$ |
| $CH_2CH_2CH_3$ | 2-Cl—$C_6H_4$ |
| $CH_2CH_2CH_3$ | 2-MeO—$C_6H_4$ |
| $CH_2CH_2CH_3$ | 2-F—$C_6H_4$ |
| $CH_2CH_2CH_3$ | 2,4—$Cl_2$—$C_6H_3$ |
| $CH_2CF_3$ | Ph |
| $CH_2CF_3$ | 4-Cl—$C_6H_4$ |
| $CH_2CF_3$ | 4-F—$C_6H_4$ |
| $CH_2CF_3$ | 4-MeO—$C_6H_4$ |
| $CH_2CF_3$ | 4-$CF_3$—$C_6H_4$ |
| $CH_2CF_3$ | 3-Cl—$C_6H_4$ |
| $CH_2CF_3$ | 3-F—$C_6H_4$ |
| $CH_2CF_3$ | 3-$CF_3$—$C_6H_4$ |
| $CH_2CF_3$ | 3-MeO—$C_6H_4$ |
| $CH_2CF_3$ | 2-Cl—$C_6H_4$ |
| $CH_2CF_3$ | 2-MeO—$C_6H_4$ |
| $CH_2CF_3$ | 2-F—$C_6H_4$ |
| $CH_2CF_3$ | 2,4-$Cl_2$—$C_6H_3$ |
| $CH_2CH_2OCH_3$ | Ph |
| $CH_2CH_2OCH_3$ | 4-Cl—$C_6H_4$ |
| $CH_2CH_2OCH_3$ | 4-F—$C_6H_4$ |
| $CH_2CH_2OCH_3$ | 4-MeO—$C_6H_4$ |
| $CH_2CH_2OCH_3$ | 4-$CF_3$—$C_6H_4$ |
| $CH_2CH_2OCH_3$ | 3-Cl—$C_6H_4$ |
| $CH_2CH_2OCH_3$ | 3-F—$C_6H_4$ |
| $CH_2CH_2OCH_3$ | 3-$CF_3$—$C_6H_4$ |
| $CH_2CH_2OCH_3$ | 3-MeO—$C_6H_4$ |
| $CH_2CH_2OCH_3$ | 2-Cl—$C_6H_4$ |
| $CH_2CH_2OCH_3$ | 2-MeO—$C_6H_4$ |
| $CH_2CH_2OCH_3$ | 2-F—$C_6H_4$ |
| $CH_2CH_2OCH_3$ | 2,4-$Cl_2$—$C_6H_3$ |
| $CH_2CH_2CH_2CH_3$ | Ph |
| $CH_2CH_2CH_2CH_3$ | 4-Cl—Ph |
| $CH_2CH_2CH_2CH_3$ | 4-F—Ph |
| $CH_2CH_2CH_2CH_3$ | 4-MeO—Ph |
| $CH_2CH_2CH_2CH_3$ | 4-$CF_3$—Ph |
| $CH_2CH_2CH_2CH_3$ | 3-Cl—Ph |
| $CH_2CH_2CH_2CH_3$ | 3-F—Ph |
| $CH_2CH_2CH_2CH_3$ | 3-$CF_3$—Ph |
| $CH_2CH_2CH_2CH_3$ | 3-MeO—Ph |
| $CH_2CH_2CH_2CH_3$ | 2-Cl—Ph |
| $CH_2CH_2CH_2CH_3$ | 2-MeO—Ph |
| $CH_2CH_2CH_2CH_3$ | 2-F—Ph |
| $CH_2CH_2CH_2CH_3$ | 2,4-$Cl_2$—Ph |
| Ph | Ph |
| Ph | 4-Cl—$C_6H_4$ |
| Ph | 4-F—$C_6H_4$ |
| Ph | 4-MeO—$C_6H_4$ |
| Ph | 4-$CF_3$—$C_6H_4$ |
| Ph | 3-Cl—$C_6H_4$ |
| Ph | 3-F—$C_6H_4$ |
| Ph | 3-$CF_3$—$C_6H_4$ |
| Ph | 3-MeO—$C_6H_4$ |
| Ph | 2-Cl—$C_6H_4$ |
| Ph | 2-MeO—$C_6H_4$ |
| Ph | 2-F—$C_6H_4$ |
| Ph | 2,4-$Cl_2$—$C_6H_3$ |
| 4-Cl—$C_6H_4$ | Ph |
| 4-Cl—$C_6H_4$ | 4-Cl—$C_6H_4$ |
| 4-Cl—$C_6H_4$ | 4-F—$C_6H_4$ |
| 4-Cl—$C_6H_4$ | 4-MeO—$C_6H_4$ |
| 4-Cl—$C_6H_4$ | 4-$CF_3$—$C_6H_4$ |
| 4-Cl—$C_6H_4$ | 3-Cl—$C_6H_4$ |
| 4-Cl—$C_6H_4$ | 3-F—$C_6H_4$ |
| 4-Cl—$C_6H_4$ | 3-$CF_3$—$C_6H_4$ |
| 4-Cl—$C_6H_4$ | 3-MeO—$C_6H_4$ |
| 4-Cl—$C_6H_4$ | 2-Cl—$C_6H_4$ |
| 4-Cl—$C_6H_4$ | 2-MeO—$C_6H_4$ |
| 4-Cl—$C_6H_4$ | 2-F—$C_6H_4$ |
| 4-Cl—$C_6H_4$ | 2,4-$Cl_2$—$C_6H_3$ |
| $CH_3$ | $CH_3$ |
| $CH_3$ | $CH_2CH_3$ |
| $CH_3$ | i-Pr |
| $CH_3$ | n-Pr |
| $CH_3$ | $CF_3$ |
| $CH_3$ | $CH_2Ph$ |
| $CH_3$ | $CH_2C_6H_4$-4-Cl |
| $CH_3$ | $CH_2C_6H_5$ |
| $CH_3$ | $CH_2C_6H_4$-4-OMe |
| $CH_3$ | $CH_2C_6H_4$-4-$CF_3$ |
| $CH_3$ | $CH_2C_6H_4$-4-F |
| $CH_3$ | 2-thienyl |
| $CH_3$ | 3-thienyl |
| $CH_3$ | 2-furyl |
| $CH_3$ | 3-furyl |
| $CH_3$ | 2-pyridyl |
| $CH_3$ | 3-pyridyl |
| $CH_3$ | 4-pyridyl |
| $CH_3$ | $CH_2CH_2Ph$ |
| $CH_2CH_3$ | $CH_3$ |
| $CH_2CH_3$ | $CH_2CH_3$ |
| $CH_2CH_3$ | i-Pr |
| $CH_2CH_3$ | n-Pr |
| $CH_2CH_3$ | $CF_3$ |
| $CH_2CH_3$ | $CH_2Ph$ |
| $CH_2CH_3$ | $CH_2C_6H_4$-4-Cl |
| $CH_2CH_3$ | $CH_2C_6H_5$ |
| $CH_2CH_3$ | $CH_2C_6H_4$-4-OMe |
| $CH_2CH_3$ | $CH_2C_6H_4$-4-$CF_3$ |
| $CH_2CH_3$ | $CH_2C_6H_3$-2,4-$Cl_2$ |
| $CH_2CH_3$ | 2-thienyl |
| $CH_2CH_3$ | 3-thienyl |
| $CH_2CH_3$ | 2-furyl |
| $CH_2CH_3$ | 3-furyl |
| $CH_2CH_3$ | 2-pyridyl |
| $CH_2CH_3$ | 3-pyridyl |
| $CH_2CH_3$ | 4-pyridyl |
| $CH_2CH_3$ | $CH_2CH_2Ph$ |
| n-Pr | $CH_3$ |
| n-Pr | $CH_2CH_3$ |
| n-Pr | i-Pr |
| n-Pr | n-Pr |
| n-Pr | $CF_3$ |
| n-Pr | $CH_2Ph$ |
| n-Pr | $CH_2C_6H_4$-4-Cl |
| n-Pr | $CH_2C_6H_5$ |
| n-Pr | $CH_2C_6H_4$-4-OMe |
| n-Pr | $CH_2C_6H_4$-4-Br |
| n-Pr | $CH_2C_6H_4$-4-F |
| n-Pr | 2-thienyl |
| n-Pr | 3-thienyl |
| n-Pr | 2-furyl |
| n-Pr | 3-furyl |
| n-Pr | 2-pyridyl |
| n-Pr | 3-pyridyl |
| n-Pr | 4-pyridyl |
| n-Pr | $CH_2CH_2Ph$ |
| n-Bu | $CH_3$ |
| n-Bu | $CH_2CH_3$ |
| n-Bu | i-Pr |
| n-Bu | n-Pr |
| n-Bu | $CF_3$ |
| n-Bu | $CH_2Ph$ |
| n-Bu | $CH_2C_6H_4$-4-Cl |
| n-Bu | $CH_2C_6H_5$ |
| n-Bu | $CH_2C_6H_4$-4-OMe |
| n-Bu | $CH_2C_6H_4$-4-$CF_3$ |
| n-Bu | $CH_2C_6H_4$-4-F |
| n-Bu | 2-thienyl |
| n-Bu | 3-thienyl |
| n-Bu | 2-furyl |
| n-Bu | 3-furyl |
| n-Bu | 2-pyridyl |
| n-Bu | 3-pyridyl |
| n-Bu | 4-pyridyl |
| $CH_2CF_3$ | $CH_3$ |
| $CH_2CF_3$ | $CH_2CH_3$ |
| $CH_2CF_3$ | i-Pr |
| $CH_2CF_3$ | n-Pr |
| $CH_2CF_3$ | $CF_3$ |
| $CH_2CF_3$ | $CH_2Ph$ |
| $CH_2CF_3$ | $CH_2C_6H_4$-4-Cl |
| $CH_2CF_3$ | $CH_2C_6H_4$-4-Cl |
| $CH_2CF_3$ | $CH_2C_6H_4$-4-OMe |
| $CH_2CF_3$ | 2-thienyl |
| $CH_2CF_3$ | 3-thienyl |

TABLE 1-continued

| X | Y |
|---|---|
| $CH_2CF_3$ | 2-furyl |
| $CH_2CF_3$ | 3-furyl |
| $CH_2CF_3$ | 2-pyridyl |
| $CH_2CF_3$ | 3-pyridyl |
| $CH_2CF_3$ | 4-pyridyl |

Me = methyl, Ph = phenyl

Especially preferred active compounds according to the invention are compounds having the radical combinations for X and Y mentioned in Table 1 and the radical combinations for A, B and D mentioned in Tables 2a and 2b:

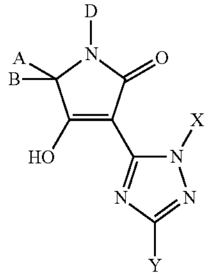

CKE = (I-1-a)

TABLE 2a

| A | B | D |
|---|---|---|
| $CH_3$ | H | H |
| $C_2H_5$ | H | H |
| $C_3H_7$ | H | H |
| i-$C_3H_7$ | H | H |
| $C_4H_9$ | H | H |
| i-$C_4H_9$ | H | H |
| s-$C_4H_9$ | H | H |
| t-$C_4H_9$ | H | H |
| $CH_3$ | $CH_3$ | H |
| $C_2H_5$ | $CH_3$ | H |
| $C_3H_7$ | $CH_3$ | H |
| i-$C_3H_7$ | $CH_3$ | H |
| $C_4H_9$ | $CH_3$ | H |
| i-$C_4H_9$ | $CH_3$ | H |
| s-$C_4H_9$ | $CH_3$ | H |
| t-$C_4H_9$ | $CH_3$ | H |
| $C_2H_5$ | $C_2H_5$ | H |
| $C_3H_7$ | $C_3H_7$ | H |
| 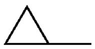 | $CH_3$ | H |
| 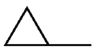 | 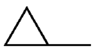 | H |
| 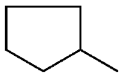 | $CH_3$ | H |
| 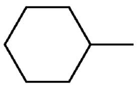 | $CH_3$ | H |
| $H_3CO—CH_2—$ | $CH_3$ | H |
| $H_5C_2O—CH_2—$ | $CH_3$ | H |
| $H_3CO—(CH_2)_2—$ | $CH_3$ | H |
| $H_5C_2O—(CH_2)_2—$ | $CH_3$ | H |

TABLE 2a-continued

| A | B | D |
|---|---|---|
| 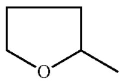 | $CH_3$ | H |
| 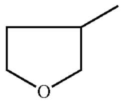 | $CH_3$ | H |
| $—(CH_2)_2—$ | | H |
| $—(CH_2)_4—$ | | H |
| $—(CH_2)_5—$ | | H |
| $—(CH_2)_6—$ | | H |
| $—(CH_2)_7—$ | | H |
| 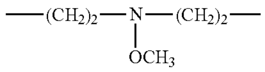 | | H |
| 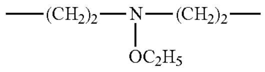 | | H |
| $—(CH_2)_2—O—(CH_2)_2—$ | | H |
| $—CH_2—O—(CH_2)_3—$ | | H |
| $—(CH_2)_2—S—(CH_2)_2—$ | | H |
| $—CH_2—CHCH_3—(CH_2)_3—$ | | H |
| $—CH_2—CHOCH_3—(CH_2)_2—$ | | H |
| $—CH_2—CHOC_2H_5—(CH_2)_2—$ | | H |
| $—CH_2—CHOC_3H_7—(CH_2)_2—$ | | H |
| $—CH_2—CHOC_4H_9—(CH_2)_2—$ | | H |
| $—CH_2—CHO(CH_2)_2OCH_3—(CH_2)_2—$ | | H |
| 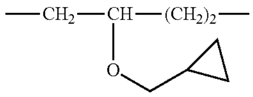 | | H |
| $—CH_2—CHOCH_3—(CH_2)_3—$ | | H |
| $—CH_2—CHOC_2H_5—(CH_2)_3—$ | | H |
| $—CH_2—CHOC_3H_7—(CH_2)_3—$ | | H |
| $—CH_2—CHOC_4H_9—(CH_2)_3—$ | | H |
| $—CH_2—CHO(CH_2)_2OCH_3—(CH_2)_3—$ | | H |
| 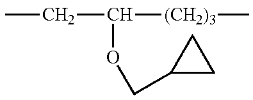 | | H |
| $—(CH_2)_2—CHCH_3—(CH_2)_2—$ | | H |
| $—(CH_2)_2—CHCF_3—(CH_2)_2—$ | | H |
| $—(CH_2)_2—CHC_2H_5—(CH_2)_2—$ | | H |
| $—(CH_2)_2—CHC_3H_7—(CH_2)_2—$ | | H |
| $—(CH_2)_2—CHi\text{-}C_3H_7—(CH_2)_2—$ | | H |
| $—(CH_2)_2—CHOCH_3—(CH_2)_2—$ | | H |
| $—(CH_2)_2—CHOC_2H_5—(CH_2)_2—$ | | H |
| $—(CH_2)_2—CHOC_3H_7—(CH_2)_2—$ | | H |
| $—(CH_2)_2—CHO—CH_2CF_3—(CH_2)_2—$ | | H |
| $—(CH_2)_2—C(CH_3)_2—(CH_2)_2—$ | | H |
| $—CH_2—(CHCH_3)_2—(CH_2)_2—$ | | H |
| 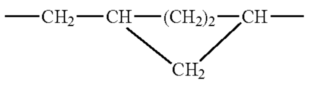 | | H |
| 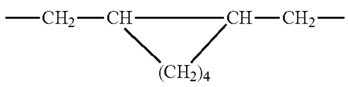 | | H |
| 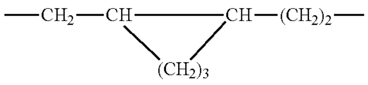 | | H |

TABLE 2a-continued
| A | B | D |
|---|---|---|
| 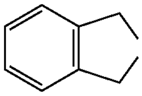 | | H |
| 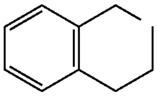 | | H |
| 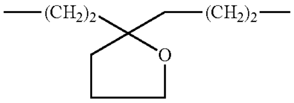 | | H |
| 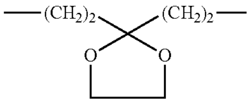 | | H |
| 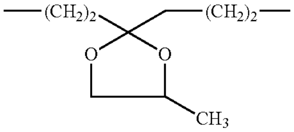 | | H |
| 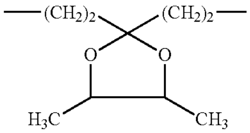 | | H |
| 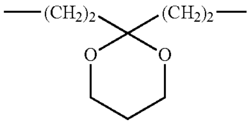 | | H |
| 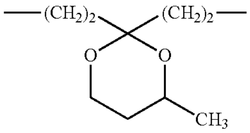 | | H |
| 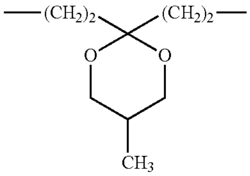 | | H |
| 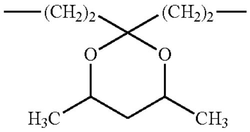 | | H |
| 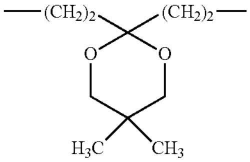 | | H |
TABLE 2a-continued
| A | B | D |
|---|---|---|
| 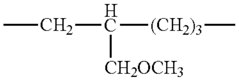 | | H |
| 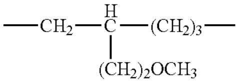 | | H |
| 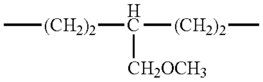 | | H |
| 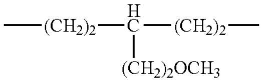 | | H |
| 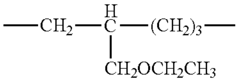 | | H |
| 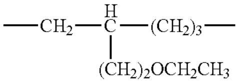 | | H |
| 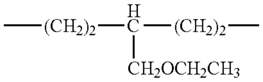 | | H |
| 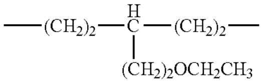 | | H |
| $-(CH_2)_2-CO-(CH_2)_2-$ | | H |
| $-(CH_2)_2-CNOMe-(CH_2)_2-$ | | H |
| $-(CH_2)_2-CNOEt-(CH_2)_2-$ | | H |
| $-(CH_2)_2-NOMe-(CH_2)_2-$ | | H |
| $-(CH_2)_2-NOEt-(CH_2)_2-$ | | H |
TABLE 2b
| A | D | B |
|---|---|---|
| $-(CH_2)_3-$ | | H |
| $-(CH_2)_4-$ | | H |
| $-CH_2-CHCH_3-CH_2-$ | | H |
| $-CH_2-CH_2-CHCH_3-$ | | H |
| $-CH_2-CHCH_3-CHCH_3-$ | | H |
| $-CH_2-CH(OCH_3)-CH_2-$ | | H |
| $-CH_2-CH{=}CH-CH_2-$ | | H |
| 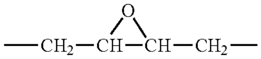 | | H |
| $-CH_2-S-CH_2-$ | | H |
| $-CH_2-S-(CH_2)_2-$ | | H |
| $-(CH_2)_2-S-CH_2-$ | | H |
| 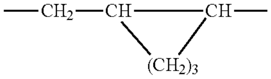 | | H |
| H | $CH_3$ | H |
| H | $C_2H_5$ | H |
| H | $C_3H_7$ | H |
| H | $i-C_3H_7$ | H |

TABLE 2b-continued

| A | D | B |
|---|---|---|
| H | 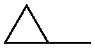 | H |
| H | 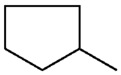 | H |
| H | 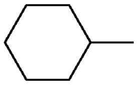 | H |
| $CH_3$ | $CH_3$ | H |
| $CH_3$ | $C_2H_5$ | H |
| $CH_3$ | $C_3H_7$ | H |
| $CH_3$ | i-$C_3H_7$ | H |
| $CH_3$ | 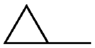 | H |
| $CH_3$ | 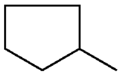 | H |
| $CH_3$ | 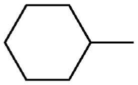 | H |
| $C_2H_5$ | $CH_3$ | H |
| $C_2H_5$ | $C_2H_5$ | H |
| H | $H_3CO—(CH_2)_2—$ | H |
| H | $H_5C_2O—(CH_2)_2—$ | H |
| H | $H_3CO—CH_2—CH(CH_3)—$ | H |
| H | $H_3CO—CHCH_3—CH_2—$ | H |
| $CH_3$ | $H_3CO—(CH_2)_2—$ | H |
| $CH_3$ | $H_5C_2O—(CH_2)_2—$ | H |
| $CH_3$ | $H_3CO—CH_2—CH(CH_3)—$ | H |
| $CH_3$ | $H_3CO—CHCH_3—CH_2—$ | H |

Especially preferred active compounds according to the invention are compounds having the radical combinations for X and Y mentioned in Table 1 and the radical combinations for A, B, D, $R_6$ and $R_7$ mentioned in Table 2c:

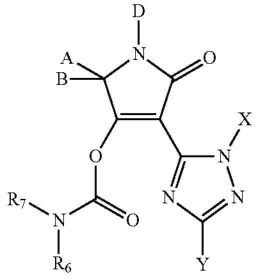

CKE = (1-1-g)

TABLE 2c

| A | B | D | $R_6$ | $R_7$ |
|---|---|---|---|---|
| $CH_3$ | $CH_3$ | H | $CH_3$ | $CH_3$ |
| $CH_3$ | $CH_3$ | H | $C_2H_5$ | $C_2H_5$ |
| $CH_3$ | $CH_3$ | H | $CH_2CH_2CH_2CH_2$ | |
| $CH_3$ | $CH_3$ | H | $CH_2CH_2CH_2CH_2CH_2$ | |
| $CH_3$ | $CH_3$ | H | $CH_2CH_2OCH_2CH_2$ | |
| $C_2H_5$ | $C_2H_5$ | H | $CH_3$ | $CH_3$ |
| $C_2H_5$ | $C_2H_5$ | H | $C_2H_5$ | $C_2H_5$ |
| $C_2H_5$ | $C_2H_5$ | H | $CH_2CH_2CH_2CH_2$ | |
| $C_2H_5$ | $C_2H_5$ | H | $CH_2CH_2CH_2CH_2CH_2$ | |

TABLE 2c-continued

| A | B | D | $R_6$ | $R_7$ |
|---|---|---|---|---|
| $C_2H_5$ | $C_2H_5$ | H | $CH_2CH_2OCH_2CH_2$ | |
| $—(CH_2)_2—O—(CH_2)_2—$ | | H | $CH_3$ | $CH_3$ |
| $—(CH_2)_2—O—(CH_2)_2—$ | | H | $C_2H_5$ | $C_2H_5$ |
| $—(CH_2)_2—O—(CH_2)_2—$ | | H | $CH_2CH_2CH_2CH_2$ | |
| $—(CH_2)_2—O—(CH_2)_2—$ | | H | $CH_2CH_2CH_2CH_2CH_2$ | |
| $—(CH_2)_2—O—(CH_2)_2—$ | | H | $CH_2CH_2OCH_2CH_2$ | |
| $—(CH_2)_2—CHOMe—(CH_2)_2—$ | | H | $CH_2CH_2CH_2CH_2$ | |
| $—(CH_2)_2—CHOMe—(CH_2)_2—$ | | H | $CH_2CH_2CH_2CH_2CH_2$ | |
| $—(CH_2)_2—CHOMe—(CH_2)_2—$ | | H | $CH_2CH_2OCH_2CH_2$ | |
| $—(CH_2)_2—CHOMe—(CH_2)_2—$ | | H | $CH_3$ | $CH_3$ |
| $—(CH_2)_2—CHOMe—(CH_2)_2—$ | | H | $C_2H_5$ | $C_2H_5$ |
| $—(CH_2)_2—N—(CH_2)_2—$<br>$OCH_3$ | | H | $CH_3$ | $CH_3$ |
| $—(CH_2)_2—N—(CH_2)_2—$<br>$OCH_3$ | | H | $C_2H_5$ | $C_2H_5$ |
| $—(CH_2)_2—N—(CH_2)_2—$<br>$OCH_3$ | | H | $CH_2CH_2CH_2CH_2$ | |
| $—(CH_2)_2—N—(CH_2)_2—$<br>$OCH_3$ | | H | $CH_2CH_2CH_2CH_2CH_2$ | |
| $—(CH_2)_2—N—(CH_2)_2—$<br>$OCH_3$ | | H | $CH_2CH_2OCH_2CH_2$ | |
| 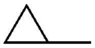 | 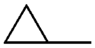 | H | $CH_3$ | $CH_3$ |
| 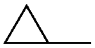 | 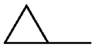 | H | $C_2H_5$ | $C_2H_5$ |
| 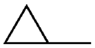 | 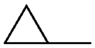 | H | $CH_2CH_2CH_2CH_2$ | |
| 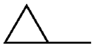 | 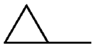 | H | $CH_2CH_2CH_2CH_2CH_2$ | |
| 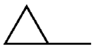 | 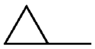 | H | $CH_2CH_2OCH_2CH_2$ | |
| $—(CH_2)_2—CHCH_3—(CH_2)_2—$ | | H | $CH_3$ | $CH_3$ |
| $—(CH_2)_2—CHCH_3—(CH_2)_2—$ | | H | $C_2H_5$ | $C_2H_5$ |
| $—(CH_2)_2—CHCH_3—(CH_2)_2—$ | | H | $CH_2CH_2CH_2CH_2$ | |
| $—(CH_2)_2—CHCH_3—(CH_2)_2—$ | | H | $CH_2CH_2CH_2CH_2CH_2$ | |
| $—(CH_2)_2—CHCH_3—(CH_2)_2—$ | | H | $CH_2CH_2OCH_2CH_2$ | |

Especially preferred active compounds according to the invention are furthermore compounds having the radical combinations for X and Y mentioned in Table 1 and the radical combinations for A and B mentioned in Table 3:

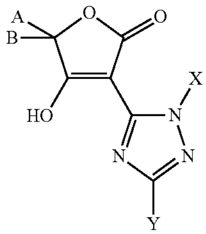

CKE = (I-2-a)

TABLE 3

| A | B |
|---|---|
| $CH_3$ | H |
| $C_2H_5$ | H |
| $C_3H_7$ | H |
| i-$C_3H_7$ | H |
| $C_4H_9$ | H |
| i-$C_4H_9$ | H |
| s-$C_4H_9$ | H |
| t-$C_4H_9$ | H |
| $CH_3$ | $CH_3$ |
| $C_2H_5$ | $CH_3$ |
| $C_3H_7$ | $CH_3$ |
| i-$C_3H_7$ | $CH_3$ |
| $C_4H_9$ | $CH_3$ |
| i-$C_4H_9$ | $CH_3$ |
| s-$C_4H_9$ | $CH_3$ |
| t-$C_4H_9$ | $CH_3$ |
| $C_2H_5$ | $C_2H_5$ |
| $C_3H_7$ | $C_3H_7$ |
| 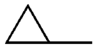 | $CH_3$ |
| 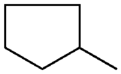 | $CH_3$ |
| 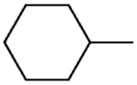 | $CH_3$ |
| $H_3CO—CH_2—$ | $CH_3$ |
| $H_5C_2O—CH_2—$ | $CH_3$ |
| $H_3CO—(CH_2)_2—$ | $CH_3$ |
| $H_5C_2O—(CH_2)_2—$ | $CH_3$ |
| 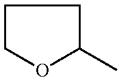 | $CH_3$ |
| 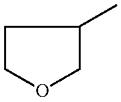 | $CH_3$ |
| $—(CH_2)_3—$ | |
| $—(CH_2)_4—$ | |
| $—(CH_2)_5—$ | |
| $—(CH_2)_6—$ | |
| $—(CH_2)_7—$ | |
| 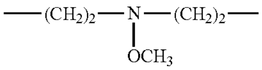 | |
| 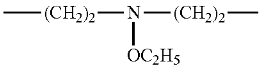 | |
| $—(CH_2)_2—O—(CH_2)_2—$ | |
| $—CH_2—O—(CH_2)_3—$ | |
| $—(CH_2)_2—S—(CH_2)_2—$ | |
| $—CH_2—CHCH_3—(CH_2)_3—$ | |
| $—CH_2—CHOCH_3—(CH_2)_3—$ | |
| $—CH_2—CHOC_2H_5—(CH_2)_3—$ | |
| $—CH_2—CHOC_3H_7—(CH_2)_3—$ | |
| $—CH_2—CHOC_4H_9—(CH_2)_3—$ | |
| $—CH_2—CHO(CH_2)_2OCH_3—(CH_2)_3—$ | |
| $—(CH_2)_2—CHCH_3—(CH_2)_2—$ | |
| $—(CH_2)_2—CHC_2H_5—(CH_2)_2—$ | |
| $—(CH_2)_2—CHC_3H_7—(CH_2)_2—$ | |
| $—(CH_2)_2—CHi\text{-}C_3H_7—(CH_2)_2—$ | |
| $—(CH_2)_2—CHOCH_3—(CH_2)_2—$ | |
| $—(CH_2)_2—CHOC_2H_5—(CH_2)_2—$ | |
| $—(CH_2)_2—CHOC_3H_7—(CH_2)_2—$ | |

TABLE 3-continued

| A | B |
|---|---|
| $—(CH_2)_2—CHO—CH_2CF_3—(CH_2)_2—$ | |
| $—(CH_2)_2—C(CH_3)_2—(CH_2)_2—$ | |
| $—CH_2—(CHCH_3)_2—(CH_2)_2—$ | |
| 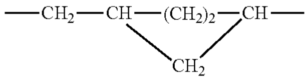 | |
| 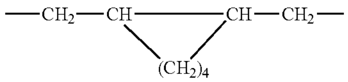 | |
| 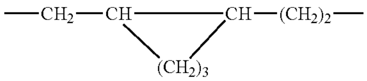 | |
| 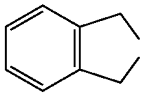 | |
| 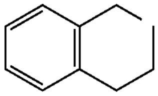 | |
| 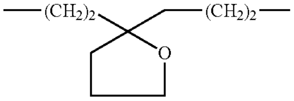 | |
| 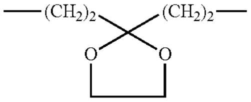 | |
| 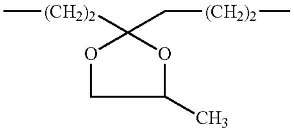 | |
| 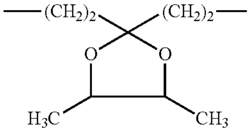 | |
| 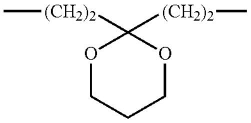 | |
| 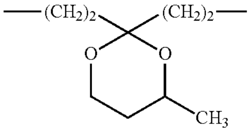 | |
| 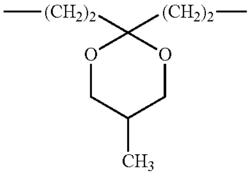 | |

TABLE 3-continued

| A | B |
|---|---|
| 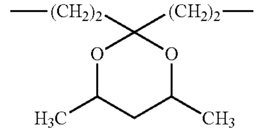 | |
| 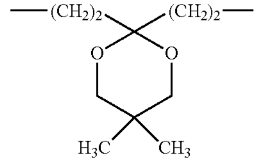 | |
| 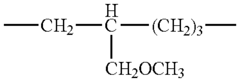 | |
| 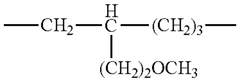 | |
| 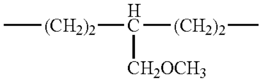 | |
| 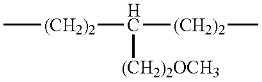 | |
| 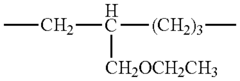 | |
| 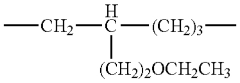 | |
| 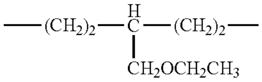 | |
| 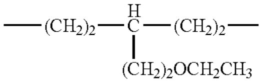 | |

Especially preferred active compounds according to the invention are compounds having the radical combinations for X and Y mentioned in Table 1 and the radical combinations for A and D mentioned in Table 4:

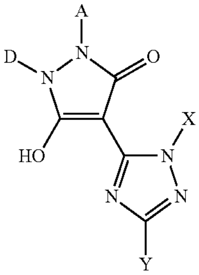

CKE = (I-8-a)

TABLE 4

| A | D |
|---|---|
| $CH_3$ | H |
| $C_2H_5$ | H |
| $C_3H_7$ | H |
| i-$C_3H_7$ | H |
| $C_4H_9$ | H |
| i-$C_4H_9$ | H |
| s-$C_4H_9$ | H |
| t-$C_4H_9$ | H |
| $CH_3$ | $CH_3$ |
| $C_2H_5$ | $CH_3$ |
| $C_3H_7$ | $CH_3$ |
| i-$C_3H_7$ | $CH_3$ |
| $C_4H_9$ | $CH_3$ |
| i-$C_4H_9$ | $CH_3$ |
| s-$C_4H_9$ | $CH_3$ |
| t-$C_4H_9$ | $CH_3$ |
| $C_2H_5$ | $C_2H_5$ |
| $C_3H_7$ | $C_3H_7$ |
| 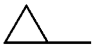 | $CH_3$ |
| 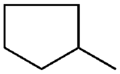 | $CH_3$ |
| 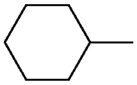 | $CH_3$ |
| $H_3CO—CH_2—$ | $CH_3$ |
| $H_5C_2O—CH_2—$ | $CH_3$ |
| $H_3CO—(CH_2)_2—$ | $CH_3$ |
| $H_5C_2O—(CH_2)_2—$ | $CH_3$ |
| 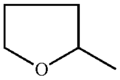 | $CH_3$ |
| 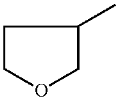 | $CH_3$ |
| $—(CH_2)_3—$ | |
| $—(CH_2)_4—$ | |
| $—(CH_2)_5—$ | |
| $—(CH_2)_6—$ | |
| $—(CH_2)_7—$ | |
| 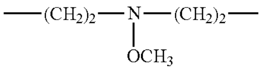 | |
| 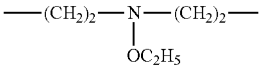 | |
| $—(CH_2)_2—O—(CH_2)_2—$ | |
| $—CH_2—O—(CH_2)_3—$ | |
| $—(CH_2)_2—S—(CH_2)_2—$ | |
| $—CH_2—CHCH_3—(CH_2)_3—$ | |
| $—(CH_2)_2—NMe—(CH_2)_2—$ | |
| $—CH_2—CHOCH_3—(CH_2)_3—$ | |
| $—CH_2—CHOC_2H_5—(CH_2)_3—$ | |
| $—CH_2—CHOC_3H_7—(CH_2)_3—$ | |
| $—CH_2—CHOC_4H_9—(CH_2)_3—$ | |
| $—CH_2—CHO(CH_2)_2OCH_3—(CH_2)_3—$ | |
| $—(CH_2)_2—CHCH_3—(CH_2)_2—$ | |
| $—(CH_2)_2—CHC_2H_5—(CH_2)_2—$ | |
| $—(CH_2)_2—CHC_3H_7—(CH_2)_2—$ | |
| $—(CH_2)_2—CHi\text{-}C_3H_7—(CH_2)_2—$ | |
| $—(CH_2)_2—CHOCH_3—(CH_2)_2—$ | |
| $—(CH_2)_2—CHOC_2H_5—(CH_2)_2—$ | |

TABLE 4-continued

| A | D |
|---|---|
| $-(CH_2)_2-CHOC_3H_7-(CH_2)_2-$ | |
| $-(CH_2)_2-CHO-CH_2CF_3-(CH_2)_2-$ | |
| $-(CH_2)_2-C(CH_3)_2-(CH_2)_2-$ | |
| $-CH_2-(CHCH_3)_2-(CH_2)_2-$ | |
| 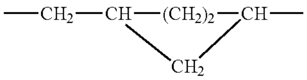 | |
| 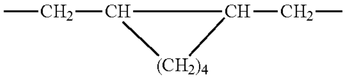 | |
| 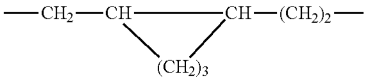 | |
| 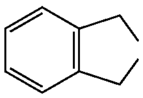 | |
| 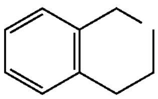 | |
| 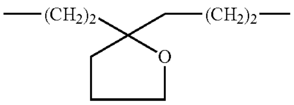 | |
| 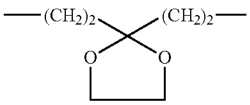 | |
| 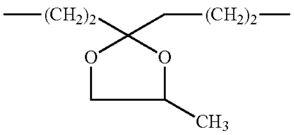 | |
| 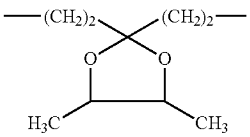 | |
| 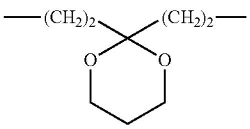 | |
| 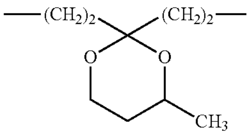 | |
| 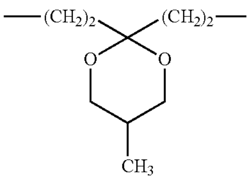 | |

TABLE 4-continued

| A | D |
|---|---|
| 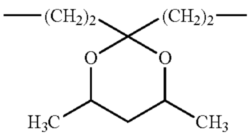 | |
| 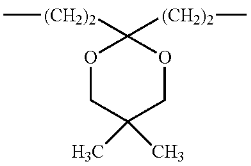 | |
| 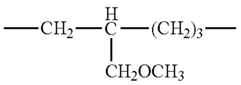 | |
| 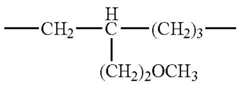 | |
| 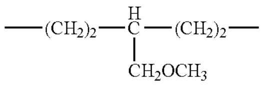 | |

The present invention further relates to formulations and use forms prepared therefrom as crop protection compositions and/or pesticides, for example drench, drip and spray liquors, comprising at least one of the active compounds according to the invention. In some cases, the use forms comprise further crop protection agents and/or pesticides and/or adjuvants which improve action, such as penetrants, e.g. vegetable oils, for example rapeseed oil, sunflower oil, mineral oils, for example paraffin oils, alkyl esters of vegetable fatty acids, for example rapeseed oil methyl ester or soya bean oil methyl ester, or alkanol alkoxylates, and/or spreaders, for example alkylsiloxanes, and/or salts, for example organic or inorganic ammonium or phosphonium salts, for example ammonium sulfate or diammonium hydrogenphosphate, and/or retention promoters, for example dioctyl sulfosuccinate or hydroxypropyl guar polymers, and/or humectants, for example glycerol, and/or fertilizers, for example ammonium-, potassium- or phosphorus-containing fertilizers.

Customary formulations are, for example, water-soluble liquids (SL), emulsion concentrates (EC), emulsions in water (EW), suspension concentrates (SC, SE, FS, OD), water-dispersible granules (WG), granules (GR) and capsule concentrates (CS); these and further possible formulation types are described, for example, by Crop Life International and in Pesticide Specifications, Manual on development and use of FAO and WHO specifications for pesticides, FAO Plant Production and Protection Papers—173, prepared by the FAO/WHO Joint Meeting on Pesticide Specifications, 2004, ISBN: 9251048576. The formulations optionally comprise, in addition to one or more active compounds according to the invention, further agrochemically active compounds.

These are preferably formulations or use forms which comprise auxiliaries, for example extenders, solvents, spontaneity promoters, carriers, emulsifiers, dispersants, antifreezes, biocides, thickeners and/or further auxiliaries, for example adjuvants. An adjuvant in this context is a component which enhances the biological effect of the formulation, without the component itself having a biological effect. Examples of adjuvants are agents which promote retention, spreading, attachment to the leaf surface or penetration.

These formulations are prepared in a known manner, for example by mixing the active compounds with auxiliaries such as, for example, extenders, solvents and/or solid carriers and/or further auxiliaries such as, for example, surfactants. The formulations are produced either in suitable production plants or else before or during application.

Auxiliaries used may be substances capable of giving the formulation of the active compound, or the application forms prepared from these formulations (such as ready-to-use crop protection agents, for example, such as spray liquors or seed dressings) particular properties, such as certain physical, technical and/or biological properties.

Suitable extenders are, for example, water, polar and non-polar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulfones and sulfoxides (such as dimethyl sulfoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulfoxide, and also water.

In principle it is possible to use all suitable solvents. Examples of suitable solvents are aromatic hydrocarbons, such as xylene, toluene or alkylnaphthalenes, chlorinated aromatic or chlorinated aliphatic hydrocarbons, such as chlorobenzene, chloroethylene or methylene chloride, aliphatic hydrocarbons, such as cyclohexane, paraffins, petroleum fractions, mineral and vegetable oils, alcohols, such as methanol, ethanol, isopropanol, butanol or glycol and their ethers and esters, ketones such as acetone, methyl ethyl ketone, methyl isobutyl ketone or cyclohexanone, strongly polar solvents, such as dimethyl sulfoxide, and also water.

In principle it is possible to use all suitable carriers. Useful carriers include in particular: for example ammonium salts and ground natural minerals such as kaolins, clays, talc, chalk, quartz, attapulgite, montmorillonite or diatomaceous earth, and ground synthetic materials such as finely divided silica, alumina and natural or synthetic silicates, resins, waxes and/or solid fertilizers. Mixtures of such carriers may also be used. Useful carriers for granules include: for example crushed and fractionated natural rocks such as calcite, marble, pumice, sepiolite, dolomite, and synthetic granules of inorganic and organic meals, and also granules of organic material such as sawdust, paper, coconut shells, corn cobs and tobacco stalks.

Liquefied gaseous extenders or solvents can also be used. Particularly suitable extenders or carriers are those which are gaseous at ambient temperature and under atmospheric pressure, for example aerosol propellant gases, such as halogenated hydrocarbons, and also butane, propane, nitrogen and carbon dioxide.

Examples of emulsifiers and/or foam formers, dispersants or wetting agents with ionic or nonionic properties, or mixtures of these surfactants, are salts of polyacrylic acid, salts of lignosulfonic acid, salts of phenolsulfonic acid or naphthalenesulfonic acid, polycondensates of ethylene oxide with fatty alcohols or with fatty acids or with fatty amines, with substituted phenols (preferably alkylphenols or arylphenols), salts of sulfosuccinic esters, taurine derivatives (preferably alkyl taurates), phosphoric esters of polyethoxylated alcohols or phenols, fatty acid esters of polyols, and derivatives of the compounds containing sulfates, sulfonates and phosphates, for example alkylaryl polyglycol ethers, alkyl sulfonates, alkylsulfates, arylsulfonates, protein hydrolysates, lignosulfite waste liquors and methylcellulose. The presence of a surfactant is advantageous if one of the active compounds and/or one of the inert carriers is insoluble in water and when the application takes place in water.

It is possible to use colorants such as inorganic pigments, for example iron oxide, titanium oxide and Prussian Blue, and organic dyes such as alizarin dyes, azo dyes and metal phthalocyanine dyes, and nutrients and trace nutrients such as salts of iron, manganese, boron, copper, cobalt, molybdenum and zinc as further auxiliaries in the formulations and the use forms derived therefrom.

Stabilizers, such as low-temperature stabilizers, preservatives, antioxidants, light stabilizers or other agents which improve chemical and/or physical stability, may also be present. Foam-formers or antifoams may also be present.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids may also be present as additional auxiliaries in the formulations and the use forms derived therefrom. Other possible auxiliaries are mineral and vegetable oils.

If appropriate, the formulations and the use forms derived therefrom may also comprise further auxiliaries. Examples of such additives include fragrances, protective colloids, binders, adhesives, thickeners, thixotropic agents, penetrants, retention promoters, stabilizers, sequestrants, complexing agents, humectants, spreaders. In general, the active compounds can be combined with any solid or liquid additive customarily used for formulation purposes.

Useful retention promoters include all those substances which reduce the dynamic surface tension, for example dioctyl sulfosuccinate, or increase the viscoelasticity, for example hydroxypropylguar polymers.

Useful penetrants in the present context are all those substances which are typically used to improve the penetration of active agrochemical compounds into plants. Penetrants are defined in this context as being able to penetrate the cuticle of the plant, from the (in general aqueous) application mixture and/or from the spray covering, and being able thereby to raise the mobility of the active compounds in the cuticle. The method described in the literature (Baur et al., 1997, Pesticide Science 51, 131-152) may be used for the purpose of determining this quality. Examples include alcohol alkoxylates such as coconut fatty ethoxylate (10) or isotridecyl ethoxylate (12), fatty acid esters, for example rapeseed oil methyl ester or soya bean oil methyl ester, fatty amine alkoxylates, for example tallowamine ethoxylate (15), or ammonium and/or phosphonium salts, for example ammonium sulfate or diammonium hydrogenphosphate.

The formulations preferably comprise between 0.00000001% and 98% by weight of active compound or, with particular preference, between 0.01% and 95% by weight of active compound, more preferably between 0.5% and 90% by weight of active compound, based on the weight of the formulation.

The active compound content of the use forms (crop protection agents) prepared from the formulations can vary within wide limits. The active compound concentration of the use forms may typically be between 0.00000001% and 95% by weight of active compound, preferably between 0.00001% and 1% by weight, based on the weight of the use form. The compounds are applied in a customary manner appropriate for the use forms.

Using, in accordance with process (A), for example ethyl 1-({[3-(4-chlorophenyl)-1-methyl-1H-1,2,4-triazol-5-yl]acetyl}amino)cyclohexanecarboxylate as starting material, the course of the process according to the invention can be represented by the following reaction scheme:

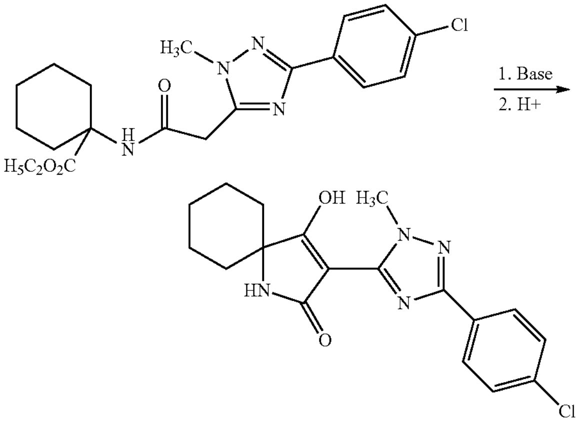

Using, in accordance with process (B), for example ethyl 2-{2-[3-(4-chlorophenyl)-1-methyl-1H-1,2,4-triazol-5-yl]acetoxy}-2-methylpropanoate, the course of the process according to the invention can be represented by the following reaction scheme:

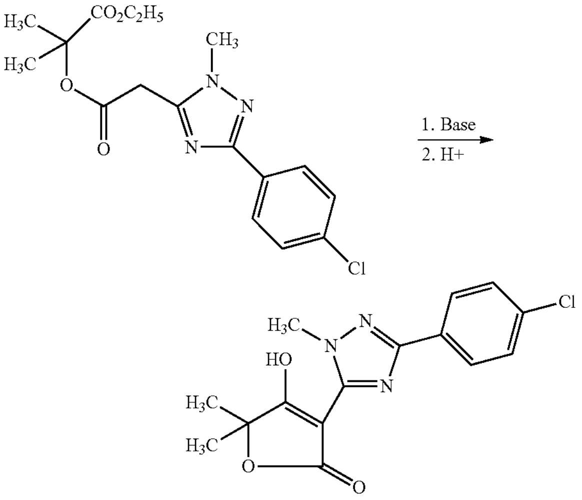

Using, in accordance with process (C), for example ethyl 2-[3-(4-chlorophenyl)-1-methyl-1H-1,2,4-triazol-5-yl]-4-[(4-methoxybenzyl)sulfanyl]-4-methyl-3-oxopentanoate, the course of the process according to the invention can be represented by the following reaction scheme:

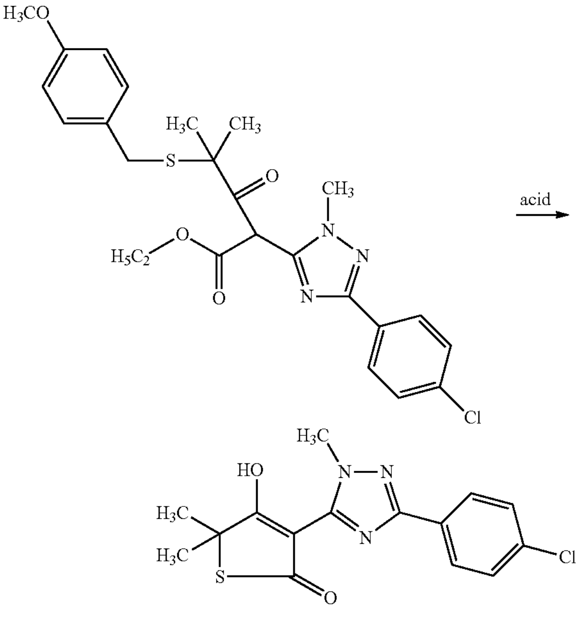

Using, in accordance with process (D), for example 2-[3-(4-chlorophenyl)-1-methyl-1H-1,2,4-triazol-5-yl]-3-oxoacryloyl chloride and acetone as starting materials, the course of the process according to the invention can be represented by the following reaction scheme:

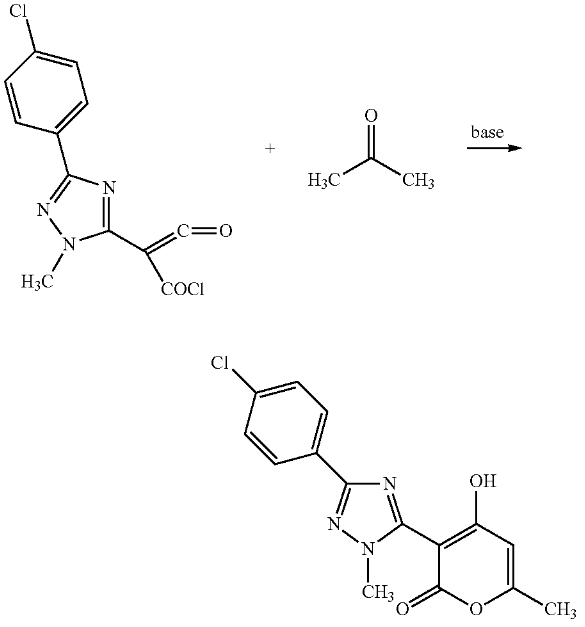

Using, in accordance with process (E), for example 2-[3-(4-chlorophenyl)-1-methyl-1H-1,2,4-triazol-5-yl]-3-oxoacryloyl chloride and thiobenzamide as starting materials, the course of the process according to the invention can be represented by the following reaction scheme:

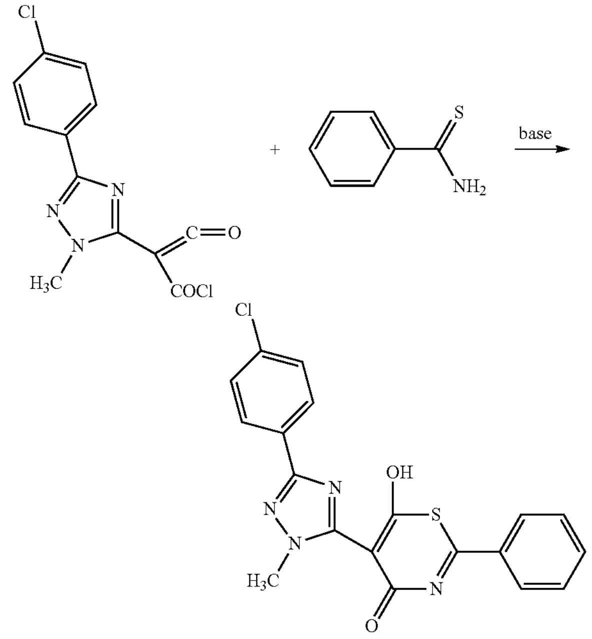

Using, in accordance with process (F), for example ethyl 2-{[3-(4-chlorophenyl)-1-methyl-1H-1,2,4-triazol-5-yl]acetyl}cyclopentanecarboxylate, the course of the process according to the invention can be represented by the following reaction scheme:

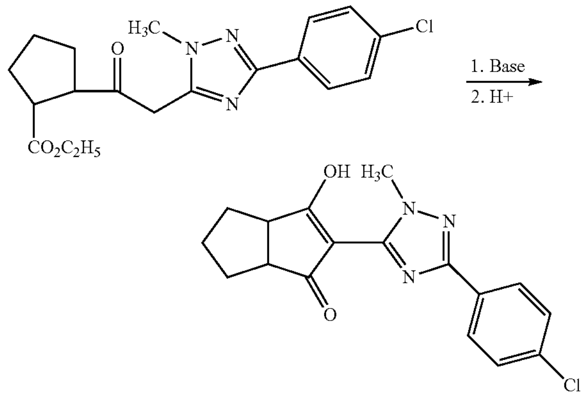

Using, in accordance with process (G), for example ethyl 6-[3-(4-chlorophenyl)-1-methyl-1H-1,2,4-triazol-5-yl]-2,2-dimethyl-5-oxohexanoate, the course of the process according to the invention can be represented by the following reaction scheme:

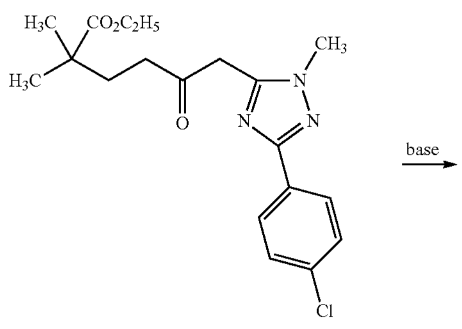

-continued

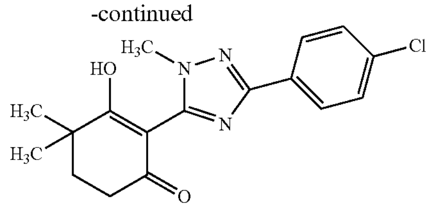

Using, in accordance with process (Hα), for example hexahydropyridazine and 2-[3-(4-chlorophenyl)-1-methyl-1H-1,2,4-triazol-5-yl]-3-oxoacryloyl chloride as starting materials, the reaction course of the process according to the invention can be represented by the following reaction scheme:

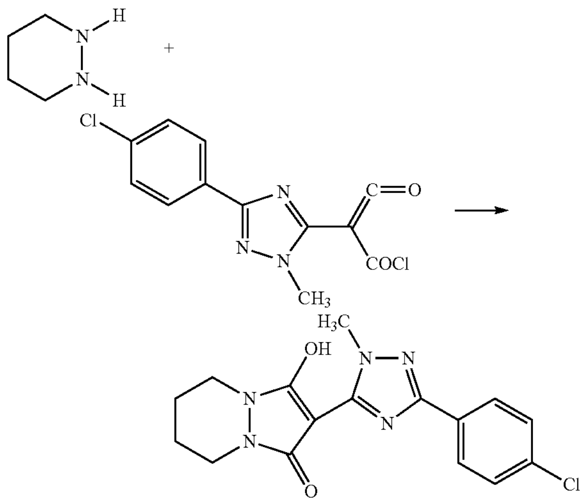

Using, in accordance with process (Hβ), for example hexahydropyridazine and dimethyl [3-(4-chlorophenyl)-1-methyl-1H-1,2,4-triazol-5-yl]malonate as starting materials, the course of the process according to the invention can be represented by the following reaction scheme:

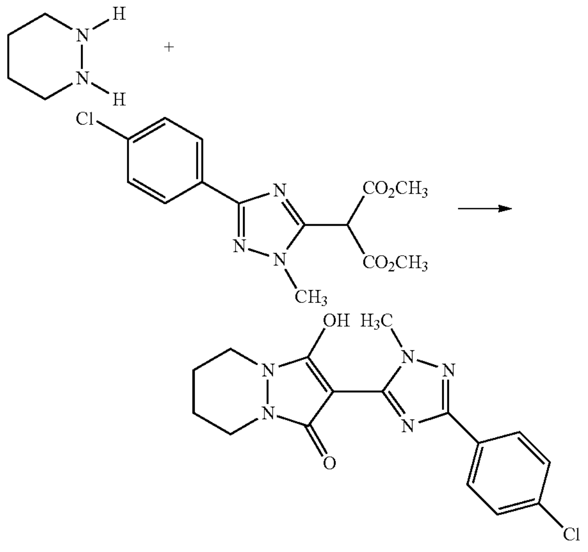

Using, in accordance with process (Hγ) ethyl 2-{[3-(4-chlorophenyl)-1-methyl-1H-1,2,4-triazol-5-yl]acetyl}tetrahydropyridazine-1(2H)-carboxylate as starting material, the course of the reaction can be represented by the following scheme:

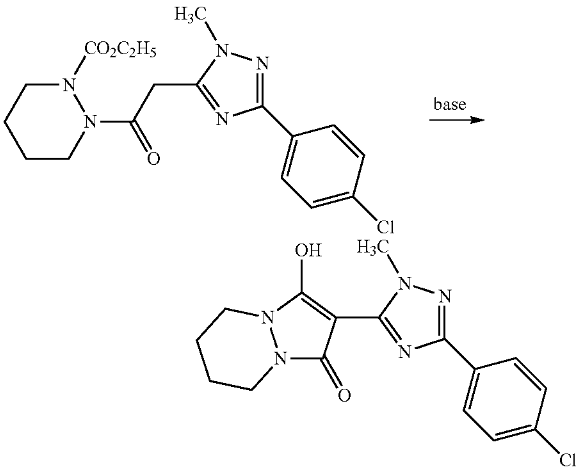

Using, in accordance with process (I), for example ethyl 1-[(({[3-(4-chlorophenyl)-1-methyl-1H-1,2,4-triazol-5-yl]acetyl}amino)methyl]cyclohexanecarboxylate as starting material, the course of the process according to the invention can be represented by the following reaction scheme:

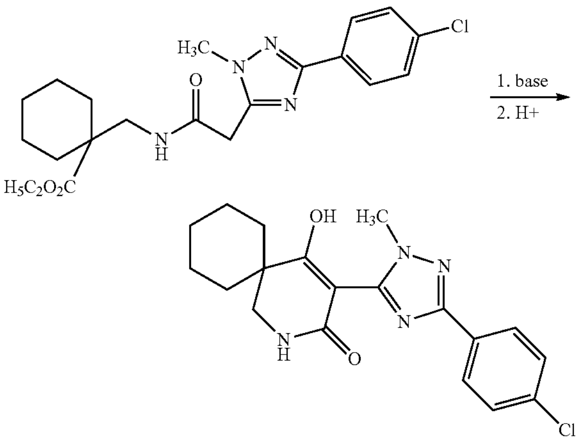

Using, in accordance with process (J), for example ethyl 3-{2-[3-(4-chlorophenyl)-1-methyl-1H-1,2,4-triazol-5-yl]acetoxy}-2,2-dimethylpropanoate, the course of the process according to the invention can be represented by the following reaction scheme:

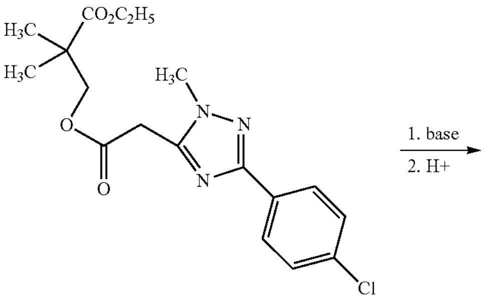

-continued

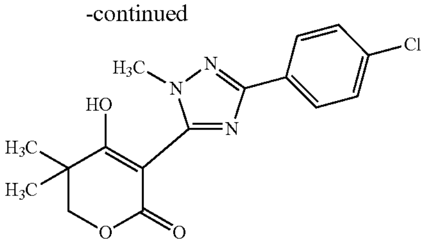

Using, in accordance with process (K), for example ethyl 1-{[{[3-(4-chlorophenyl)-1-methyl-1H-1,2,4-triazol-5-yl]acetyl}(methyl)amino]oxy}cyclopentanecarboxylate as starting material, the course of the process according to the invention can be represented by the following reaction scheme:

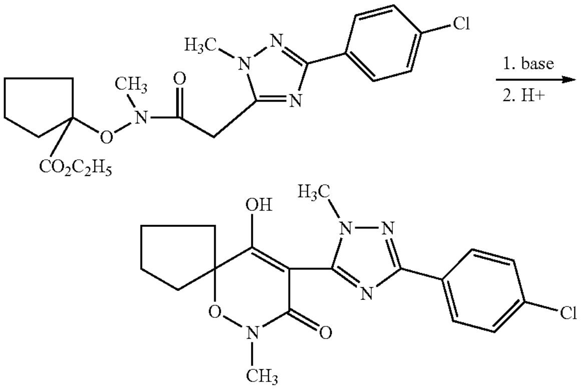

Using, in accordance with process (Lα), for example 3-[3-(4-chlorophenyl)-1-methyl-1H-1,2,4-triazol-5-yl]-4-hydroxy-5,5-dimethyl-1,5-dihydro-2H-pyrrol-2-one and pivaloyl chloride as starting materials, the course of the process according to the invention can be represented by the following reaction scheme:

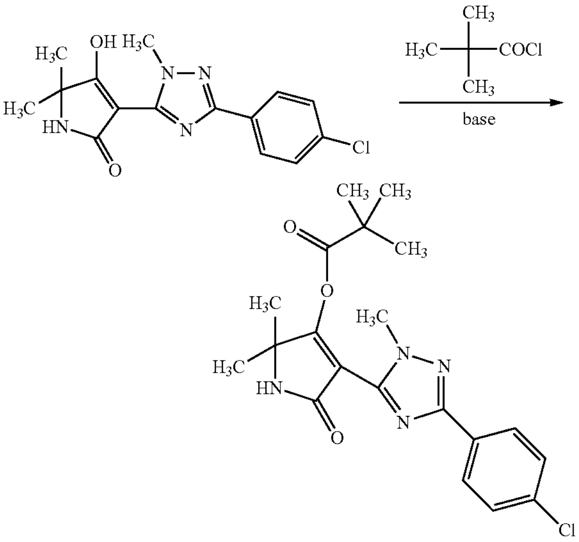

Using, in accordance with process (Lβ) α), for example 3-[3-(4-chlorophenyl)-1-methyl-1H-1,2,4-triazol-5-yl]-4- hydroxy-5,5-dimethyl-1,5-dihydro-2H-pyrrol-2-one and acetic anhydride as starting materials, the course of the process according to the invention can be represented by the following reaction scheme:

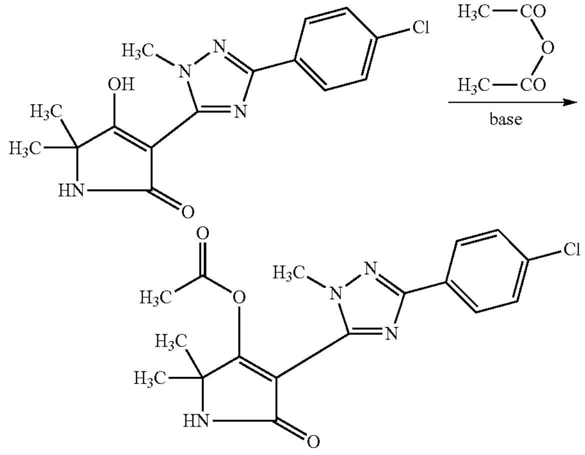

Using, in accordance with process (M), for example 2-[3-(4-chlorophenyl)-1-methyl-1H-1,2,4-triazol-5-yl]-1-hydroxy-6,7,8,8a-tetrahydroindolizin-3(5H)-one and ethyl chloroformate as starting materials, the course of the process according to the invention can be represented by the following reaction scheme:

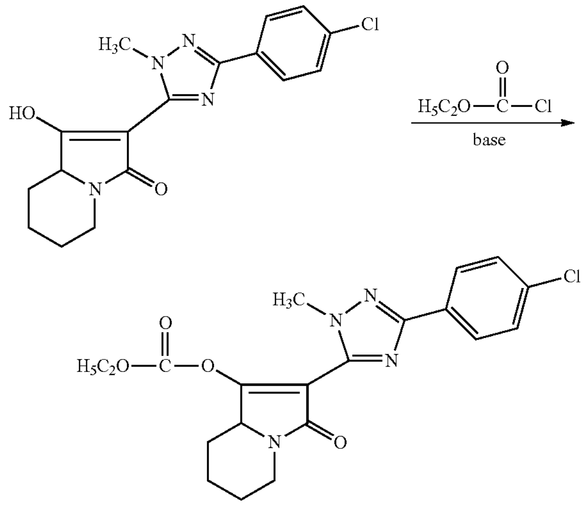

Using, in accordance with process (N), for example 3-[3-(4-chlorophenyl)-1-methyl-1H-1,2,4-triazol-5-yl]-4-hydroxy-5-methyl-6-phenyl-2H-pyran-2-one and methyl chloromonothioformate as starting materials, the course of the reaction can be represented as follows:

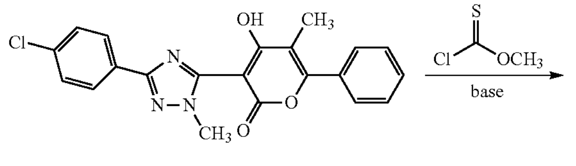

-continued

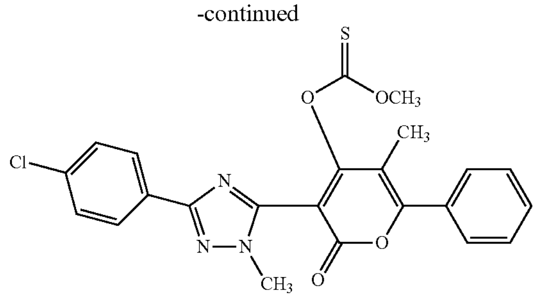

Using, in accordance with process (O), for example 3-[3-(4-chlorophenyl)-1-methyl-1H-1,2,4-triazol-5-yl]-4-hydroxy-1-azaspiro[4.5]dec-3-en-2-one and methanesulfonyl chloride as starting material, the course of the reaction can be represented by the following reaction scheme:

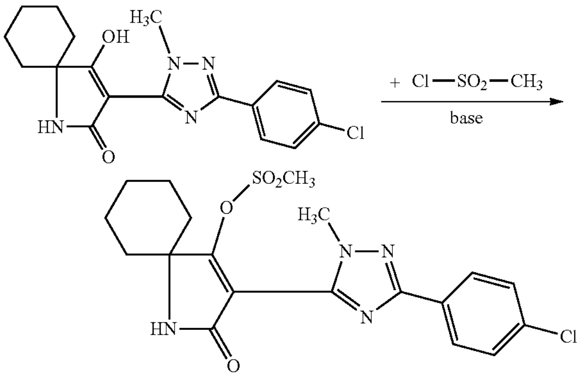

Using, in accordance with process (P), for example 3-[3-(4-chlorophenyl)-1-methyl-1H-1,2,4-triazol-5-yl]-4-hydroxy-5,5-dimethyl-1,5-dihydro-2H-pyrrol-2-one and 2,2,2-trifluoroethyl methanethiophosphonyl chloride as starting materials, the course of the reaction can be represented by the following reaction scheme:

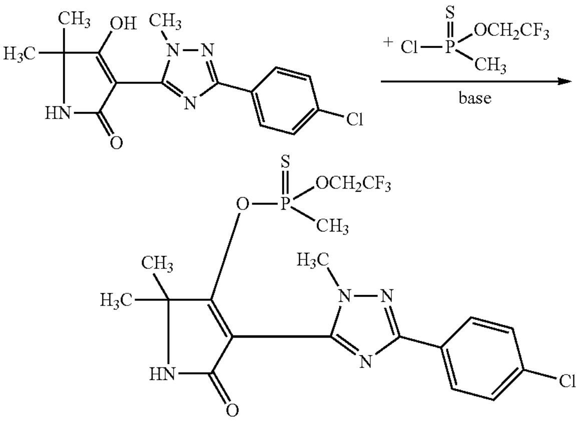

Using, in accordance with process (Q), for example 3-[3-(4-chlorophenyl)-1-methyl-1H-1,2,4-triazol-5-yl]-5-cyclopropyl-4-hydroxy-5-methyl-1,5-dihydro-2H-pyrrol-2-one and NaOH as components, the course of the process according to the invention can be represented by the following reaction scheme:

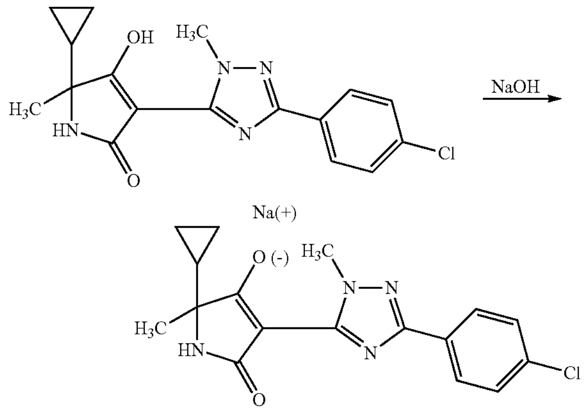

Using, in accordance with process (R) variant α, for example 3-[3-(4-chlorophenyl)-1-methyl-1H-1,2,4-triazol-5-yl]-4-hydroxy-1-oxaspiro[4.4]non-3-en-2-one and ethyl isocyanate as starting materials, the course of the reaction can be represented by the following reaction scheme:

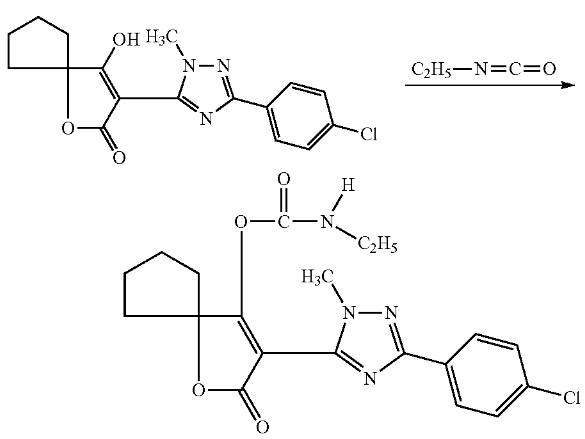

Using, in accordance with process (R) variant β, for example 3-[3-(4-chlorophenyl)-1-methyl-1H-1,2,4-triazol-5-yl]-4-hydroxy-5-methyl-1,5-dihydro-2H-pyrrol-2-one and dimethylcarbamoyl chloride as starting materials, the course of the reaction can be represented by the following scheme:

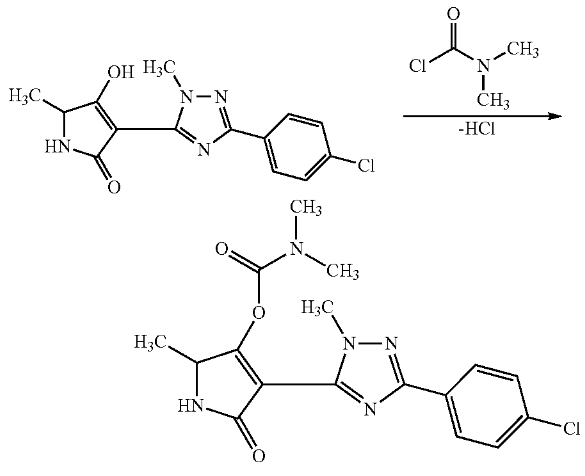

The compounds of the formula (II) which are required as starting materials in process (A) according to the invention (II)

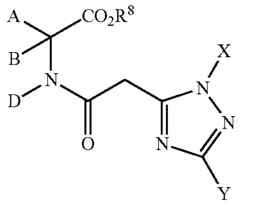

in which

A, B, D, X, Y and $R^8$ have the meanings given above are novel.

The acylamino acid esters of the formula (II) are obtained, for example, when amino acid derivatives of the formula (XXVII)

(XXVII)

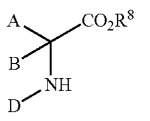

in which

A, B, $R^8$ and D have the meanings given above are acylated with substituted 1,2,4-triazolylacetic acid derivatives of the formula (XXVIII)

(XXVIII)

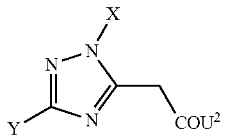

in which

X and Y have the meanings given above and $U^2$ represents a leaving group introduced by reagents for the activation of carboxylic acids, such as carbonyldiimidazole, carbonyldiimides (such as, for example, dicyclohexylcarbodiimide), propanephosphonic anhydride (T3P), phosphorylating agents (such as, for example, $POCl_3$, BOP—Cl), halogenating agents, for example thionyl chloride, oxalyl chloride, phosgene or chloroformic esters, (Chem. Reviews 52, 237-416 (1953); Bhattacharya, Indian J. Chem. 6, 341-5, 1968)

or when acylamino acids of the formula (XXIX)

(XXIX)

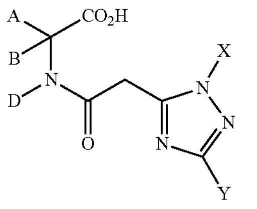

in which

A, B, D, X and Y have the meanings given above are esterified (Chem. Ind. (London) 1568 (1968)).

The compounds of the formula (XXIX)

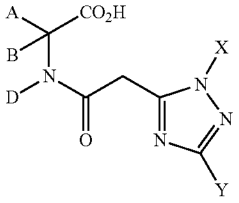

(XXIX)

in which

A, B, D, X and Y have the meanings given above are novel.

The compounds of the formula (XXIX) are obtained when amino acids of the formula (XXX)

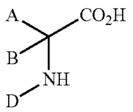

(XXX)

in which

A, B and D have the meanings given above are acylated with substituted triazolylacetic acid derivatives of the formula (XXVIII)

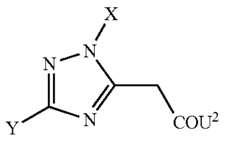

(XXVIII)

in which

X and Y have the meanings given above and $U^2$ has the meaning given above, for example following the method of Schotten-Baumann (Organikum [Organic Chemistry], VEB Deutscher Verlag der Wissenschaften, Berlin 1977, p. 505).

The compounds of the formula (XXVIII) are novel. They can be prepared by processes known in principle (see, for example, H. Henecka, Houben-Weyl, Methoden der Organischen Chemie [Methods of Organic Chemistry], Vol. 8, pp. 467-469 (1952)) WO 97/02243, WO 99/43699, or they are generated in situ using the reagents mentioned above.

The compounds of the formula (XXVIII) are obtained, for example, by reacting substituted triazolylacetic acids of the formula (XXXI)

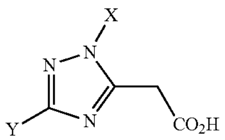

(XXXI)

in which

X and Y have the meaning given above with halogenating agents (for example thionyl chloride, thionyl bromide, oxalyl chloride, phosgene, phosphorus trichloride, phosphorus tribromide or phosphorus pentachloride), phosphonylating agents such as (for example $POCl_3$, BOP—Cl), carbonyldiimidazole, carbonyldiimides (for example dicyclohexylcarbonyldiimide) optionally in the presence of a diluent (for example optionally chlorinated aliphatic or aromatic hydrocarbons such as toluene or methylene chloride or ethers, for example tetrahydrofuran, dioxane, methyl tert-butyl ether) at temperatures of from −20° C. to 150° C., preferably from −10° C. to 100° C.

Some of the compounds of the formula (XXVII) and (XXX) are known from the patent literature cited at the outset, and/or they can be prepared by known processes (see, for example, Compagnon, Miocque Ann. Chim. (Paris) [14] 5, pp. 11-22, 23-27 (1970)).

The substituted cyclic aminocarboxylic acids of the formula (XXX) in which A and B form a ring can generally be obtained by the Bucherer-Bergs synthesis or by the Strecker synthesis, where they are obtained in different isomeric forms. Thus, under the conditions of the Bucherer-Bergs synthesis, the isomers (for simplicity called β below) in which the radicals R and the carboxyl group are equatorial are predominantly obtained, while under the conditions of the Strecker synthesis the isomers (for simplicity called α below) in which the amino group and the radicals R are equatorial are predominantly obtained.

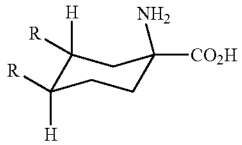

Bucherer-Bergs synthesis
(β isomer)

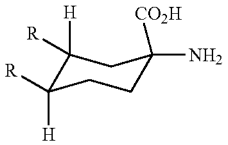

Strecker synthesis
(α isomer)

(L. Munday, J. Chem. Soc. 4372 (1961); J. T. Eward, C. Jitrangeri, Can. J. Chem. 53, 3339 (1975).

Furthermore, the starting materials, used in the above process (A), of the formula (II)

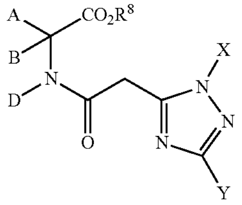

(II)

in which

A, B, D, X, Y and $R^8$ have the meanings given above can be prepared when aminonitriles of the formula (XXXII)

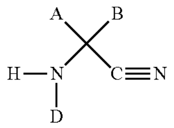

(XXXII)

in which

A, B and D have the meanings given above are reacted with substituted triazolylacetic acid derivatives of the formula (XXVIII)

(XXVIII)

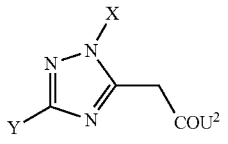

in which

X, Y and $U^2$ have the meanings given above to give compounds of the formula (XXXIII)

(XXXIII)

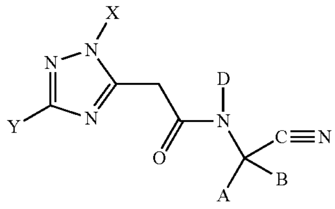

in which

A, B, D, X and Y have the meanings given above and these are subsequently subjected to acidic alcoholysis.

The compounds of the formula (XXXIII) are likewise novel.

The compounds, required as starting materials in the process (B) according to the invention, of the formula (III)

(III)

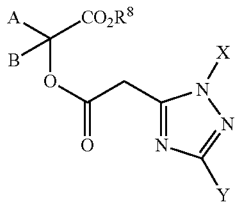

in which

A, B, X, Y and $R^8$ have the meanings given above are novel.

They can be prepared by methods known in principle.

Thus, the compounds of the formula (III) are obtained, for example, when 2-hydroxycarboxylic esters of the formula (XXXIV-A)

(XXXIV-A)

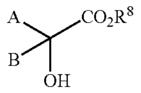

in which

A, B and $R^8$ have the meanings given above.

are acylated with substituted triazolylacetic acid derivatives of the formula (XXVIII)

(XXVIII)

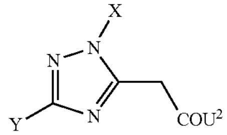

in which

X, Y and $U^2$ have the meanings given above (Chem. Reviews 52, 237-416 (1953)).

Furthermore, the compounds of the formula (III) are obtained when substituted triazolylacetic acids of the formula (XXXI)

(XXXI)

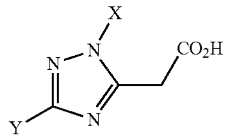

in which

X and Y have the meanings given above are alkylated with α-halocarboxylic esters of the formula (XXXIV-B)

(XXXIV-B)

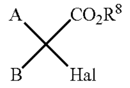

in which

A, B and $R^8$ have the meanings given above and

Hal represents chlorine or bromine

Some of the compounds of the formula (XXXIV-A) are commercially available, or they are known from the disclosures mentioned at the outset.

The compounds of the formula (XXXIV-B) are commercially available.

The compounds of the formula (XXXI) are novel.

For example, the compounds of the formula (XXXI)

(XXXI)

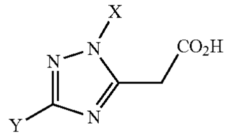

in which

X and Y have the meanings given above are obtained when triazolylacetic esters of the formula (XXXV)

(XXXV)

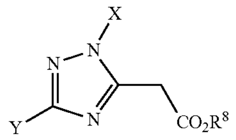

in which

X, Y and $R^8$ have the meaning given above are hydrolyzed in the presence of acids or bases, in the presence of a solvent under generally known standard conditions.

Except for the compound XXXV-1, the compounds of the formula (XXXV) are novel.

XXXV-1

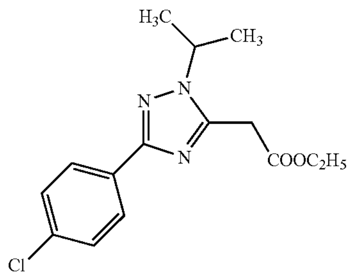

The compounds of the formula (XXXV) in which X Y and $R^8$ have the meaning given above are obtained when triazolylacetic esters of the formula (XXXV-A)

(XXXV-A)

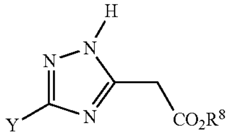

in which $R^8$ and Y have the meaning given above are reacted in the presence an alkylating agent (for example alkyl halide) in the presence of a base and optionally in a suitable solvent, for example as described in Plant Physiology 144, 1303, Supplement Materials and Methods S1.

Except for the compound XXXV-A1 (see Plant Physiology 144, 1303, Supplement Materials and Methods S1), the compounds of the formula (XXXV-A) are novel.

XXXV-A1

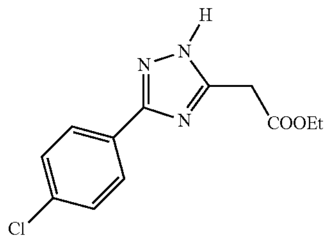

The preparation of the triazolylacetic esters of the formula (XXXV-A) is known in principle, for example from Synthesis 1999, 483-486 and Plant Physiology 144, 1303, Supplement Materials and Methods 51, and they can be prepared by the processes described therein.

The compounds, required as starting materials in process (C) above, of the formula (IV)

(IV)

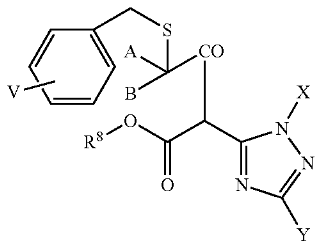

in which

A, B, V, X, Y and $R^8$ have the meanings given above are novel.

They can be prepared by methods known in principle.

The compounds of the formula (IV) are obtained, for example, when substituted triazolylacetic esters of the formula (XXXV)

(XXXV)

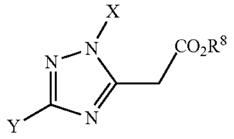

in which

X, Y and $R^8$ have the meanings given above are acylated with 2-benzylthiocarbonyl halides of the formula (XXXVI)

(XXXVI)

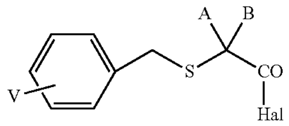

in which

A, B and V have the meanings given above and

Hal represents halogen (in particular chlorine or bromine), in the presence of strong bases (see, for example, M. S. Chambers, E. J. Thomas, D. J. Williams, J. Chem. Soc. Chem. Commun., (1987), 1228).

Some of the benzylthiocarbonyl halides of the formula (XXXVI) are known, and/or they can be prepared by known processes (J. Antibiotics (1983), 26, 1589).

The halocarbonyl ketenes of the formula (VI) required as starting materials in the above processes (D), (E) and (H-α) are novel. They can be prepared by methods known in principle (cf., for example, Org. Prep. Proced. Int., 7, (4), 155-158, 1975 and DE 1 945 703). Thus, for example, the compounds of the formula (VI)

(VI)

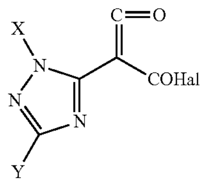

in which

X and Y have the meanings given above and

Hal represents chlorine or bromine, are obtained when substituted triazolylmalonic acids of the formula (XXXVII)

(XXXVII)

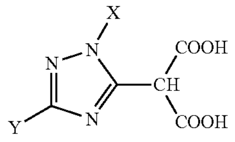

in which

X and Y have the meanings given above are reacted with acid halides such as, for example, thionyl chloride, phosphorus(V) chloride, phosphorus(III) chloride, oxalyl chloride, phosgene or thionyl bromide, optionally in the presence of catalysts such as, for example, dimethylformamide, methylstearylformamide or triphenylphosphine, and optionally in the presence of bases such as, for example, pyridine or triethylamine.

The substituted phenylmalonic acids of the formula (XXXVII) are novel. They can be prepared in a simple manner by known processes (cf., for example, Organikum [Organic Chemistry], VEB Deutscher Verlag der Wissenschaften, Berlin 1977, p. 517 ff, EP-A-528 156, WO 96/35 664, WO 97/02 243, WO 97/01535, WO 97/36868 and WO 98/05638).

Thus, triazolylmalonic acids of the formula (XXXVII)

(XXXVII)

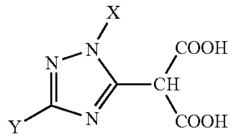

in which

X and Y have the meanings given above are obtained when triazolylmalonic esters of the formula (XI)

(XI)

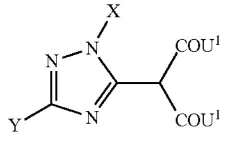

in which

X and Y have the meaning given above and $U^1$ represents $OR^8$, where $R^8$ has the meaning given above, are initially hydrolyzed in the presence of a base and a solvent and then carefully acidified (see, for example, EP-A-528 156, WO 96/35 664, WO 97/02 243).

The malonic esters of the formula (XI)

(XI)

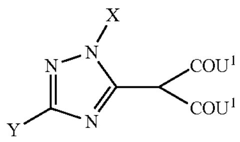

in which

X and Y have the meaning given above and $U^1$ represents $OR^8$, where $R^8$ has the meaning given above, are novel.

They can be prepared by generally known methods of organic chemistry (cf., for example, Tetrahedron Lett. 27, 2763 (1986), Organikum [Organic Chemistry] VEB Deutscher Verlag der Wissenschaften, Berlin 1977, p. 587 ff., WO 96/35664, WO 97/02243, WO 97/01535, WO 97/36868, WO 98/05638 and WO 99/47525).

The carbonyl compounds of the formula (V) required as starting materials in process (D) according to the invention (V)

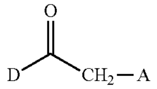

in which

A and D have the meanings given above, or silylenol ethers thereof of the formula (Va)

(Va)

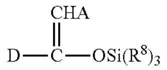

in which

A, D and $R^8$ have the meanings given above are compounds which are commercially available, generally known or obtainable by known processes.

The principles of the preparation of the ketene acid chlorides required as starting materials for carrying out the process (E) according to the invention have already been described in connection with process (D). The thioamides of the formula (VII) required for carrying out process (E) according to the invention (VII)

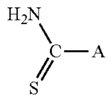

in which

A has the meaning given above are compounds generally known in organic chemistry.

The compounds, required as starting materials in process (F) above, of the formula (VIII)

(VIII)

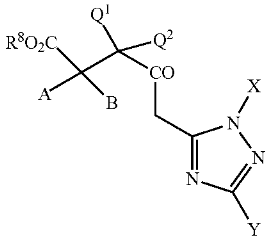

in which
A, B, $Q^1$, $Q^2$, X, Y and $R^8$ have the meaning given above are novel.

They can be prepared by methods known in principle.

The 5-triazolyl-4-ketocarboxylic esters of the formula (VIII) are obtained, for example, when 5-aryl-4-ketocarboxylic acids of the formula (XXXVIII)

(XXXVIII)

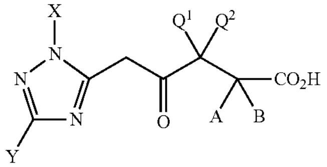

in which
X, Y, A, B, $Q^1$ and $Q^2$ have the meaning given above
are esterified (cf., for example, Organikum [Organic Chemistry], 15. edition, Berlin, 1977, page 499) or alkylated (see preparation example).

The 5-triazolyl-4-ketocarboxylic acids of the formula (XXXVIII)

(XXXVIII)

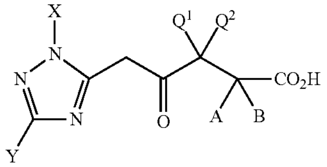

in which
A, B, $Q^1$, $Q^2$, X and Y have the meaning given above
are novel; however, they can be prepared by methods known in principle (WO 96/01 798, WO 97/14667, WO 98/39281).

The 5-triazolyl-4-ketocarboxylic acids of the formula (XXXVIII) are obtained, for example, when 2-triazolyl-3-oxoadipinic esters of the formula (XXXIX)

(XXXIX)

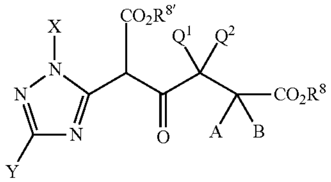

in which
A, B, $Q^1$, $Q^2$, X and Y have the meaning given above and
$R^8$ and $R^{8'}$ represent alkyl (in particular $C_1$-$C_8$-alkyl) and,
when the compound of the formula (XLI-a) is used, $R^8$ represents hydrogen,
are decarboxylated, optionally in the presence of a diluent and optionally in the presence of a base or acid (cf., for example, Organikum [Organic Chemistry], 15. edition, Berlin, 1977, pages 519 to 521, WO 96/01798, WO 97/14667, WO 98/39281).

The compounds of the formula (XXXIX)

(XXXIX)

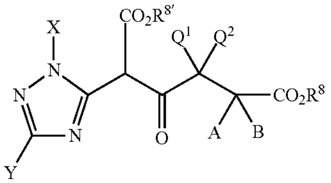

in which
A, B, $Q^1$, $Q^2$, X, Y, $R^8$ and $R^{8'}$ have the meaning given above and,
when the compound of the formula (XLI-a) is used, $R^8$ represents hydrogen,
are novel.

The compounds of the formula (XXXIX) are obtained, for example,
when dicarboxylic hemiester chlorides of the formula (XL)

(XL)

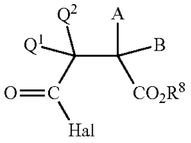

in which
A, B, $Q^1$, $Q^2$ and $R^8$ have the meaning given above and
Hal represents chlorine or bromine,
or carboxylic anhydrides of the formula (XLI-a)

(XLI-a)

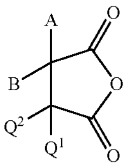

in which
A, B, $Q^1$ and $Q^2$ have the meaning given above
are acylated with a triazolylacetic ester of the formula (XXXV)

(XXXV)

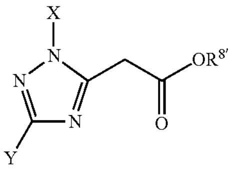

in which

X, Y and $R^{8'}$ have the meaning given above in the presence of a diluent and in the presence of a base (cf., for example, M. S. Chambers, E. J. Thomas, D. J. Williams, J. Chem. Soc. Chem. Commun., (1987), 1228, cf. also the preparation example).

Some of the compounds of the formulae (XL) and (XLI-a) are known compounds of organic chemistry and/or can be prepared in a simple manner by methods known in principle.

The compounds, required as starting materials in process (G) above, of the formula (IX)

(IX)

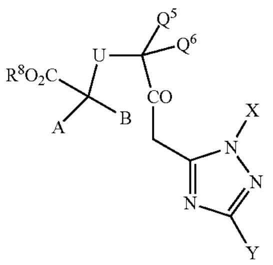

in which

A, B, $Q^5$, $Q^6$, U, X, Y and $R^8$ have the meaning given above are novel.

They can be prepared by methods known in principle.

The 6-aryl-5-ketocarboxylic esters of the formula (IX) are obtained, for example, when 6-triazolyl-5-ketocarboxylic acids of the formula (XLII)

(XLII)

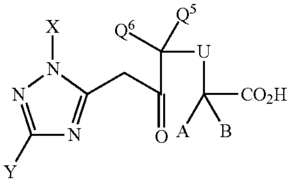

in which

A, B, $Q^5$, $Q^6$, U, X and Y have the meaning given above are esterified (cf., for example, Organikum [Organic Chemistry], 15. edition, Berlin, 1977, page 499, WO 99/43649, WO 99/48869).

The 6-triazolyl-5-ketocarboxylic acids of the formula (XLII)

(XLII)

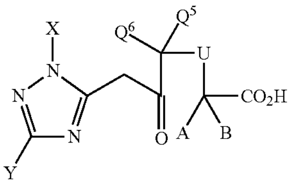

in which

A, B, $Q^5$, $Q^6$, U, X and Y have the meaning given above are novel. They can be prepared by methods known in principle (WO 99/43649, WO 99/48869), for example by hydrolyzing and decarboxylating substituted 2-triazolyl-3-oxoheptanediacid esters of the formula (XLIII)

(XLIII)

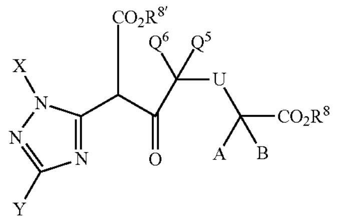

in which

A, B, $Q^5$, $Q^6$, U, X and Y have the meaning given above and $R^8$ and $R^{8'}$ represent alkyl (preferably $C_1$-$C_6$-alkyl) and, when the compound of the formula (XLI-b) is used, $R^8$ represents hydrogen, optionally in the presence of a diluent and optionally in the presence of a base or acid (cf., for example, Organikum [Organic Chemistry], 15. edition, Berlin, 1977, pages 519 to 521, WO 99/43649, WO 99/48869).

The compounds of the formula (XLIII)

(XLIII)

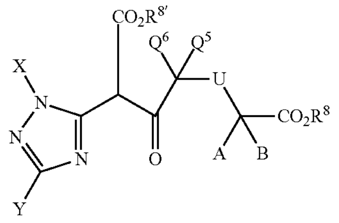

in which

A, B, $Q^5$, $Q^6$, U, X, Y, $R^8$ and $R^{8'}$ have the meaning given above are novel and can be obtained by condensing dicarboxylic esters of the formula (XLIV)

(XLIV)

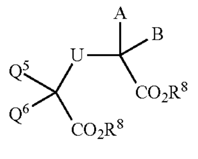

in which

A, B, $Q^5$, $Q^6$, U and $R^8$ have the meaning given above or carboxylic anhydrides of the formula (XLI-b)

(XLI-b)

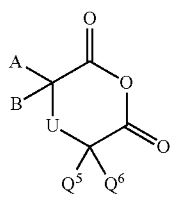

in which A, B, $Q^5$, $Q^6$ and U have the meaning given above with a substituted triazolylacetic ester of the formula (XXXV)

(XXXV)

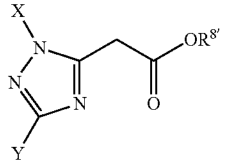

in which

X, Y and $R^{8'}$ have the meaning given above in the presence of a diluent and in the presence of a base.

Some of the compounds of the formula (XLIV) are known and/or can be prepared by known processes.

Some of the hydrazines of the formula (X) required as starting materials for the process (H-α) and (H-β) according to the invention

A-NH—NH-D (X)

in which

A and D have the meanings given above are known, and/or they can be prepared by methods known from the literature (cf., for example, Liebigs Ann. Chem. 585, 6 (1954); Reaktionen der organischen Synthese [Reactions of Organic Synthesis], C. Ferri, page 212, 513; Georg Thieme Verlag Stuttgart, 1978; Liebigs Ann. Chem. 443, 242 (1925); Chem. Ber. 98, 2551 (1965), EP-A-508 126, WO 92/16510, WO 99/47 525, WO 01/17 972).

The compounds of the formula (XII) required for the process (H-γ) according to the invention (XII)

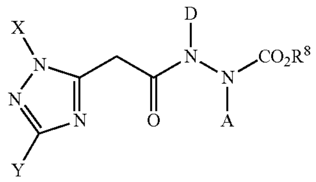

in which

A, D, X, Y and $R^8$ have the meaning given above are novel.

The acylcarbazates of the formula (XII) are obtained, for example, when carbazates of the formula (XLV)

(XLV)

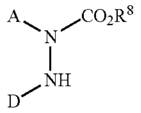

in which

A, $R^8$ and D have the meanings given above are acylated with substituted triazolylacetic acid derivatives of the formula (XXVIII)

(XXVIII)

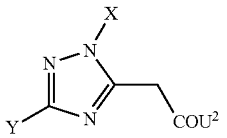

in which

X, Y and $U^2$ have the meanings given above (Chem. Reviews 52, 237-416 (1953); Bhattacharya, Indian J. Chem. 6, 341-5, 1968).

Some of the carbazates of the formula (XLV) are commercially available and some are known, or they can be prepared by processes of organic chemistry which are known in principle.

The compounds of the formula (XXVIII) have already been described under the precursors for process (A) and (B).

The compounds of the formula (XIII) required as starting materials for process (I) according to the invention (XIII)

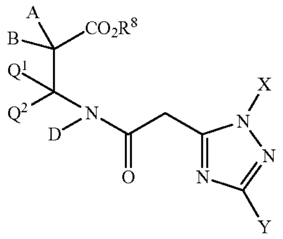

in which

A, B, D, $Q^1$, $Q^2$, X, Y and $R^8$ have the meanings given above are novel.

The acylamino acid esters of the formula (XIII) are obtained, for example, when amino acid derivatives of the formula (XLVI)

(XLVI)

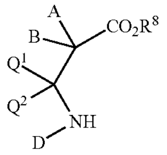

in which

A, B, $Q^1$, $Q^2$, $R^8$ and D have the meanings given above are acylated with substituted hetarylacetic acid derivatives of the formula (XXVIII)

(XXVIII)

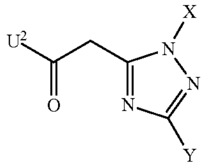

in which

X, Y and $U^2$ have the meaning given above (Chem. Reviews 52, 237-416 (1953); Bhattacharya, Indian J. Chem. 6, 341-5, 1968)

or when acylamino acids of the formula (XLVII)

(XLVII)

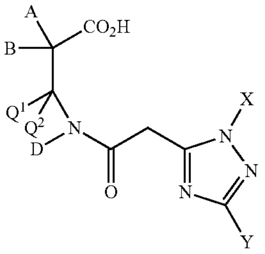

in which

A, B, D, $Q^1$, $Q^2$, X and Y have the meanings given above are esterified (Chem. Ind. (London) 1568 (1968)).

The compounds of the formula (XLVII)

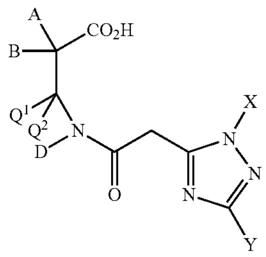

(XLVII)

in which

A, B, D, $Q^1$, $Q^2$, X and Y have the meanings given above are novel.

The compounds of the formula (XLVII) are obtained when β-amino acids of the formula (XLVIII)

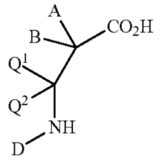

(XLVIII)

in which

A, B, $Q^1$, $Q^2$ and D have the meanings given above are acylated with substituted triazolylacetic acid derivatives of the formula (XXVIII)

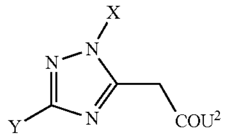

(XXVIII)

in which

X, Y and $U^2$ have the meanings given above, for example following the method of Schotten-Baumann (Organikum [Organic Chemistry], VEB Deutscher Verlag der Wissenschaften, Berlin 1977, p. 505).

Some of the compounds of the formula (XLVI) and (XLVIII) are known from WO 01/79204 or can be prepared by the process which is mentioned therein and is known in principle.

The compounds of the formula (XIV) required as starting materials for process (J) according to the invention

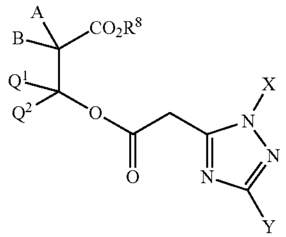

(XIV)

in which

A, B, $Q^1$, $Q^2$, X, Y and $R^8$ have the meanings given above are novel.

The acylhydroxycarboxylic esters of the formula (XIV) are obtained, for example, when hydroxycarboxylic esters of the formula (XLIX)

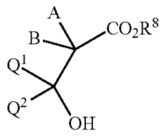

(XLIX)

in which

A, B, $Q^1$, $Q^2$ and $R^8$ have the meanings given above are acylated with substituted triazolylacetic acid derivatives of the formula (XXVIII)

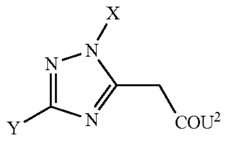

(XXVIII)

in which

X, Y and $U^2$ have the meanings given above (see preparation example of compounds of the formula (II)).

Some of the compounds of the formula (XLIX) are known from WO 01/98288 or can be prepared by processes known in principle, for example by Reformatskij synthesis (Organikum [Organic Chemistry], VEB Deutscher Verlag der Wissenschaften, Berlin 1990, 18th Ed., p. 501 ff.)

The compounds of the formula (XV) required as starting materials for process (K) according to the invention

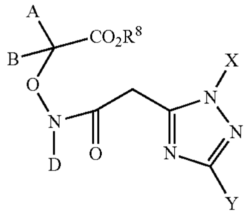

(XV)

in which

A, B, D, X, Y and $R^8$ have the meanings given above are novel.

The acylhydroxyamino acid esters of the formula (XV) are obtained, for example, when amino acid derivatives of the formula (L)

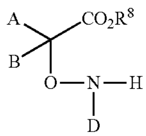

(L)

in which

A, B, $R^8$ and D have the meanings given above are acylated with substituted triazolylacetic acid derivatives of the formula (XXVIII)

(XXVIII)

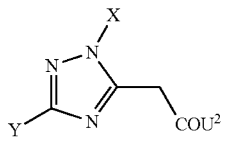

in which

X, Y and $U^2$ have the meanings given above (Chem. Reviews 52, 237-416 (1953); Bhattacharya, Indian J. Chem. 6, 341-5, 1968).

Some of the hydroxylamino acid esters, required as starting materials for preparing compounds of the formula (XV), of the formula (L)

(L)

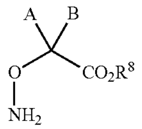

in which

A, B, and $R^8$ have the meaning given above are novel and can be prepared by known processes (N. A. Porter et. al. J. Org. Chem. 63 5547 (1998), WO 03/048138).

Thus, for example, hydroxylamino acid esters of the formula (L)

(L)

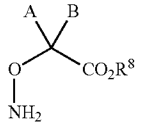

in which

A, B and $R^8$ have the meaning given above are obtained when N-hydroxyphthalimide of the formula (LI)

(LI)

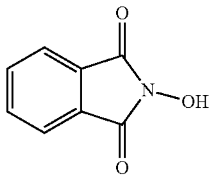

are reacted with haloalkyl esters of the formula (LII)

(LII)

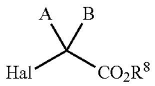

in which

A, B and $R^8$ have the meaning given above and

Hal represents chlorine, bromine or iodine, preferably bromine, to give O-alkoxyphthalimides of the formula (LIII)

(LIII)

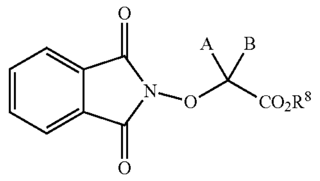

in which

A, B and $R^8$ have the meaning given above, and the compounds of the formula (L) are then released, for example, by hydrazinolysis.

The compounds of the formulae (LII) and (LI) are likewise known amd can be prepared by known processes (N. A. Porter et. al. J. Org. Chem. 63, 5547-5554, 1998).

Furthermore, for example, acylhydroxylamino acid esters of the formula (XV)

(XV)

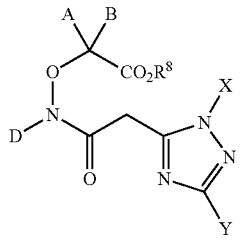

in which

A, B, D, X, Y and $R^8$ have the meaning given above

D, however, preferably not being hydrogen, are obtained, for example, when triazolylacetic acid derivatives of the formula (XXVIII)

(XXVIII)

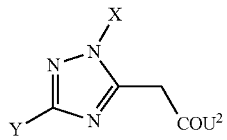

in which

X, Y and $U^2$ have the meaning given above are reacted with hydroxylamines of the formula (LIV)

(LIV)

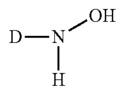

in which

D has the meaning given above, but is preferably not hydrogen, to give compounds of the formula (LV)

(LV)

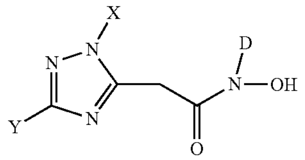

in which

D, X and Y have the meaning given above and these are alkylated with haloalkyl esters of the formula (LII)

(LII)

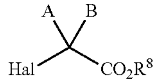

in which

A, B and $R^8$ have the meaning given above and

Hal represents chlorine, bromine or iodine, preferably bromine, to give compounds of the formula (XV) (E. K. Ryo et. al., Bull. Korean Chem. Soc. 20 965 (1999)).

Some of the compounds of the formula (LIV) are commercially available, some are known and can be prepared by known processes.

Moreover, compounds of the formula (XV) in which D is not hydrogen are obtained when compounds of the formula (XV-a)

(XV-a)

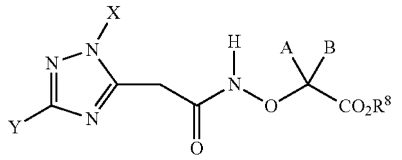

in which

A, B, X, Y and $R^8$ have the meaning given above are alkylated with compounds of the formula (LVI)

D-LG (LVI)

in which

D has the meaning given above, but is not hydrogen, and

LG represents a leaving group such as, for example, chlorine, bromine, iodine, mesylate, tosylate or triflate to give compounds of the formula (XV) (WO 03/048138).

Some of the compounds of the formula (LVI) are commercially available, some are known and can be prepared by known processes.

The compounds of the formulae (LIII) and (LV) are known and can be prepared in accordance with the literature cited at the outset.

The acid halides of the formula (XVI), carboxylic anhydrides of the formula (XVII), chloroformic esters or chloroformic thioesters of the formula (XVIII), chloromonothioformic esters or chlorodithioformic esters of the formula (XIX), sulfonyl chlorides of the formula (XX), phosphorus compounds of the formula (XXI) and metal hydroxides, metal alkoxides or amines of the formulae (XXII) and (XXIII) and isocyanates of the formula (XXIV) and carbamoyl chlorides of the formula (XXV) furthermore required as starting materials for carrying out the processes (L), (M), (N), (O), (P), (O) and (R) according to the invention are generally known compounds of organic or inorganic chemistry.

In addition, the compounds of the formulae (V), (VII), (X), (XXVII), (XXX), (XXXII), (XXXIV-A), (XXXIV-B), (XXXVI), (XL), (XLI-a), (XLI-b), (XLIV), (XLV), (XLVI), (XLVIII), (XLIX), (LI), (LII), (LIV) and (LVI) are known from the patent applications cited at the outset Process (A) is characterized in that compounds of the formula (II) in which A, B, D, X, Y and $R^8$ have the meanings given above are subjected to an intramolecular condensation in the presence of a base.

Diluents which can be employed in process (A) according to the invention are all inert organic solvents. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulfoxide, sufolane, dimethylformamide and N-methylpyrrolidone, and also alcohols, such as methanol, ethanol, propanol, isopropanol, butanol, isobutanol and tert-butanol.

Bases (deprotonating agents) which can be employed when carrying out process (A) according to the invention are all customary proton acceptors. The following can preferably be used: the oxides, hydroxides and carbonates of alkali metals and alkaline earth metals, such as sodium hydroxide, potassium hydroxide, magnesium oxide, calcium oxide, sodium carbonate, potassium carbonate and calcium carbonate, all of which can also be employed in the presence of phase-transfer catalysts such as, for example, triethylbenzylammonium chloride, tetrabutylammonium bromide, Adogen 464 (=methyltrialkyl($C_8$-$C_{10}$)ammonium chloride) or TDA 1 (=tris-(methoxyethoxyethyl)amine). Alkali metals such as sodium or potassium can also be used. Furthermore, alkali metal and alkaline earth metal amides and hydrides, such as sodium amide, sodium hydride and calcium hydride, and additionally also alkali metal alkoxides, such as sodium methoxide, sodium ethoxide and potassium tert-butoxide can be employed.

When carrying out the process (A) according to the invention, the reaction temperatures can be varied within a relatively wide range. In general, the process is carried out at temperatures between 0° C. and 250° C., preferably between 50° C. and 150° C.

Process (A) according to the invention is generally carried out under atmospheric pressure.

When carrying out process (A) according to the invention, the reactants of the formula (II) and the deprotonating bases are generally employed in approximately twice the equimolar amounts. However, it is also possible to employ one or the other component in a larger excess (of up to 3 mol).

Process (B) is characterized in that compounds of the formula (III) in which A, B, X, Y and $R^8$ have the meanings given above are subjected to an intramolecular condensation in the presence of a diluent and in the presence of a base.

Diluents which can be employed in process (B) according to the invention are all inert organic solvents. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulfoxide, sulfolane, dimethylformamide and N-methylpyrrolidone. It is also possible to employ alcohols, such as methanol, ethanol, propanol, isopropanol, butanol, isobutanol and tert-butanol.

Bases (deprotonating agents) which can be employed when carrying out process (B) according to the invention are all customary proton acceptors. The following can preferably be used: the oxides, hydroxides and carbonates of alkali metals and alkaline earth metals, such as sodium hydroxide, potassium hydroxide, magnesium oxide, calcium oxide, sodium carbonate, potassium carbonate and calcium carbonate, all of which can also be employed in the presence of phase-transfer catalysts such as, for example, triethylbenzylammonium chloride, tetrabutylammonium bromide, Adogen 464 (=methyltrialkyl($C_8$-$C_{10}$)ammonium chloride) or TDA 1 (=tris-(methoxyethoxyethyl)amine). Alkali metals such as sodium or potassium can also be used. Furthermore, alkali metal and alkaline earth metal amides and hydrides, such as sodium amide, sodium hydride and calcium hydride, and additionally also alkali metal alkoxides, such as sodium methoxide, sodium ethoxide and potassium tert-butoxide can be employed.

When carrying out the process (B) according to the invention, the reaction temperatures can be varied within a relatively wide range. In general, the process is carried out at temperatures between 0° C. and 250° C., preferably between 50° C. and 150° C.

Process (B) according to the invention is generally carried out under atmospheric pressure.

When carrying out process (B) according to the invention, the reactants of the formula (II) and the deprotonating bases are generally employed in approximately equimolar amounts. However, it is also possible to employ one or the other component in a larger excess (of up to 3 mol).

Process (C) is characterized in that compounds of the formula (IV) in which A, B, V, X, Y and $R^8$ have the meanings given above are cyclized intramolecularly in the presence of an acid and optionally in the presence of a diluent.

Diluents which can be employed in process (C) according to the invention are all inert organic solvents. Preference is given to using hydrocarbons, such as toluene and xylene, furthermore halogenated hydrocarbons, such as dichloromethane, chloroform, ethylene chloride, chlorobenzene, dichlorobenzene, moreover polar solvents, such as dimethyl sulfoxide, sulfolane, dimethylformamide and N-methylpyrrolidone. It is also possible to employ alcohols, such as methanol, ethanol, propanol, isopropanol, butanol, isobutanol, tert-butanol.

If appropriate, the acid employed may also serve as diluent.

Suitable for use as acid in process (C) according to the invention are all inorganic and organic acids such as, for example, hydrohalic acids, sulfuric acid, alkyl-, aryl- and haloalkylsulfonic acids, in particular halogenated alkylcarboxylic acids such as, for example, trifluoroacetic acid.

When carrying out process (C) according to the invention, the reaction temperatures can be varied within a relatively wide range. In general, the process is carried out at temperatures between 0° C. and 250° C., preferably between 50° C. and 150° C.

Process (C) according to the invention is generally carried out under atmospheric pressure.

When carrying out process (C) according to the invention, the reactants of the formula (IV) and the acid are generally employed, for example, in equimolar amounts. However, it is also possible to use the acid as solvent or as catalyst.

Process (D) according to the invention is characterized in that carbonyl compounds of the formula (V) or enol ethers thereof of the formula (V-a) are reacted with ketene acid halides of the formula (VI) in the presence of a diluent and optionally in the presence of an acid acceptor.

Diluents which can be employed in process (D) according to the invention are all inert organic solvents. Preference is given to using optionally halogenated hydrocarbons such as toluene, xylene, mesitylene, chlorobenzene and dichlorobenzene, furthermore ethers, such as dibutyl ether, glycol dimethyl ether, diglycol dimethyl ether and diphenyl ether, moreover polar solvents, such as dimethyl sulfoxide, sulfolane, dimethylformamide or N-methylpyrrolidone.

Suitable acid acceptors for carrying out process variant (D) according to the invention are all customary acid acceptors.

Preference is given to using tertiary amines such as triethylamine, pyridine, diazabicyclooctane (DABCO), diazabicycloundecane (DBU), diazabicyclononene (DBN), Hünig base and N,N-dimethylaniline.

When carrying out process variant (D) according to the invention, the reaction temperatures can be varied within a relatively wide range. Expediently, the process is carried out at temperatures between 0° C. and 250° C., preferably between 50° C. and 220° C.

Process (D) according to the invention is expediently carried out under atmospheric pressure.

When carrying out process (D) according to the invention, the reactants of the formulae (V) and (VI) in which A, D, X and Y have the meanings given above and Hal represents halogen and optionally the acid acceptors are generally employed in approximately equimolar amounts. However, it is also possible to employ one or the other component in a relatively large excess (of up to 5 mol).

Process (E) according to the invention is characterized in that thioamides of the formula (VII) are reacted with ketene acid halides of the formula (VI) in the presence of a diluent and optionally in the presence of an acid acceptor.

Diluents which can be employed in process variant (E) according to the invention are all inert organic solvents. Preference is given to using hydrocarbons, such as toluene and xylene, furthermore ethers, such as dibutyl ether, glycol dimethyl ether and diglycol dimethyl ether, moreover polar solvents, such as dimethyl sulfoxide, sulfolane, dimethylformamide and N-methylpyrrolidone.

Suitable acid acceptors for carrying out process (E) according to the invention are all customary acid acceptors.

Preference is given to using tertiary amines such as triethylamine, pyridine, diazabicyclooctane (DABCO), diazabicycloundecane (DBU), diazabicyclononene (DBN), Hünig base and N,N-dimethylaniline.

When carrying out the process (E) according to the invention, the reaction temperatures can be varied within a relatively wide range. Expediently, the process is carried out at temperatures between 0° C. and 250° C., preferably between 20° C. and 220° C.

Process (E) according to the invention is expediently carried out under atmospheric pressure.

When carrying out process (E) according to the invention, the reactants of the formulae (VII) and (VI) in which A, X and Y have the meanings given above and Hal represents halogen and optionally the acid acceptors are generally employed in approximately equimolar amounts. However, it is also possible to employ one or the other component in a relatively large excess (of up to 5 mol).

Process (F) is characterized in that compounds of the formula (VIII) in which A, B, $Q^1$, $Q^2$, X, Y and $R^8$ have the meaning given above are subjected to an intramolecular condensation in the presence of a base.

Suitable diluents for process (F) according to the invention are all organic solvents which are inert toward the reaction participants. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as collidine, dimethyl sulfoxide, sulfolane, dimethylformamide and N-methylpyrrolidone. It is also possible to employ alcohols, such as methanol, ethanol, propanol, isopropanol, butanol, isobutanol, tert-butanol.

Bases (deprotonating agents) which can be employed when carrying out process (F) according to the invention are all customary proton acceptors. The following can preferably be used: the oxides, hydroxides and carbonates of alkali metals and alkaline earth metals, such as sodium hydroxide, potassium hydroxide, magnesium oxide, calcium oxide, sodium carbonate, potassium carbonate and calcium carbonate, all of which can also be employed in the presence of phase-transfer catalysts such as, for example, triethylbenzylammonium chloride, tetrabutylammonium bromide, Adogen 464 (methyltrialkyl($C_8$-$C_{10}$)ammonium chloride) or TDA 1 (tris-(methoxyethoxyethyl)amine). Alkali metals such as sodium or potassium can also be used. Furthermore, alkali metal and alkaline earth metal amides and hydrides, such as sodium amide, sodium hydride and calcium hydride, and additionally also alkali metal alkoxides, such as sodium methoxide, sodium ethoxide and potassium tert-butoxide can be employed.

When carrying out the process (F) according to the invention, the reaction temperatures can be varied within a relatively wide range. In general, the process is carried out at temperatures between −75° C. and 250° C., preferably between −50° C. and 150° C.

Process (F) according to the invention is generally carried out under atmospheric pressure.

When carrying out process (F) according to the invention, the reactants of the formula (VIII) and the deprotonating bases are generally employed in approximately equimolar amounts. However, it is also possible to employ one or the other component in a larger excess (of up to 3 mol).

Process (G) is characterized in that compounds of the formula (IX) in which A, B, $Q^5$, $Q^6$, U, X, Y and R8 have the meaning given above are subjected to an intramolecular condensation in the presence of bases.

Suitable diluents for process (G) according to the invention are all organic solvents which are inert toward the reaction participants. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulfoxide, sulfolane, dimethylformamide and N-methylpyrrolidone. It is also possible to employ alcohols, such as methanol, ethanol, propanol, isopropanol, butanol, isobutanol, tert-butanol.

Bases (deprotonating agents) which can be employed when carrying out process (G) according to the invention are all customary proton acceptors.

The following can preferably be used: the oxides, hydroxides and carbonates of alkali metals and alkaline earth metals, such as sodium hydroxide, potassium hydroxide, magnesium oxide, calcium oxide, sodium carbonate, potassium carbonate and calcium carbonate, all of which can also be employed in the presence of phase-transfer catalysts such as, for example, triethylbenzylammonium chloride, tetrabutylammonium bromide, Adogen 464 (methyltrialkyl($C_8$-$C_{10}$)ammonium chloride) or TDA 1 (tris-(methoxyethoxyethyl)amine). Alkali metals such as sodium or potassium can also be used. Furthermore, alkali metal and alkaline earth metal amides and hydrides, such as sodium amide, sodium hydride and calcium hydride, and additionally also alkali metal alkoxides, such as sodium methoxide, sodium ethoxide and potassium tert-butoxide can be employed.

When carrying out the process (G) according to the invention, the reaction temperatures can be varied within a relatively wide range. In general, the process is carried out at temperatures between 0° C. and 250° C., preferably between 50° C. and 150° C.

Process (G) according to the invention is generally carried out under atmospheric pressure.

When carrying out process (G) according to the invention, the reactants of the formula (IX) and the deprotonating bases are generally employed in approximately equimolar amounts. However, it is also possible to employ one or the other component in a relatively large excess (of up to 3 mol).

Process (H-α) according to the invention is characterized in that hydrazines of the formula (X) or salts of these compounds are reacted with ketene acid halides of the formula (VI) in the presence of a diluent and optionally in the presence of an acid acceptor.

Diluents which can be employed in process (H-α) according to the invention are all inert organic solvents. Preference is given to using optionally chlorinated hydrocarbons, such as, for example, mesitylene, chlorobenzene and dichlorobenzene, toluene, xylene, furthermore ethers, such as dibutyl ether, glycol dimethyl ether, diglycol dimethyl ether and diphenylethane, moreover polar solvents, such as dimethyl sulfoxide, sulfolane, dimethylformamide or N-methylpyrrolidone.

Suitable acid acceptors for carrying out process (H-α) according to the invention are all customary acid acceptors.

Preference is given to using tertiary amines such as triethylamine, pyridine, diazabicyclooctane (DABCO), diazabicycloundecane (DBU), diazabicyclononene (DBN), Hünig base and N,N-dimethylaniline.

When carrying out process variant (H-α) according to the invention, the reaction temperatures can be varied within a relatively wide range. Expediently, the process is carried out at temperatures between 0° C. and 250° C., preferably between 50° C. and 220° C.

Process (H-α) according to the invention is expediently carried out under atmospheric pressure.

When carrying out process (H-α) according to the invention, the reactants of the formulae (VI) and (X) in which A, D, X and Y have the meanings given above and Hal represents halogen and optionally the acid acceptors are generally employed in approximately equimolar amounts. However, it is also possible to employ one or the other component in a relatively large excess (of up to 5 mol).

Process (H-β) is characterized in that hydrazines of the formula (X) or salts of this compound in which A and D have the meanings given above are subjected to a condensation with malonic esters or malonamides of the formula (XI) in which $U^1$, X, Y and $R^8$ have the meaning given above in the presence of a base.

Diluents which can be employed in process (H-β) according to the invention are all inert organic solvents. Preference is given to using optionally halogenated hydrocarbons, such as toluene, xylene, mesitylene, chlorobenzene and dichlorobenzene, furthermore ethers, such as dibutyl ether, tetrahydrofuran, dioxane, diphenyl ether, glycol dimethyl ether and diglycol dimethyl ether, moreover polar solvents, such as dimethyl sulfoxide, sufolane, dimethylformamide, dimethylacetamide and N-methylpyrrolidone, and also alcohols, such as methanol, ethanol, propanol, isopropanol, butanol, isobutanol and tert-butanol.

Bases (deprotonating agents) which can be employed when carrying out process (H-β) according to the invention are all customary proton acceptors. The following can preferably be used: the oxides, hydroxides and carbonates of alkali metals and alkaline earth metals, such as sodium hydroxide, potassium hydroxide, magnesium oxide, calcium oxide, sodium carbonate, potassium carbonate and calcium carbonate, all of which can also be employed in the presence of phase-transfer catalysts such as, for example, triethylbenzylammonium chloride, tetrabutylammonium bromide, Adogen 464 (=methyltrialkyl($C_8$-$C_{10}$)ammonium chloride) or TDA 1 (=tris-(methoxyethoxyethyl)amine). Alkali metals such as sodium or potassium can also be used. Furthermore, alkali metal and alkaline earth metal amides and hydrides, such as sodium amide, sodium hydride and calcium hydride, and additionally also alkali metal alkoxides, such as sodium methoxide, sodium ethoxide and potassium tert-butoxide can be employed.

Preference is also given to using tertiary amines such as triethylamine, pyridine, diazabicyclooctane (DABCO), diazabicycloundecane (DBU), diazabicyclononene (DBN), Hünig base and N,N-dimethylaniline.

When carrying out process (H-β) according to the invention, the reaction temperatures can be varied within a relatively wide range. In general, the process is carried out at temperatures between 0° C. and 280° C., preferably between 50° C. and 180° C.

Process (H-β) according to the invention is generally carried out under atmospheric pressure.

When carrying out process (H-β) according to the invention, the reactants of the formula (XI) and (X) and the deprotonating bases are generally employed in approximately equimolar amounts. However, it is also possible to employ one or the other component in a relatively large excess (of up to 3 mol).

Process (H-γ) is characterized in that compounds of the formula (XII) in which A, D, X, Y and $R^8$ have the meanings given above are subjected to an intramolecular condensation in the presence of a base.

Diluents which can be employed in process (H-γ) according to the invention are all inert organic solvents. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulfoxide, sufolane, dimethylformamide and N-methylpyrrolidone, and also alcohols, such as methanol, ethanol, propanol, isopropanol, butanol, isobutanol and tert-butanol.

Bases (deprotonating agents) which can be employed when carrying out process (H-γ) according to the invention are all customary proton acceptors. The following can preferably be used: the oxides, hydroxides and carbonates of alkali metals and alkaline earth metals, such as sodium hydroxide, potassium hydroxide, magnesium oxide, calcium oxide, sodium carbonate, potassium carbonate and calcium carbonate, all of which can also be employed in the presence of phase-transfer catalysts such as, for example, triethylbenzylammonium chloride, tetrabutylammonium bromide, Adogen 464 (=methyltrialkyl($C_8$-$C_{10}$)ammonium chloride) or TDA 1 (=tris-(methoxyethoxyethyl)amine). Alkali metals such as sodium or potassium can also be used. Furthermore, alkali metal and alkaline earth metal amides and hydrides, such as sodium amide, sodium hydride and calcium hydride, and additionally also alkali metal alkoxides, such as sodium methoxide, sodium ethoxide and potassium tert-butoxide can be employed.

When carrying out process (H-γ) according to the invention, the reaction temperatures can be varied within a relatively wide range. In general, the process is carried out at temperatures between 0° C. and 250° C., preferably between 50° C. and 150° C.

Process (H-γ) according to the invention is generally carried out under atmospheric pressure.

When carrying out process (H-γ) according to the invention, the reactants of the formula (XII) and the deprotonating bases are generally employed in approximately twice the equimolar amounts. However, it is also possible to employ one or the other component in a larger excess (of up to 3 mol).

Process (I) is characterized in that compounds of the formula (XIII) in which A, B, D, $Q^1$, $Q^2$, X, Y and R8 have the meanings given above are subjected to an intramolecular condensation in the presence of a base.

Diluents which can be employed in process (I) according to the invention are all inert organic solvents. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulfoxide, sufolane, dimethylformamide, dimethylacetamide and N-methylpyrrolidone, and also alcohols, such as methanol, ethanol, propanol, isopropanol, butanol, isobutanol and tert-butanol.

Bases (deprotonating agents) which can be employed when carrying out process (I) according to the invention are all customary proton acceptors. The following can preferably be used: the oxides, hydroxides and carbonates of alkali metals and alkaline earth metals, such as sodium hydroxide, potassium hydroxide, magnesium oxide, calcium oxide, sodium carbonate, potassium carbonate and calcium carbonate, all of which can also be employed in the presence of phase-transfer catalysts such as, for example, triethylbenzylammonium chloride, tetrabutylammonium bromide, Adogen 464 (=methyltrialkyl($C_8$-$C_{10}$)ammonium chloride) or TDA 1 (=tris-(methoxyethoxyethyl)amine). Alkali metals such as sodium or potassium can also be used. Furthermore, alkali metal and alkaline earth metal amides and hydrides, such as sodium amide, sodium hydride and calcium hydride, and additionally also alkali metal alkoxides, such as sodium methoxide, sodium ethoxide and potassium tert-butoxide can be employed.

When carrying out process (I) according to the invention, the reaction temperatures can be varied within a relatively wide range. In general, the process is carried out at temperatures between −80° C. and 180° C., preferably between −50° C. and 120° C.

Process (I) according to the invention is generally carried out under atmospheric pressure.

When carrying out process (I) according to the invention, the reactants of the formula (XIII) and the deprotonating bases are generally employed in approximately twice the equimolar amounts. However, it is also possible to employ one or the other component in a larger excess (of up to 3 mol).

Process (J) is characterized in that compounds of the formula (XIV) in which A, B, $Q^1$, $Q^2$, X, Y and R8 have the meanings given above are subjected to an intramolecular condensation in the presence of a base.

Diluents which can be employed in process (J) according to the invention are all inert organic solvents. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulfoxide, sufolane, dimethylformamide and N-methylpyrrolidone, and also alcohols, such as methanol, ethanol, propanol, isopropanol, butanol, isobutanol and tert-butanol.

Bases (deprotonating agents) which can be employed when carrying out process (J) according to the invention are all customary proton acceptors. The following can preferably be used: the oxides, hydroxides and carbonates of alkali metals and alkaline earth metals, such as sodium hydroxide, potassium hydroxide, magnesium oxide, calcium oxide, sodium carbonate, potassium carbonate and calcium carbonate, all of which can also be employed in the presence of phase-transfer catalysts such as, for example, triethylbenzylammonium chloride, tetrabutylammonium bromide, Adogen 464 (=methyltrialkyl($C_8$-$C_{10}$)ammonium chloride) or TDA 1 (=tris-(methoxyethoxyethyl)amine). Alkali metals such as sodium or potassium can also be used. Furthermore, alkali metal and alkaline earth metal amides and hydrides, such as sodium amide, sodium hydride and calcium hydride, and additionally also alkali metal alkoxides, such as sodium methoxide, sodium ethoxide and potassium tert-butoxide can be employed.

When carrying out process (J) according to the invention, the reaction temperatures can be varied within a relatively wide range. In general, the process is carried out at temperatures between 0° C. and 250° C., preferably between 50° C. and 150° C.

Process (J) according to the invention is generally carried out under atmospheric pressure.

When carrying out process (J) according to the invention, the reactants of the formula (XIV) and the deprotonating bases are generally employed in approximately twice the equimolar amounts. However, it is also possible to employ one or the other component in a larger excess (of up to 3 mol).

Process (K) is characterized in that compounds of the formula (XV) in which A, B, D, X, Y and $R^8$ have the meanings given above are subjected to an intramolecular condensation in the presence of a base.

Diluents which can be employed in process (K) according to the invention are all inert organic solvents. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulfoxide, sufolane, dimethylformamide and N-methylpyrrolidone, and also alcohols, such as methanol, ethanol, propanol, isopropanol, butanol, isobutanol and tert-butanol.

Bases (deprotonating agents) which can be employed when carrying out process (K) according to the invention are all customary proton acceptors. The following can preferably be used: the oxides, hydroxides and carbonates of alkali metals and alkaline earth metals, such as sodium hydroxide, potassium hydroxide, magnesium oxide, calcium oxide, sodium carbonate, potassium carbonate and calcium carbonate, all of which can also be employed in the presence of phase-transfer catalysts such as, for example, triethylbenzylammonium chloride, tetrabutylammonium bromide, Adogen 464 (=methyltrialkyl($C_8$-$C_{10}$)ammonium chloride) or TDA 1 (=tris-(methoxyethoxyethyl)amine). Alkali metals such as sodium or potassium can also be used. Furthermore, alkali metal and alkaline earth metal amides and hydrides, such as sodium amide, sodium hydride and calcium hydride, and additionally also alkali metal alkoxides, such as sodium methoxide, sodium ethoxide and potassium tert-butoxide can be employed.

When carrying out process (K) according to the invention, the reaction temperatures can be varied within a relatively wide range. In general, the process is carried out at temperatures between −78° C. and 250° C., preferably between 0° C. and 150° C.

Process (K) according to the invention is generally carried out under atmospheric pressure.

When carrying out process (K) according to the invention, the reactants of the formula (XV) and the deprotonating bases are generally employed in approximately twice the equimolar amounts. However, it is also possible to employ one or the other component in a larger excess (of up to 3 mol).

Process (L-α) is characterized in that compounds of the formulae (I-1-a) to (I-11-a) are in each case reacted with carbonyl halides of the formula (XVI), if appropriate in the presence of a diluent and if appropriate in the presence of an acid binder.

Suitable diluents for the process (L-α) according to the invention are all solvents which are inert to the acid halides. Preference is given to using hydrocarbons, such as benzine, benzene, toluene, xylene and tetraline, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, and also strongly polar solvents, such as dimethyl sulfoxide and sulfolane. If the acid halide is sufficiently stable to hydrolysis, the reaction may also be carried out in the presence of water.

Suitable acid binders when carrying out the reaction in accordance with process (L-α) according to the invention are all customary acid acceptors. The following can preferably be used: tertiary amines such as triethylamine, pyridine, diazabicyclooctane (DABCO), diazabicycloundecene (DBU), diazabicyclononene (DBN), Hünig base and N,N-dimethylaniline, furthermore alkaline earth metal oxides such as magnesium oxide and calcium oxide, moreover alkali metal carbonates and alkaline earth metal carbonates such as sodium carbonate, potassium carbonate and calcium carbonate, and alkali metal hydroxides such as sodium hydroxide and potassium hydroxide.

In the process (L-α) according to the invention, the reaction temperatures can be varied within a relatively wide range. In general, the process is carried out at temperatures between −20° C. and +150° C., preferably between 0° C. and 100° C.

When carrying out the process (L-α) according to the invention, the starting materials of the formulae (I-1-a) to (I-11-a) and the carbonyl halide of the formula (XVI) are generally in each case employed in approximately equivalent amounts. However, it is also possible to employ the carbonyl halide in a relatively large excess (of up to 5 mol). Work-up is carried out by customary methods.

Process (L-β) is characterized in that compounds of the formulae (I-1-a) to (I-11-a) are reacted with carboxylic anhydrides of the formula (XVII), if appropriate in the presence of a diluent and if appropriate in the presence of an acid binder.

Preferred diluents for the process (L-β) according to the invention are those diluents which are also preferred when acid halides are used. Besides, a carboxylic anhydride used in excess may also simultaneously act as diluent.

In the process (L-β), acid binders which are added, if appropriate, are preferably those acid binders which are also preferred when acid halides are used.

In the process (L-β) according to the invention, the reaction temperatures can be varied within a relatively wide range. In general, the process is carried out at temperatures between −20° C. and +150° C., preferably between 0° C. and 100° C.

When carrying out the process (L-β) according to the invention, the starting materials of the formulae (I-1-a) to (I-11-a) and the carboxylic anhydride of the formula (XVII) are generally in each case employed in approximately equivalent amounts. However, it is also possible to employ the carboxylic anhydride in a relatively large excess (of up to 5 mol). Work-up is carried out by customary methods.

In general, a procedure is followed in which diluent, excess carboxylic anhydride and the carboxylic acid which forms are removed by distillation or by washing with an organic solvent or with water.

Process (M) is characterized in that compounds of the formulae (I-1-a) to (I-11-a) are reacted in each case with chloroformic esters or chloroformic thioesters of the formula (XVIII), if appropriate in the presence of a diluent and if appropriate in the presence of an acid binder.

Suitable acid binders when carrying out the reaction in accordance with process (M) according to the invention are all customary acid acceptors. The following can preferably be used: tertiary amines such as triethylamine, pyridine, DABCO, DBU, DBN, Hünig base and N,N-dimethylaniline, furthermore alkaline earth metal oxides such as magnesium oxide and calcium oxide, moreover alkali metal carbonates and alkaline earth metal carbonates such as sodium carbonate, potassium carbonate and calcium carbonate, and alkali metal hydroxides such as sodium hydroxide and potassium hydroxide.

Diluents which can be employed in the process (M) according to the invention are all solvents which are inert to the chloroformic esters or chloroformic thioesters. Preference is given to using hydrocarbons, such as benzine, benzene, toluene, xylene and tetraline, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, and also strongly polar solvents, such as dimethyl sulfoxide and sulfolane.

When carrying out process (M) according to the invention, the reaction temperatures can be varied within a relatively wide range. If the process is carried out in the presence of a diluent and of an acid binder, the reaction temperatures are generally between −20° C. and +100° C., preferably between 0° C. and 50° C.

Process (M) according to the invention is generally carried out under atmospheric pressure.

When carrying out process (M) according to the invention, the starting materials of the formulae (I-1-a) to (I-11-a) and the corresponding chloroformic ester or chloroformic thioester of the formula (XVIII) are generally used in each case in approximately equivalent amounts. However, it is also possible to employ one or the other component in a larger excess (of up to 2 mol). Work-up is carried out by customary methods. In general, a procedure is followed in which the salts which have precipitated are removed and the reaction mixture which remains is concentrated by stripping off the diluent.

Process (N) according to the invention is characterized in that compounds of the formula (I-1-a) to (I-11-a) are in each case reacted with compounds of the formula (XIX), in the presence of a diluent and if appropriate in the presence of an acid binder.

In preparation process (N), approximately 1 mol of chloromonothioformic ester or chlorodithioformic ester of the formula (XIX) is reacted at from 0 to 120° C., preferably at from 20 to 60° C., per mole of starting compound of the formulae (I-1-a) to (I-11-a).

Suitable diluents which are added, if appropriate, are all inert polar organic solvents, such as ethers, amides, sulfones, sulfoxides, but also haloalkanes.

Preference is given to using dimethyl sulfoxide, tetrahydrofuran, dimethylformamide or methylene chloride.

If, in a preferred embodiment, the enolate salt of the compounds (I-1-a) to (I-11-a) is synthesized by addition of strong deprotonating agents (such as, for example, sodium hydride or potassium tertiary-butoxide), the further addition of acid binders can be dispensed with.

If acid binders are employed, these are customary inorganic or organic bases, for example sodium hydroxide, sodium carbonate, potassium carbonate, pyridine and triethylamine.

The reaction can be carried out under atmospheric pressure or under elevated pressure and is preferably carried out under atmospheric pressure. Work-up is carried out by customary methods.

Process (O) according to the invention is characterized in that compounds of the formula (I-1-a) to (I-11-a) are in each case reacted with sulfonyl chlorides of the formula (XX), if appropriate in the presence of a diluent and if appropriate in the presence of an acid binder.

In preparation process (O), about 1 mol of sulfonyl chloride of the formula (XX) is reacted per mole of starting material of the formula (I-1-a) to (I-11-a), at from −20 to 150° C., preferably from 20 to 70° C.

Suitable diluents which are optionally added are all inert polar organic solvents such as ethers, amides, nitriles, sulfones, sulfoxides or halogenated hydrocarbons such as methylene chloride.

Preference is given to using dimethyl sulfoxide, tetrahydrofuran, dimethylformamide, methylene chloride.

If, in a preferred embodiment, the enolate salt of the compounds (I-1-a) to (I-11-a) is synthesized by addition of strong deprotonating agents (such as, for example, sodium hydride or potassium tert-butoxide), the further addition of acid binders can be dispensed with.

If acid binders are employed, these are customary inorganic or organic bases, for example sodium hydroxide, sodium carbonate, potassium carbonate, pyridine and triethylamine.

The reaction can be carried out under atmospheric pressure or under elevated pressure and is preferably carried out under atmospheric pressure. Work-up is carried out by customary methods.

Process (P) according to the invention is characterized in that compounds of the formulae (I-1-a) to (I-11-a) are in each case reacted with phosphorus compounds of the formula (XXI), if appropriate in the presence of a diluent and if appropriate in the presence of an acid binder.

In preparation process (P), 1 to 2, preferably 1 to 1.3, mol of the phosphorus compound of the formula (XXI) are reacted at temperatures of between −40° C. and 150° C., preferably between −10 and 110° C., per mole of the compounds (I-1-a) to (I-11-a) in order to obtain compounds of the formulae (I-1-e) to (I-11-e).

Suitable diluents which are optionally added are all inert polar organic solvents such as ethers, amides, nitriles, alcohols, sulfides, sulfones, sulfoxides and the like.

Substances which are preferably employed are acetonitrile, dimethyl sulfoxide, tetrahydrofuran, dimethylformamide, methylene chloride.

Suitable acid binders which are optionally added are customary inorganic or organic bases such as hydroxides, carbonates or amines. Examples which may be mentioned are sodium hydroxide, sodium carbonate, potassium carbonate, pyridine, triethylamine.

The reaction can be carried out under atmospheric pressure or under elevated pressure, preferably under atmospheric pressure. Work-up is carried out by customary methods of organic chemistry. The resulting end products are preferably purified by crystallization, chromatography or by what is known as "incipient distillation", that is to say removal of the volatile components in vacuo.

The process (Q) is characterized in that compounds of the formula (I-1-a) to (I-11-a) are in each case reacted with metal hydroxides or metal alkoxides of the formula (XXII) or amines of the formula (XXII), if appropriate in the presence of a diluent.

Preferred diluents for the process (Q) according to the invention are ethers, such as tetrahydrofuran, dioxane, diethyl ether, or else alcohols, such as methanol, ethanol, isopropanol, but also water.

Process (Q) according to the invention is generally carried out under atmospheric pressure.

In general, the reaction temperatures are between −20° C. and 100° C., preferably between 0° C. and 50° C.

Process (R) according to the invention is characterized in that compounds of the formulae (I-1-a) to (I-11-a) are in each case reacted with (R-α) compounds of the formula (XXIV), if appropriate in the presence of a diluent and if appropriate in the presence of a catalyst, or (R-β) with compounds of the formula (XXV), if appropriate in the presence of a diluent and if appropriate in the presence of an acid binder.

In preparation process (R-α), approximately 1 mol of isocyanate of the formula (XXIV) is reacted per mole of starting material of the formulae (I-1-a) to (I-11-a), at from 0 to 100° C., preferably at from 20 to 50° C.

Suitable diluents which are optionally added are all inert organic solvents, such as ethers, amides, nitriles, sulfones, sulfoxides.

If appropriate, catalysts may be added to accelerate the reaction. Catalysts which can be employed very advantageously are organotin compounds such as, for example, dibutyltin dilaurate. The process is preferably carried out under atmospheric pressure.

In preparation process (R-β), about 1 mol of carbamoyl chloride of the formula (XXV) is reacted per mole of starting material of the formula (I-1-a) to (I-11-a), at from −20 to 150° C., preferably from 0 to 70° C.

Suitable diluents which are optionally added are all inert polar organic solvents such as ethers, amides, sulfones, sulfoxides or halogenated hydrocarbons.

Preference is given to using dimethyl sulfoxide, tetrahydrofuran, dimethylformamide or methylene chloride.

If, in a preferred embodiment, the enolate salt of the compounds (I-1-a) to (I-11-a) is synthesized by addition of strong deprotonating agents (such as, for example, sodium hydride or potassium tert-butoxide), the further addition of acid binders can be dispensed with.

If acid binders are employed, these are customary inorganic or organic bases, for example sodium hydroxide, sodium carbonate, potassium carbonate, triethylamine or pyridine.

The reaction can be carried out under atmospheric pressure or under elevated pressure and is preferably carried out under atmospheric pressure. Work-up is carried out by customary methods.

The active compounds according to the invention, in combination with good plant tolerance and favorable toxicity to warm-blooded animals and being tolerated well by the environment, are suitable for protecting plants and plant organs, for increasing the harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They can be used with preference as crop protection agents. They are effective against normally sensitive and resistant species and against all or some stages of development. The abovementioned pests include:

pests from the phylum of the Arthropoda, more particularly from the class of the Arachnida, for example *Acarus* spp., *Aceria sheldoni, Aculops* spp., *Aculus* spp., *Amblyomma* spp., Amphi*tetranychus viennensis, Argas* spp., *Boophilus* spp., *Brevipalpus* spp., *Bryobia graminum, Bryobia praetiosa, Centruroides* spp., *Chorioptes* spp., *Dermanyssus gallinae, Dermatophagoides pteronyssinus, Dermatophagoides farinae, Dermacentor* spp., *Eotetranychus* spp., *Epitrimerus pyri, Eutetranychus* spp., *Eriophyes* spp., *Glycyphagus domesticus, Halotydeus destructor, Hemitarsonemus* spp., *Hyalomma* spp., *Ixodes* spp., *Latrodectus* spp., *Loxosceles* spp., *Metatetranychus* spp., *Neutrombicula autumnalis, Nuphersa* spp., *Oligonychus* spp., *Ornithodorus* spp., *Ornithonyssus* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Steneotarsonemus* spp., *Steneotarsonemus spinki, Tarsonemus* spp., *Tetranychus* spp., *Trombicula alfreddugesi, Vaejovis* spp., *Vasates lycopersici;* from the class of the Chilopoda, for example *Geophilus* spp., *Scutigera* spp.;

from the order or the class of the Collembola, for example *Onychiurus armatus.;* from the class of the Diplopoda, for example *Blaniulus guttulatus;* from the class of the Insecta, for example from the order of the Blattodea, for example *Blattella asahinai, Blattella germanica, Blatta orientalis, Leucophaea maderae, Panchlora* spp., *Parcoblatta* spp., *Periplaneta* spp., *Supella longipalpa;* from the order of the Coleoptera, for example *Acalymma vittatum, Acanthoscelides obtectus, Adoretus* spp., *Agelastica alni, Agriotes* spp., *Alphitobius diaperinus, Amphimallon solstitialis, Anobium punctatum, Anoplophora* spp., *Anthonomus* spp., *Anthrenus* spp., *Apion* spp., *Apogonia* spp., *Atomaria* spp., *Attagenus* spp., *Bruchidius obtectus, Bruchus* spp., *Cassida* spp., *Cerotoma trifurcata, Ceutorrhynchus* spp., *Chaetocnema* spp., *Cleonus mendicus, Conoderus* spp., *Cosmopolites* spp., *Costelytra zealandica, Ctenicera* spp., *Curculio* spp., *Cryptolestes ferrugineus, Cryptorhynchus lapathi, Cylindrocopturus* spp., *Dermestes* spp., *Diabrotica* spp., *Dichocrocis* spp., *Dicladispa armigera, Diloboderus* spp., *Epilachna* spp., *Epitrix* spp., *Faustinus* spp., *Gibbium psylloides, Gnathocerus cornutus, Hellula undalis, Heteronychus arator, Heteronyx* spp., *Hylamorpha elegans, Hylotrupes bajulus, Hypera postica, Hypomeces squamosus, Hypothenemus* spp., *Lachnosterna consanguinea, Lasioderma serricorne, Latheticus oryzae, Lathridius* spp., *Lema* spp., *Leptinotarsa decemlineata, Leucoptera* spp., *Lissorhoptrus oryzophilus, Lixus* spp., *Luperodes* spp., *Lyctus* spp., *Megascelis* spp., *Melanotus* spp., *Meligethes aeneus, Melolontha* spp.,

*Migdolus* spp., *Monochamus* spp., *Naupactus xanthographus, Necrobia* spp., *Niptus hololeucus, Oryctes rhinoceros, Oryzaephilus surinamensis, Oryzaphagus oryzae, Otiorrhynchus* spp., *Oxycetonia jucunda, Phaedon cochleariae, Phyllophaga* spp., *Phyllophaga helleri, Phyllotreta* spp., *Popillia japonica, Premnotrypes* spp., *Prostephanus truncatus, Psylliodes* spp., *Ptinus* spp., *Rhizobius ventralis, Rhizopertha dominica, Sitophilus* spp., *Sitophilus oryzae, Sphenophorus* spp., *Stegobium paniceum, Sternechus* spp., *Symphyletes* spp., *Tanymecus* spp., *Tenebrio molitor, Tenebrioides mauretanicus, Tribolium* spp., *Trogoderma* spp., *Tychius* spp., *Xylotrechus* spp., *Zabrus* spp.;

from the order of the Diptera, for example *Aedes* spp., *Agromyza* spp., *Anastrepha* spp., *Anopheles* spp., *Asphondylia* spp., *Bactrocera* spp., *Bibio hortulanus, Calliphora erythrocephala, Calliphora vicina, Ceratitis capitata, Chironomus* spp., *Chrysomyia* spp., *Chrysops* spp., *Chrysozona pluvialis, Cochliomyia* spp., *Contarinia* spp., *Cordylobia anthropophaga, Cricotopus sylvestris, Culex* spp., *Culicoides* spp., *Culiseta* spp., *Cuterebra* spp., *Dacus oleae, Dasyneura* spp., *Delia* spp., *Dermatobia hominis, Drosophila* spp., *Echinocnemus* spp., *Fannia* spp., *Gasterophilus* spp., *Glossina* spp., *Haematopota* spp., *Hydrellia* spp., *Hydrellia griseola, Hylemya* spp., *Hippobosca* spp., *Hypoderma* spp., *Liriomyza* spp., *Lucilia* spp., *Lutzomyia* spp., *Mansonia* spp., *Musca* spp., *Oestrus* spp., *Oscinella frit, Paratanytarsus* spp., *Paralauterborniella subcincta, Pegomyia* spp., *Phlebotomus* spp., *Phorbia* spp., *Phormia* spp., *Piophila casei, Prodiplosis* spp., *Psila rosae, Rhagoletis* spp., *Sarcophaga* spp., *Simulium* spp., *Stomoxys* spp., *Tabanus* spp., *Tetanops* spp., *Tipula* spp.;

from the order of the Heteroptera, for example *Anasa tristis, Antestiopsis* spp., *Boisea* spp., *Blissus* spp., *Calocoris* spp., *Campylomma livida, Cavelerius* spp., *Cimex* spp., *Collaria* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptocorisa varicornis, Leptoglossus phyllopus, Lygus* spp., *Macropes excavatus, Miridae, Monalonion atratum, Nezara* spp., *Oebalus* spp., *Pentomidae, Piesma quadrata, Piezodorus* spp., *Psallus* spp., Pseudacysta *persea, Rhodnius* spp., *Sahlbergella singularis, Scaptocoris castanea, Scotinophora* spp., *Stephanitis nashi, Tibraca* spp., *Triatoma* spp.;

from the order of the Homoptera, for example *Acizzia acaciaebaileyanae, Acizzia dodonaeae, Acizzia uncatoides, Acrida turrita, Acyrthosipon* spp., *Acrogonia* spp., *Aeneolamia* spp., *Agonoscena* spp., *Aleyrodes proletella, Aleurolobus barodensis, Aleurothrixus floccosus, Allocaridara malayensis, Amrasca* spp., *Anuraphis cardui, Aonidiella* spp., *Aphanostigma piri, Aphis* spp., *Arboridia apicalis, Arytainilla* spp., *Aspidiella* spp., *Aspidiotus* spp., *Atanus* spp., *Aulacorthum solani, Bemisia tabaci, Blastopsylla occidentalis, Boreioglycaspis melaleucae, Brachycaudus helichrysi, Brachycolus* spp., *Brevicoryne brassicae, Cacopsylla* spp., *Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chondracris rosea, Chromaphis juglandicola, Chrysomphalus ficus, Cicadulina mbila, Coccomytilus halli, Coccus* spp., *Cryptomyzus ribis, Cryptoneossa* spp., *Ctenarytaina* spp., *Dalbulus* spp., *Dialeurodes citri, Diaphorina citri, Diaspis* spp., *Drosicha* spp., *Dysaphis* spp., *Dysmicoccus* spp., *Empoasca* spp., *Eriosoma* spp., *Erythroneura* spp., *Eucalyptolyma* spp., *Euphyllura* spp., *Euscelis bilobatus, Ferrisia* spp., *Geococcus coffeae, Glycaspis* spp., *Heteropsylla*

*cubana, Heteropsylla spinulosa, Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Macrosteles facifrons, Mahanarva* spp., *Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nettigoniclla spectra, Nilaparvata lugens, Oncometopia* spp., *Orthezia praelonga, Oxya chinensis, Pachypsylla* spp., *Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Prosopidopsylla flava, Protopulvinaria pyriformis, Pseudaulacaspis pentagona, Pseudococcus* spp., *Psyllopsis* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoideus titanus, Schizaphis graminum, Selenaspidus articulatus, Sogata* spp., *Sogatella furcifera, Sogatodes* spp., *Stictocephala festina, Siphoninus phillyreae, Tenalaphara malayensis, Tetragonocephela* spp., *Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii, Zygina* spp.;

from the order of the Hymenoptera, for example *Acromyrmex* spp., *Athalia* spp., *Atta* spp., *Diprion* spp., *Hoplocampa* spp., *Lasius* spp., *Monomorium pharaonis, Sirex* spp., *Solenopsis* invicta, *Tapinoma* spp., *Urocerus* spp., *Vespa* spp., *Xeris* spp.;

from the order of the Isopoda, for example *Armadillidium vulgare, Oniscus asellus, Porcellio scaber;* from the order of the Isoptera, for example *Coptotermes* spp., *Cornitermes cumulans, Cryptotermes* spp., *Incisitermes* spp., *Microtermes obesi, Odontotermes* spp., *Reticulitermes spp.;* from the order of the Lepidoptera, for example *Achroia grisella, Acronicta major, Adoxophyes* spp., *Aedia leucomelas, Agrotis* spp., *Alabama* spp., *Amyelois transitella, Anarsia* spp., *Anticarsia* spp., *Argyroploce* spp., *Barathra brassicae, Borbo cinnara, Bucculatrix thurberiella, Bupalus piniarius, Busseola* spp., *Cacoecia* spp., *Caloptilia theivora, Capua reticulana, Carpocapsa pomonella, Carposina niponensis, Chematobia brumata, Chilo* spp., *Choristoneura* spp., *Clysia ambiguella, Cnaphalocerus* spp., *Cnaphalocrocis medinalis, Cnephasia* spp., *Conopomorpha* spp., *Conotrachelus* spp., *Copitarsia* spp., *Cydia* spp., *Dalaca noctuides, Diaphania* spp., *Diatraea saccharalis, Earias* spp., *Ecdytolopha aurantium, Elasmopalpus lignosellus, Eldana saccharina, Ephestia* spp., *Epinotia* spp., *Epiphyas postvittana, Etiella* spp., *Eulia* spp., *Eupoecilia ambiguella, Euproctis* spp., *Euxoa* spp., *Feltia* spp., *Galleria mellonella, Gracillaria* spp., *Grapholitha* spp., *Hedylepta* spp., *Helicoverpa* spp., *Heliothis* spp., *Hofmannophila pseudospretella, Homoeosoma* spp., *Homona* spp., *Hyponomeuta padella, Kakivoria flavofasciata, Laphygma* spp., *Laspeyresia molesta, Leucinodes orbonalis, Leucoptera* spp., *Lithocolletis* spp., *Lithophane antennata, Lobesia* spp., *Loxagrotis albicosta, Lymantria* spp., *Lyonetia* spp., *Malacosoma neustria, Maruca testulalis, Mamstra brassicae, Melanitis leda, Mocis* spp., *Monopis obviella, Mythimna separata, Nemapogon cloacellus, Nymphula* spp., *Oiketicus* spp., *Oria* spp., *Orthaga* spp., *Ostrinia* spp., *Oulema oryzae, Panolis flammea, Parnara* spp., *Pectinophora* spp., *Perileucoptera* spp., *Phthorimaea* spp., *Phyllocnistis citrella, Phyllonorycter* spp., *Pieris* spp., *Platynota stultana, Plodia interpunctella,*

*Plusia* spp., *Plutella xylostella, Prays* spp., *Prodenia* spp., *Protoparce* spp., *Pseudaletia* spp., *Pseudaletia unipuncta, Pseudoplusia includens, Pyrausta nubilalis, Rachiplusia nu, Schoenobius* spp., *Scirpophaga* spp., *Scirpophaga innotata, Scotia segetum, Sesamia* spp., *Sesamia inferens, Sparganothis* spp., *Spodoptera* spp., *Spodoptera praefica, Stathmopoda* spp., *Stomopteryx subsecivella, Synanthedon* spp., *Tecia solanivora, Thermesia gemmatalis, Tinea cloacella, Tinea pellionella, Tineola bisselliella, Tortrix* spp., *Trichophaga tapetzella, Trichoplusia* spp., *Tryporyza incertulas, Tuta absoluta, Virachola* spp.;

from the order of the Orthoptera or Saltatoria, for example *Acheta domesticus, Dichroplus* spp., *Gryllotalpa* spp., *Hieroglyphus* spp., *Locusta* spp., *Melanoplus* spp., *Schistocerca gregaria;* from the order of the Phthiraptera, for example *Damalinia* spp., *Haematopinus* spp., *Linognathus* spp., *Pediculus* spp., *Phylloera vastatrix, Phtirus pubis, Trichodectes* spp.;

from the order of the Psocoptera, for example *Lepinotus* spp., *Liposcelis* spp.;

from the order of the Siphonaptera, for example *Ceratophyllus* spp., *Ctenocephalides* spp., *Pulex irritans, Tunga penetrans, Xenopsylla* cheopsis;

from the order of the Thysanoptera, for example *Anaphothrips obscurus, Baliothrips biformis, Drepanothrips reuteri, Enneothrips flavens, Frankliniella* spp., *Heliothrips* spp., *Hercinothrips femoralis, Rhipiphorothrips cruentatus, Scirtothrips* spp., *Taeniothrips cardamomi, Thrips* spp.;

from the order of the Zygentoma (=Thysanura), for example *Ctenolepisma* spp., *Lepisma saccharina, Lepismodes inquilinus, Thermobia domestica;* from the class of the Symphyla, for example *Scutigerella* spp.;

pests from the phylum of the Mollusca, more particularly from the class of the Bivalvia, for example *Dreissena* spp., and also from the class of the Gastropoda, e.g. *Anion* spp., *Biomphalaria* spp., *Bulinus* spp., *Deroceras* spp., *Galba* spp., *Lymnaea* spp., *Oncomelania* spp., *Pomacea* spp., *Succinea* spp.;

animal parasites from the phyla of the Plathelminthes and Nematoda, for example *Ancylostoma duodenale, Ancylostoma ceylanicum, Ancylostoma braziliensis, Ancylostoma* spp., *Ascaris* spp., *Brugia malayi, Brugia timori, Bunostomum* spp., *Chabertia* spp., *Clonorchis* spp., *Cooperia* spp., *Dicrocoelium* spp., *Dictyocaulus filaria, Diphyllobothrium latum, Dracunculus* medinensis, *Echinococcus granulosus, Echinococcus multilocularis, Enterobius vermicularis, Faciola* spp., *Haemonchus* spp., *Heterakis* spp., *Hymenolepis nana, Hyostrongulus* spp., Loa Loa, *Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Strongyloides* spp., *Taenia saginata, Taenia solium, Trichinella spiralis, Trichinella* nativa, *Trichinella britovi, Trichinella nelsoni, Trichinella pseudopsiralis, Trichostrongulus* spp., *Trichuris trichuria, Wuchereria bancrofti;* plant pests from the phylum of the Nematoda, i.e. plant-parasitic nematodes, more particularly *Aphelenchoides* spp., *Bursaphelenchus* spp., *Ditylenchus* spp., *Globodera* spp., *Heterodera* spp., *Longidorus* spp., *Meloidogyne* spp., *Pratylenchus* spp., *Radopholus* spp., *Trichodorus* spp., *Tylenchulus* spp., *Xiphinema* spp., *Helicotylenchus* spp., *Tylenchorhynchus* spp., *Scutellonema* spp., *Paratrichodorus* spp., *Meloinema* spp., *Paraphelenchus* spp., *Aglenchus* spp., *Belonolaimus* spp., *Nacobbus* spp., *Rotylenchulus* spp., *Rotylenchus* spp., *Neotylenchus* spp., *Paraphelenchus* spp., *Dolichodorus* spp., *Hoplolaimus* spp., *Punctodera* spp., *Criconemella* spp., *Quinisulcius* spp., *Hemicycliophora* spp., *Anguina* spp., *Subanguina* spp., *Hemicriconemoides* spp., *Psilenchus* spp., *Pseudohalenchus* spp., *Criconemoides* spp., *Cacopaurus* spp.

Furthermore, from the sub-kingdom of the Protozoa, the order of the Coccidia, for example *Eimeria* spp. can be controlled.

If appropriate, the compounds according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (mycoplasma-like organisms) and RLO (rickettsia-like organisms). If appropriate, they can also be used as intermediates or precursors for the synthesis of other active compounds.

The invention can be used to treat all plants and parts of plants. Plants are understood here to mean all plants and plant populations, such as wanted and unwanted wild plants or crop plants (including naturally occurring crop plants). Crop plants may be plants obtainable by conventional breeding and optimization methods or by biotechnological and gene-technological methods, or combinations of these methods, including the transgenic plants and including the plant cultivars protectable or not protectable by plant breeders' rights. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. The plant parts also include harvested material and vegetative and generative propagation material, for example cuttings, tubers, rhizomes, slips and seeds.

Treatment according to the invention of the plants and plant parts with the active compounds is carried out directly or by allowing the compounds to act on their surroundings, environment or storage space by the customary treatment methods, for example by immersion, spraying, evaporation, fogging, scattering, painting on, injection and, in the case of propagation material, in particular in the case of seeds, also by applying one or more coats.

The active compounds can be converted to the customary formulations, such as solutions, emulsions, wettable powders, water- and oil-based suspensions, powders, dusts, pastes, soluble powders, soluble granules, granules for broadcasting, suspoemulsion concentrates, natural substances impregnated with active compound, synthetic substances impregnated with active compound, fertilizers, and microencapsulations in polymeric substances.

These formulations are produced in a known manner, for example by mixing the active compounds with extenders, i.e. liquid solvents, and/or solid carriers, optionally with the use of surfactants, i.e. emulsifiers and/or dispersants, and/or foam formers. The formulations are produced either in suitable production plants or else before or during application.

The auxiliaries used may be those substances which are suitable for imparting particular properties to the composition itself and/or to preparations derived therefrom (for example spray liquors, seed dressings), such as certain technical properties and/or also particular biological properties. Typical auxiliaries include: extenders, solvents and carriers.

Suitable extenders are, for example, water, polar and non-polar organic chemical liquids, for example from the classes of the aromatic and nonaromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulfones and sulfoxides (such as dimethyl sulfoxide).

If the extender used is water, it is also possible to use, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulfoxide, and also water.

According to the invention, a carrier is a natural or synthetic, organic or inorganic substance which may be solid or liquid and with which the active compounds are mixed or bonded for better applicability, in particular for application to plants or plant parts. The solid or liquid carrier is generally inert and should be suitable for use in agriculture.

Suitable solid carriers are:

for example ammonium salts and natural rock meals, such as kaolins, clays, talc, chalk, quartz, attapulgite, montmorillonite or diatomaceous earth, and synthetic rock flours, such as finely divided silica, alumina and silicates; useful solid carriers for granules include: for example, crushed and fractionated natural rocks such as calcite, marble, pumice, sepiolite and dolomite, and also synthetic granules of inorganic and organic flours, and granules of organic material such as paper, sawdust, coconut shells, corn cobs and tobacco stalks; useful emulsifiers and/or foam-formers include: for example nonionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates and also protein hydrolysates; suitable dispersants are nonionic and/or ionic substances, for example from the classes of the alcohol-POE and/or -POP ethers, acid and/or POP POE esters, alkylaryl and/or POP POE ethers, fat and/or POP POE adducts, POE- and/or POP-polyol derivatives, POE- and/or POP-sorbitan or -sugar adducts, alkyl or aryl sulfates, alkyl- or arylsulfonates and alkyl or aryl phosphates or the corresponding PO-ether adducts. Furthermore, suitable oligomers or polymers, for example those derived from vinylic monomers, from acrylic acid, from EO and/or PO alone or in combination with, for example, (poly)alcohols or (poly)amines. It is also possible to employ lignin and its sulfonic acid derivatives, unmodified and modified celluloses, aromatic and/or aliphatic sulfonic acids and also their adducts with formaldehyde.

Tackifiers such as carboxymethylcellulose and natural and synthetic polymers in the form of powders, granules or lattices, such as gum arabic, polyvinyl alcohol and polyvinyl acetate, or else natural phospholipids such as cephalins and lecithins and synthetic phospholipids can be used in the formulations.

It is possible to use dyes such as inorganic pigments, for example iron oxide, titanium oxide and Prussian Blue, and organic dyes such as alizarin dyes, azo dyes and metal phthalocyanine dyes, and trace nutrients such as salts of iron, manganese, boron, copper, cobalt, molybdenum and zinc.

Further additives may be perfumes, mineral or vegetable, optionally modified oils, waxes and nutrients (including trace nutrients), such as salts of iron, manganese, boron, copper, cobalt, molybdenum and zinc.

Stabilizers, such as low-temperature stabilizers, preservatives, antioxidants, light stabilizers or other agents which improve chemical and/or physical stability, may also be present.

The formulations generally comprise between 0.01 and 98% by weight of active compound, preferably between 0.5 and 90%.

The active compound according to the invention can be present in its commercially available formulations and in the use forms, prepared from these formulations, as a mixture with other active compounds, such as insecticides, attractants, sterilizing agents, bactericides, acaricides, nematicides, fungicides, growth-regulating substances, herbicides, safeners, fertilizers or semiochemicals.

A mixture with other known active compounds, such as herbicides, fertilizers, growth regulators, safeners, semiochemicals, or else with agents for improving the plant properties, is also possible.

When used as insecticides, the active compounds according to the invention may also be present in their commercially available formulations and in the use forms, prepared from these formulations, as a mixture with synergists. Synergists are compounds which increase the action of the active compounds, without it being necessary for the synergist added to be active itself.

When used as insecticides, the active compounds according to the invention may also be present in their commercially available formulations and in the use forms, prepared from these formulations, as a mixture with inhibitors which reduce degradation of the active compound after use in the environment of the plant, on the surface of parts of plants or in plant tissues.

The active compound content of the use forms prepared from the commercially available formulations may vary within wide limits. The active compound concentration of the application forms may be from 0.00000001 to 95% by weight of active compound, preferably between 0.00001 and 1% by weight.

The compounds are applied in a customary manner appropriate for the use forms.

The active compounds according to the invention act not only against plant, hygiene and stored product pests, but also in the veterinary medicine sector against animal parasites (ecto- and endoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp. and *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example, *Pulex* spp., *Ctenocephalides* spp., *Xenopsylla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example, *Blatta orientalis, Periplaneta americana, Blattela germanica* and *Supella* spp.

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The active compounds of the formula (I) according to the invention are also suitable for controlling arthropods which attack agricultural livestock, for example cattle, sheep, goats, horses, pigs, donkeys, camels, buffaloes, rabbits, chickens, turkeys, ducks, geese, honey-bees, other domestic animals such as, for example, dogs, cats, caged birds, aquarium fish, and experimental animals, for example hamsters, guinea pigs, rats and mice. The control of these arthropods is intended to reduce cases of death and reduced productivity (of meat, milk, wool, hides, eggs, honey etc.), and so more economic and easier animal husbandry is possible by use of the active compound according to the invention.

The active compounds according to the invention are used in the veterinary sector and in animal husbandry in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of molded articles containing the active compound, such as collars, ear marks, tail marks, limb bands, halters, marking devices and the like.

When used for livestock, poultry, domestic animals and the like, the active compounds of the formula (I) can be used as formulations (for example powders, emulsions, flowables) comprising the active compounds in an amount of 1 to 80% by weight, either directly or after 100 to 10 000-fold dilution, or they may be used as a chemical bath.

It has also been found that the compounds according to the invention have strong insecticidal action against insects which destroy industrial materials.

Preferred but nonlimiting examples include the following insects:

beetles, such as *Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec., *Tryptodendron* spec., *Apate monachus, Bostrychus capucins, Heterobostrychus brunneus, Sinoxylon* spec., *Dinoderus minutus;*

Dermapterans, such as *Sirex juvencus, Urocerus gigas, Urocerus gigas taignus, Urocerus augur;* termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus;* bristletails, such as *Lepisma saccarina.*

Industrial materials in the present connection are understood to mean inanimate materials, such as preferably plastics, adhesives, sizes, papers and cards, leather, wood, processed wood products and coating compositions.

The ready-to-use compositions may optionally also comprise other insecticides, and optionally one or more fungicides.

With respect to possible additional partners for mixing, reference is made to the insecticides and fungicides mentioned above.

Moreover, the compounds according to the invention can be employed for protecting objects which come into contact with saltwater or brackish water, in particular hulls, screens, nets, buildings, moorings and signaling systems, against fouling.

In addition, the compounds according to the invention can be used as antifouling compositions, alone or in combinations with other active compounds.

The active compounds are also suitable for controlling animal pests in the domestic sector, in the hygiene sector and in the protection of stored products, especially insects, arachnids and mites, which are found in enclosed spaces, for example homes, factory halls, offices, vehicle cabins and the like. They can be used to control these pests alone or in combination with other active compounds and auxiliaries in domestic insecticide products. They are effective against sensitive and resistant species, and against all developmental stages. These pests include:

From the order of the Scorpionidea, for example, *Buthus occitanus.*

From the order of the Acarina, for example, *Argas persicus, Argas reflexus, Bryobia* spp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae.*

From the order of the Araneae, for example, *Aviculariidae, Araneidae.*

From the order of the Opiliones, for example, *Pseudoscorpiones chelifer, Pseudoscorpiones cheiridium, Opiliones phalangium.*

From the order of the Isopoda, for example, *Oniscus asellus, Porcellio scaber.*

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus.*

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.*

From the order of the Saltatoria, for example, *Acheta domesticus.*

From the order of the Dermaptera, for example, *Forficula auricularia*.

From the order of the Isoptera, for example, *Kalotermes* spp., *Reticulitermes* spp.

From the order of the Psocoptera, for example, *Lepinatus* spp., *Liposcelis* spp.

From the order of the Coleoptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum*.

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa*.

From the order of the Lepidoptera, for example, *Achroia grisella, Galleria mellonella, Plodia interpunctella, Tinea cloacella, Tinea pellionella, Tineola bisselliella*.

From the order of the Siphonaptera, for example, *Ctenocephalides canis, Ctenocephalides felis, Pulex irritans, Tunga penetrans, Xenopsylla cheopis*.

From the order of the Hymenoptera, for example, *Camponotus herculeanus, Lasius fuliginosus, Lasius niger, Lasius umbratus, Monomorium pharaonis, Paravespula* spp., *Tetramorium caespitum*.

From the order of the Anoplura, for example, *Pediculus humanus capitis, Pediculus humanus corporis, Pemphigus* spp., *Phylloera vastatrix, Phthirus pubis*.

From the order of the Heteroptera, for example, *Cimex hemipterus, Cimex lectularius, Rhodinus prolixus, Triatoma infestans*.

In the field of household insecticides, they are used alone or in combination with other suitable active compounds, such as phosphoric acid esters, carbamates, pyrethroids, neonicotinoids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or in bait stations.

The compounds of the formula (I) according to the invention (active compounds) have excellent herbicidal activity against a broad spectrum of economically important mono- and dicotyledonous annual harmful plants. The active compounds act efficiently even on perennial harmful plants which produce shoots from rhizomes, root stocks and other perennial organs and which are difficult to control.

The amount of active compound used can vary within a relatively wide range. It depends essentially on the nature of the desired effect. In general, the amounts used are between 1 g and 10 kg of active compound per hectare of soil surface, preferably between 5 g and 5 kg per ha.

The advantageous effect of the compatibility with crop plants of the active compound combinations according to the invention is particularly pronounced at certain concentration ratios. However, the weight ratios of the active compounds in the active compound combinations can be varied within relatively wide ranges. In general, amounts of 0.001 to 1000 parts by weight, preferably from 0.01 to 100 parts by weight, particularly preferably 0.05 to 20 parts by weight, of one of the compounds which improves crop plant compatibility (antidotes/safeners) mentioned above under (b') are present per part by weight of active compound of the formula (I).

The active compound combinations according to the invention are generally applied in the form of finished formulations. However, the active compounds contained in the active compound combinations can, as individual formulations, also be mixed during use, i.e. be applied in the form of tank mixes.

For certain applications, in particular by the post-emergence method, it may furthermore be advantageous to include, as further additives in the formulations, mineral or vegetable oils which are tolerated by plants (for example the commercial preparation "Rako Binol"), or ammonium salts, such as, for example, ammonium sulfate or ammonium thiocyanate.

The novel active compound combinations can be used as such, in the form of their formulations or in the use forms prepared therefrom by further dilution, such as ready-to-use solutions, suspensions, emulsions, powders, pastes and granules. They are used in a customary manner, for example by watering, spraying, atomizing, dusting or broadcasting.

The application rates of the active compound combinations according to the invention can be varied within a certain range; they depend, inter alia, on the weather and on soil factors. In general, the application rates are between 0.001 and 5 kg per ha, preferably between 0.005 and 2 kg per ha, particularly preferably between 0.01 and 0.5 kg per ha.

Depending on their properties, the safeners to be used according to the invention can be used for pretreating the seed of the crop plant (seed dressing) or can be introduced into the seed furrows prior to sowing or be used separately prior to the herbicide or together with the herbicide, before or after emergence of the plants.

Examples of plants which may be mentioned are the important crop plants, such as cereals (wheat, barley, rice), corn, soybeans, potatoes, cotton, oilseed rape, beet, sugar cane and also fruit plants (with the fruits apples, pears, citrus fruits and grapevines), greater emphasis being given to cereals, corn, soybeans, potatoes, cotton and oilseed rape.

The active compounds according to the invention can be used to treat all plants and parts of plants. Plants are understood here to mean all plants and plant populations, such as wanted and unwanted wild plants or crop plants (including naturally occurring crop plants). Crop plants may be plants obtainable by conventional breeding and optimization methods or by biotechnological and gene-technological methods, or combinations of these methods, including the transgenic plants and including the plant cultivars protectable or not protectable by plant breeders' rights. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. The plant parts also include harvested material and vegetative and generative propagation material, for example cuttings, tubers, rhizomes, slips and seeds.

Treatment according to the invention of the plants and plant parts with the active compounds is carried out directly or by allowing the compounds to act on their surroundings, environment or storage space by the customary treatment methods, for example by immersion, spraying, evaporation, fogging, scattering, painting on, injection and, in the case of propagation material, in particular in the case of seeds, also by applying one or more coats.

The present invention therefore also relates to a method for controlling unwanted plants or for regulating the growth of plants, preferably in crops of plants, where one or more compound(s) according to the invention is/are applied to the plants (for example harmful plants such as monocotyledonous or dicotyledonous weeds or undesired crop plants), to the seeds (for example grains, seeds or vegetative propagules such as tubers or shoot parts with buds) or to the area on which the plants grow (for example the area under cultivation). The compounds according to the invention can be deployed, for example, prior to sowing (if appropriate also by incorporation into the soil), prior to emergence or after emergence. Specific examples of some representatives of the monocotyledonous and dicotyledonous weed flora which can be controlled by the inventive compounds are as follows, though there is no intention to restrict the enumeration to particular species:

Monocotyledonous weed plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

The plants listed can be treated in accordance with the invention in a particularly advantageous manner with the compounds of the general formula I and/or the active compound mixtures according to the invention. The preferred ranges stated above for the active ingredients or mixtures also apply to the treatment of these plants. Particular emphasis is given to the treatment of plants with the compounds or mixtures specifically mentioned in the present text.

When the compounds according to the invention are applied to the soil surface before germination, either the weed seedlings are prevented completely from emerging or the weeds grow until they have reached the cotyledon stage, but then stop growing and eventually, after three to four weeks have elapsed, die completely.

If the active compounds are applied post-emergence to the green parts of the plants, growth stops after the treatment, and the harmful plants remain at the growth stage of the time of application, or die completely after a certain time, such that competition by the weeds, which is harmful to the crop plants, is thus eliminated very early and in a lasting manner.

Although the compounds according to the invention display an outstanding herbicidal activity against monocotyledonous and dicotyledonous weeds, crop plants of economically important crops, for example dicotyledonous crops of the genera *Arachis, Beta, Brassica, Cucumis, Cucurbita, Helianthus, Daucus, Glycine, Gossypium, Ipomoea, Lactuca, Linum, Lycopersicon, Miscanthus, Nicotiana, Phaseolus, Pisum, Solanum, Vicia*, or monocotyledonous crops of the genera *Allium, Ananas, Asparagus, Avena, Hordeum, Oryza, Panicum, Saccharum, Secale, Sorghum, Triticale, Triticum, Zea*, are damaged only to an insignificant extent, or not at all, depending on the structure of the respective compound according to the invention and its application rate. This is why the present compounds are highly suitable for the selective control of unwanted plant growth in plant crops such as agriculturally useful plants or ornamentals.

In addition, the compounds according to the invention (depending on their particular structure and the application rate deployed) have outstanding growth-regulating properties in crop plants. They engage in the plant's metabolism in a regulatory fashion and can therefore be employed for the influencing, in a targeted manner, of plant constituents and for facilitating harvesting, such as, for example, by triggering desiccation and stunted growth. Moreover, they are also suitable for generally controlling and inhibiting unwanted vegetative growth without destroying the plants in the process. Inhibiting the vegetative growth plays an important role in many monocotyledonous and dicotyledonous crops since for example lodging can be reduced, or prevented completely, hereby.

As already mentioned above, it is possible to treat all plants and their parts in accordance with the invention. In a preferred embodiment, wild plant species and plant cultivars, or those obtained by conventional biological breeding methods, such as crossing or protoplast fusion, and also parts thereof, are treated. In a further preferred embodiment, transgenic plants and plant cultivars obtained by genetic engineering, if appropriate in combination with conventional methods (Genetically Modified Organisms), and parts thereof are treated. The terms "parts" or "parts of plants" or "plant parts" have been explained above.

More preferably, plants of the plant cultivars which are commercially available or are in use are treated in accordance with the invention. Plant cultivars are understood to mean plants having new properties ("traits") and which have been obtained by conventional breeding, by mutagenesis or by recombinant DNA techniques. They may be cultivars, biotypes and genotypes.

Depending on the plant species or plant cultivars, and the location and growth conditions (soils, climate, vegetation period, diet) thereof, the treatment according to the invention may also result in superadditive ("synergistic") effects. For example, possibilities include reduced application rates and/or broadening of the activity spectrum and/or an increase in the activity of the compounds and compositions usable in accordance with the invention, better plant growth, increased tolerance to high or low temperatures, increased tolerance to drought or to levels of water or soil salinity, enhanced flowering performance, easier harvesting, accelerated ripening, higher yields, higher quality and/or higher nutritional value of the harvested products, increased storage life and/or processibility of the harvested products, which exceed the effects normally to be expected.

Because of their herbicidal and plant growth-regulating properties, the active compounds can also be used to control harmful plants in crops of known genetically modified plants or of those yet to be developed. In general, the transgenic plants are notable for special advantageous properties, for example for resistances to certain pesticides, in particular certain herbicides, resistances to plant diseases or organisms that cause plant diseases, such as certain insects, nematodes or microorganisms such as fungi, bacteria or viruses. Other particular properties relate, for example, to the harvested material with regard to quantity, quality, storability, composition and specific constituents. For instance, there are known transgenic plants with an elevated starch content or altered starch quality, or with a different fatty acid composition in the harvested material. Further special properties may be tolerance or resistance to abiotic stress factors, for example heat, cold, drought, salinity and ultraviolet radiation. The active compounds can also be used in transgenic plants distinguished by higher yields, for example an improved photosynthesis performance or an improved nutrient uptake.

Preference is given to the use of the compounds of the formula (I) according to the invention or salts thereof in economically important transgenic crops of useful plants and ornamental plants, for example of cereals such as wheat, barley, rye, oats, millet, rice, cassaya and corn, or else crops of sugar beet, cotton, soybean, oilseed rape, potatoes, tomatoes, peas and other vegetables.

The compounds of the formula (I) can preferably be used as herbicides in crops of useful plants which are resistant, or have been made resistant by recombinant means, to the phytotoxic effects of the herbicides.

Conventional methods of generating novel plants which have modified properties in comparison to plants occurring to date consist, for example, in traditional breeding methods and the generation of mutants. Alternatively, novel plants with altered properties can be generated with the aid of recombinant methods (see, for example, EP 0221044, EP 0131624). For example, there have been many descriptions of:

- genetic modifications of crop plants for the purpose of modifying the starch synthesized in the plants (for example WO 92/011376 A, WO 92/014827 A, WO 91/019806 A),
- transgenic crop plants which are resistant to certain herbicides of the glufosinate type (cf., for example, EP 0242236 A, EP 0242246 A) or of the glyphosate type (WO 92/000377A) or of the sulphonylurea type (EP 0257993 A, U.S. Pat. No. 5,013,659) or to combinations or mixtures of these herbicides through "gene stacking", such as transgenic crop plants, for example corn or soybean with the tradename or the designation Optimum™ GAT™ (glyphosate ALS tolerant). Also described were transgenic plants resistant to synthetic auxins (e.g. 2,4 D) HRAC mode of action Class Oand aryloxyphenoxy propionates (fops, HRAC, Class A) (DHT, Dow Agroscience Herbicide Tolerance Trait),
- transgenic crop plants, for example cotton, which are capable of producing *Bacillus thuringiensis* toxins (Bt toxins), which make the plants resistant to certain pests (EP 0142924 A, EP 0193259 A),
- transgenic crop plants having a modified fatty acid composition (WO 91/013972 A),
- genetically modified plants having novel insect resistances based, for example, on the expression of toxins from *Photorhabdus, Xenorhabdus* symbionts from entomopathogenic nematodes and toxins from spiders, scorpions, ants, parasitic wasps,
- genetically modified crop plants with novel constituents or secondary metabolites, for example novel phytoalexins, which bring about an increased disease resistance (EP 0309862 A, EP 0464461 A),
- genetically modified plants having reduced photorespiration, which have higher yields and higher stress tolerance (EP 0305398 A),
- transgenic crop plants which produce pharmaceutically or diagnostically important proteins ("molecular pharming"),
- transgenic crop plants which are distinguished by higher yields or better quality,
- transgenic crop plants distinguished by increased tolerances to abiotic and biotic stress factors,
- transgenic crop plants which are distinguished by a combination, for example of the abovementioned novel properties ("gene stacking").

Numerous molecular biology techniques which can be used to produce novel transgenic plants with modified properties are known in principle; see, for example, I. Potrykus and G. Spangenberg (eds.) Gene Transfer to Plants, Springer Lab Manual (1995), Springer Verlag Berlin, Heidelberg, or Christou, "Trends in Plant Science" 1 (1996) 423-431.

To carry out such recombinant manipulations, nucleic acid molecules which allow mutagenesis or a sequence change by recombination of DNA sequences can be introduced into plasmids. With the aid of standard methods, it it possible, for example, to undertake base exchanges, remove parts of sequences or add natural or synthetic sequences. For the joining of the DNA fragments to one another, adaptors or linkers can be attached to the fragments; see, for example, Sambrook et al., 1989, Molecular Cloning, A Laboratory Manual, 2nd ed. Cold Spring Harbor Laboratory Press, Cold Spring Harbor, N.Y.; or Winnacker "Gene and Klone" [Genes and Clones], VCH Weinheim 2nd edition 1996.

The production of plant cells with a reduced activity of a gene product can be achieved, for example, by the expression of at least one appropriate antisense RNA, or of a sense RNA for achievement of a cosuppression effect, or the expression of at least one appropriately constructed ribozyme which specifically cleaves transcripts of the abovementioned gene product.

To this end, it is possible to use DNA molecules which encompass the entire coding sequence of a gene product inclusive of any flanking sequences which may be present, and also DNA molecules which only encompass portions of the coding sequence, in which case it is necessary for these portions to be long enough to have an antisense effect in the cells. The use of DNA sequences which have a high degree of homology to the coding sequences of a gene product, but are not completely identical to them, is also possible.

When expressing nucleic acid molecules in plants, the protein synthesized can be localized in any desired compartment of the plant cell. However, to achieve localization in a particular compartment, it is possible, for example, to join the coding region to DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give whole plants. In principle, the transgenic plants can be plants of any desired plant species, i.e. not only monocotyledonous, but also dicotyledonous, plants.

Thus, transgenic plants can be obtained whose properties are altered by overexpression, suppression or inhibition of homologous (=natural) genes or gene sequences or the expression of heterologous (=foreign) genes or gene sequences.

It is preferred to employ the compounds (I) according to the invention in transgenic crops which are resistant to growth regulators such as, for example, 2,4 D, dicamba, or against herbicides which inhibit essential plant enzymes, for example acetyl CoA carboxylases, acetolactate synthases (ALS), EPSP synthases, glutamine synthases (GS) or hydroxyphenylpyruvate dioxygenases (HPPD), or against herbicides from the group of the FOPs, sulfonylureas, glyphosates, glufosinates or benzoylisoxazoles and analogous active compounds, or against any combinations of these active compounds.

The compounds according to the invention can be used with particular preference in transgenic crop plants which are resistant to a combination of glyphosates and glufosinates, glyphosates and sulfonylureas or imidazolinones. The compounds according to the invention can be used with very particular preference in transgenic crop plants, for example corn or soybeans with the trade name or the designation Optimum™ GAT™ (glyphosate ALS tolerant). Furthermore and particularly preferably, the compounds according to the invention can be employed in transgenic plants resistant to synthetic auxins (for example 2, 4 D) having "HRAC mode of action Class " and aryloxyphenoxy propionate (fops) having "HRAC mode of action Class A" (for example DHT, Dow Agroscience Herbicide Tolerance Trait).

On employment of the active compounds according to the invention in transgenic crops, not only do the effects toward harmful plants observed in other crops occur, but often also effects which are specific to application in the particular transgenic crop, for example an altered or specifically widened spectrum of weeds which can be controlled, altered application rates which can be used for the application, preferably good combinability with the herbicides to which the transgenic crop is resistant, and influencing of growth and yield of the transgenic crop plants.

The invention therefore also relates to the use of the compounds of the formula (I) according to the invention as herbicides for controlling harmful plants in transgenic crop plants.

The compounds according to the invention can be applied in the form of wettable powders, emulsifiable concentrates, sprayable solutions, dusting products or granules in the customary formulations. The invention therefore also provides herbicidal and plant growth-regulating compositions which comprise the compounds according to the invention.

The compounds according to the invention can be formulated in various ways, according to the biological and/or physicochemical parameters required. Examples of possible formulations include: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), oil- or water-based dispersions, oil-miscible solutions, capsule suspensions (CS), dusting products (DP), seed-dressing products, granules for scattering and soil application, granules (GR) in the form of microgranules, spray granules, coated granules and adsorption granules, water-dispersible granules (WG), water-soluble granules (SG), ULV formulations, microcapsules and waxes.

These individual types of formulation are known in principle and are described, for example, in: Winnacker-Küchler, "Chemische Technologie" [Chemical Technology], Volume 7, C. Hanser Verlag Munich, 4. ed. 1986; Wade van Valkenburg, "Pesticide Formulations", Marcel Dekker, N.Y., 1973; K. Martens, "Spray Drying" Handbook, 3rd ed. 1979, G. Goodwin Ltd. London.

The necessary formulation assistants, such as inert materials, surfactants, solvents and further additives, are likewise known and are described, for example, in: Watkins, "Handbook of Insecticide Dust Diluents and Carriers", 2nd ed., Darland Books, Caldwell N.J., H. v. Olphen, "Introduction to Clay Colloid Chemistry"; 2nd ed., J. Wiley & Sons, N.Y.; C. Marsden, "Solvents Guide"; 2nd ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Interface-active Ethylene Oxide Adducts], Wiss. Verlagsgesell., Stuttgart 1976; Winnacker-Küchler, "Chemische Technologie" [Chemical Engineering], volume 7, C. Hanser Verlag Munich, 4th ed. 1986.

Based on these formulations, it is also possible to produce combinations with other pesticidally active compounds, such as, for example, insecticides, acaricides, herbicides, fungicides, and also with safeners, fertilizers and/or growth regulators, for example in the form of a finished formulation or as a tank mix.

Wettable powders are preparations which can be dispersed uniformly in water and, in addition to the active ingredient, apart from a diluent or inert substance, also comprise surfactants of the ionic and/or nonionic type (wetting agents, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleoylmethyltaurate. To produce the wettable powders, the herbicidal active compounds are ground finely, for example in customary apparatus such as hammer mills, blower mills and air-jet mills, and simultaneously or subsequently mixed with the formulation assistants.

Emulsifiable concentrates are produced by dissolving the active ingredient in an organic solvent, for example butanol, cyclohexanone, dimethylformamide, xylene, or else relatively high-boiling aromatics or hydrocarbons or mixtures of the organic solvents, with addition of one or more ionic and/or nonionic surfactants (emulsifiers). The emulsifiers used may be, for example: calcium alkylarylsulfonates such as calcium dodecylbenzenesulfonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters, or polyoxyethylene sorbitan esters, for example polyoxyethylene sorbitan fatty acid esters.

Dusts are obtained by grinding the active compound with finely distributed solid substances, for example talc, natural clays, such as kaolin, bentonite and pyrophyllite, or diatomaceous earth.

Suspension concentrates may be water- or oil-based. They may be prepared, for example, by wet grinding by means of commercial bead mills and optional addition of surfactants as have, for example, already been listed above for the other formulation types.

Emulsions, for example oil-in-water emulsions (EW), can be produced, for example, by means of stirrers, colloid mills and/or static mixers using aqueous organic solvents and optionally surfactants as already listed above, for example, for the other formulation types.

Granules can be prepared either by spraying the active compound onto granulated inert material capable of adsorption or by applying active compound concentrates to the surface of carrier substances, such as sand, kaolinites or granulated inert material, by means of adhesives, for example polyvinyl alcohol, sodium polyacrylate or mineral oils. Suitable active compounds can also be granulated in the manner customary for the production of fertilizer granules—if desired as a mixture with fertilizers.

Water-dispersible granules are prepared generally by the customary processes such as spray-drying, fluidized bed granulation, pan granulation, mixing with high-speed mixers and extrusion without solid inert material.

For the production of pan granules, fluidized bed granules, extruder granules and spray granules, see, for example, processes in "Spray-Drying Handbook" 3rd ed. 1979, G. Goodwin Ltd., London, J. E. Browning, "Agglomeration", Chemical and Engineering 1967, pages 147 ff.; "Perry's Chemical Engineer's Handbook", 5th Ed., McGraw-Hill, New York 1973, pp. 8-57.

For further details regarding the formulation of crop protection agents, see, for example, G. C. Klingman, "Weed Control as a Science", John Wiley and Sons, Inc., New York, 1961, pages 81-96 and J. D. Freyer, S. A. Evans, "Weed Control Handbook", 5th ed., Blackwell Scientific Publications, Oxford, 1968, pages 101-103.

The agrochemical formulations contain generally 0.1 to 99% by weight, especially 0.1 to 95% by weight, of compounds according to the invention.

In wettable powders, the active compound concentration is, for example, from about 10 to 90% by weight, the remainder to 100% by weight consisting of customary formulation components. In the case of emulsifiable concentrates, the active compound concentration can be from about 1 to 90, preferably from 5 to 80, % by weight. Dust-type formulations contain 1 to 30% by weight of active compound, preferably usually 5 to 20% by weight of active compound; sprayable solutions contain about 0.05 to 80% by weight, preferably from 2 to 50% by weight, of active compound. In the case of water-dispersible granules, the active ingredient content depends partly on whether the active compound is present in liquid or solid form and on which granulation assistants, fillers, etc., are used. In the water-dispersible granules, the content of active compound is, for example, between 1 and 95% by weight, preferably between 10 and 80% by weight.

In addition, the active compound formulations mentioned optionally comprise the respective customary tackifiers, wetting agents, dispersants, emulsifiers, penetrants, preservatives, antifreeze agents and solvents, fillers, carriers and dyes, defoamers, evaporation inhibitors and agents which influence the pH and the viscosity.

The treatment method according to the invention is preferably employed for genetically modified organisms such as, for example, plants or plant parts.

Genetically modified plants, so-called transgenic plants, are plants in which a heterologous gene has been stably integrated into the genome.

The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example antisense technology, cosuppression technology or RNAi technology [RNA interference]). A heterologous gene that is located in the genome is also referred to as a transgene. A transgene that is defined by its specific presence in the plant genome is called a transformation or transgenic event.

Depending on the plant species or plant cultivars, their location and growth conditions (soils, climate, vegetation period, diet), the treatment according to the invention may also result in superadditive ("synergistic") effects. For example, the following effects which exceed the effects actually to be expected are possible: reduced application rates and/or widened spectrum of activity and/or increased efficacy of the active compounds and compositions which can be used in accordance with the invention, better plant growth, increased tolerance to high or low temperatures, increased tolerance to drought or to water or soil salinity, increased flowering performance, easier harvesting, accelerated maturation, higher harvest yields, bigger fruits, greater plant height, greener leaf colour, earlier flowering, higher quality and/or a higher nutritional value of the harvested products, higher sugar concentration within the fruits, better storage stability and/or processability of the harvested products.

At certain application rates, the active compound combinations according to the invention may also have a strengthening effect in plants. Accordingly, they are suitable for mobilizing the defence system of the plant against attack by unwanted phytopathogenic fungi and/or microorganisms and/or viruses. This may be one of the reasons for the enhanced activity of the combinations according to the invention, for example against fungi. Plant-strengthening (resistance-inducing) substances are to be understood as meaning, in the present context, also those substances or combinations of substances which are capable of stimulating the defence system of plants in such a way that, when subsequently inoculated with unwanted phytopathogenic fungi and/or microorganisms and/or viruses, the treated plants display a substantial degree of resistance to these unwanted phytopathogenic fungi and/or microorganisms and/or viruses. In the present case, unwanted phytopathogenic fungi and/or microorganisms and/or viruses are understood as meaning phytopathogenic fungi, bacteria and viruses. The substances according to the invention can therefore be used for protection of plants from attack by the pathogens mentioned within a certain period after treatment. The period within which protection is achieved generally extends for from 1 to 10 days, preferably 1 to 7 days, after the treatment of the plants with the active compounds.

Plants which are furthermore preferably treated according to the invention are resistant against one or more biotic stress factors, i.e. said plants have a better defence against animal and microbial pests, such as against nematodes, insects, mites, phytopathogenic fungi, bacteria, viruses and/or viroids.

In addition to the plants and plant cultivars mentioned above, is also possible to treat those according to the invention which are resistant to one or more abiotic stress factors.

The abiotic stress conditions may include, for example, drought, cold and hot conditions, osmotic stress, waterlogging, elevated soil salinity, elevated exposure to minerals, ozone conditions, strong light conditions, limited availability of nitrogen nutrients, limited availability of phosphorus nutrients or avoidance of shade.

Plants and plant cultivars which can likewise be treated in accordance with the invention are those plants which are characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristics of heterosis, or hybrid vigor, which results in generally higher yield, increased vigor, better health and better resistance towards biotic and abiotic stress factors. Such plants are typically made by crossing an inbred male-sterile parent line (the female parent) with another inbred male-fertile parent line (the male parent). Hybrid seed is typically harvested from the male-sterile plants and sold to growers. Male-sterile plants can sometimes (e.g. in corn) be produced by detasseling (i.e. the mechanical removal of the male reproductive organs or male flowers) but, more typically, male sterility is the result of genetic determinants in the plant genome. In that case, and especially when seed is the desired product to be harvested from the hybrid plants, it is typically useful to ensure that male fertility in hybrid plants, which contain the genetic determinants responsible for male sterility, is fully restored. This can be accomplished by ensuring that the male parents have appropriate fertility restorer genes which are capable of restoring the male fertility in hybrid plants that contain the genetic determinants responsible for male sterility. Genetic determinants for male sterility may be located in the cytoplasm. Examples of cytoplasmic male sterility (CMS) were for instance described for *Brassica* species. However, genetic determinants for male sterility can also be located in the nuclear genome. Male-sterile plants can also be obtained by plant biotechnology methods such as genetic engineering. A particularly useful means of obtaining male-sterile plants is described in WO 89/10396 in which, for example, a ribonuclease such as a barnase is selectively expressed in the tapetum cells in the stamens. Fertility can then be restored by expression in the tapetum cells of a ribonuclease inhibitor such as barstar.

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium*, the CP4 gene of the bacterium *Agrobacterium* sp., the genes encoding a petunia EPSPS, a tomato EPSPS, or an eleusine EPSPS. It can also be a mutated EPSPS. Glyphosate-tolerant plants can also be obtained by expressing a gene that encodes a glyphosate oxido-reductase enzyme. Glyphosate-tolerant plants can also be obtained by expressing a gene that encodes a glyphosate acetyl transferase enzyme. Glyphosate-tolerant plants can also be obtained by selecting plants containing naturally-occurring mutations of the above-mentioned genes.

Other herbicide-resistant plants are, for example, plants that have been made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is an enzyme encoding a phosphinothricin acetyltransferase (such as the bar or pat protein from *Streptomyces* species). Plants expressing an exogenous phosphinothricin acetyltransferase have been described.

Further herbicide-tolerant plants are also plants that are made tolerant to the herbicides inhibiting the enzyme hydroxyphenylpyruvate dioxygenase (HPPD). Hydroxyphenylpyruvate dioxygenases are enzymes that catalyze the reaction in which para-hydroxyphenylpyruvate (HPP) is transformed into homogentisate. Plants tolerant to HPPD inhibitors can be transformed with a gene encoding a naturally occurring resistant HPPD enzyme, or a gene encoding a mutated HPPD enzyme. Tolerance to HPPD inhibitors can also be obtained by transforming plants with genes encoding certain enzymes enabling the formation of homogentisate despite the inhibition of the native HPPD enzyme by the HPPD inhibitor. Tolerance of plants to HPPD inhibitors can also be improved by transforming plants with a gene encoding an enzyme prephenate dehydrogenase in addition to a gene encoding an HPPD-tolerant enzyme.

Further herbicide-resistant plants are plants that have been made tolerant to acetolactate synthase (ALS) inhibitors. Known ALS inhibitors include, for example, sulfonylurea, imidazolinone, triazolopyrimidines, pyrimidinyl oxy(thio) benzoates and/or sulfonylaminocarbonyltriazolinone herbicides. Different mutations in the ALS enzyme (also known as acetohydroxy acid synthase, AHAS) are known to confer tolerance to different herbicides and groups of herbicides. The production of sulfonylurea-tolerant plants and imidazolinone-tolerant plants is described in international publication WO 1996/033270. Further sulfonylurea- and imidazolinone-tolerant plants are also described, for example in WO 2007/024782.

Further herbicide-resistant plants are plants that have been made tolerant to ACCase inhibitors.

Other plants tolerant to imidazolinone and/or sulfonylurea can be obtained by induced mutagenesis, by selection in cell cultures in the presence of the herbicide or by mutation breeding.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

In the present context, the term "insect-resistant transgenic plant" includes any plant containing at least one transgene comprising a coding sequence encoding the following:

1) an insecticidal crystal protein from *Bacillus thuringiensis* or an insecticidal portion thereof, such as the insecticidal crystal proteins described compiled online at: http://www.lifesci.sussex.ac.uk/Home/Neil_Crickmore/Bt/, or insecticidal portions thereof, e.g., proteins of the Cry protein classes Cry1Ab, Cry1Ac, Cry1F, Cry2Ab, Cry3Ae, or Cry3Bb or insecticidal portions thereof; or
2) a crystal protein from *Bacillus thuringiensis* or a portion thereof which is insecticidal in the presence of a second other crystal protein from *Bacillus thuringiensis* or a portion thereof, such as the binary toxin made up of the Cy34 and Cy35 crystal proteins; or
3) a hybrid insecticidal protein comprising portions of two different insecticidal crystal proteins from *Bacillus thuringiensis*, such as a hybrid of the proteins of 1) above or a hybrid of the proteins of 2) above, for example the Cry1A.105 protein produced by corn event MON98034 (WO 2007/027777); or 4) a protein of any one of points 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation, such as the Cry3Bb1 protein in corn events MON863 or MON88017, or the Cry3A protein in corn event MIR604; or 5) an insecticidal secreted protein from *Bacillus thuringiensis* or *Bacillus cereus*, or an insecticidal portion thereof, such as the vegetative insecticidal proteins (VIP) listed at: http://www.lifesci.sussex.ac.uk/Home/Neil_Crickmore/Bt/vip.html, for example proteins from the VIP3Aa protein class; or 6) a secreted protein from *Bacillus thuringiensis* or *Bacillus cereus* which is insecticidal in the presence of a second secreted protein from *Bacillus thuringiensis* oder *B. cereus*, such as the binary toxin made up of the VIP1A and VIP2A proteins; or 7) a hybrid insecticidal protein comprising portions from different secreted proteins from *Bacillus thuringiensis* or *Bacillus cereus*, such as a hybrid of the proteins in 1) above or a hybrid of the proteins in 2) above; or 8) a protein of any one of points 1) to 3) above wherein some, particularly 1 to 10, amino acids have been replaced by another amino acid to obtain a higher insecticidal activity to a target insect species, and/or to expand the range of the target insect species affected, and/or because of changes induced in the encoding DNA during cloning or transformation (while still encoding an insecticidal protein), such as the VIP3Aa protein in cotton event COT 102.

Of course, an insect-resistant transgenic plant, as used herein, also includes any plant comprising a combination of genes encoding the proteins of any one of the above classes 1 to 8. In one embodiment, an insect-resistant plant contains more than one transgene encoding a protein of any one of the above classes 1 to 8, to expand the range of target insect species affected, or to delay insect resistance development to the plants by using different proteins insecticidal to the same target insect species but having a different mode of action, such as binding to different receptor binding sites in the insect.

Plants or plant cultivars (obtained by plant biotechnology methods such as genetic engineering) which may also be treated according to the invention are tolerant to abiotic stress factors. Such plants can be obtained by genetic transformation, or by selection of plants containing a mutation imparting such stress resistance. Particularly useful stress-tolerant plants include the following:

a. plants which contain a transgene capable of reducing the expression and/or the activity of the poly(ADP-ribose) polymerase (PARP) gene in the plant cells or plants;

b. plants which contain a stress tolerance enhancing transgene capable of reducing the expression and/or the activity of the PARG encoding genes of the plants or plants cells;

c. plants which contain a stress tolerance-enhancing transgene coding for a plant-functional enzyme of the nicotinamide adenine dinucleotide salvage biosynthesis pathway, including nicotinamidase, nicotinate phosphoribosyltransferase, nicotinic acid mononucleotide adenyltransferase, nicotinamide adenine dinucleotide synthetase or nicotinamide phosphoribosyltransferase.

Plants or plant cultivars (obtained by plant biotechnology methods such as genetic engineering) which may also be treated according to the invention show altered quantity, quality and/or storage stability in the harvested product and/or altered properties of specific components of the harvested product such as, for example:

1) Transgenic plants which synthesize a modified starch, which in its physical-chemical characteristics, in particular the amylose content or the amylose/amylopectin ratio, the degree of branching, the average chain length, the side chain distribution, the viscosity behavior, the gelling strength, the starch grain size and/or the starch grain morphology, is changed in comparison with the synthesised starch in wild-type plant cells or plants, so that this is better suited for special applications.

2) Transgenic plants which synthesize non-starch carbohydrate polymers or which synthesize non-starch carbohydrate polymers with altered properties in comparison to wild-type plants without genetic modification. Examples are plants which produce polyfructose, especially of the inulin and levan type, plants which produce alpha-1,4-glucans, plants which produce alpha-1,6-branched alpha-1,4-glucans, and plants producing alternan.

3) Transgenic plants which produce hyaluronan

Plants or plant cultivars (obtained by plant biotechnology methods such as genetic engineering) which may also be treated according to the invention are plants, such as cotton plants, with altered fiber characteristics. Such plants can be obtained by genetic transformation, or by selection of plants containing a mutation imparting such altered fiber characteristics and include:

a) plants, such as cotton plants, containing an altered form of cellulose synthase genes;

b) plants, such as cotton plants, containing an altered form of rsw2 or rsw3 homologous nucleic acids;

c) plants, such as cotton plants, with increased expression of sucrose phosphate synthase;

d) plants, such as cotton plants, with increased expression of sucrose synthase;

e) plants, such as cotton plants, wherein the timing of the plasmodesmatal gating at the basis of the fiber cell is altered, e.g. through downregulation of fiber-selective β-1,3-glucanase;

f) plants, such as cotton plants, having fibers with altered reactivity, e.g. through the expression of N-acetylglucosaminetransferase gene including nodC, and chitin synthase genes.

Plants or plant cultivars (obtained by plant biotechnology methods such as genetic engineering) which may also be treated according to the invention are plants, such as oilseed rape or related *Brassica* plants, with altered oil profile characteristics. Such plants can be obtained by genetic transformation, or by selection of plants containing a mutation imparting such altered oil characteristics, and include:

a) plants, such as oilseed rape plants, which produce oil having a high oleic acid content;

b) plants, such as oilseed rape plants, which produce oil having a low linolenic acid content;

c) plants, such as oilseed rape plants, producing oil having a low level of saturated fatty acids.

Particularly useful transgenic plants which may be treated according to the invention are plants which comprise one or more genes which encode one or more toxins and are the transgenic plants available under the following trade names: YIELD GARD® (for example corn, cotton, soybeans), KnockOut® (for example corn), BiteGard® (for example corn), BT-Xtra® (for example corn), StarLink® (for example corn), Bollgard® (cotton), Nucotn® (cotton), Nucotn 33B®

(cotton), NatureGard® (for example corn), Protecta® and NewLeaf® (potatoes). Examples of herbicide-tolerant plants which may be mentioned are corn varieties, cotton varieties and soybean varieties which are available under the following trade names: Roundup Ready® (glyphosate tolerance, for example corn, cotton, soybean), Liberty Link® (phosphinotricin tolerance, for example oilseed rape), IMI® (imidazolinone tolerance) and SCS® (sulfonylurea tolerance), for example corn. Herbicide-resistant plants (plants bred in a conventional manner for herbicide tolerance) which should be mentioned include the varieties sold under the Clearfield® name (for example corn).

Particularly useful transgenic plants which may be treated according to the invention are plants containing transformation events, or a combination of transformation events, and that are listed for example in the databases for various national or regional regulatory agencies (see for example http://gmoinfo.jrc.it/gmp_browse.aspx and http://www.agbios.com/dbase.php).

The term "active compounds" or "compounds" always also includes the active compound combinations mentioned here.

PREPARATION EXAMPLES

Example I-1-a1-1=(I-1-a-1)

Process A

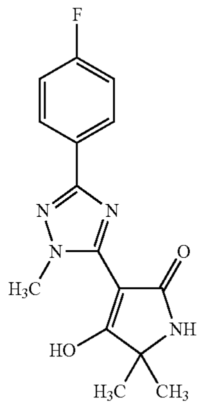 [SMILES: Cn1nc(-c2ccc(F)cc2)nc1C1=C(O)C(C)(C)NC1=O]

At room temperature, 0.5 mmol (167 mg) of methyl N-{[3-(4-fluorophenyl)-1-methyl-1H-1,2,4-triazol-5-yl]acetyl}-2-methylalaninate (compound according to Example II-1-a-1) in 0.5 ml of anhydrous DMF are added dropwise to a solution of 2.1 mmol (236 mg) of potassium tert-butoxide in 1 ml of anhydrous DMF, and the mixture is stirred at room temperatur for 2 h. 2.1 mmol (239 mg) of trifluoroacetic acid in 0.5 ml of acetonitrile are added to the reaction. The crude product is purified by HPLC. Yield: 114 mg (76% of theory).

$^1$H NMR (400 MHz, $CDCl_3$): δ=1.4 (s, 6H), 4.5 (s, 3H), 7.2 (m, 2H), 7.9 (m, 2H).

Example I-1-a4-4=(I-1-a-43)

Process A

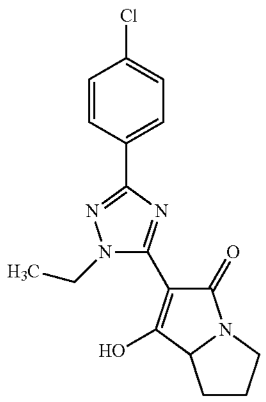 [SMILES: CCn1nc(-c2ccc(Cl)cc2)nc1C1=C(O)C2CCCN2C1=O]

At room temperature, 0.5 mmol (188 mg) of methyl 1-{[3-(4-chlorophenyl)-1-ethyl-1H-1,2,4-triazol-5-yl]acetyl}prolinate in 0.5 ml of anhydrous DMF are added dropwise to a solution of 1.6 mmol (180 mg) of potassium tert-butoxide in 1 ml of anhydrous DMF, and the mixture is stirred at room temperatur for 2 h. 182 mg (1.6 mmol) of trifluoroacetic acid in 0.5 ml of acetonitrile are added to the reaction mixture. The reaction is then purified by HPLC. Yield: 139 mg (81% of theory).

$^1$H NMR (400 MHz, $CDCl_3$): δ=1.5 (t, 3H), 2.2 (m, 3H), 3.2 (M, 1H), 3.7 (M, 1H), 4.2 (M, 1H), 5.0 (m, 2H), 7.5 (m, 2H), 7.8 (m, 2H).

The following compounds of the formula (I-1-a) are obtained analogously to Example I-1-a1-1 and Example I-1-a-4-4 and following the general preparation instructions:

(I-1-a)

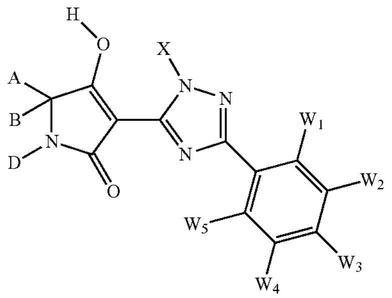

| Ex. No. | X | $W_1$ | $W_2$ | $W_3$ | $W_4$ | $W_5$ | D | A | B | Analysis | Isomer |
|---|---|---|---|---|---|---|---|---|---|---|---|
| I-1-a1-2 (I-1-a-2) | $C_2H_5$ | H | H | F | H | H | H | $CH_3$ | $CH_3$ | 1H NMR (400 MHz, $CDCl_3$): δ = 1.4 (s, 6H), 1.5 (t, 3H), 5.0 (q, 2H), 7.2 (m, 2H), 7.9 (m, 2H) | |

-continued (I-1-a)

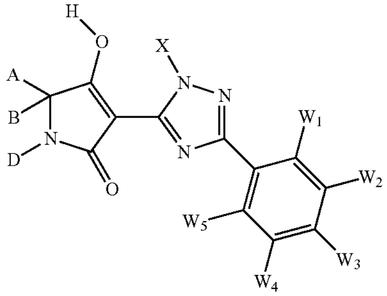

| Ex. No. | X | $W_1$ | $W_2$ | $W_3$ | $W_4$ | $W_5$ | D | A | B | Analysis | Isomer |
|---|---|---|---|---|---|---|---|---|---|---|---|
| I-1-a1-3 (I-1-a-3) | $CH_3$ | H | H | Cl | H | H | H | $CH_3$ | $CH_3$ | 1H NMR (400 MHz, $CDCl_3$: δ = 1.4 (s, 6H), 4.5 (s, 3H), 7.5 (d, 2H), 7.8 (d, 2H) | |
| I-1-a1-4 (I-1-a-4) | $C_2H_5$ | H | H | Cl | H | H | H | $CH_3$ | $CH_3$ | 1H NMR (400 MHz, $CDCl_3$: δ = 1.4 (s, 6H), 1.5 (t, 3H), 5.0 (q, 2H), 7.5 (d, 2H), 7.8 (d, 2H) | |
| I-1-a1-5 (I-1-a-5) | $CH_3$ | H | H | H | H | H | H | $CH_3$ | $CH_3$ | 1H NMR (400 MHz, $CDCl_3$: δ = 1.4 (s, 6H), 4.5 (s, 3H), 7.5 (m, 3H), 7.9 (d, 2H) | |
| I-1-a1-6 (I-1-a-6) | $C_2H_5$ | H | H | H | H | H | H | $CH_3$ | $CH_3$ | 1H NMR (400 MHz, $CDCl_3$: δ = 1.4 (s, 6H), 1.5 (t, 3H), 5.0 (q, 2H), 7.5 (t, 2H), 7.9 (d, 2H) | |
| I-1-a1-7 (I-1-a-7) | i-Pr | H | H | H | H | H | H | $CH_3$ | $CH_3$ | 1H-NMR (400 MHz, $CDCl_3$: δ = 1.4 (s, 6H), 1.6 (d, 6H), 6.4 (m, 1H), 7.5 (m, 3H), 7.9 (d, 2H) | |
| I-1-a1-8 (I-1-a-8) | i-Pr | H | H | F | H | H | H | $CH_3$ | $CH_3$ | 1H NMR (400 MHz, $CDCl_3$: δ = 1.4 (s, 6H), 1.6 (d, 6H), 6.4 (m, 1H), 7.2 (t, 2H), 7.9 (m, 2H) | |
| I-1-a1-9 (I-1-a-9) | i-Pr | H | H | Cl | H | H | H | $CH_3$ | $CH_3$ | 1H NMR (400 MHz, $CDCl_3$: δ = 1.4 (s, 6H), 1.6 (d, 6H), 6.4 (m, 1H), 7.5 (d, 2H), 7.8 (d, 2H) | |
| I-1-a1-10 (I-1-a-10) | n-Pr | H | H | H | H | H | H | $CH_3$ | $CH_3$ | 1H NMR (400 MHz, $CDCl_3$: δ = 1.0 (t, 3H), 1.4 (s, 6H), 2.0 (m, 2H), 5.0 (t, 2H), 7.5 (m, 3H), 7.8 (d, 2H) | |
| I-1-a1-12 (I-1-a-11) | n-Pr | H | H | Cl | H | H | H | $CH_3$ | $CH_3$ | 1H NMR (400 MHz, $CDCl_3$: δ = 1.0 (t, 3H), 1.4 (s, 6H), 2.0 (m, 2H), 5.0 (t, 2H), 7.5 (d, 2H), 7.8 (d, 2H) | |
| I-1-a1-16 (I-1-a-12) | Me | Cl | H | Cl | H | H | H | $CH_3$ | $CH_3$ | 1H NMR (400 MHz, $CDCl_3$: δ = 1.40 (s, 6H), 4.52 (s, 3H), 5.32 (s, br, 1H), 7.38-7.41 (m, 1H), 7.56 (s, 1H), 7.98-7.8.00 (m, 1H) | |
| I-1-a2-1 (I-1-a-13) | $CH_3$ | H | H | F | H | H | H | $—(CH_2)_2—CH(OCH_3)—(CH_2)_2—$ | | 1H NMR (400 MHz, $CDCl_3$): δ = 1.4 (m, 2H), 1.7 (m, 2H), 1.9 (m, 2H), 2.2 (m, 2H), 3.3 (m, 1H), 3.4 (s, 3H), 4.5 (s, 3H), 7.2 (t, 2H), 7.9 (m, 2H) | cis |
| I-1-a2-2 (I-1-a-14) | $C_2H_5$ | H | H | F | H | H | H | $—(CH_2)_2—CH(OCH_3)—(CH_2)_2—$ | | 1H NMR (400 MHz, DMSO-$d_6$): δ = 1.4 (t, 3H), 1.5 (m, 4H), 1.9 (m, 2H), 2.0 (m, 2H), 3.2 (m, 1H), 3.3 (s, 3H), 4.5 (q, 2H), 7.3 (t, 2H), 8.0 (m, 2H) | cis |
| I-1-a2-3 (I-1-a-15) | $CH_3$ | H | H | Cl | H | H | H | $—(CH_2)_2—CH(OCH_3)—(CH_2)_2—$ | | 1H NMR (400 MHz, $CDCl_3$): δ = 1.4 (m, 2H), 1.7 (m, 2H), 1.9 (m, 2H), 2.2 (m, 2H), 3.3 (m, 1H), 3.4 (s, 3H), 4.5 (s, 3H), 7.2 (t, 2H), 7.9 (m, 2H) | cis |
| I-1-a2-4 (I-1-a-16) | $C_2H_5$ | H | H | Cl | H | H | H | $—(CH_2)_2—CH(OCH_3)—(CH_2)_2—$ | | 1H NMR (400 MHz, $CDCl_3$): δ = 1.4 (m, 2H), 1.5 (t, 3H), 1.7 (m, 2H), 1.9 (m, | cis |

-continued (I-1-a)

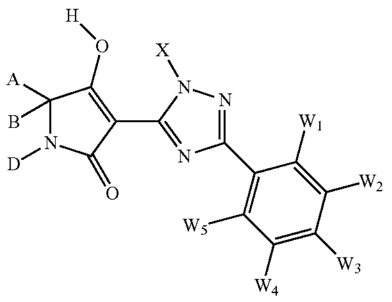

| Ex. No. | X | $W_1$ | $W_2$ | $W_3$ | $W_4$ | $W_5$ | D | A | B | Analysis | Isomer |
|---|---|---|---|---|---|---|---|---|---|---|---|
| | | | | | | | | | | 2H), 2.2 (m,2H), 3.3 (m, 1H), 3.4 (s, 3H), 5.0 (q, 2H), 7.5 (m, 3H), 7.8 (m, 2H) | |
| I-1-a2-5 (I-1-a-17) | $CH_3$ | H | H | H | H | H | H | $—(CH_2)_2—CH(OCH_3)—(CH_2)_2—$ | | 1H NMR (400 MHz, $CDCl_3$): δ = 1.4 (m, 2H), 1.7 (m, 2H), 1.9 (m, 2H), 2.2 (m, 2H), 3.3 (m, 1H), 3.4 (s, 3H), 4.5 (s, 3H), 7.5 (m, 3H), 7.9 (m, 2H) | cis |
| I-1-a2-6 (I-1-a-18) | $C_2H_5$ | H | H | H | H | H | H | $—(CH_2)_2—CH(OCH_3)—(CH_2)_2—$ | | 1H NMR (400 MHz, $CDCl_3$): δ = 1.4 (m, 2H), 1.5 (t, 3H), 1.7 (m, 2H), 1.9 (m, 2H), 2.2 (m, 2H), 3.3 (m, 1H), 3.4 (s, 3H), 5.0 (q, 2H), 7.5 (m, 3H), 7.8 (m, 2H) | cis |
| I-1-a2-7 (I-1-a-19) | i-Pr | H | H | H | H | H | H | $—(CH_2)_2—CH(OCH_3)—(CH_2)_2—$ | | 1H NMR (400 MHz, $CDCl_3$): δ = 1.4 (m, 2H), 1.5 (d, 6H), 1.7 (m, 2H), 1.9 (m, 2H), 2.2 (m, 2H), 3.3 (m, 1H), 3.4 (s, 3H), 6.5 (m, 1H), 7.5 (m, 3H), 7.8 (m, 2H) | cis |
| I-1-a2-8 (I-1-a-20) | i-Pr | H | H | F | H | H | H | $—(CH_2)_2—CH(OCH_3)—(CH_2)_2—$ | | 1H NMR (400 MHz, $CDCl_3$): δ = 1.4 (m, 2H), 1.5 (d, 6H), 1.7 (m, 2H), 1.9 (m, 2H), 2.2 (m, 2H), 3.3 (m, 1H), 3.4 (s, 3H), 6.4 (m, 1H), 7.2 (t, 2H), 7.9 (m, 2H) | cis |
| I-1-a2-9 (I-1-a-21) | i-Pr | H | H | Cl | H | H | H | $—(CH_2)_2—CH(OCH_3)—(CH_2)_2—$ | | 1H NMR (400 MHz, $CDCl_3$): δ = 1.4 (m, 2H), 1.5 (d, 6H), 1.7 (m, 2H), 1.9 (m, 2H), 2.2 (m, 2H), 3.3 (m, 1H), 3.4 (s, 3H), 6.4 (m, 1H), 7.5 (d, 2H), 7.9 (d, 2H) | cis |
| I-1-a2-10 (I-1-a-22) | n-Pr | H | H | H | H | H | H | $—(CH_2)_2—CH(OCH_3)—(CH_2)_2—$ | | 1H NMR (400 MHz, $CDCl_3$): δ = 1.0 (t, 3H), 1.4 (m, 2H), 1.7 (m, 2H), 1.9 (m, 4H), 2.2 (m, 2H), 3.3 (m, 1H), 3.4 (s, 3H), 5.0 (t, 2H), 7.5 (m, 3H), 7.9 (d, 2H) | cis |
| I-1-a2-11 (I-1-a-23) | n-Pr | H | H | F | H | H | H | $—(CH_2)_2—CH(OCH_3)—(CH_2)_2—$ | | 1H NMR (400 MHz, $CDCl_3$): δ = 1.0 (t, 3H), 1.4 (m, 2H), 1.7 (m, 2H), 1.9 (m, 4H), 2.2 (m, 2H), 3.3 (m, 1H), 3.4 (s, 3H), 5.0 (t, 2H), 7.2 (t, 2H), 7.9 (m, 2H) | cis |
| I-1-a2-12 (I-1-a-24) | n-Pr | H | H | Cl | H | H | H | $—(CH_2)_2—CH(OCH_3)—(CH_2)_2—$ | | 1H NMR (400 MHz, $CDCl_3$): δ = 1.0 (t, 3H), 1.4 (m, 2H), 1.7 (m, 2H), 1.9 (m, 4H), 2.2 (m, 2H), 3.3 (m, 1H), 3.4 (s, 3H), 5.0 (t, 2H), 7.5 (d, 2H), 7.8 (d, 2H) | cis |
| I-1-a2-13 (I-1-a-25) | $CH_2CF_3$ | H | H | F | H | H | H | $—(CH_2)_2—CH(OCH_3)—(CH_2)_2—$ | | 1H NMR (400 MHz, $CDCl_3$): δ = 1.5 (m, 2H), 1.7 (m, 2H), 1.9 (m, 2H), 2.2 (m, 2H), 2.2 (m, 2H), 3.3 (m, 1H), 3.4 (s, 3H), 5.9 (q, 2H), 7.2 (t, 2H), 8.0 (m, 2H) | cis |
| I-1-a2-14 (I-1-a-26) | n-Bu | H | H | F | H | H | H | $—(CH_2)_2—CH(OCH_3)—(CH_2)_2—$ | | 1H NMR (400 MHz, $CDCl_3$): δ = 1.0 (t, 3H), 1.4 (m, 4H), 1.7 (m, 2H), 1.9 (m, 4H), 2.2 (m, 2H), 3.3 | cis |

-continued (I-1-a)

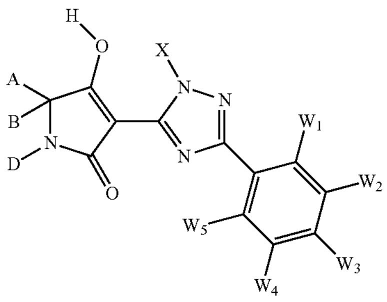

| Ex. No. | X | $W_1$ | $W_2$ | $W_3$ | $W_4$ | $W_5$ | D | A | B | Analysis | Isomer |
|---|---|---|---|---|---|---|---|---|---|---|---|
| | | | | | | | | | | (m, 1H), 3.4 (s, 3H), 5.0 (t, 2H), 7.2 (t, 2H), 7.9 (m, 2H) | |
| I-1-a2-15 (I-1-a-27) | $CH_3$ | H | H | Cl | H | H | H | $—(CH_2)_2—CH(OCH_3)—(CH_2)_2—$ | | 1H NMR (400 MHz, $CDCl_3$): δ = 1.4 (m, 2H), 1.7 (m, 2H), 1.9 (m, 2H), 2.2 (m, 2H), 3.3 (m, 1H), 3.3 (s, 3H), 3.4 (s, 3H), 3.9 (t, 2H), ), 5.2 (t, 2H), 7.5 (d, 2H), 7.8 (d, 2H) | cis |
| I-1-a2-16 (I-1-a-28) | $CH_3$ | H | H | Cl | H | H | H | $—(CH_2)_2—CH(OCH_3)—(CH_2)_2—$ | | 1H NMR (400 MHz, $CDCl_3$): δ = 1.46-1.49 (m, 2H), 1.84-1.87 (m, 2H), 1.95-1.98 (m, 2H), 2.20-2.24 (m, 2H), 3.18-3.28 (m, 1H), 3.32 (s, 3H), 3.67 (s, 3H), 3.88 (s, 2H), 3.97 (s, 3H), 7.32-7.35 (m, 1H), 7.52 (s, 1H), 7.81-7.83 (m, 1H), 8.47 (s, br, 1H) | cis |
| I-1-a3-1 (I-1-a-29) | $CH_3$ | H | H | F | H | H | H | $—(CH_2)_2—O—(CH_2)_2—$ | | 1H NMR (400 MHz, $CDCl_3$): δ = 1.5 (d, 2H), 2.2 (m, 2H), 3.6 (m, 2H), 4.2 (m, 2H), 4.5 (s, 3H), 7.2 (t, 2H), 7.9 (m, 2H) | |
| I-1-a3-2 (I-1-a-30) | $C_2H_5$ | H | H | F | H | H | H | $—(CH_2)_2—O—(CH_2)_2—$ | | 1H NMR (400 MHz, $d_6$-DMSO): δ = 1.3 (d, 2H), 1.4 (t, 3H), 2.0 (m, 2H), 3.7 (m, 2H), 3.9 (m, 2H), 4.5 (s, 3H), 7.2 (t, 2H), 7.9 (m, 2H) | |
| I-1-a3-3 (I-1-a-31) | $CH_3$ | H | H | Cl | H | H | H | $—(CH_2)_2—O—(CH_2)_2—$ | | 1H NMR (400 MHz, $CDCl_3$): δ = 1.5 (m, 2H), 2.2 (m, 2H), 3.6 (m, 2H), 4.2 (m, 2H), 4.5 (s, 3H), 7.5 (d, 2H), 7.8 (d, 2H) | |
| I-1-a3-4 (I-1-a-32) | $C_2H_5$ | H | H | Cl | H | H | H | $—(CH_2)_2—O—(CH_2)_2—$ | | 1H-NMR (400 MHz, $d_6$-DMSO): δ = 1.3 (d, 2H), 1.4 (t, 3H), 2.0 (m, 2H), 3.7 (m, 2H), 3.9 (m, 2H), 4.4 (q, 2H), 7.6 (d, 2H), 8.0 (m, 2H) | |
| I-1-a3-5 (I-1-a-33) | $CH_3$ | H | H | H | H | H | H | $—(CH_2)_2—O—(CH_2)_2—$ | | 1H NMR (400 MHz, $CDCl_3$): δ = 1.5 (d, 2H), 2.2 (m, 2H), 3.6 (m, 2H), 4.2 (m, 2H), 4.5 (s, 3H), 7.5 (m, 3H), 7.9 (m, 2H) | |
| I-1-a3-6 (I-1-a-34) | $C_2H_5$ | H | H | H | H | H | H | $—(CH_2)_2—O—(CH_2)_2—$ | | 1H NMR (400 MHz, $CDCl_3$): δ = 1.5 (m, 5H), 2.2 (m, 2H), 3.6 (m, 2H), 4.2 (m, 2H), 5.1 (q, 2H), 7.5 (m, 3H), 7.9 (m, 2H) | |
| I-1-a3-7 (I-1-a-35) | i-Pr | H | H | H | H | H | H | $—(CH_2)_2—O—(CH_2)_2—$ | | 1H NMR (400 MHz, $CDCl_3$): δ = 1.5 (m, 5H), 2.2 (m, 2H), 3.6 (m, 2H), 4.1 (m, 2H), 6.5 (m, 1H), 7.5 (m, 3H), 7.9 (m, 2H) | |
| I-1-a3-8 (I-1-a-36) | i-Pr | H | H | F | H | H | H | $—(CH_2)_2—O—(CH_2)_2—$ | | 1H NMR (400 MHz, $CDCl_3$): δ = 1.5 (m, 5H), 2.2 (m, 2H), 3.6 (m, 2H), 4.1 (m, 2H), 6.5 (m, 1H), 7.2 (t, 2H), 7.9 (m, 2H) | |

-continued (I-1-a)

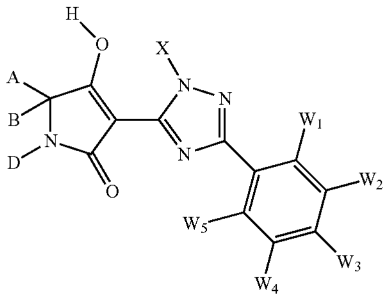

| Ex. No. | X | $W_1$ | $W_2$ | $W_3$ | $W_4$ | $W_5$ | D | A | B | Analysis | Isomer |
|---|---|---|---|---|---|---|---|---|---|---|---|
| I-1-a3-9 (I-1-a-37) | i-Pr | H | H | Cl | H | H | H | $—(CH_2)_2—O—(CH_2)_2—$ | | 1H NMR (400 MHz, $CDCl_3$): δ = 1.5 (m, 5H), 2.2 (m, 2H), 3.6 (m, 2H), 4.1 (m, 2H), 6.4 (m, 1H), 7.5 (d, 2H), 7.9 (d, 2H) | |
| I-1-a3-10 (I-1-a-38) | n-Pr | H | H | H | H | H | H | $—(CH_2)_2—O—(CH_2)_2—$ | | 1H NMR (400 MHz, $CDCl_3$): δ = 1.0 (t, 3H), 1.5 (m, 2H), 2.0 (m, 2H), 2.2 (m, 2H), 3.6 (m, 2H), 4.1 (m, 2H), 5.0 (t, 2H), 7.5 (m, 3H), 7.9 (d, 2H) | |
| I-1-a3-11 (I-1-a-39) | n-Pr | H | H | F | H | H | H | $—(CH_2)_2—O—(CH_2)_2—$ | | 1H NMR (400 MHz, $CDCl_3$): δ = 1.0 (t, 3H), 1.5 (m, 2H), 2.0 (m, 2H), 2.2 (m, 2H), 3.6 (m, 2H), 4.1 (m, 2H), 5.0 (t, 2H), 7.2 (t, 2H), 7.9 (m, 2H) | |
| I-1-a4-1 (I-1-a-40) | $CH_3$ | H | H | F | H | H | $—(CH_2)_3—$ | | H | 1H NMR (400 MHz, $CDCl_3$): δ = 1.6 (m, 1H), 2.1 (m, 2H), 2.2 (m, 1H), 3.2 (m, 1H), 3.6 (m, 1H), 4.1 (m, 1H), 4.5 (s, 3H), 7.2 (t, 2H), 7.9 (m, 2H) | |
| I-1-a4-2 (I-1-a-41) | $C_2H_5$ | H | H | F | H | H | $—(CH_2)_3—$ | | H | 1H NMR (400 MHz, $CDCl_3$): δ = 1.5 (t, 3H), 1.6 (m, 1H), 2,.1 (m, 2H), 2.2 (m, 1H), 3.2 (m, 1H), 3.7 (m, 1H), 4.1 (m, 1H), 5.0 (m, 2H), 7.2 (t, 2H), 7.9 (m, 2H) | |
| I-1-a4-3 (I-1-a-42) | $CH_3$ | H | H | Cl | H | H | $—(CH_2)_3—$ | | H | 1H NMR (400 MHz, $CDCl_3$): δ = 1.6 (m, 1H), 2.1 (m, 2H), 2.2 (m, 1H), 3.3 (m, 1H), 3.6 (m, 1H), 4.2 (m, 1H), 4.4 (s, 3H), 7.5 (d, 2H), 7.8 (d, 2H) | |
| I-1-a4-4 (I-1-a-43) | $C_2H_5$ | H | H | Cl | H | H | $—(CH_2)_3—$ | | H | 1H NMR (400 MHz, $CDCl_3$): δ = 1.5 (t, 3H), 1.6 (m, 1H), 2.1 (m, 2H), 2.2 (m, 1H), 3.3 (m, 1H), 3.6 (m, 1H), 4.2 (m, 1H), 5.0 (m, 2H), 7.5 (d, 2H), 7.8 (d, 2H) | |
| I-1-a4-6 (I-1-a-44) | $C_2H_5$ | H | H | H | H | H | $—(CH_2)_3—$ | | H | 1H NMR (400 MHz, $CDCl_3$): δ = 1.5 (t, 3H), 2.1 (m, 2H), 2.2 (m, 1H), 3.3 (m, 1H), 3.6 (m, 1H), 4.1 (m, 1H), 5.0 (m, 2H), 7.5 (m, 3H), 7.8 (d, 2H) | |
| I-1-a4-7 (I-1-a-45) | i-Pr | H | H | H | H | H | $—(CH_2)_3—$ | | H | 1H NMR (400 MHz, $CDCl_3$): δ = 1.5 (d, 3H), 1.6 (d, 3H), 2.1 (m, 2H), 2.2 (m, 1H), 3.3 (m, 1H), 3.6 (m, 1H), 4.1 (m, 1H), 6.3 (m, 1H), 7.5 (m, 3H), 7.8 (d, 2H) | |

-continued (I-1-a)

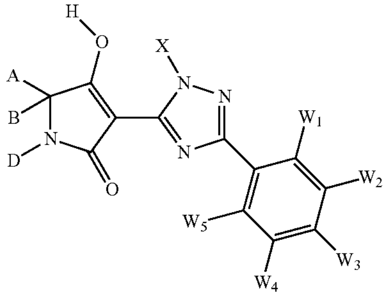

| Ex. No. | X | $W_1$ | $W_2$ | $W_3$ | $W_4$ | $W_5$ | D | A | B | Analysis | Isomer |
|---|---|---|---|---|---|---|---|---|---|---|---|
| I-1-a4-8 (I-1-a-46) | i-Pr | H | H | F | H | H | | $-(CH_2)_3-$ | H | 1H NMR (400 MHz, $CDCl_3$): δ = 1.5 (d, 3H), 1.6 (d, 3H), 2.1 (m, 2H), 2.2 (m, 1H), 3.3 (m, 1H), 3.6 (m, 1H), 4.1 (m, 1H), 6.3 (m, 1H), 7.2 (t, 2H), 7.9 (m, 2H) | |
| I-1-a4-9 (I-1-a-47) | i-Pr | H | H | Cl | H | H | | $-(CH_2)_3-$ | H | 1H NMR (400 MHz, $CDCl_3$): δ = 1.5 (d, 3H), 1.6 (d, 3H), 2.1 (m, 2H), 2.2 (m, 1H), 3.3 (m, 1H), 3.6 (m, 1H), 4.1 (m, 1H), 6.3 (m, 1H), 7.5 (d, 2H), 7.8 (d, 2H) | |
| I-1-a4-10 (I-1-a-48) | n-Pr | H | H | H | H | H | | $-(CH_2)_3-$ | H | 1H NMR (400 MHz, $CDCl_3$): δ = 1.0 (t, 3H), 1.6 (m, 1H), 2.0 (m, 2H), 2.1 (m, 2H), 2.2 (m, 1H), 3.3 (m, 1H), 3.6 (m, 1H), 4.1 (m, 1H), 4.9 (m, 1H), 5.0 (m, 1H), 7.5 (m, 3H), 7.8 (d, 2H) | |
| I-1-a4-11 (I-1-a-49) | n-Pr | H | H | F | H | H | | $-(CH_2)_3-$ | H | 1H NMR (400 MHz, $CDCl_3$): δ = 1.0 (t, 3H), 1.6 (m, 1H), 2.0 (m, 2H), 2.1 (m, 2H), 2.2 (m, 1H), 3.3 (m, 1H), 3.6 (m, 1H), 4.1 (m, 1H), 4.9 (m, 1H), 5.0 (m, 1H), 7.2 (t, 2H), 7.9 (m, 2H) | |
| I-1-a5-1 (I-1-a-50) | $CH_3$ | H | H | F | H | H | c-Pr | H | H | 1H NMR (400 MHz, $CDCl_3$): δ = 0.8 (m, 4H), 2.7 (m, 1H), 3.8 (s, 2H), 4.5 (s, 3H), 7.2 (m, 2H), 7.9 (m, 2H) | |
| I-1-a5-2 (I-1-a-51) | $C_2H_5$ | H | H | F | H | H | c-Pr | H | H | 1H NMR (400 MHz, $CDCl_3$): δ = 0.8 (m, 4H), 1.5 (t, 3H), 2.7 (m, 1H), 3.8 (s, 2H), 5.0 (q, 2H), 7.2 (m, 2H), 7.9 (m, 2H) | |
| I-1-a5-3 (I-1-a-52) | $CH_3$ | H | H | Cl | H | H | c-Pr | H | H | 1H NMR (400 MHz, $CDCl_3$): δ = 0.8 (m, 4H), 2.7 (m, 1H), 3.8 (s, 2H), 4.5 (s, 3H), 7.2 (m, 2H), 7.9 (m, 2H) | |
| I-1-a5-4 (I-1-a-53) | $C_2H_5$ | H | H | Cl | H | H | c-Pr | H | H | 1H NMR (400 MHz, $CDCl_3$): δ = 0.8 (m, 4H), 1.5 (t, 3H), 2.7 (m, 1H), 3.8 (s, 2H), 5.0 (q, 2H), 7.5 (d, 2H), 7.8 (d, 2H) | |
| I-1-a5-5 (I-1-a-54) | $CH_3$ | H | H | H | H | H | c-Pr | H | H | 1H NMR (400 MHz, $CDCl_3$): δ = 0.8 (m, 4H), 2.7 (m, 1H), 3.8 (s, 2H), 4.5 (s, 3H), 7.5 (m, 3H), 7.9 (m, 2H) | |

-continued (I-1-a)

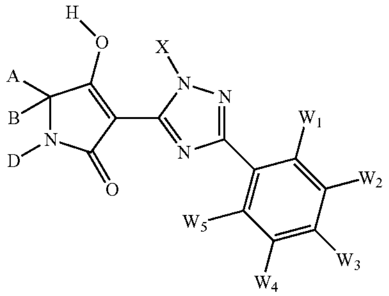

| Ex. No. | X | $W_1$ | $W_2$ | $W_3$ | $W_4$ | $W_5$ | D | A | B | Analysis | Isomer |
|---|---|---|---|---|---|---|---|---|---|---|---|
| I-1-a5-6 (I-1-a-55) | $C_2H_5$ | H | H | H | H | H | c-Pr | H | H | 1H NMR (400 MHz, $CDCl_3$): δ = 0.8 (m, 4H), 1.5 (t, 3H), 2.7 (m, 1H), 3.8 (s, 2H), 5.0 (q, 2H), 7.5 (m, 3H), 7.9 (m, 2H) | |
| I-1-a5-7 (I-1-a-56) | i-Pr | H | H | H | H | H | c-Pr | H | H | 1H NMR (400 MHz, $CDCl_3$): δ = 0.8 (m, 4H), 1.5 (d, 6H), 2.7 (m, 1H), 3.7 (s, 2H), 6.5 (m, 1H), 7.5 (m, 3H), 7.9 (m, 2H) | |
| I-1-a5-8 (I-1-a-57) | i-Pr | H | H | F | H | H | c-Pr | H | H | 1H NMR (400 MHz, $CDCl_3$): δ = 0.8 (m, 4H), 1.5 (d, 6H), 2.7 (m, 1H), 3.7 (s, 2H), 6.5 (m, 1H), 7.2 (t, 2H), 7.9 (d, 2H) | |
| I-1-a5-9 (I-1-a-58) | i-Pr | H | H | Cl | H | H | c-Pr | H | H | 1H NMR (400 MHz, $CDCl_3$): δ = 0.8 (m, 4H), 1.5 (d, 6H), 2.7 (m, 1H), 3.7 (s, 2H), 6.4 (m, 1H), 7.5 (d, 2H), 7.9 (d, 2H) | |
| I-1-a5-10 (I-1-a-59) | n-Pr | H | H | H | H | H | c-Pr | H | H | 1H NMR (400 MHz, $CDCl_3$): δ = 0.8 (m, 4H), 1.0 (t, 3H), 2.0 (m, 2H), 2.7 (m, 1H), 3.7 (s, 2H), 5.0 (t, 2H), 7.5 (d, 2H), 7.9 (d, 2H) | |
| I-1-a5-11 (I-1-a-60) | n-Pr | H | H | F | H | H | c-Pr | H | H | 1H NMR (400 MHz, $CDCl_3$): δ = 0.8 (m, 4H), 1.0 (t, 3H), 2.0 (m, 2H), 2.7 (m, 1H), 3.7 (s, 2H), 5.0 (t, 2H), 7.2 (t, 2H), 7.9 (m, 2H) | |
| I-1-a6-3 (I-1-a-61) | $CH_3$ | H | H | Cl | H | H | H | $—(CH_2)_2—CH(On\text{-}Pr)—(CH_2)_2—$ | | 1H NMR (400 MHz, $CDCl_3$): δ = 0.9 (t, 3H), 1.4 (m, 2H), 1.7 (m, 4H), 1.9 (m, 2H), 2.2 (m, 2H), 3.3 (m, 1H), 3.5 (t, 2H), 4.5 (s, 3H), 7.5 (d, 2H), 7.8 (d, 2H) | cis |
| I-1-a7-2 (I-1-a-62) | $C_2H_5$ | H | H | F | H | H | H | $—(CH_2)_2—CH(Me)—(CH_2)_2—$ | | 1H NMR (400 MHz, $CDCl_3$): δ = 1.0 (d, 3H), 1.1 (m, 2H), 1.5 (t, 3H), 1.6 (m, 2H), 1.9 (m, 4H), 5.0 (q, 2H), 7.2 (t, 2H), 7.9 (m, 2H) | cis |
| I-1-a7-3 (I-1-a-63) | $CH_3$ | H | H | Cl | H | H | H | $—(CH_2)_2—CH(Me)—(CH_2)_2—$ | | 1H NMR (400 MHz, $CDCl_3$): δ = 1.0 (d, 3H), 1.1 (m, 2H), 1.6 (m, 3H), 1.9 (m, 4H), 4.5 (s, 3H), 7.5 (d, 2H), 7.8 (d, 2H) | cis |
| I-1-a7-7 (I-1-a-64) | i-Pr | H | H | H | H | H | H | $—(CH_2)_2—CH(Me)—(CH_2)_2—$ | | 1H NMR (400 MHz, $CDCl_3$): δ = 1.0 (d, 3H), 1.1 (m, 2H), 1.6 (m, 3H), 1.9 (m, 4H), 6.4 (m, 1H), 7.5 (m, 3H), 7.9 (m, 2H) | |

-continued (I-1-a)

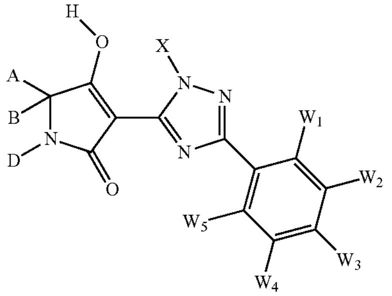

| Ex. No. | X | $W_1$ | $W_2$ | $W_3$ | $W_4$ | $W_5$ | D | A | B | Analysis | Isomer |
|---|---|---|---|---|---|---|---|---|---|---|---|
| I-1-a7-11 (I-1-a-65) | n-Pr | H | H | F | H | H | H | $-(CH_2)_2-CH(Me)-(CH_2)_2-$ | | 1H NMR (400 MHz, $CDCl_3$): δ = 1.0 (m, 6H), 1.5 (m, 1H), 1.6 (m, 2H), 1.9 (m, 6H), 5.0 (t, 2H), 7.2 (t, 2H), 7.9 (m, 2H) | |
| I-1-a8-3 (I-1-a-66) | $CH_3$ | H | H | Cl | H | H | H | $-(CH_2)_2-CH(CF_3)-(CH_2)_2-$ | | 1H NMR (400 MHz, $CDCl_3$): δ = 1.6 (m, 2H), 1.7 (m, 2H), 1.9 (m, 2H), 2.1 (m, 2H), 4.5 (s, 3H), 7.5 (d, 2H), 7.8 (d, 2H) | |
| I-1-a9-3 (I-1-a-67) | $CH_3$ | H | H | Cl | H | H | H | $-(CH_2)_2-N(OEt)-(CH_2)_2-$ | | 1H NMR (400 MHz, $CDCl_3$): δ = 1.2 (t, 3H), 1.6 (m, 2H), 2.2 (m, 2H), 2.5 (m, 2H), 3.4 (m, 2H), 3.8 (q, 2H), 4.5 (s, 3H), 7.5 (d, 2H), 7.8 (d, 2H) | |
| I-1-a10-3 (I-1-a-68) | $CH_3$ | H | H | Cl | H | H | H | $-(CH_2)_2-N(OMe)-(CH_2)_2-$ | | 1H NMR (400 MHz, $CDCl_3$): δ = 1.8 (m, 2H), 2.2 (m, 2H), 4.5 (s, 3H), 7.5 (d, 2H), 7.8 (d, 2H) | |
| I-1-a11-3 (I-1-a-69) | $CH_3$ | H | H | Cl | H | H | H | $-(CH_2)_2-C(O-CH_2CHCH_2)-(CH_2)_2-$ | | 1H NMR (400 MHz, $CDCl_3$): δ = 3.9 (m, 2H), 4.5 (s, 3H), 7.5 (d, 2H), 7.8 (d, 2H) | |
| I-1-a12-3 (I-1-a-70) | $CH_3$ | H | H | Cl | H | H | H | $-(CH_2)_2-C(Et)(OMe)-(CH_2)_2-$ | | 1H NMR (400 MHz, $CDCl_3$): δ = 0.9 (t, 3H), 1.5 (q, 2H), 2.0 (m, 2H), 2.2 (m, 2H), 3.2 (s, 3H), 4.5 (s, 3H), 7.5 (d, 2H), 7.8 (d, 2H) | |
| I-1-a13-3 (I-1-a-71) | $CH_3$ | H | H | Cl | H | H | H | $-(CH_2)_2-C(OCH_2CHMeCH_2O)-(CH_2)_2-$ | | 1H NMR (400 MHz, $CDCl_3$): δ = 0.8 (d, 3H), 1.6 (m, 4H), 1.7 (m, 2H), 2.2 (m, 4H), 3.5 (t, 2H), 3.6 (t, 2H), 3.8 (t, 2H), 4.5 (s, 3H), 7.5 (d, 2H), 7.8 (d, 2H) | |
| I-1-a14-3 (I-1-a-72) | $CH_3$ | H | H | Cl | H | H | H | c-Pr | c-Pr | 1H NMR (400 MHz, $CDCl_3$): δ = 0.3 (m, 5H), 0.6 (m, 2H), 1.3 (m, 3H), 4.5 (s, 3H), 7.5 (d, 2H), 7.8 (d, 2H) | |
| I-1-a14-11 (I-1-a-73) | n-Pr | H | H | F | H | H | H | c-Pr | c-Pr | 1H NMR (400 MHz, $CDCl_3$): δ = 0.3 (m, 5H), 0.6 (m, 2H), 1.0 (t, 3H), 1.3 (m, 2H), 2.0 (m, 2H), 4.9 (m, 2H), 7.2 (t, 2H), 7.9 (m, 2H) | |

c-Pr = cyclopropyl;
i-Pr = isopropyl;
n-Pr = n-propyl;
n-Bu = n-butyl,
Pr = propyl,
Me = methyl,
Et = ethyl

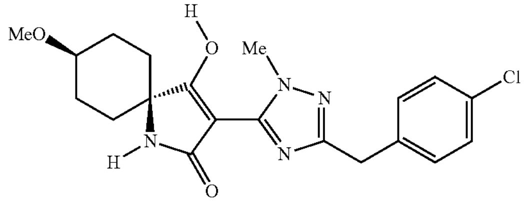

Bsp. 1-15-a2-4 = (I-1-a-74)

1H NMR ($CDCl_3$): δ=1.3 (m, 2H), 1.6 (m, 2H), ), 1.8 (m, 2H), 2.2 (m, 2H), 3.2 (m, 1H), 3.4 (s, 3H), 4.0 (s, 2H), 4.4 (s, 3H), 7.2 (d, 2H), 7.4 (d, 2H)

Example I-1-b2-4=(I-1-g-1)

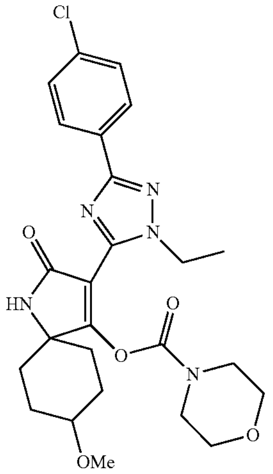 [SMILES: CCn1nc(-c2ccc(Cl)cc2)nc1C1=C(OC(=O)N2CCOCC2)C2(CCC(OC)CC2)NC1=O]

70 mg (0.17 mmol) of 1-8-a1 are dissolved in 5 ml of dichloromethane. 35.2 mg (0.347 mmol) of triethylamine are added successively to this solution, and the mixture is cooled to 0° C. A solution of 52.0 mg (0.347 mmol) of morpholine-4-carbonyl chloride in 1 ml of dichlormethane is then added dropwise. The mixture is stirred at room temperature overnight. The mixture is then washed with water and dried over magnesium sulfate. The solution is concentrated under reduced pressure and purified by HPLC. Yield: 78 mg (87%).

1H NMR ($CDCl_3$): δ=1.5 (t, 3H), 1.9 (m, 4H), ), 2.2 (m, 2H), 3.2 (m, 2H), 3.3 (m, 3H), 3.4 (s, 3H), 3.7 (m, 2H), 3.8 (m, 2H), ), 4.3 (s, 2H), 7.2 (d, 2H), 8.0 (m, 2H)

Example II-1-a3-4=(II-1)

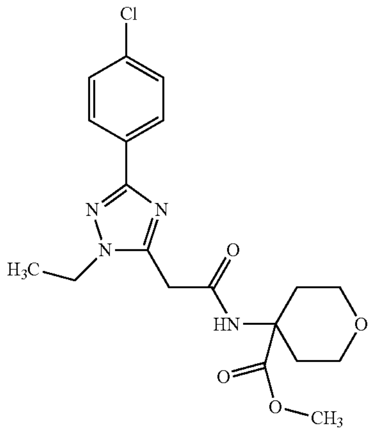 [SMILES: CCn1nc(-c2ccc(Cl)cc2)nc1CC(=O)NC1(C(=O)OC)CCOCC1]

1.2 mmol (318 mg) of [3-(4-chlorophenyl)-1-ethyl-1H-1,2,4-triazol-5-yl]acetic acid and 0.1 mmol (7 mg) of DMF are dissolved in 5 ml of anhydrous dichloromethane 1.3 mmol of oxalyl chloride (163 mg) in 3 ml of anhydrous dichloromethane are added dropwise. The solution is stirred at room temperature for 8 h and then concentrated under reduced pressure. The [3-(4-chlorophenyl)-1-ethyl-1H-1,2,4-triazol-5-yl]acetyl chloride obtained in this manner is processed further in crude form.

1.2 mmol (234 mg) of 4-(methoxycarbonyl)tetrahydro-2H-pyran-4-aminium chloride and 0.1 mmol (12 mg) of N,N-dimethylpyridine-4-amine (DMAP) are taken up in 5 ml of dichloromethane and cooled to 0-5° C. 2.8 mmol (282 mg) of triethylamine in 2 ml of dichloromethane are then added dropwise, and the mixture is stirred at room temperature for 0.25 h. The solution obtained in this manner is added dropwise to the solution, described above, of [3-(4-chlorophenyl)-1-ethyl-1H-1,2,4-triazol-5-yl]acetyl chloride in 5 ml of dichloromethane and stirred at room temperature for 16 h. The reaction is poured onto ice-water and extracted with dichloromethane. The combined organic phases are dried over $MgSO_4$ and concentrated by rotary evaporation. The crude product is purified by HPLC. Yield: 438 mg (90.0% of theory).

$^1$H NMR (400 MHz, $CDCl_3$): δ=2.0 (m, 2H), 3.6 (s, 3H), 3.7 (m, 2H), 3.9 (m, 2H), 4.0 (s, 3H), 4.1 (s, 2H), 7.4 (d, 2H), 8.0 (d, 2H).

The following compounds of the formula (II) are obtained analogously to Example (II-1-a3-4) and following the general preparation instructions:

(II)

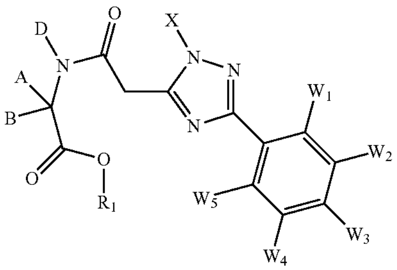

| Ex. No. | X | $W_1$ | $W_2$ | $W_3$ | $W_4$ | $W_5$ | $W_5$ | $R_1$ | D | A | B | Analysis | Isomer |
|---|---|---|---|---|---|---|---|---|---|---|---|---|---|
| II-1-a1-5 (II-2) | $CH_3$ | H | H | H | H | H | H | $CH_3$ | H | $CH_3$ | $CH_3$ | 1H NMR (400 MHz, $CDCl_3$: δ = 1.5 (s, 6H), 3.7 (s, 3H), 3.8 (s, 2H), 3.9 (s, 3H), 7.4 (m, 3H), 8.1 (d, 2H) | cis |

-continued (II)

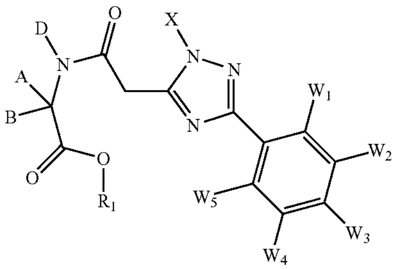

| Ex. No. | X | $W_1$ | $W_2$ | $W_3$ | $W_4$ | $W_5$ | $W_5$ | $R_1$ | D | A | B | Analysis | Isomer |
|---|---|---|---|---|---|---|---|---|---|---|---|---|---|
| II-1-a1-6 (II-3) | $C_2H_5$ | H | H | H | H | H | H | $CH_3$ | H | $CH_3$ | $CH_3$ | 1H NMR (400 MHz, $CDCl_3$: δ = 1.5 (t, 3H), 1.5 (s, 6H), 3.7 (s, 3H), 3.8 (s, 2H), 4.2 (q, 2H), 7.4 (m, 3H), 8.1 (d, 2H) | cis |
| II-1-a1-7 (II-4) | i-Pr | H | H | H | H | H | H | $CH_3$ | H | $CH_3$ | $CH_3$ | 1H NMR (400 MHz, $CDCl_3$: δ = 1.5 (d, 6H), 1.6 (s, 6H), 3.7 (s, 3H), 3.8 (s, 2H), 4.6 (m, 1H), 7.4 (m, 3H), 8.1 (d, 2H) | cis |
| II-1-a1-8 (II-5) | i-Pr | H | H | F | H | H | H | $CH_3$ | H | $CH_3$ | $CH_3$ | 1H NMR (400 MHz, $CDCl_3$: δ = 1.5 (d, 6H), 1.6 (s, 6H), 3.7 (s, 3H), 3.8 (s, 2H), 4.6 (m, 1H), 7.1 (t, 2H), 8.1 (m, 2H) | cis |
| II-1-a1-9 (II-6) | i-Pr | H | H | Cl | H | H | H | $CH_3$ | H | $CH_3$ | $CH_3$ | 1H NMR (400 MHz, $CDCl_3$: δ = 1.5 (d, 6H), 1.6 (s, 6H), 3.7 (s, 3H), 3.8 (s, 2H), 4.6 (m, 1H), 7.4 (d, 2H), 8.0 (d, 2H) | cis |
| II-1-a1-10 (II-7) | n-Pr | H | H | H | H | H | H | $CH_3$ | H | $CH_3$ | $CH_3$ | 1H NMR (400 MHz, $CDCl_3$: δ = 1.0 (t, 3H), 1.5 (s, 6H), 1.9 (m, 2H), 3.7 (s, 3H), 3.8 (s, 2H), 4.1 (t, 2H), 7.4 (m, 3H), 8.1 (d, 2H) | cis |
| II-1-a1-11 (II-8) | n-Pr | H | H | F | H | H | H | $CH_3$ | H | $CH_3$ | $CH_3$ | 1H NMR (400 MHz, $CDCl_3$: δ = 1.0 (t, 3H), 1.6 (s, 6H), 1.9 (m, 2H), 3.7 (s, 3H), 3.7 (s, 2H), 4.1 (t, 2H), 7.1 (t, 2H), 8.1 (m, 2H) | cis |
| II-1-a2-4 (II-9) | $C_2H_5$ | H | H | Cl | H | H | H | $CH_3$ | H | $-(CH_2)_2-CH(OCH_3)-(CH_2)_2-$ | | 1H NMR (400 MHz, $CDCl_3$): δ = 1.5 (t, 3H), 1.9 (m, 2H), 2.0 (m, 2H), 2.3 (m, 2H), 3.2 (m, 1H), 3.3 (s, 3H), 3.7 (s, 3H), 3.8 (s, 2H), 4.2 (q, 2H), 7.4 (d, 2H), 8.0 (d, 2H) | cis |
| II-1-a2-5 (II-10) | $CH_3$ | H | H | H | H | H | H | $CH_3$ | H | $-(CH_2)_2-CH(OCH_3)-(CH_2)_2-$ | | 1H NMR (400 MHz, $CDCl_3$): δ = 1.5 (m, 2H), 1.9 (m, 2H), 2.0 (m, 2H), 2.3 (m, 2H), 3.2 (m, 1H), 3.3 (s, 3H), 3.7 (s, 3H), 3.8 (s, 2H), 4.5 (m, 1H), 7.4 (m, 3H), 8.0 (d, 2H) | cis |
| II-1-a2-6 (II-11) | $C_2H_5$ | H | H | H | H | H | H | $CH_3$ | H | $-(CH_2)_2-CH(OCH_3)-(CH_2)_2-$ | | 1H NMR (400 MHz, $CDCl_3$): δ = 1.5 (t, 3H), 1.9 (m, 2H), 2.0 (m, 2H), 2.3 (m, 2H), 3.2 (m, 1H), 3.3 (s, 3H), 3.7 (s, 3H), 3.8 (s, 2H), 4.2 (q, 2H), 7.4 (m, 3H), 8.0 (d, 2H) | cis |
| II-1-a2-7 (II-12) | i-Pr | H | H | H | H | H | H | $CH_3$ | H | $-(CH_2)_2-CH(OCH_3)-(CH_2)_2-$ | | 1H NMR (400 MHz, $CDCl_3$): δ = 1.5 (d, 6H), 1.9 (m, 2H), 2.0 (m, 2H), 2.3 (m, 2H), 3.2 (m, 1H), 3.3 (s, 3H), 3.7 (s, 3H), 3.8 (s, 2H), 3.9 (s, 3H), 7.4 (m, 3H), 8.0 (d, 2H) | cis |
| II-1-a2-8 (II-13) | i-Pr | H | H | F | H | H | H | $CH_3$ | H | $-(CH_2)_2-CH(OCH_3)-(CH_2)_2-$ | | 1H NMR (400 MHz, $CDCl_3$): δ = 1.5 (d, 6H), 1.9 (m, 2H), 2.0 (m, 2H), 2.3 (m, 2H), 3.2 (m, 1H), 3.3 (s, 3H), 3.7 (s, 3H), 3.8 (s, 2H), 4.5 (m, 1H), 7.1 (t, 2H), 8.0 (m, 2H) | cis |
| II-1-a2-9 (II-14) | i-Pr | H | H | Cl | H | H | H | $CH_3$ | H | $-(CH_2)_2-CH(OCH_3)-(CH_2)_2-$ | | 1H NMR (400 MHz, $CDCl_3$): δ = 1.5 (d, 6H), 1.9 (m, 2H), 2.0 (m, 2H), 2.3 (m, 2H), 3.2 (m, 1H), 3.3 (s, 3H), 3.7 (s, 3H), 3.8 (s, 2H), 4.5 (m, 1H), 7.4 (d, 2H), 8.0 (d, 2H) | cis |
| II-1-a2-10 (II-15) | n-Pr | H | H | H | H | H | H | $CH_3$ | H | $-(CH_2)_2-CH(OCH_3)-(CH_2)_2-$ | | 1H NMR (400 MHz, $CDCl_3$): δ = 1.0 (t, 3H), 1,5 (m, 2H), 2.3 (m, 2H), 3.2 (m, 1H), 3.3 (s, 3H), 3.7 (s, 3H), 3.8 (s, 2H), 4.1 (t, 2H), 7.4 (d, 2H), 8.0 (d, 2H) | cis |
| II-1-a2-11 (II-16) | n-Pr | H | H | F | H | H | H | $CH_3$ | H | $-(CH_2)_2-CH(OCH_3)-(CH_2)_2-$ | | 1H NMR (400 MHz, $CDCl_3$): δ = 1.0 (t, 3H), 1,5 (m, 2H), 2.3 (m, 2H), 3.2 (m, 1H), 3.3 (s, 3H), 3.7 (s, 3H), 3.8 (s, 2H), 4.1 (t, 2H), 7.1 (t, 2H), 8.0 (m, 2H) | cis |
| II-1-a6-3 (II-17) | $CH_3$ | H | H | Cl | H | H | H | $CH_3$ | H | $-(CH_2)_2-CH(On-Pr)-(CH_2)_2-$ | | 1H NMR (400 MHz, $CDCl_3$): δ = 0.9 (t, 3H), 2.3 (m, 2H), 3.2 (m, 1H), 3.4 (t, 2H), 3.7 (s, 3H), 3.9 (s, 3H), 7.4 (d, 2H), 8.0 (d, 2H) | |

-continued (II)

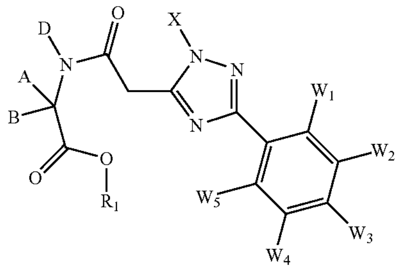

| Ex. No. | X | $W_1$ | $W_2$ | $W_3$ | $W_4$ | $W_5$ | $W_5$ | $R_1$ | D | A | B | Analysis | Isomer |
|---|---|---|---|---|---|---|---|---|---|---|---|---|---|
| II-1-a7-2 (II-18) | $C_2H_5$ | H | H | F | H | H | H | $CH_3$ | H | $—(CH_2)_2—CH(Me)—(CH_2)_2—$ | | 1H NMR (400 MHz, $CDCl_3$): δ = 0.9 (d, 3H), 1,2 (m, 2H), 1.4 (m, 1H), 1.5 (t, 3H), 1.6 (m, 2H), 1.8 (m, 2H), 2.2 (m, 2H), 3.6 (s, 3H), 4.1 (s, 2H), 4.3 (t, 2H), 7.2 (t, 2H), 8.1 (m, 2H) | |
| II-1-a7-3 (II-19) | $CH_3$ | H | H | Cl | H | H | H | $CH_3$ | H | $—(CH_2)_2—CH(Me)—(CH_2)_2—$ | | 1H NMR (400 MHz, $CDCl_3$): δ = 0.9 (d, 3H), 1,2 (m, 2H), 1.4 (m, 1H), 1.6 (m, 2H), 1.8 (m, 2H),), 2.2 (m, 2H), 3.6 (s, 3H), 4.0 (s, 2H), 4.3 (q, 2H), 7.4 (d, 2H), 8.0 (m, 2H) | |
| II-1-a7-7 (II-20) | i-Pr | H | H | H | H | H | H | $CH_3$ | H | $—(CH_2)_2—CH(Me)—(CH_2)_2—$ | | 1H NMR (400 MHz, $CDCl_3$): δ = 0.9 (d, 3H), 1,2 (m, 2H), 1.4 (m, 1H), 1.6 (m, 2H), 1.8 (m, 2H), 2.0 (m, 2H), 2.2 (m, 2H), 3.6 (s, 3H), 4.1 (s, 2H), 4.3 (t, 2H), 7.2 (t, 2H), 8.1 (m, 2H) | |
| II-1-Ia7-11 (II-21) | n-Pr | H | H | F | H | H | H | $CH_3$ | H | $—(CH_2)_2—CH(Me)—(CH_2)_2—$ | | 1H NMR (400 MHz, $CDCl_3$): δ = 0.9 (d, 3H), 1.0 (t, 3H), 1,2 (m, 2H), 1.4 (m, 1H), 1.6 (d, 6H), 1.8 (m, 2H), 2.0 (m, 2H), 2.2 (m, 2H), 4.8 (m, 1H), 7.5 (m, 3H), 8.1 (m, 2H) | |
| II-1-a9-3 (II-22) | $CH_3$ | H | H | Cl | H | H | H | $CH_3$ | H | $—(CH_2)_2—N(OEt)—(CH_2)_2—$ | | 1H NMR (400 MHz, $CDCl_3$): δ = 1,2 (t, 3H), 2.2 (m, 2H), 3.7 (s 3H), 3.8 (s, 2H), 3.9 (s, 3H), 7.4 (d, 2H), 8.0 (d, 2H) | |
| II-1-a10-3 (II-23) | $CH_3$ | H | H | Cl | H | H | H | $CH_3$ | H | $—(CH_2)_2—N(OMe)—(CH_2)_2—$ | | 1H NMR (400 MHz, $CDCl_3$): δ = 2.2 (m, 2H), 3.5 (s, 3H), 3.7 (s 3H), 3.8 (s, 2H), 3.9 (s, 3H), 7.4 (d, 2H), 8.0 (d, 2H) | |
| II-1-a3-11 (II-24) | n-Pr | H | H | F | H | H | H | $CH_3$ | H | $—(CH_2)_2—O—(CH_2)_2—$ | | 1H NMR (400 MHz, $CDCl_3$): δ = 1.0 (t, 3H), 1.9 (m, 2H), 2.0 (m, 2H), 2.2 (m, 2H), 3.7 (m, 2H), 3.7 (s, 3H), 3.8 (s, 2H), 3.9 (m, 2H), 4.1 (t, 2H), 7.1 (t, 2H), 8.0 (m, 2H) | |

Example (XXXI-4)

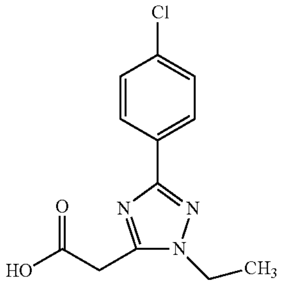 [SMILES: CCn1nc(-c2ccc(Cl)cc2)nc1CC(=O)O]

14.3 mmol (4.2 g) of ethyl [1-ethyl-3-(4-chlorophenyl)-1H-1,2,4-triazol-5-yl]acetate are dissolved in 30 ml of ethanol. 15 ml of a 15% strength aqueous sodium hydroxide solution are added dropwise, and the mixture is stirred at 45° C. for three hours. The reaction is concentrated and the residue is taken up in 50 ml of ice-water. 2N 10% strength hydrochloric acid is added dropwise until pH=2 is reached. The resulting precipitate is filtered off with suction, washed with water and dried. This gives 3.6 g (=95.2% of theory).

$^1$H NMR (400 MHz) in (DMSO-$d_6$): δ=1.4 (t, 3H), 4.0 (s, 2H), 4.2 (q, 2H), 7.5 (d, 2H), 8.0 (d, 2H)

Example (XXXI-10)

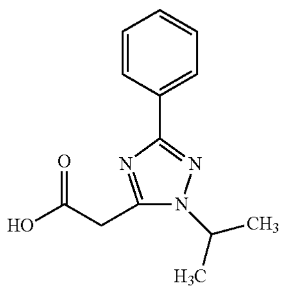 [SMILES: CC(C)n1nc(-c2ccccc2)nc1CC(=O)O]

19.4 mmol (5.3 g) of ethyl (1-isopropyl-3-phenyl-1H-1,2,4-triazol-5-yl)acetate are dissolved in 40 ml of ethanol. 20 ml of a 15% strength aqueous sodium hydroxide solution are added dropwise, and the mixture is stirred at 45° C. for three hours. The reaction is concentrated and the residue is taken up in 50 ml of ice-water. 2N 10% strength hydrochloric acid is added dropwise until pH=2 is reached. The resulting precipitate is filtered off with suction, washed with water and dried. This gives 4.5 g (=94.7% of theory).

$^1$H NMR (400 MHz) in (DMSO-$d_6$): δ=1.4 (d, 6H), 4.0 (s, 2H), 4.6 (m, 1H), 7.4 (m, 3H), 8.0 (d, 2H)

The following compounds of the formula (XXXI) are obtained analogously to Example (XXXI-4) and (XXXI-10) and following the general preparation instructions:

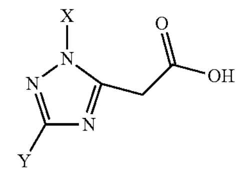

| No. | Y | X |
|---|---|---|
| XXXI-1 | 4-F—Ph | $CH_3$ |
| XXXI-2 | 4-F—Ph | $C_2H_5$ |
| XXXI-3 | 4-Cl—Ph | $CH_3$ |
| XXXI-5 | Ph | $CH_3$ |
| XXXI-6 | Ph | $C_2H_5$ |
| XXXI-7 | 4-F—Ph | i-Pr |
| XXXI-8 | 4-F—Ph | n-Pr |
| XXXI-9 | Ph | n-Pr |
| XXXI-11 | 4-F—Ph | $CH_2CF_3$ |
| XXXI-12 | 4-F—Ph | n-Bu |
| XXXI-13 | 4-Cl—Ph | $CH_2CH_2OCH_3$ |

Ph = phenyl, Pr = propyl, Bu = butyl $^1$H NMR (400 MHz) of XXXI-1 in (DMSO-$d_6$): δ=3.8 (s, 3H), 4.0 (s, 2H), 7.3 (m, 2H), 8.0 (m, 2H)

$^1$H NMR (400 MHz) of XXXI-2 in (DMSO-$d_6$): δ=1.4 (t, 3H), 4.0 (s, 2H), 4.2 (q, 2H), 7.3 (m, 2H), 8.0 (m, 2H)

$^1$H NMR (400 MHz) of XXXI-3 in (DMSO-$d_6$): δ=3.8 (s, 3H), 4.0 (s, 2H), 7.5 (d, 2H), 7.9 (d, 2H)

$^1$H NMR (400 MHz) of XXXI-5 in (DMSO-$d_6$): δ=3.8 (s, 3H), 4.0 (s, 2H), 7.4 (m, 3H), 7.9 (d, 2H)

$^1$H NMR (400 MHz) of XXXI-6 in (DMSO-$d_6$): δ=1.4 (t, 3H), 4.0 (s, 2H), 4.2 (q, 2H), 7.4 (m, 3H), 8.0 (d, 2H)

$^1$H NMR (400 MHz) of XXXI-7 in (DMSO-$d_6$): δ=1.4 (d, 6H), 4.0 (s, 2H), 4.6 (septet, 1H), 7.3 (m, 3H), 8.0 (m, 2H)

$^1$H NMR (400 MHz) of XXXI-8 in (DMSO-$d_6$): δ=0.9 (t, 3H), 1.3 (m, 2H), 4.0 (s, 2H), 4.1 (t, 2H), 7.3 (m, 2H), 8.0 (m, 2H)

$^1$H NMR (400 MHz) of XXXI-9 in (DMSO-$d_6$): δ=0.9 (t, 3H), 1.3 (m, 2H), 4.0 (s, 2H), 4.1 (t, 2H), 7.4 (m, 3H), 8.0 (d, 2H)

$^1$H NMR (400 MHz) of XXXI-11 in ($CDCl_3$): δ=4.0 (s, 2H), 4.8 (m, 2H), 7.1 (m, 2H), 8.1 (m, 2H)

$^1$H NMR (400 MHz) of XXXI-12 in ($CDCl_3$): δ=1.0 (t, 3H), 1.4 (m, 2H), 1.9 (s, 2H), 4.1 (m, 4H), 7.1 (m, 2H), 8.1 (m, 2H)

$^1$H NMR (400 MHz) of XXXI-13 in (DMSO-$d_6$): δ=3.3 (s, 3H), 3.7 (t, 2H), 4.0 (s, 2H), 4.4 (t, 2H), 7.5 (d, 2H), 8.0 (d, 2H)

Example (XXXV-1)

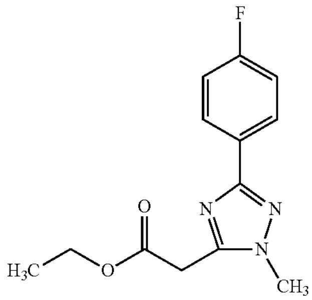 [SMILES: CCOC(=O)Cc1nc(-c2ccc(F)cc2)nn1C]

0.0915 mol (22.8 g) of ethyl [5-(4-fluorophenyl)-1H-1,2,4-triazol-3-yl]acetate are dissolved in 225 ml of acetonitrile. Under argon, 0.183 mol (25.2 g) of potassium carbonate are added over a period of 15 minutes. 0.091 mol (13.0 g) of iodomethane, dissolved in 40 ml of acetonitrile, are then added dropwise over 15 min. The reaction is shaken for 16 h. The reaction solution is filtered through a glass frit and the filtrate is concentrated. The crude product is purified by column chromatography on silica gel. The mobile phase used is a mixture of hexane:ethyl acetate=3:1. This gives 13.7 g (=56% of theory).

$^1$H NMR (400 MHz) of XXXV-1 in ($CDCl_3$): δ=1.3 (t, 3H), 3.9 (s, 3H), 3.9 (s, 2H), 4.2 (q, 2H), 7.1 (m, 2H), 8.0 (m, 2H)

Example (XXXV-6)

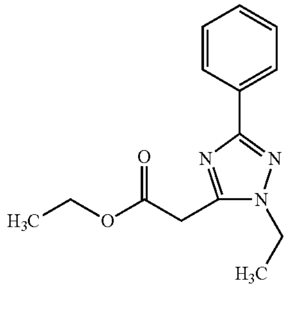 [SMILES: CCOC(=O)Cc1nc(-c2ccccc2)nn1CC]

0.030 mol (7.0 g) of ethyl (5-phenyl-1H-1,2,4-triazol-3-yl) acetate are dissolved in 60 ml of DMSO. Under argon, 0.091 mol (12.5 g) of potassium carbonate are added over a period of 15 minutes. 0.033 mol (5.2 g) of iodoethane, dissolved in 40 ml of DMSO, are then added dropwise over 15 min. The reaction is stirred for 1.5 h at 60° C. The reaction solution is filtered through a glass frit and the filtrate is concentrated under high vacuum. The crude product is purified by HPLC. This gives 5.3 g (=68.8% of theory).

$^1$H NMR (400 MHz) of XXXV-6 in ($CDCl_3$): δ=1.3 (t, 3H), 1.5 (t, 3H), 3.9 (s, 2H), 4.2 (m, 2H), 7.3 (m, 3H), 8.1 (d, 2H)

The following compounds of the formula (XXXI) are obtained analogously to Example (XXXV-1) and (XXXV-6) and following the general preparation instructions:

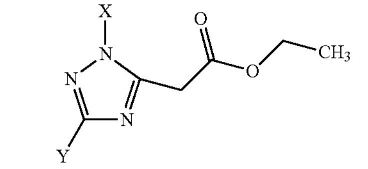

| No. | Y | X |
|---|---|---|
| XXXV-2 | 4-F—Ph | $C_2H_5$ |
| XXXV-3 | 4-Cl—Ph | $CH_3$ |
| XXXV-4 | 4-Cl—Ph | $C_2H_5$ |
| XXXV-5 | Ph | $CH_3$ |
| XXXV-7 | 4-F—Ph | i-Pr |
| XXXV-8 | 4-F—Ph | n-Pr |
| XXXV-9 | Ph | n-Pr |
| XXXV-10 | Ph | i-Pr |
| XXXV-11 | 4-F—Ph | $CH_2CF_3$ |
| XXXV-12 | 4-F—Ph | n-Bu |
| XXXV-13 | 4-Cl—Ph | $CH_2CH_2OCH_3$ |

$^1$H NMR (400 MHz) of XXXV-2 in ($CDCl_3$): δ=1.3 (t, 3H), 1.5 (t, 3H), 3.9 (s, 2H), 4.2 (m, 4H), 7.1 (m, 2H), 8.0 (m, 2H)

$^1$H NMR (400 MHz) of XXXV-3 in ($CDCl_3$): δ=1.3 (t, 3H), 3.9 (s, 3H), 3.9 (s, 2H), 4.2 (q, 2H), 7.4 (m, 2H), 8.0 (d, 2H)

$^1$H NMR (400 MHz) of XXXV-4 in ($CDCl_3$): δ=1.3 (t, 3H), 1.5 (t, 3H), 3.8 (s, 2H), 4.2 (m, 4H), 7.5 (d, 2H), 7.6 (d, 2H)

$^1$H NMR (400 MHz) of XXXV-5 in ($CDCl_3$): δ=1.3 (t, 3H), 3.9 (s, 3H), 3.9 (s, 2H), 4.2 (q, 2H), 7.4 (m, 3H), 8.1 (d, 2H)

$^1$H NMR (400 MHz) of XXXV-7 in ($CDCl_3$): δ=1.3 (t, 3H), 1.5 (d, 6H), 3.8 (s, 2H), 4.2 (q, 2H), 4.6 (septett, 1H), 7.2 (m, 2H), 7.6 (m, 2H)

$^1$H NMR (400 MHz) of XXXV-8 in ($CDCl_3$): δ=0.9 (t, 3H), 1.3 (t, 3H), 1.9 (m, 1H), 3.8 (s, 2H), 4.1 (t, 2H), 4.2 (q, 2H), 7.2 (m, 2H), 7.6 (m, 2H)

$^1$H NMR (400 MHz) of XXXV-9 in ($CDCl_3$): δ=1.0 (t, 3H), 1.3 (t, 3H), 2.0 (m, 1H), 3.8 (s, 2H), 4.1 (t, 2H), 4.2 (q, 2H), 7.4 (m, 3H), 8.1 (d, 2H)

$^1$H NMR (400 MHz) of XXXV-10 in ($CDCl_3$): δ=1.3 (t, 3H), 1.6 (d, 6H), 3.9 (s, 2H), 4.2 (q, 2H), 4.5 (septett, 1H), 7.4 (m, 3H), 8.1 (m, 2H)

$^1$H NMR (400 MHz) of XXXV-11 in ($CDCl_3$): δ=1.3 (t, 3H), 4.2 (q, 2H), 4.9 (q, 2H), 7.1 (m, 2H), 8.1 (m, 2H)

$^1$H NMR (400 MHz) of XXXV-12 in ($CDCl_3$): δ=1.0 (t, 3H), 1.3 (t, 3H), 1.4 (m, 2H), 2.0 (m, 2H), 4.2 (t, 2H), 4.3 (q, 2H), 4.3 (s, 2H), 7.1 (m, 2H), 8.2 (m, 2H)

$^1$H NMR (400 MHz) of XXXI-13 in ($CDCl_3$): δ=1.3 (t, 3H), 3.3 (s, 3H), 3.7 (t, 2H), 4.0 (s, 2H), 4.2 (q, 2H), 4.4 (t, 2H), 7.4 (d, 2H), 8.0 (d, 2H)

Example (XXXV-A-1)

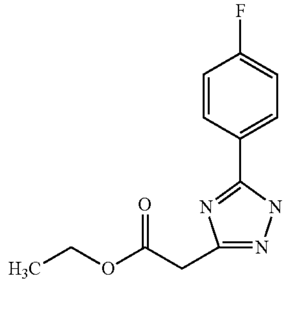 [SMILES: CCOC(=O)Cc1n[nH]c(-c2ccc(F)cc2)n1]

0.46 mol (89.7 g) of 1,3-diethoxy-3-oxopropane-1-iminium chloride is added to a well-stirred mixture of 500 ml of chloroform and 300 ml of saturated sodium bicarbonate solution. After 15 minutes, the organic phase is separated off, washed with sodium chloride solution and dried over magnesium sulfate, and the filtrate is concentrated.

The residue is taken up in toluene, placed under argon and, at 0° degrees, first 0.74 mol (74.5 g) of triethylamine and then, dropwise, a solution of 0.80 mol (126.4 g) of 4-fluorobenzoyl chloride in toluene are added. Stirring is continued at RT overnight. The precipitate is filtered off and the filtrate is concentrated. The residue is dissolved in 500 ml of dichloromethane, and 500 ml of an anhydrous 1N hydrazine solution in THF are then added dropwise. The mixture is stirred at room temperature for 16 h. The reaction solution is washed twice with ice-water. The combined organic phases are dried over magnesium sulfate and concentrated. The crude product is purified by column chromatography on silica gel. The mobile phase used is a mixture of hexane:ethyl acetate=1:1. Yield: 48.2 g (42.1% of theory)

$^1$H NMR (400 MHz) in (DMSO-$d_6$): δ=1.2 (t, 3H), 3.9 (s, 2H), 4.3 (m, 2H), 7.4 (m, 2H), 8.0 (m, 2H)

Example (XXXV-A-2)

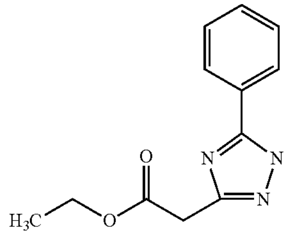 [SMILES: CCOC(=O)Cc1n[nH]c(-c2ccccc2)n1]

0.46 mol (89.7 g) of 1,3-diethoxy-3-oxopropane-1-iminium chloride is added to a well-stirred mixture of 500 ml of chloroform and 300 ml of saturated sodium bicarbonate solution. After 15 minutes, the organic phase is separated off, washed with sodium chloride solution and dried over magnesium sulfate, and the filtrate is concentrated.

The residue is taken up in toluene, placed under argon and, at 0° degrees, first 0.048 mol (74.5 g) of triethylamine and then, dropwise, a solution of 0.80 mol (140.0 g) of 4-chlorobenzoyl chloride in toluene are added. Stirring is continued at RT overnight. The precipitate is filtered off and the filtrate is concentrated. The residue is dissolved in 500 ml of dichloromethane, and 500 ml of an anhydrous 1N hydrazine solution in THF are then added dropwise. The mixture is stirred at room temperature for 16 h.

The reaction solution is washed 2× with ice-water. The combined organic phases are dried over magnesium sulfate and concentrated. The crude product is purified by column chromatography on silica gel. The mobile phase used is a mixture of hexane:ethyl acetate=1:1. Yield: 47.3 g (44.5% of theory)

$^1$H NMR (400 MHz) in ($CDCl_3$): δ=1.3 (t, 3H), 4.0 (s, 2H), 4.3 (q, 2H), 7.4 (m, 3H), 8.0 (m, 2H)

Example I-2a3-2=(I-2-a-1)

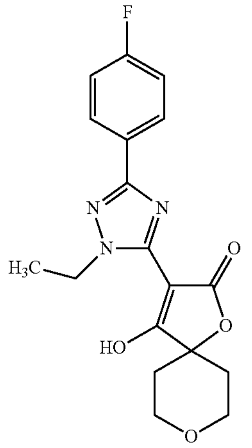 [SMILES: CCn1nc(-c2ccc(F)cc2)nc1C1=C(O)C2(CCOCC2)OC1=O]

208 mg (1.85 mmol) of potassium t-butoxide are initially charged in 3 ml of DMF and cooled to 0° C. A solution of 300 mg (0.74 mmol) of ethyl 4-ethoxy-2-{2-[1-ethyl-3-(4-fluorophenyl)-1H-1,2,4-triazol-5-yl]acetoxy}butanoate in 3 ml of DMF is added dropwise at RT and stirred at room temperature overnight.

For work-up, the DMF is removed on a rotary evaporator, the residue is stirred with water, the alk. phase is extracted with methyl t-butyl ether, the aqueous phase is extracted with hydrochloric acid, with dichloromethane, dried, filtered off and concentrated. The crude product is purified by chromatography on silica gel (mobile phase ethyl acetate/cyclohexane). Yield: 195 mg (73% of theory)

1H NMR ($CDCl_3$): δ=1.5 (t, 3H), 2.2 (m, 2H), 3.9 (m, 2H), 4.0 (m, 2H), 5.0 (q, 2H), 7.3 (m, 2H), 7.9 (m, 2H)

The following compounds of the formula (I-2-a) are obtained analogously to Example (I-2-a3-2) and following the general preparation instructions (I-2-a)

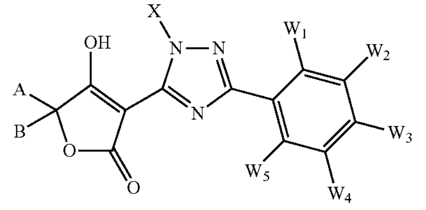

| Ex. no. | X | $W_1$ | $W_2$ | $W_3$ | $W_4$ | $W_5$ | A | B | Analysis | Isomer |
|---|---|---|---|---|---|---|---|---|---|---|
| I-2-a1-2 (I-2-a-2) | $C_2H_5$ | H | H | F | H | H | $CH_3$ | $CH_3$ | a) | |
| I-2-a2-3a (I-2-a-3) | $CH_3$ | H | H | Cl | H | H | $—(CH_2)_2—CHOCH_3—(CH_2)_2—$ | | b) | cis |
| I-2-a2-3b (I-2-a-4) | $CH_3$ | H | H | Cl | H | H | $—(CH_2)_2—CHOCH_3—(CH_2)_2—$ | | c) | trans |
| I-2-a6-3 (I-2-a-5) | $CH_3$ | H | H | Cl | H | H | $—(CH_2)_2—CHCH_2CH_3—(CH_2)_2—$ | | d) | |
| I-2-a2-12a (I-2-a-6) | n-Pr | H | H | F | H | H | $—(CH_2)_2—CHOCH_3—(CH_2)_2—$ | | e) | cis |
| I-2-a2-12b (I-2-a-7) | n-Pr | H | H | F | H | H | $—(CH_2)_2—CHOCH_3—(CH_2)_2—$ | | f) | trans |

a) 1H NMR ($CDCl_3$): δ=1.5 (s, 6H), 1.5 (t, 3H), 2.0 (m, 4H), 5.0 (q, 2H), 7.3 (m, 2H), 7.9 (m, 2H)

b) 1H NMR ($CDCl_3$): δ=1.7 (m, 2H), 1.8 (m, 2H), 1.9 (m, 2H), 2.1 (m, 2H), 3.3 (m, 1H), 3.4 (s, 3H), 4.5 (s, 3H), 7.5 (d, 2H), 7.8 (d, 2H)

c) 1H NMR ($CDCl_3$): δ=1.5 (m, 2H), 1.9 (m, 2H), 2.0 (m, 2H), 2.2 (m, 2H), 3.3 (s, 3H), 3.6 (m, 1H), 4.5 (s, 3H), 7.5 (d, 2H), 7.8 (d, 2H)

d) 1H NMR ($CDCl_3$): δ=0.9 (t, 3H), 1.4 (m, 2H), 1.7 (m, 4H), 1.9 (m, 2H), 2.0 (m, 2H), 4.5 (s, 3H), 7.5 (d, 2H), 7.8 (d, 2H)

e) 1H NMR ($CDCl_3$): δ=1.0 (t, 3H), 1.7 (m, 2H), 1.9 (m, 2H), 3.3 (m, 1H), 3.4 (s, 3H), 4.5 (t, 2H), 7.1 (t, 2H), 8.1 (m, 2H)

f) 1H NMR ($CDCl_3$): δ=1.0 (t, 3H), 1.5 (m, 2H), 1.9 (m, 2H), 2.2 (m, 2H), 3.3 (s, 3H), 3.6 (m, 1H), 4.8 (t, 3H), 7.2 (t, 2H), 8.0 (m, 2H)

Example III-1-a2-3=(III-1)

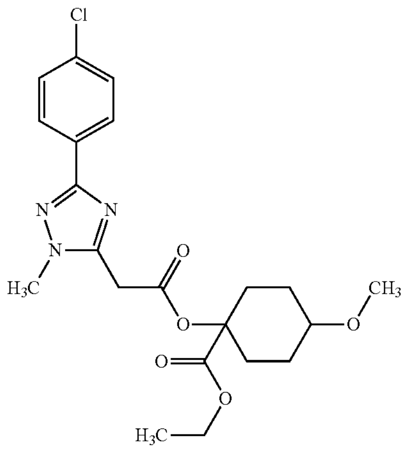

500 mg (1.9 mmol) of triazolylacetic acid XXXI-3, 442 mg (2.2 mmol) of ethyl 1-hydroxy-4-methoxycyclohexanecarboxylate and 513 mg (4.0 mmol) of N-ethyl-diisopropylamine are dissolved in 5 ml of dichloromethane and cooled to 0° C. With stirring, 1.52 g of 2,4,6-tripropyl-1,3,5,2,4,6-trioxatriphosphinane 2,4,6-trioxide (T3P) in 3 ml of THF are slowly added dropwise, and the mixture is shaken overnight. The reaction is concentrated and purified by HPLC: Yield: 435 mg (67%)

1H NMR ($CDCl_3$): δ=1.2 (t, 3H), 1.5 (m, 2H), 1.8 (m, 2H), 1.9 (m, 2H), 2.3 (m, 2H), 3.2 (m, 1H), 3.3 (s, 3H), 3.9 (s, 3H), 4.0 (s, 2H), 4.2 (q, 2H), 7.4 (d, 2H), 8.0 (d, 2H)

Example (I-8-a1)

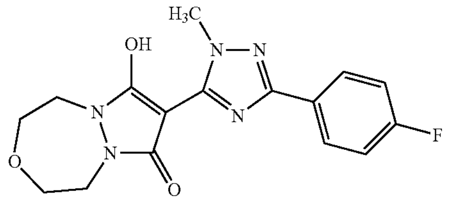 [SMILES: Cn1nc(-c2ccc(F)cc2)nc1-c1c(O)n2n(c1=O)CCOCC2]

308 mg (2.74 mmol) of potassium t-butoxide are initially charged in 3 ml of DMF and cooled to 0° C. A solution of 300 mg (0.74 mmol) of methyl 5-{[3-(4-fluorophenyl)-1-methyl-1H-1,2,4-triazol-5-yl]acetyl}-1,4,5-oxadiazepan-4-carboxylate in 3 ml of DMF is added dropwise at RT and stirred at room temperature overnight. For work-up, the DMF is removed on a rotary evaporator, the residue is stirred with water, the alk. phase is extracted with methyl t-butyl ether, the aqueous phase is extracted with hydrochloric acid, with dichloromethane, dried, filtered off and concentrated. The crude product is purified by chromatography on silica gel (mobile phase ethyl acetate/cyclohexane). Yield: 188 mg (69% of theory)

1H NMR ($CDCl_3$): δ=3.9 (m, 4H), 4.0 (m, 4H), 4.5 (s, 3H), 7.2 (t, 2H), 7.9 (m, 2H)

The following compounds of the formula (I-8-a) are obtained analogously to Example (I-8-a1) and following the general preparation instructions (I-8-a)

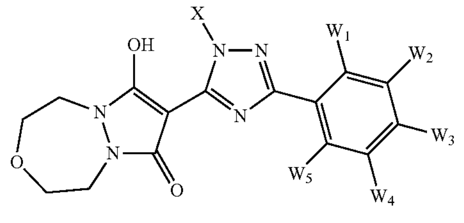

| Ex. no. | X | $W_1$ | $W_2$ | $W_3$ | $W_4$ | $W_5$ | Analysis |
|---|---|---|---|---|---|---|---|
| I-8-a-2 | i-Pr | H | H | H | H | H | a) |
| I-8-a-3 | $CH_3$ | H | H | Cl | H | H | b) |
| I-8-a-4 | n-Pr | H | H | F | H | H | c) |
| I-8-a-5 | $C_2H_5$ | H | H | F | H | H | d) |

a) 1H NMR ($CDCl_3$): δ = 1.5 (d, 6H), 3.9 (m, 4H), 4.0 (m, 4H), 6.5 (m, 1H), 7.2 (m, 2H), 7.9 (m, 2H)
b) 1H NMR (DMSO-$d_6$): δ = 3.6 (m, 4H), 3.8 (m, 4H), 4.0 (s, 3H), 7.5 (d, 2H), 8.0 (d, 2H)
c) 1H NMR ($CDCl_3$): δ = 1.0 (t, 3H), 2.0 (m, 2H), 3.9 (m, 4H), 4.1 (m, 4H), 4.8 (t, 2H), 7.2 (m, 2H), 8.0 (m, 2H)
d) 1H NMR ($CDCl_3$): δ = 1.5 (t, 3H), 3.9 (m, 4H), 5.0 (q, 2H), 7.2 (m, 2H), 7.9 (m, 2H)

Example I-8-b1=(I-8-g-1)

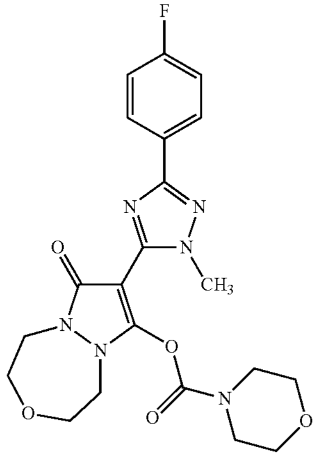 [SMILES: Cn1nc(-c2ccc(F)cc2)nc1-c1c(OC(=O)N2CCOCC2)n2n(c1=O)CCOCC2]

45 mg (0.13 mmol) of 1-8-a1 are dissolved in 5 ml of dichloromethane. 19.8 mg (0.195 mmol) of triethylamine are added successively to this solution, and the mixture is cooled to 0° C. A solution of 21 mg (0.143 mmol) of morpholine-4-carbonyl chloride in 1 ml of dichlormethane is then added dropwise. The mixture is stirred at room temperature overnight. The mixture is then washed with water and dried over magnesium sulfate. The solution is concentrated under reduced pressure and purified by HPLC. Yield: 54 mg (92%).

1H NMR ($CDCl_3$): δ=3.4 (m, 2H), 3.6 (m, 2H), 3.7 (m, 4H), 4.0 (m, 4H), 4.1 (s, 3H), 4.2 (m, 2H), 4.3 (m, 2H), 7.2 (t, 2H), 7.9 (m, 2H)

Example XII-8-a1=(XII-1)

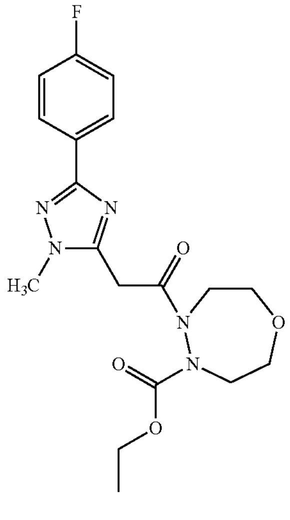 [SMILES: CCOC(=O)N1CCOCCN1C(=O)Cc1nc(-c2ccc(F)cc2)nn1C]

500 mg (2.13 mmol) of triazolylacetic acid XXXI-1, 403 mg (2.32 mmol) of ethyl 1,4,5-oxadiazepane-4-carboxylate and 824 mg (6.4 mmol) of N-ethyl-diisopropylamine are dissolved in 5 ml of dichloromethane and cooled to 0° C. With stirring, 1.52 g of 2,4,6-tripropyl-1,3,5,2,4,6-trioxatriphosphinane 2,4,6-trioxide (T3P) in 3 ml of THF are slowly added dropwise, and the mixture is shaken overnight. The reaction is concentrated and purified by HPLC: Yield: 673 mg (81%)

1H NMR ($CDCl_3$): δ=1.3 (m, 3H), 3.9 (s, 3H), 7.1 (t, 2H), 8.0 (m, 2H)

The following compounds of the formula (XII) are obtained analogously to Example (XII-8-a-1) and following the general preparation instructions (XII)

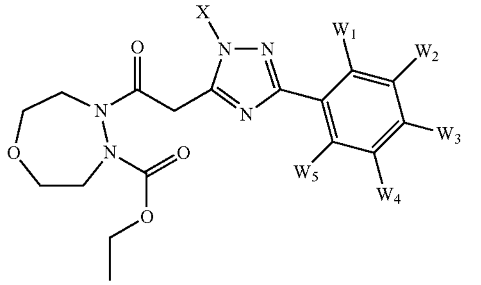

| Ex. no. | X | $W_1$ | $W_2$ | $W_3$ | $W_4$ | $W_5$ | Analysis |
|---|---|---|---|---|---|---|---|
| XII-8-a2 (XII-2) | i-Pr | H | H | H | H | H | a) |
| XII-8-a3 (XII-3) | $CH_3$ | H | H | Cl | H | H | b) |
| XII-8-a4 (XII-4) | n-Pr | H | H | F | H | H | c) |
| XII-8-a5 (XII-5) | Et | H | H | F | H | H | d) |

a) 1H NMR ($CDCl_3$): δ = 1.3 (m, 3H), 1.5 (d, 3H), ), 1.6 (d, 3H), 4.6 (septet, 1H), 7.4 (m, 3H), 8.1 (d, 2H)
b) 1H NMR ($CDCl_3$): δ = 1.3 (m, 3H), 3.9 (s, 3H), 7.4 (d, 2H), 8.0 (d, 2H)
c) 1H NMR ($CDCl_3$): δ = 1.0 (t, 3H), 1.3 (m, 3H), ), 2.0 (m, 2H), 4.6 (septet, 1H), 7.1 (m, 2H), 8.0 (m, 2H)
d) 1H NMR ($CDCl_3$): δ = 1.3 (m, 3H), 1.5 (t, 3H), ), 4.2 (q, 2H), 7.1 (m, 2H), 8.0 (m, 2H)

In Preparation Examples having two example numbers, the second number refers to the illustrations in the description.

Example 1

1. Herbicidal Pre-emergence Action

Seeds of monocotyledonous and dicotyledonous weed plants and crop plants are placed in wood-fiber pots in sandy loam and covered with soil. The test compounds, formulated in the form of wettable powders (WP), are then, as an aqueous suspension with a water application rate of 600 l/ha (converted), with 0.2% of wetting agent added, applied at various dosages to the surface of the covering soil.

After the treatment, the pots are placed in a greenhouse and kept under good growth conditions for the test plants. The visual assessment of the damage to the test plants is carried out after a trial period of about 3 weeks by comparison with untreated controls (herbicidal activity in percent: 100% activity=the plants have died, 0% activity=like control plants).

In addition to the compounds mentioned above, the following compounds show an activity of ≥80% against *Alopecurus myosuroides, Avena fatua, Echinocloa crus-galli, Lolium multiflorum* and *Setaria viridis* when applied by the pre-emergence method at 320 g/ha of a.i.: I-1-a1-1, I-1-a1-2, I-1-a1-4, I-1-a1-9, I-1-a1-10, I-1-a2-1, I-1-a2-2, I-1-a2-3, I-1-a2-4, I-1-a2-6, I-1-a2-7, I-1-a2-9, I-1-a2-10, I-1-a3-2, I-1-a3-3, I-1-a3-4, I-1-a3-6, I-1-a4-3, I-1-a4-2, I-1-a4-4, I-1-a4-11, I-1-a5-8, I-1-a6-3, I-1-a7-3, I-1-a8-3, I-1-a9-3, I-1-a10-3, I-1-a11-3, I-1-a12-3, I-1-a13-3, I-2-a2-12a.

Example 2

Herbicidal Post-emergence Action

Seeds of monocotyledonous and dicotyledonous weed and crop plants are placed in sandy loam in wood-fiber pots, covered with soil and cultivated in a greenhouse under good growth conditions. 2 to 3 weeks after sowing, the test plants are treated at the one-leaf stage. The test compounds, formulated as wettable powders (WP), are then, with a water application rate of 600 l/ha (converted), with 0.2% of wetting agent added, sprayed at various dosages onto the green parts of the plants. After the test plants have been kept in the greenhouse under optimum growth conditions for about 3 weeks, the activity of the preparations is rated visually in comparison to untreated controls (herbicidal activity in percent: 100% activity=the plants have died, 0% activity=like control plants).

In addition to the compounds mentioned above, the following compounds show an activity of ≥80% against *Alopecurus myosuroides, Avena fatua, Echinocloa crus-galli, Lolium multiflorum* and *Setaria viridis* when applied by the post-emergence method at 320 g/ha: I-1-a1-1, I-1-a1-2, I-1-a1-4, I-1-a2-1, I-1-a2-2, I-1-a2-3, I-1-a2-4, I-1-a2-6, I- 1-a2-9, I-1-a2-10, I-1-a3-1, I-1-a3-2, I-1-a3-3, I-1-a3-4, I-1-a4-1, I-1-a4-2, I-1-a4-3, I-1-a4-4, I-1-a5-4, I-1-a7-3, I-1-a8-3, I-1-a9-3, I-1-a10-3, I-2a3-2.

Example 3

*Lucilia Cuprina* (48 h)

Solvent: dimethyl sulfoxide

To produce a suitable preparation of active compound, 10 mg of active compound are mixed with 0.5 ml of dimethyl sulfoxide, and the concentrate is diluted with water to the desired concentration.

Vessels containing horse meat treated with the active compound preparation of the desired concentration are populated with about 20 *Lucilia* cuprina larvae.

After 48 hours, the kill in % is determined 100% means that all larvae have been killed; 0% means that no larvae have been killed.

In this test, for example, the following compounds of the Preparation Examples show an efficacy of 90% at an application rate of 100 ppm: I-1-a1-3.

Example 4

*Tetranychus* Spray Test, OP-resistant (TETRUR)

Solvents: 78.0 parts by weight of acetone 1.5 parts by weight of dimethylformamide Emulsifer: 0.5 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Discs of bean leaves (*Phaseolus vulgaris*) which are infested by all stages of the greenhouse red spider mite (*Tetranychus urticae*) are sprayed with an active compound preparation of the desired concentration.

After 6 days, the effect in % is determined 100% here means that all of the spider mites have been killed; 0% means that none of the spider mites have been killed.

In this test, for example, the following compounds of the Preparation Examples show an efficacy of 100% at an application rate of 500 g/ha: I-1-a1-3, I-1-a2-1, I-1-a2-3, I-1-a3-1, I-1-a-4-4, I-1-a8-3, I-2-a2-3a, I-2-a2-3b.

In this test, for example, the following compounds of the Preparation Examples show an efficacy of 90% at an application rate of 500 g/ha: I-1-a6-3, I-1-a7-3, I-2-a2-12a.

In this test, for example, the following compounds of the Preparation Examples show an efficacy of 80% at an application rate of 500 g/ha: I-1-a1-4.

In this test, for example, the following compounds of the Preparation Examples show an efficacy of 90% at an application rate of 100 g/ha: I-1-a1-9, I-1-a9-3, I-1-a10-3, I-1-a11-3, I-8-a3, I-8-a5.

Example 5

*Myzus persicae* Spray Test (MYZUPE)

Solvents: 78 parts by weight of acetone
1.5 parts by weight of dimethylformamide
Emulsifier: 0.5 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Disks of Chinese cabbage (*Brassica pekinensis*) infested by all stages of the green peach aphid (*Myzus persicae*) are sprayed with an active compound formulation of the desired concentration.

After 6 days, the effect in % is determined 100% here means that all of the aphids have been killed; 0% means that none of the aphids have been killed.

In this test, for example, the following compounds from the Preparation Examples show an efficacy of 100% at an application rate of 500 g/ha: I-1-a2-1, I-1-a2-3, I-1-a2-5, I-1-a3-5, I-2-a2-3a, I-2-a2-3b.

In this test, for example, the following compounds from the Preparation Examples show an efficacy of 90% at an application rate of 500 g/ha: I-1-a6-3, I-1-a7-3, I-1-a9-3, I-1-a10-3, I-1-a11-3, I-1-a13-3, I-2-a2-12a, I-8-a3.

In this test, for example, the following compounds from the Preparation Examples show an efficacy of 80% at an application rate of 500 g/ha:: I-1-a1-4.

Example 6

*Phaedon Cochleariae* Spray Test (PHAECO)

Solvents: 78.0 parts by weight of acetone
1.5 parts by weight of dimethylformamide
Emulsifier: 0.5 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Disks of Chinese cabbage leaves (*Brassica pekinensis*) are sprayed with an active compound preparation of the desired concentration and, after drying, populated with larvae of the mustard beetle (*Phaedon cochleariae*).

After 7 days, the effect in % is determined 100% means that all beetle larvae have been killed; 0% means that none of the beetle larvae have been killed.

In this test, for example, the following compounds of the Preparation Examples show an efficacy of 100% at an application rate of 500 g/ha: I-1-a6-3.

The invention claimed is:

1. A compound of formula (I)

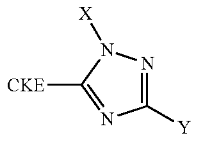

(I)

in which

X represents methyl, ethyl, n-propyl, isopropyl, n-butyl, $-CH_2CF_3$ or cyclopropyl, Y represents phenyl, 4-Cl-benzyl, 4-F-phenyl, 4-Cl-phenyl or 2,4-$Cl_2$-phenyl, CKE represents one of the groups

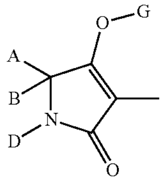

, (1)

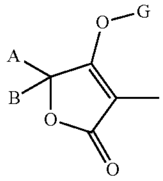

, or (2)

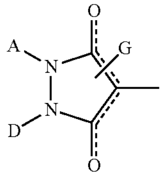

, (8)

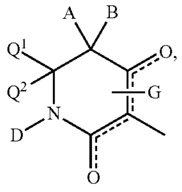

(9)

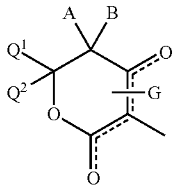

or (10)

-continued (11)

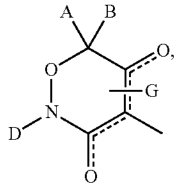

A represents hydrogen, methyl, ethyl or cyclopropyl,

B represents hydrogen, methyl or cyclopropyl, or

A, B and the carbon atom to which they are attached together represent saturated $C_5$-$C_6$-cyclo-alkyl in which optionally one ring member is replaced by oxygen or nitrogen and which is optionally mono- or disubstituted by methyl, ethyl, methoxymethyl, methoxy, ethoxy, propoxy, butoxy, trifluoroethoxy, trifluoromethyl or —O—$CH_2CHCH_2$, where methoxy or ethoxy are suitable as ring N-substituents, or A, B and the carbon atom to which they are attached together represent $C_6$-cycloalkyl which is optionally substituted by an alkylenedioxy group which contains two oxygen atoms that are not directly adjacent, thus forming a further 5- or 6-membered ring which is optionally mono- or disubstituted by methyl, D represents hydrogen or cyclopropyl, or A and D together represent $C_3$-$C_5$-alkanediyl in which optionally one carbon atom is replaced by oxygen, or A and D together represent $C_3$-$C_5$-alkanediyl which is optionally substituted by an alkylenedioxy group which optionally contains two oxygen atoms that are not directly adjacent and is optionally mono- to disubstituted by methyl, thus forming a further 5-membered ring, and G represents hydrogen (a) or represents one of the groups (b)

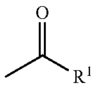

or (c)

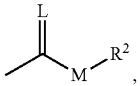

, in which

L represents oxygen,

M represents oxygen, $R^1$ represents $C_1$-$C_6$-alkyl, and $R^2$ represents $C_1$-$C_6$-alkyl, or G represents group (g)

(g)

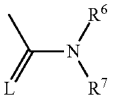

in which

L represents oxygen and $R^6$ and $R^7$ together represent a $C_5$-alkylene radical in which one carbon atom is replaced by oxygen.

2. The compound of the formula (I) as claimed in claim 1 in which

X represents methyl or ethyl,

Y represents 4-F-phenyl or 4-Cl-phenyl,

CKE represents one of the groups (1)

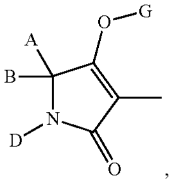

, (2)

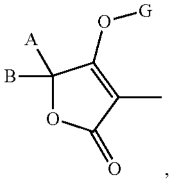

,

A represents hydrogen or methyl,

B represents hydrogen or methyl,

A, B and the carbon atom to which they are attached represent saturated $C_6$-cycloalkyl in which optionally one ring member is replaced by oxygen and which is optionally monosubstituted by methyl or methoxy, D represents hydrogen or cyclopropyl, or A and D together represent $C_3$-alkanediyl, and G represents hydrogen.

3. The compound of the formula (I) as claimed in claim 1 in which

X represents methyl, ethyl, isopropyl, n-propyl, n-butyl or —$CH_2$—$CF_3$,

Y represents phenyl, 4-Cl-benzyl, 4-F-phenyl, 4-Cl-phenyl or 2,4-$Cl_2$-phenyl,

CKE represents one of the groups (1)

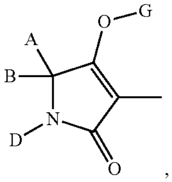

, (2)

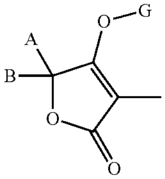

or (8)

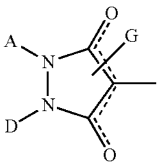

,

A represents hydrogen, methyl or cyclopropyl,

B represents hydrogen, methyl or cyclopropyl,

A, B and the carbon atom to which they are attached represent saturated $C_6$-cycloalkyl in which optionally one ring member is replaced by oxygen or nitrogen and which is optionally mono- or disubstituted by methyl, ethyl, methoxy, ethoxy, n-propoxy, trifluoromethyl or —O—$CH_2CHCH_2$, where methoxy or ethoxy are suitable as ring N-substituents, or A, B and the carbon atom to which they are attached represent $C_6$-cycloalkyl which is optionally substituted by an alkylenedioxy group which contains two oxygen atoms that are not directly adjacent, thus forming a further 6-membered ring which is optionally monosubstituted by methyl, D represents hydrogen or cyclopropyl, or A and D together represent C3-alkanediyl or when CKE=group (8) together optionally also represent —$(CH_2)_2$—O—$(CH_2)_2$—, and G represents hydrogen (a) or represents group (g)

(g)

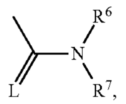

in which

L represents oxygen and $R^6$ and $R^7$ together represent a $C_5$-alkylene radical in which one carbon atom is replaced by oxygen.

4. A process for preparing compounds of the formula (I) as claimed claim 1, wherein to obtain (A) a compound of formula (I-1-a)

(I-1-a)

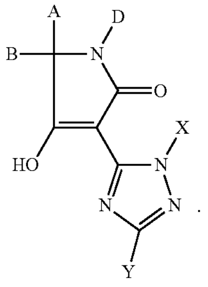

a compound of formula (II)

(II)

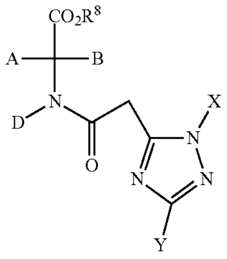

in which $R^8$ represents alkyl, is condensed intramolecularly in the presence of a diluent and in the presence of a base, (B) a compound of formula (I-2-a)

(I-2-a)

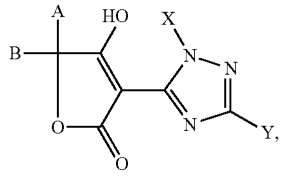

a compound of formula (III)

(III)

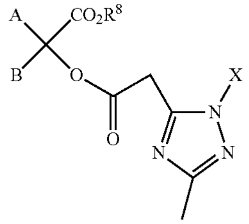

in which $R^8$ represents alkyl, is condensed intramolecularly in the presence of a diluent and in the presence of a base, (H) a compound of formula (I-8-a)

(I-8-a)

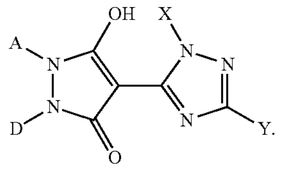

a compound of formula (X)

(X)

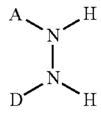

α) is reacted with a compound of formula (VI)

(VI)

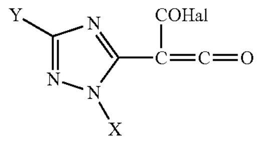

in which Hal represents halogen, optionally in the presence of a diluent and optionally in the presence of an acid acceptor, or β) is reacted with a compound of formula (XI)

(XI)

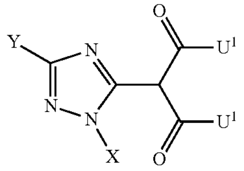

in which $U^1$ represents $NH_2$ or O—$R^8$, where $R^8$ has the meaning mentioned above, optionally in the presence of a diluent and optionally in the presence of a base, or γ) a compound of formula (XII)

(XII)

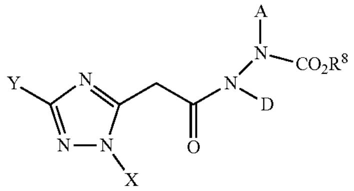

in which $R^8$ represents alkyl, is reacted optionally in the presence of a diluent and optionally in the presence of a base, (L) a compound of formula (I) as defined in claim 1 in which G is group (b), a compound of the formulae (I-1-a), (I-2-a), or (I-8-a) shown above is in each case reacted (α) with an acid halide of formula (XVI)

(XVI)

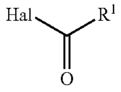

in which Hal represents halogen, or (β) with a carboxylic anhydride of formula (XVII)

$R^1$—CO—O—CO—$R^1$ (XVII)

optionally in the presence of a diluent and optionally in the presence of an acid binder;

(M) a compound of formula (I) as defined in claim 1 in which G is group (c), a compound of formulae (I-1-a), (I-2-a), or (I-8-a) in which is in each case reacted with a chloroformic ester or chloroformic thioester of formula (XVIII)

$R^2$-M-CO—Cl (XVIII)

in which $R^2$ and M have the meanings given in claim 1, optionally in the presence of a diluent and optionally in the presence of an acid binder, and (R) a compound of formula (I) as defined in claim 1 in which G is group (g), a compound of the formulae (I-1-a), (I-2-a), or (I-8-a) shown above is in each case (α) reacted with an isocyanate or isothiocyanate of formula (XXIV)

R6-N═C=L (XXIV)

optionally in the presence of a diluent and optionally in the presence of a catalyst, or (β) reacted with a carbamoyl chloride or thiocarbamoyl chloride of formula (XXV)

(XXV)

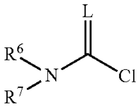

optionally in the presence of a diluent and optionally in the presence of an acid binder.

5. A composition for controlling pests and/or unwanted vegetation, comprising at least one compound of the formula (I) as claimed in claim 1.

6. A method of controlling animal pests and/or unwanted vegetation, comprising allowing a compound of formula (I) as claimed in claim 1 to act on a pest, unwanted vegetation and/or a habitat thereof.

7. A process for preparing a composition for controlling one or more pests and/or unwanted vegetation, comprising mixing a compound of formula (I) as claimed in claim 1 with an extender and/or surfactant.

8. A compound of formula (I) as claimed in claim 1 capable of being used for preparing a composition for controlling a pest and/or unwanted vegetation.

9. A composition comprising an effective amount of an active compound combination comprising, as components, (a') at least one compound of formula (I) as claimed in claim 1 and (b') at least one crop plant compatibility-improving compound selected from the group consisting of S1) a compound of the formula (S1)

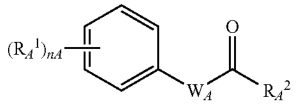

where $n_A$ is a natural number from 0 to 5, $R_A^1$ is halogen, $(C_1-C_4)$-alkyl, $(C_1-C_4)$-alkoxy, nitro or $(C_1-C_4)$-haloalkyl, $W_A$ is an unsubstituted or substituted divalent heterocyclic radical selected from the group consisting of the partially unsaturated or aromatic five-membered heterocycles having 1 to 3 ring heteroatoms of the N or O type, where at least one nitrogen atom and at most one oxygen atom is present in the ring, $m_A$ is 0 or 1, $R_A^2$ is $OR_A^3$, $SR_A^3$ or $NR_A^3R_A^4$ or a saturated or unsaturated 3- to 7-membered heterocycle having at least one nitrogen atom and up to 3 heteroatoms selected from the group consisting of O and S, which is joined to the carbonyl group in (S1) via the nitrogen atom and is unsubstituted or substituted by radicals selected from the group consisting of $(C_1-C_4)$-alkyl, $(C_1-C_4)$-alkoxy or optionally substituted phenyl, $R_A^3$ is hydrogen or an unsubstituted or substituted aliphatic hydrocarbyl radical having a total of 1 to 18 carbon atoms, $R_A^4$ is hydrogen, $(C_1-C_6)$-alkyl, $(C_1-C_6)$-alkoxy or substituted or unsubstituted phenyl, $R_A^5$ is H, $(C_1-C_8)$-alkyl, $(C_1-C_8)$-haloalkyl, $(C_1-C_4)$-alkoxy-$(C_1-C_8)$-alkyl, cyano or $COOR_A^9$, where $R_A^9$ hydrogen, $(C_1-C_8)$-alkyl, $(C_1-C_8)$-haloalkyl, $(C_1-C_4)$-alkoxy-$(C_1-C_4)$-alkyl, $(C_1-C_6)$-hydroxy-alkyl, $(C_3-C_{12})$-cycloalkyl or tri-$(C_1-C_4)$-alkylsilyl, and $R_A^6$, $R_A^7$, and $R_A^8$ are identical or different and are hydrogen, $(C_1-C_8)$-alkyl, $(C_1-C_8)$-haloalkyl, $(C_3-C_{12})$-cycloalkyl or substituted or unsubstituted phenyl;

S2) a compound of the formula (S2)

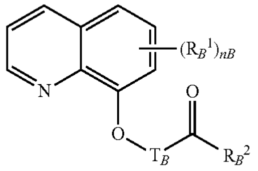

where $R_B^1$ is halogen, $(C_1-C_4)$-alkyl, $(C_1-C_4)$-alkoxy, nitro or $(C_1-C_4)$-haloalkyl, $n_B$ is a natural number from 0 to 5, $R_B^2$ is $OR_B^3$, $SR_B^3$ or $NR_B^3R_B^4$ or a saturated or unsaturated 3- to 7-membered heterocycle having at least one nitrogen atom and up to 3 heteroatoms selected from the group consisting of O and S, which is joined to the carbonyl group in (S2) via the nitrogen atom and is unsubstituted or substituted by radicals selected from the group consisting of $(C_1-C_4)$-alkyl, $(C_1-C_4)$-alkoxy or optionally substituted phenyl, $R_B^3$ is hydrogen or an unsubstituted or substituted aliphatic hydrocarbyl radical having a total of 1 to 18 carbon atoms, $R_B^4$ is hydrogen, $(C_1-C_6)$-alkyl, $(C_1-C_6)$-alkoxy or substituted or unsubstituted phenyl; and $T_B$ is a ($C_1$ or $C_2$)-alkanediyl chain which is unsubstituted or substituted by one or two $(C_1-C_4)$-alkyl radicals or by $[(C_1-C_3)$-alkoxy]carbonyl;

S3) a compound of the formula (S3)

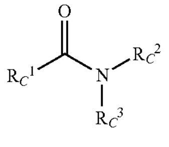

where $R_C^1$ is $(C_1-C_4)$-alkyl, $(C_1-C_4)$-haloalkyl, $(C_2-C_4)$-alkenyl, $(C_2-C_4)$-haloalkenyl or $(C_3-C_7)$-cycloalkyl, and $R_C^2$ and $R_C^3$ are identical or different and are hydrogen, $(C_1-C_4)$-alkyl, $(C_2-C_4)$-alkenyl, $(C_2-C_4)$-alkynyl, $(C_1-C_4)$-haloalkyl, $(C_2-C_4)$-haloalkenyl, $(C_1-C_4)$-alkylcarbamoyl-$(C_1-C_4)$-alkyl, $(C_2-C_4)$-alkenylcarbamoyl-$(C_1-C_4)$alkyl, $(C_1-C4)$-alkoxy-$(C_1-C_4)$-alkyl, dioxolanyl-$(C_1-C_4)$-alkyl, thiazolyl, furyl, furylalkyl, thienyl, piperidyl, or substituted or unsubstituted phenyl, or $R_C^2$ and $R_C^3$ together form a substituted or unsubstituted heterocyclic ring, S4) a compound of the formula (S4)

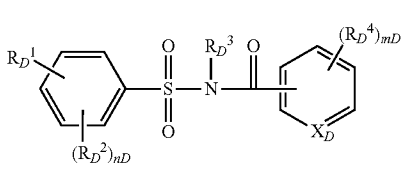

where $X_D$ is CH or N, $R_D^1$ is CO—$NR_D^5R_D^6$ or NHCO—$R_D^7$, $R_D^2$ is halogen, $(C_1-C_4)$-haloalkyl, $(C_1-C_4)$-haloalkoxy, nitro, $(C_1-C_4)$-alkyl, $(C_1-C_4)$-alkoxy, $(C_1-C_4)$-alkylsulfonyl, $(C_1-C_4)$-alkoxycarbonyl or $(C_1-C_4)$-alkylcarbonyl, $R_D^3$ is hydrogen, $(C_1-C_4)$-alkyl, $(C_2-C_4)$-alkenyl or $(C_2-C_4)$-alkynyl, $R_D^4$ is halogen, nitro, $(C_1-C_4)$-alkyl, $(C_1-C_4)$-haloalkyl, $(C_1-C_4)$-haloalkoxy, $(C_3-C_6)$-cycloalkyl, phenyl, $(C_1-C_4)$-alkoxy, cyano, $(C_1-C_4)$-alkylthio, $(C_1-C_4)$-alkylsulfinyl, $(C_1-C_4)$-alkylsulfonyl, $(C_1-C_4)$-alkoxycarbonyl or $(C_1-C_4)$-alkylcarbonyl, $R_D^5$ is hydrogen, $(C_1-C_6)$-alkyl, $(C_3-C_6)$-cycloalkyl, $(C_2-C_6)$-alkenyl, $(C_2-C_6)$-alkynyl, $(C_5-C_6)$-cycloalkenyl, phenyl or 3- to 6-membered heterocyclyl containing $v_D$ heteroatoms selected from the group consisting of nitrogen, oxygen and sulfur, where the seven latter radicals are each substituted by $v_D$ substituents selected from the group consisting of halogen, $(C_1-C_6)$-alkoxy, $(C_1-C_6)$-haloalkoxy, $(C_1-C_2)$-alkylsulfinyl, $(C_1-C_2)$-alkylsulfonyl, $(C_3-C_6)$-cycloalkyl, $(C_1-C_4)$-alkoxycarbonyl, $(C_1-C_4)$-alkylcarbonyl and phenyl, and in the case of cyclic radicals also $(C_1-C_4)$-alkyl and $(C_1-C_4)$-haloalkyl, $R_D^6$ is hydrogen, $(C_1-C_6)$-alkyl, $(C_2-C_6)$-alkenyl or $(C_2-C_6)$-alkynyl, where the three latter radicals are each substituted by $v_D$ radicals selected from the group consisting of halogen, hydroxyl, $(C_1-C_4)$-alkyl, $(C_1-C_4)$-alkoxy and $(C_1-C_4)$-alkylthio, or $R_D^5$ and $R_D^6$ together with the nitrogen atom which bears them form a pyrrolidinyl or piperidinyl radical, $R_D^7$ is hydrogen, $(C_1-C_4)$-alkylamino, di-$(C_1-C_4)$-alkylamino, $(C_1-C_6)$-alkyl, or $(C_3-C_6)$-cycloalkyl, where the 2 latter radicals are substituted by $v_D$ substituents selected from the group consisting of halogen, $(C_1-C_4)$-alkoxy, $(C_1-C_6)$-haloalkoxy and $(C_1-C_4)$-alkylthio, and in the case of cyclic radicals also $(C_1-C_4)$-alkyl and $(C_1-C_4)$-haloalkyl, $n_D$ is 0, 1 or 2, $m_D$ is 1 or 2, and $v_D$ is 0, 1, 2 or 3;

S5) a hydroxyaromatic or aromatic-aliphatic carboxylic acid derivative (S5) selected from the group consisting of ethyl 3,4,5-triacetoxybenzoate, 3,5-dimethoxy-4-hydroxybenzoic acid, 3,5-dihydroxybenzoic acid, 4-hydroxysalicylic acid, 4-fluorosalicyclic acid, 2-hydroxycinnamic acid, 1,2- dihydro-2-oxo-6-trifluoro-methylpyridine-3-carboxamide, and 2,4-dichlorocinnamic acid;

S6) a 1,2-dihydroquinoxalin-2-one (S6) selected from the group consisting of 1-methyl-3-(2-thienyl)-1,2-dihydroquinoxalin-2-one, 1-methyl-3-(2-thienyl)-1,2-dihydroquinoxaline-2-thione, 1-(2-aminoethyl)-3-(2-thienyl)-1,2-dihydro-quinoxalin-2-one hydrochloride, 1-[2-(diethylamino)ethyl]-6,7-dimethyl-3-thiophen-2-ylquinoxalin-2(1H)-one, and 1-(2-methylsulfonylaminoethyl)-3-(2-thienyl)-1,2-dihydroquinoxalin-2-one;

S7) a compound of the formula (S7)

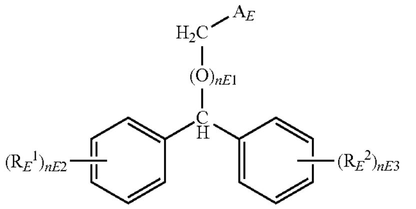

where $R_E^1$, $R_E^2$ are each independently of one another halogen, $(C_1-C_4)$-alkyl, $(C_1-C_4)$-alkoxy, $(C_1-C_4)$-haloalkyl, $(C_1-C_4)$-alkylamino, di-$(C_1-C_4)$-alkylamino or nitro;

$A_E$ is $COOR_E^3$ or $COSR_E^4$, $R_E^3$, $R_E^4$ are each independently of one another hydrogen, $(C_1-C_4)$-alkyl, $(C_2-C_6)$-alkenyl, $(C_2-C_4)$-alkynyl, cyanoalkyl, $(C_1-C_4)$-haloalkyl, phenyl, nitrophenyl, benzyl, halobenzyl, pyridinylalkyl or alkylammonium, $n_E^1$ is 0 or 1, and $n_E^2$, $n_E^3$ are each independently of one another 0, 1 or 2;

S8) a compound of the formula (S8)

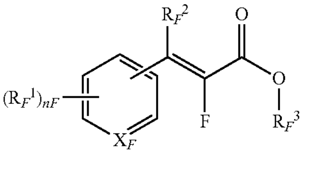

where $X_F$ is CH or N, $n_F$ in the case that $X_F$=N is an integer from 0 to 4 and in the case that $X_F$=CH is an integer from 0 to 5, $R_F^1$ is halogen, $(C_1-C_4)$-alkyl, $(C_1-C_4)$-haloalkyl, $(C_1-C_4)$-alkoxy, $(C_1-C_4)$-haloalkoxy, nitro, $(C_1-C_4)$-alkylthio, $(C_1-C_4)$-alkylsulfonyl, $(C_1-C_4)$-alkoxycarbonyl, optionally substituted phenyl, or optionally substituted phenoxy, $R_F^2$ is hydrogen or $(C_1-C_4)$-alkyl, and $R_F^3$ is hydrogen, $(C_1-C_8)$-alkyl, $(C_2-C_4)$-alkenyl, $(C_2-C_4)$-alkynyl, or aryl, where each of the aforementioned carbon-containing radicals is unsubstituted or substituted by one or more identical or different radicals selected from the group consisting of halogen and alkoxy, or salts thereof;

S9) a 3-(5-tetrazolylcarbonyl)-2-quinolone (S9) selected from the group consisting of 1,2-dihydro-4-hydroxy-1-ethyl-3-(5-tetrazolylcarbonyl)-2-quinolone and 1,2-dihydro-4-hydroxy-1-methyl-3-(5-tetrazolylcarbonyl)-2-quinolone;

S10) a compound of the formula (S10a)

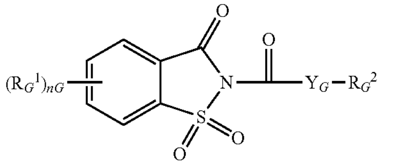

or ($S10^b$)

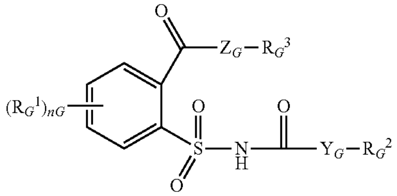

where $R_G^1$ is halogen, $(C_1-C_4)$-alkyl, methoxy, nitro, cyano, $CF_3$, or $OCF_3$, $Y_G$ and $Z_G$ are each independently of one another O or S, $n_G$ is an integer from 0 to 4, $R_G^2$ is $(C_1-C_{16})$-alkyl, $(C_2-C_6)$-alkenyl, $(C_3-C_6)$-cycloalkyl, aryl, benzyl, or halobenzyl, and $R_G^3$ is hydrogen or $(C_1-C_6)$-alkyl;

S11) an oxyimino compound (S11) seed dressing selected from the group consisting of oxabetrinil ((Z)-1,3-dioxolan-2-ylmethoxyimino(phenyl)acetonitrile) (S11-1) used as seed dressing safener for millet against metolachlor damage, fluxofenim (1-(4-chlorophenyl)-2,2,2-trifluoro-1-ethanone O-(1,3-dioxolan-2-ylmethyl)-oxime) (S11-2) used as seed dressing safener for millet against metolachlor damage, and cyometrinil (CGA-43089, (Z)-cyanomethoxyimino(phenyl)-acetonitrile) (S11-3) used as seed dressing safener for millet against metolachlor damage;

S12) an isothiochromanone (S12) that is methyl [(3-oxo-1H-2-benzothiopyran-4(3H)-ylidene)methoxyl] acetate (S12-1);

S13) naphthalic anhydride (1,8-naphthalenedicarboxylic anhydride) (S13-1) used as seed dressing safener for corn against thiocarbamate herbicide damage, fenclorim (4,6-dichloro-2-phenylpyrimidine) (S13-2) used as safener for pretilachlor in sown rice, flurazole (benzyl 2-chloro-4-trifluoromethyl-1,3-thiazole-5-carboxylate) (S13-3) used as seed dressing safener for millet against alachlor and metolachlor damage, CL 304415 (4-carboxy-3,4-dihydro-2H-1-benzopyran-4-acetic acid) (S13-4) used as a safener for corn against damage by imidazolinones, MG 191 (2-dichloromethyl-2-methyl-1,3-dioxolane) (S13-5)) used as a safener for corn, MG-838 (2-propenyl 1-oxa-4-azaspiro[4.5]decane-4-carbodithioate) (S13-6), disulfoton (O,O-diethyl S-2-ethylthioethyl phosphorodithioate) (S13-7), dietholate (O,O-diethyl O-phenyl phosphorothioate) (S13-8), or mephenate (4-chlorophenyl methylcarbamate) (S13-9);

S14) an active compound which, in addition to herbicidal action against harmful plants, also has safener action on crop plants selected from the group consisting of dimepiperate (MY-93, S-1-methyl-1-phenylethylpiperidine-1-carbothioate) used as a safener for rice against damage by the herbicide molinate, daimuron (SK 23, 1-(1-methyl-1-phenylethyl)-3-p-tolylurea) used as a safener for rice against imazosulfuron herbicide damage, cumyluron (JC-940, 3-(2-chlorophenylmethyl)-1-(1-methyl-1-phenylethyl) urea) used as a safener for rice against damage by some herbicides, methoxyphenone (NK 049, 3,3'-dimethyl-4-methoxybenzo-phenone) used as a safener for rice, and CSB (1-bromo-4-(chloromethylsulfonyl)benzene) used as a safener for rice; and S15) an active compound which is used primarily as an herbicide but also having safener action on crop plants selected from the group consisting of (2,4-dichlorophenoxy)acetic acid (2,4-D), (4-chlorophenoxy) acetic acid, (R,S)-2-(4-chloro-o-tolyloxy)propionic acid (mecoprop), 4-(2,4-dichloro-phenoxy)butyric acid (2,4-DB), (4-chloro-o-tolyloxy)acetic acid (MCPA), 4-(4-chloro-o-tolyloxy)butyric acid, 4-(4-chlorophenoxy)butyric acid, 3,6-dichloro-2-methoxybenzoic acid (digamma), and 1-(ethoxycarbonyl) ethyl 3,6-dichloro-2-methoxybenzoate (lactidichlor-ethyl).

10. The composition as claimed in claim 9 where the crop plant compatibility-improving compound is mefenpyr-diethyl.

11. A method for controlling unwanted vegetation, comprising allowing a composition as claimed in claim 9 to act on a plant and/or surroundings thereof.

12. A composition as claimed in claim 9 capable of being used for controlling unwanted vegetation.

13. A method for controlling unwanted vegetation, comprising allowing a compound of formula (I) as claimed in claim 1 and a crop plant compatibility-improving compound to act separately, in close temporal succession, on a plant and/or surroundings thereof.

14. A compound of the formula (I-1-a')

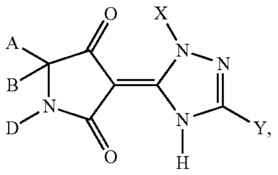

(I-2-a')

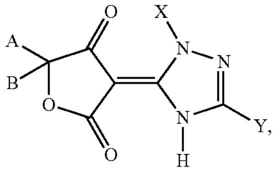

or

-continued (I-8-a')

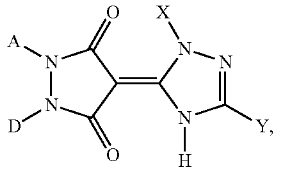

where

X represents methyl, ethyl, n-propyl, isopropyl, n-butyl, —$CH_2CF_3$ or cyclopropyl, Y represents phenyl, 4-Cl-benzyl, 4-F-phenyl, 4-Cl-phenyl or 2,4-$Cl_2$-phenyl, A represents hydrogen, methyl, ethyl or cyclopropyl, B represents hydrogen, methyl or cyclopropyl, or A, B and the carbon atom to which they are attached together represent saturated $C_5$-$C_6$-cyclo-alkyl in which optionally one ring member is replaced by oxygen or nitrogen and which is optionally mono- or disubstituted by methyl, ethyl, methoxymethyl, methoxy, ethoxy, propoxy, butoxy, trifluoroethoxy, trifluoromethyl or —O—$CH_2CHCH_2$, where methoxy or ethoxy are suitable as ring N-substituents, or A, B and the carbon atom to which they are attached together represent $C_6$-cycloalkyl which is optionally substituted by an alkylenedioxy group which contains two oxygen atoms that are not directly adjacent, thus forming a further 5- or 6-membered ring which is optionally mono- or disubstituted by methyl, and D represents hydrogen or cyclopropyl, or A and D together represent $C_3$-$C_5$-alkanediyl in which optionally one carbon atom is replaced by oxygen, or A and D together represent $C_3$-$C_5$-alkanediyl which is optionally substituted by an alkylenedioxy group which optionally contains two oxygen atoms that are not directly adjacent and is optionally mono- to disubstituted by methyl, thus forming a further 5-membered ring.

15. A compound according to claim 1 of the formula

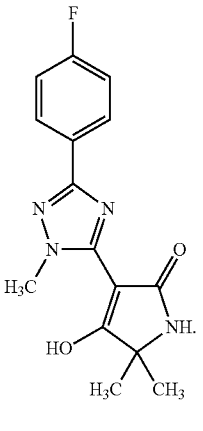 [SMILES: Cn1nc(-c2ccc(F)cc2)nc1C1=C(O)C(C)(C)NC1=O]

* * * * *